US010501454B2

(12) United States Patent
Yang et al.

(10) Patent No.: US 10,501,454 B2
(45) Date of Patent: Dec. 10, 2019

(54) MONOCYCLIC β-LACTAM-SIDEROPHORE CONJUGATE, AND PREPARATION METHOD AND USE THEREOF

(71) Applicants: Yushe Yang, Shanghai (CN); Liang Tan, Shanghai (CN); Qunhuan Kou, Shanghai (CN)

(72) Inventors: Yushe Yang, Shanghai (CN); Liang Tan, Shanghai (CN); Qunhuan Kou, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/251,486

(22) Filed: Jan. 18, 2019

(65) Prior Publication Data

US 2019/0233407 A1 Aug. 1, 2019

Related U.S. Application Data

(63) Continuation of application No. PCT/CN2017/093279, filed on Jul. 18, 2017.

(30) Foreign Application Priority Data

Jul. 21, 2016 (CN) .......................... 2016 1 0578272

(51) Int. Cl.
*C07D 417/14* (2006.01)
*A61P 31/04* (2006.01)

(52) U.S. Cl.
CPC ............ *C07D 417/14* (2013.01); *A61P 31/04* (2018.01)

(58) Field of Classification Search
CPC .................................................... C07D 471/14
USPC .......................................................... 546/243
See application file for complete search history.

(56) References Cited

U.S. PATENT DOCUMENTS 4,883,879 A 11/1989 Zama et al.

FOREIGN PATENT DOCUMENTS

| | | |
|---|---|---|
| CN | 1458932 | 11/2003 |
| CN | 101641095 | 2/2010 |
| CN | 103724330 | 4/2014 |
| WO | WO 2008/116813 | 10/2008 |
| WO | WO 2012/073138 | 6/2012 |
| WO | WO 2013/110643 | 8/2013 |

OTHER PUBLICATIONS

Page et al., "In Vitro Properties of BAL30072 . . . ", Antimicrob. Agents Chemother. 2010, 54, 2291-2302.
Sakagami et al., "Synthetic Cephalosporins. VII . . . ", Chemical & Pharmaceutical Bulletin 1990, 38(12), 3476-3479.
Performance Standards for Antimicrobial Susceptibility Testing; Twenty-Third Informational Supplement, M02-A11, M07-A9 and M11-A8, 2013; Jan. 2013.
Yamawaki et al., "A novel series of parenteral . . . ", Bioorg. Med. Chem. 15 (2007) 6716-6732.

*Primary Examiner* — Taofiq A Solola
(74) *Attorney, Agent, or Firm* — Reinhart Boerner Van Deuren P.C.

(57) ABSTRACT

The present disclosure relates to the field of pharmaceutical synthesis, and more particularly, relates to a monocyclic β-lactam-siderophore conjugate as well as a method for synthesizing same and its use in the treatment of bacterial infectious diseases. Provided are a monocyclic β-lactam-siderophore conjugate represented by formula (I) as described herein, an optical isomer thereof or a pharmaceutically acceptable salt thereof, and a method for synthesizing same, and a use thereof in treating bacterial infectious diseases.

11 Claims, No Drawings

MONOCYCLIC β-LACTAM-SIDEROPHORE CONJUGATE, AND PREPARATION METHOD AND USE THEREOF

CROSS-REFERENCE TO RELATED PATENT APPLICATIONS

This patent application is a continuation of PCT/CN2017/093279, filed Jul. 18, 2017, which claims priority to Chinese Application No. 201610578272.9, filed Jul. 21, 2016, the entire teachings and disclosure of which are incorporated herein by reference thereto.

TECHNICAL FIELD

The present invention belongs to the field of pharmaceutical synthesis, and more particularly, relates to a monocyclic β-lactam-siderophore conjugate as well as a method for synthesizing same and its use in the treatment of bacterial infectious diseases.

BACKGROUND OF ART

The discovery and use of antibiotics is considered to be one of the most important breakthroughs in modern medicine, and plays an extremely important role in safeguarding human health and prolonging human life. However, with the widespread use and even abuse of antibiotics in medicine, agriculture, aquaculture, etc., the problem of bacterial resistance has become one of the most pressing major threats to human health in the past two decades. In the past decade, the lag in the development of new antibacterial drugs and the reduction in investment in research and development of new antibacterial drugs by large pharmaceutical companies have exacerbated the severity of the "antibiotic crisis". In 2014, the World Health Organization pointed out that the world is going towards the "post-antibiotic era". If the problem of serious lack of effective antibiotics is not effectively alleviated as soon as possible, there may be a terrible possibility that people will die from common infections once again. At present, the main Gram-positive and negative bacteria have been generally resistant to existing antibiotics. Gram-positive bacteria are mainly methicillin-resistant *Staphylococcus aureus* (MRSA) and *Staphylococcus epidermidis* (MRSE), penicillin-resistant *Streptococcus pneumoniae* (PRSP) and vancomycin-resistant enterococci (VRE). Among them, MRSA and VRE are the most harmful. For multidrug-resistant positive bacteria infections, there are still a few drugs such as linezolid, tigecycline, glycopeptides (vancomycin and teicoplanin), so Gram-positive bacteria resistance is still a controllable crisis. The resistance of Gram-negative bacteria is more serious than that of Gram-positive bacteria. Except for the increasing community-acquired multidrug resistant (MDR) Gram-negative bacteria such as *Escherichia coli* and *Neisseria gonorrhoeae*, hospital-acquired extensive drug resistant (XDR) and total drug resistant (TDR) Gram-negative bacteria such as *Pseudomonas aeruginosa, Acinetobacter baumannii* and *Klebsiella pneumoniae* are extremely refractory and almost no drug is available, resulting in high mortality of hospital-acquired XDR and TDR infections. Therefore, Gram-negative bacterial resistance is a crisis that has been out of control. It can be seen that the development of drugs that are effective against drug-resistant Gram-negative bacteria is a significant and imminent scientific task for scientists. The resistance mechanisms of Gram-negative bacteria are more complicated than those of Gram-positive bacteria, including bacteria producing β-lactam hydrolase; the expression of the efflux pump pumping the drug out of the bacteria; the mutation of the membrane pore protein leading to the decrease of permeability; the mutations in binding sites and lateral transfer of drug resistance genes. A drug that can treat a drug-resistant negative bacterial infection should have the following characteristics: 1) it can pass through an outer membrane of the negative bacteria; 2) it is not recognized by the efflux pump and is not excreted out of the bacteria; and 3) it is not hydrolyzed by various hydrolases before reaching the target. Therefore, it is very difficult to develop drugs for multidrug-resistant negative bacteria. At present, no substantial progress has been made worldwide, and the drug candidates in clinical research are new structural derivatives of existing class antibiotics such as CAX101, Avibactam (NXL-104), Plazomicin (ACHN-490) and Eravacycline (TP-434). Looking for a new compound that can enter the bacteria with a new mechanism and overcome the mechanisms of bacterial efflux pump and membrane pore protein mutation is the most important direction for the development of new anti-multidrug resistance drug.

Free iron is almost a nutrient for all microorganisms, but it is extremely low in human plasma and body fluids, only $10^{-9}$ M, which is much lower than the needs of bacterial colonization and growth. In order to survive and maintain infectious toxicity, bacteria secrete various siderophores (molecules that can efficiently complex iron) to take iron from the host, transport the siderophore into the bacterial cells and release iron through the corresponding siderophore receptor on the outer membrane of the bacteria. Based on the principle of iron uptake of bacteria, the organic combination of the antibacterial drug and the siderophore in an ingenious way makes bacteria actively transport the antibiotics and iron together into the body while taking iron, which will effectively overcome the difficulty of pass through the outer membrane of Gram-negative bacteria and kill the bacteria quickly.

(1)

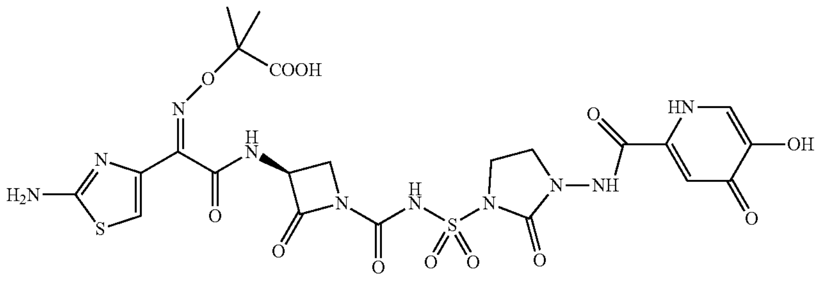

Pirazmonam

-continued (2)

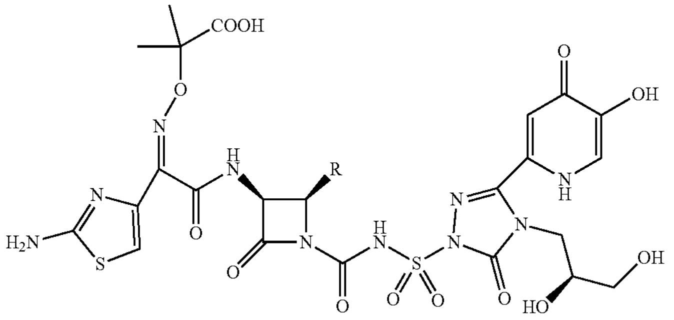

MC-1 R = H (3)

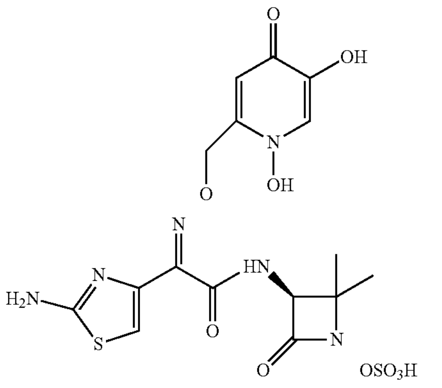

BAL30072

(4)

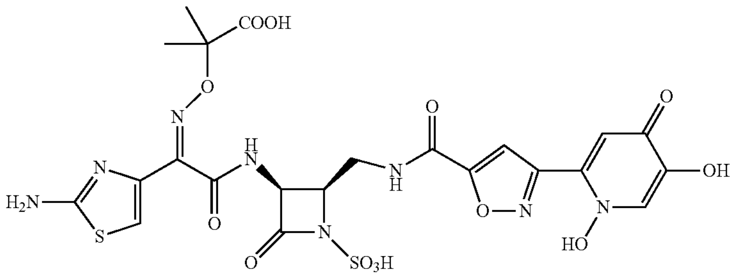

(5)

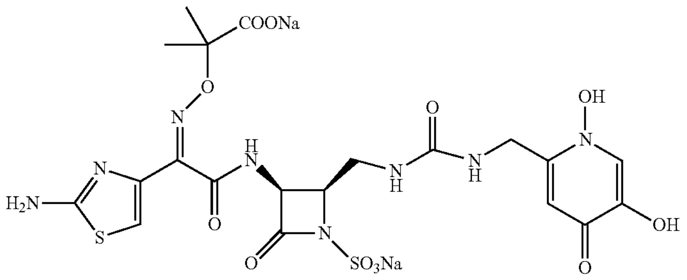

Efforts to design new antibiotics based on the principle of iron uptake of bacteria began in the late 1980s. In 1985, the compound Pirazmonam reported by Bristol-Myers Squibb is better in vitro and in vivo activities against *Enterobacter, Pseudomonas aeruginosa* and *Acinetobacter baumannii* than the similar aztreonam and ceftazidime. In 2007, Basilea reported the first siderophore antibiotic, BAL30072, which entered the clinical study. The compound has good antibacterial activity against multidrug-resistant *Pseudomonas aeruginosa* and *Acinetobacter baumannii*, but has less activity against the resistant Gram-negative bacteria that produce cephalosporinase (AmpC) or Class A or Class D extended-spectrum lactamases (ESBLs). At present, the treatment of drug-resistant Gram-negative bacteria infection with BAL30072 and meropenem in combination is in phase I clinical stage. Pfizer reported the Pirazmonam analogue MC-1 in 2011. MC-1 has a $MIC_{90}$ of 0.5 μg/mL for multi-drug-resistant *Pseudomonas aeruginosa*, a $MIC_{90}$ of 2 μg/mL for *Escherichia coli*, and a $MIC_{90}$ of 8 μg/mL for *Klebsiella pneumoniae*. Unfortunately, MC-1 is essentially ineffective against *Acinetobacter* with a $MIC_{90}$ greater than 64 μg/mL. In addition, MC-1 is chemically unstable and is susceptible to hydrolysis, which limits its further research. In 2012 to 2013, Pfizer reported compounds 4 and 5 in which a hydroxypyridone structure is introduced at the 2-position of the β-lactam ring. The compounds have good activity against *Pseudomonas aeruginosa, Klebsiella pneumoniae* and *Escherichia coli*. But the activity against *Acinetobacter baumannii* is still low ($MIC_{90}$>64 μg/mL).

In summary, the monocyclic β-lactam-siderophore conjugates are currently in the preclinical research stage, and only a few individual compounds such as BAL30072 are in the early stages of clinical research. The existing monocyclic β-lactam-siderophore conjugates have obvious deficiencies, and ubiquitously (such as the representative compound BAL30072) the antibacterial activity is not strong, and the antibacterial spectrum is not broad enough to cover the four most important multidrug-resistant Gram-negative bacteria, *Escherichia coli, Klebsiella pneumoniae, Acinetobacter baumannii* and *Pseudomonas aeruginosa*. In particular, they have no antibacterial activity against important *Klebsiella pneumoniae* [Antimicrob. Agents Chemother. 2010, 54, 2291-2302], which is a major obstacle to the clinical application of such compounds.

In view of the above problems, the present invention provides a novel monocyclic β-lactam-siderophore conjugate having a novel structure, a stronger antibacterial activity and a broader antibacterial spectrum. The structure of such conjugate is characterized by introducing a substituent at the alpha position of the oxime ether for the first time. The introduction of the substituent makes the compound of the present invention have stronger activity against Gram-negative bacteria, and more importantly, the compounds of the present invention have a broader antibacterial spectrum, and have strong activity against the four most important multidrug resistant Gram-negative bacteria, *Escherichia coli, Klebsiella pneumoniae, Acinetobacter baumannii* and *Pseudomonas aeruginosa.*

BRIEF SUMMARY

One aspect of the present invention provides a monocyclic β-lactam-siderophore conjugate represented by formula (I), an enantiomer, a diastereomer, a racemate thereof, or a mixture thereof, or a pharmaceutically acceptable salt thereof:

(I)

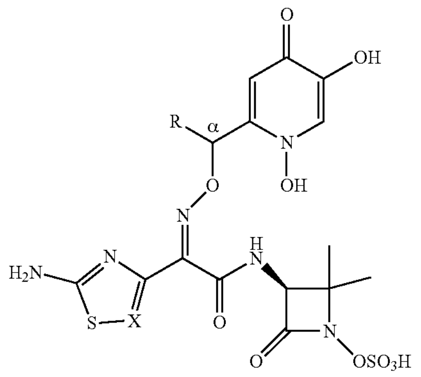

wherein X=CY or N, Y is H or a halogen;

R is (1) a carboxyl group, —$COOR_1$ or —$CONR_2R_3$;

(2) an unsubstituted $C_{1-6}$ linear alkyl group, an unsubstituted $C_{3-6}$ branched alkyl group, a $C_{3-6}$ cycloalkyl group or an unsubstituted $C_{2-7}$ alkenyl group;

(3) a mono- or poly-substituted $C_{1-4}$ linear alkyl group or $C_{3-6}$ branched alkyl group, wherein the substituent is a hydroxyl group, an amino group, a cyano group, —$OR_1$, —$SR_1$, —$S(O_2)R_1$, —$NR_2R_3$, and a halogen;

(4) a substituted or unsubstituted phenyl group, wherein the substituent in the substituted phenyl group is 1 to 3 substituents independently selected from the group consisting of a hydroxyl group, a cyano group, —$R_1$, —$OR_1$, —$NR_2R_3$ and a halogen; or (5) a substituted or unsubstituted 5- or 6-membered heteroaryl ring group having 1 to 4 hetero atoms independently selected from the group consisting of N, S and O, wherein the substituent in the 5- or 6-membered heteroaryl ring group is independently selected from the group consisting of a hydroxyl group, a cyano group, —$R_1$, —$OR_1$, —$NR_2R_3$, and a halogen;

$R_1$ is a $C_{1-6}$ linear alkyl group, a $C_{3-6}$ branched alkyl group or a $C_{3-6}$ cycloalkyl group;

$R_2$ and $R_3$ are each independently a hydrogen, a $C_{1-6}$ linear alkyl group, a $C_{3-6}$ branched alkyl group or a $C_{3-6}$ cycloalkyl group;

the halogen is F, Cl, Br or I; preferably F, Cl or Br;

a stereo configuration of an alpha carbon may be of S type or R type or (R,S) type.

Preferably, Y is H, Cl or Br.

Preferably, when R is a mono- or poly-substituted $C_{1-4}$ linear alkyl group or $C_{3-6}$ branched alkyl group, the substituent is preferably a hydroxyl group, —$OR_1$, —$SR_1$, —$S(O_2)R_1$;

Preferably, R is selected from the group consisting of a methyl group, an ethyl group, a propyl group, a butyl group, an isopropyl group, an isobutyl group, a cyclopropyl group and a vinyl group; a mono- or poly-substituted $C_{1-4}$ linear alkyl group and $C_{3-6}$ branched alkyl group, wherein the substituent is selected from the group consisting of a hydroxyl group, —$OR_1$, —$SR_1$ and —$S(O_2)R_1$; a phenyl group; a substituted or unsubstituted 5- or 6-membered heteroaryl ring group having 1 to 2 heteroatoms independently selected from the group consisting of N, S and O, wherein the substituent in the 5- or 6-membered heteroaryl ring group is independently selected from the group consisting of a hydroxyl group, a cyano group, —$R_1$, —$OR_1$, —$NR_2R_3$, and a halogen.

Preferably, $R_1$ is a methyl group, an ethyl group, a propyl group, an isopropyl group, a n-butyl group, an isobutyl group, a sec-butyl group, a tert-butyl group or a cyclopropyl group.

Preferably, $R_2$ and $R_3$ are each independently a hydrogen, a methyl group, an ethyl group, a propyl group, an isopropyl group, a n-butyl group, an isobutyl group, a sec-butyl group, a tert-butyl group or a cyclopropyl group.

Further preferably, $R_1$ is a methyl group, an ethyl group, a propyl group, an isopropyl group.

Further preferably, $R_2$ and $R_3$ are each independently a hydrogen, a methyl group, an ethyl group, a propyl group, an isopropyl group.

Preferably, the representative compound of formula (I) of the present invention is one of the following compounds:

-continued
compound 1
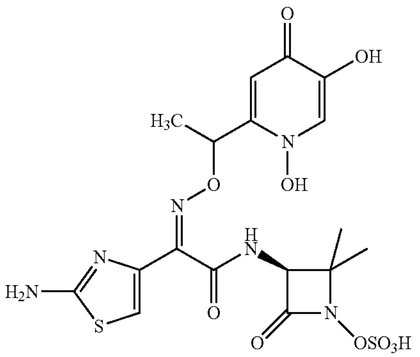
compound 2
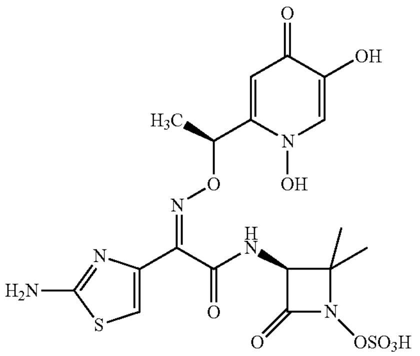
compound 3
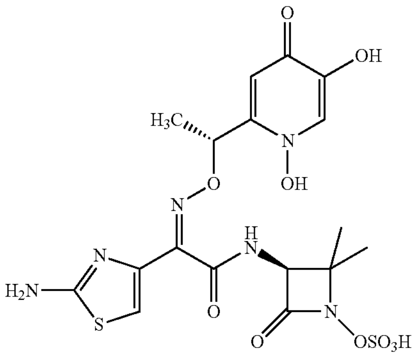
compound 4
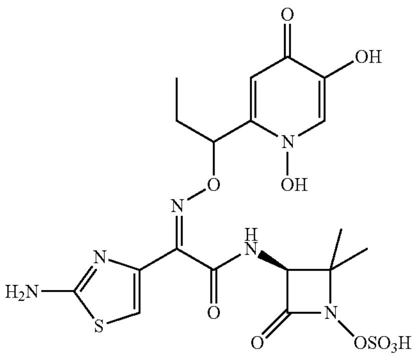
compound 5
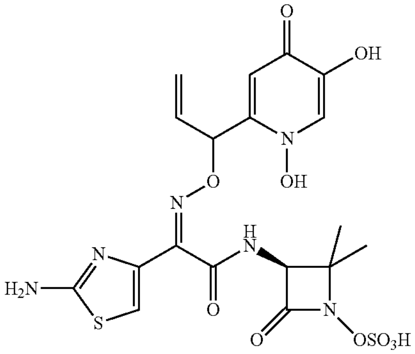
compound 6
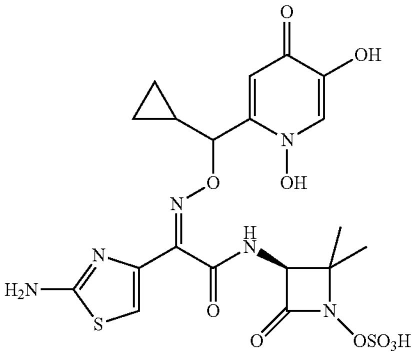
compound 7
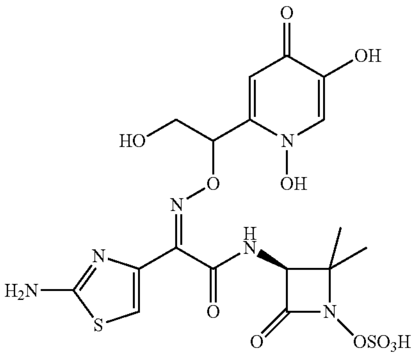
compound 8
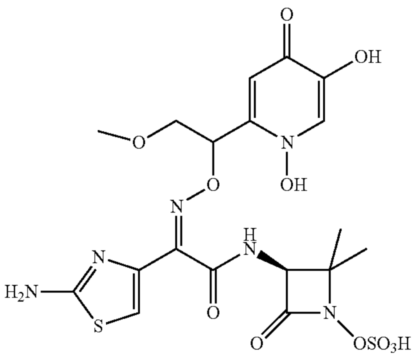

-continued
compound 9
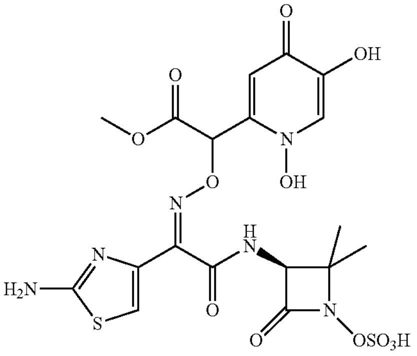
compound 10
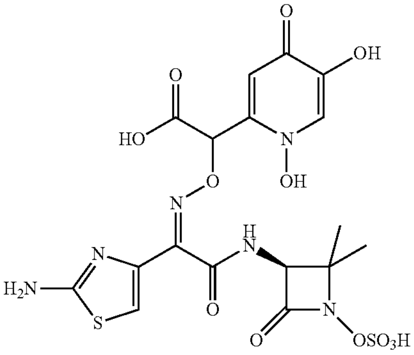
compound 11
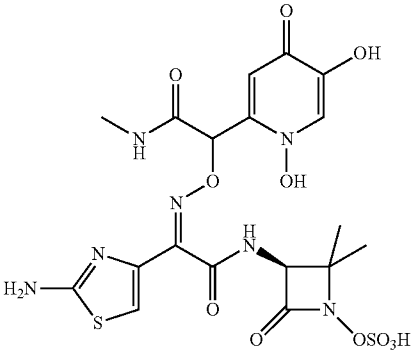
compound 12
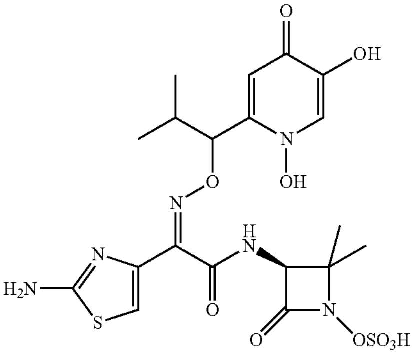
-continued
compound 13
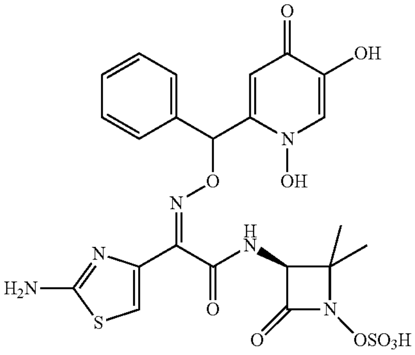
compound 14
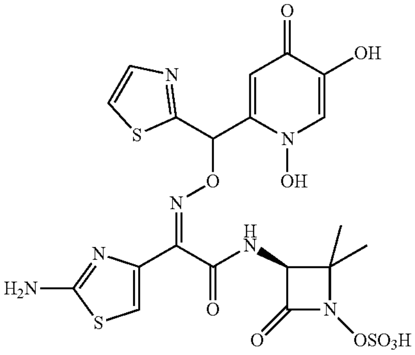
compound 15
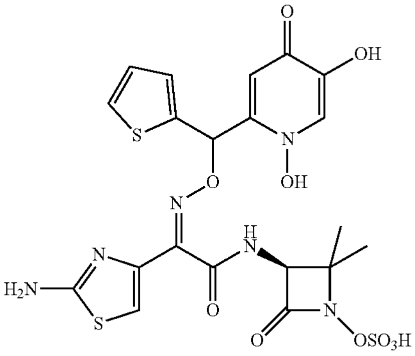
compound 16
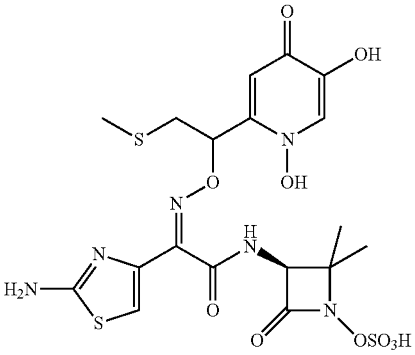

-continued
compound 17
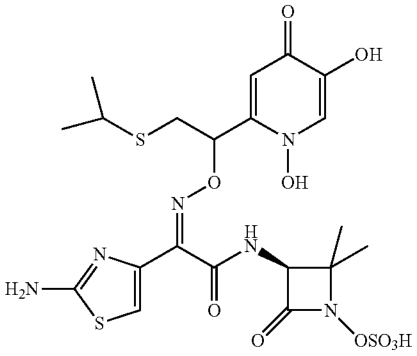
compound 18
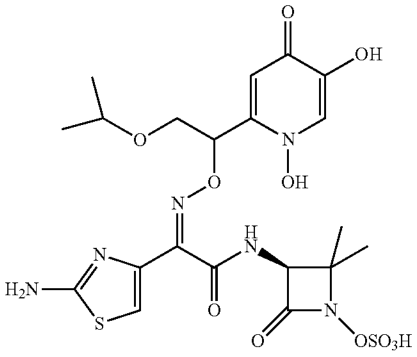
compound 19
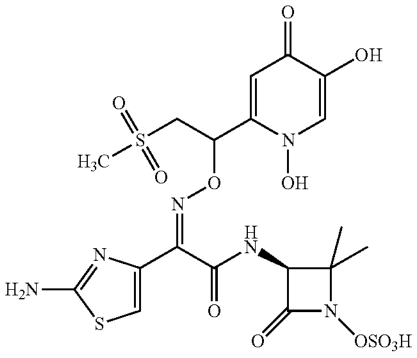
compound 20
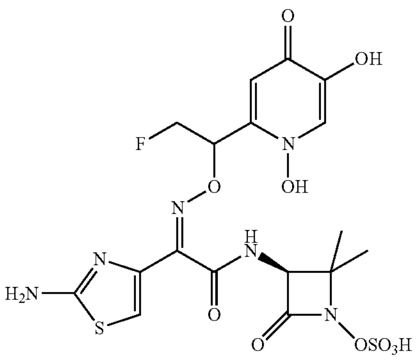
-continued
compound 21
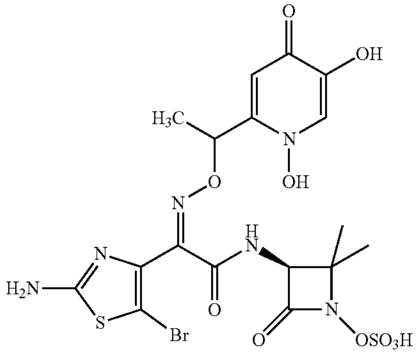
compound 22
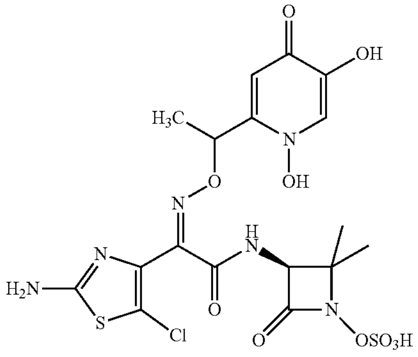
compound 23
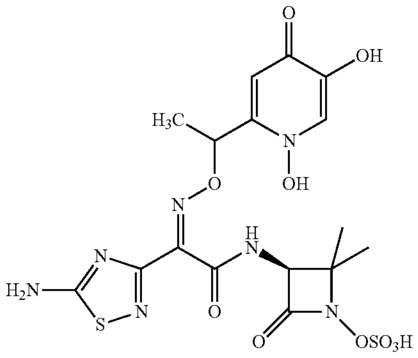
compound 24
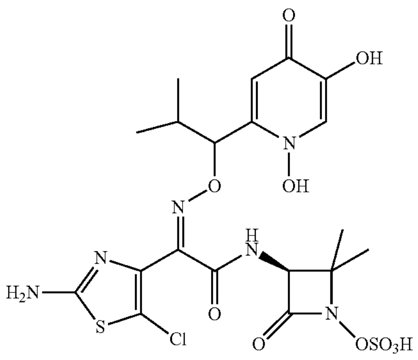

-continued
compound 25
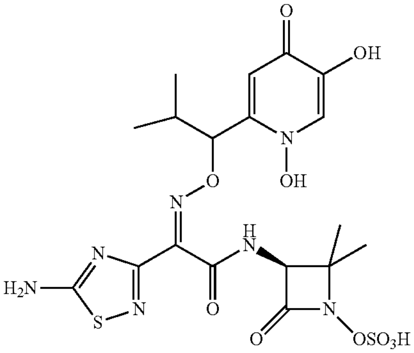
compound 26
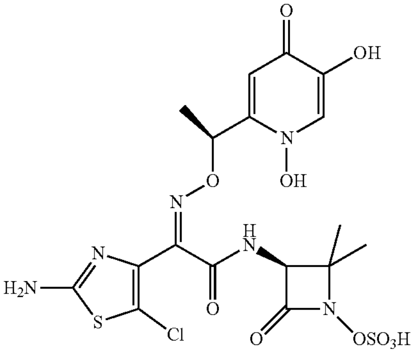
compound 27
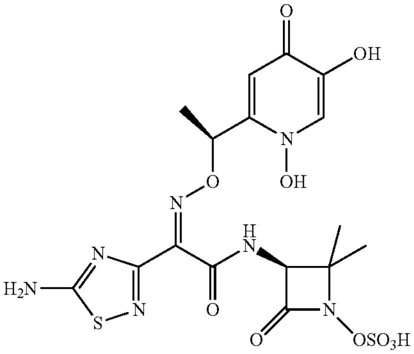
compound 28
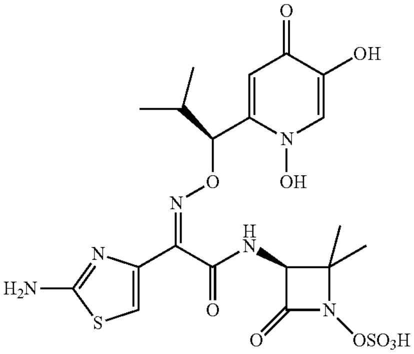
-continued
compound 29
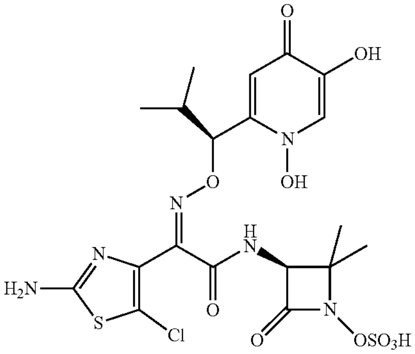
compound 30
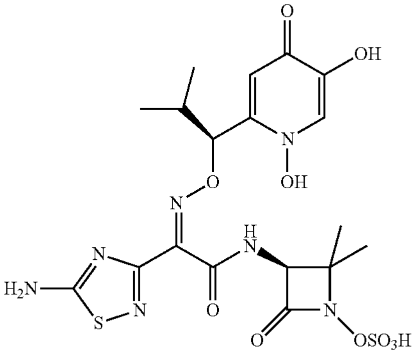
compound 31
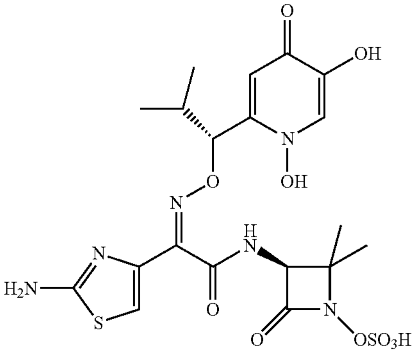
compound 32
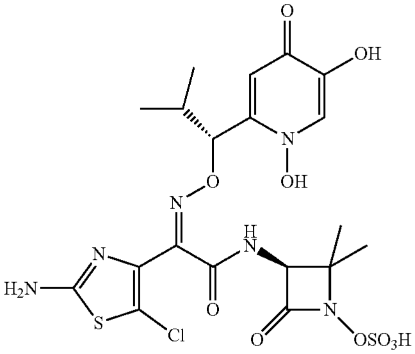

-continued compound 33

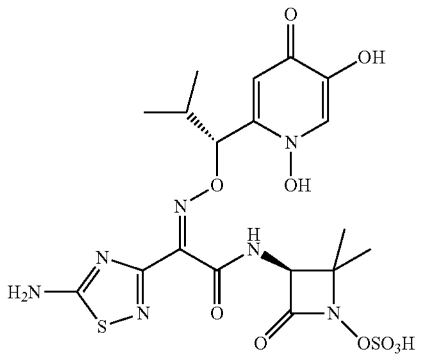

compound 34

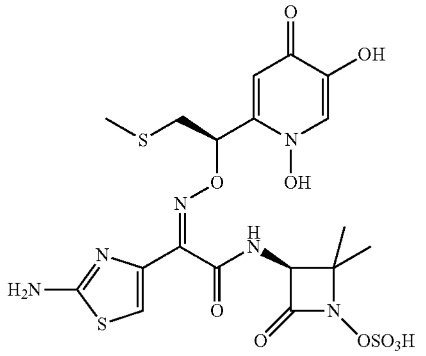

compound 35

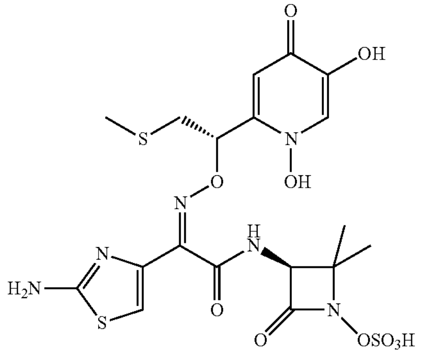

compound 36

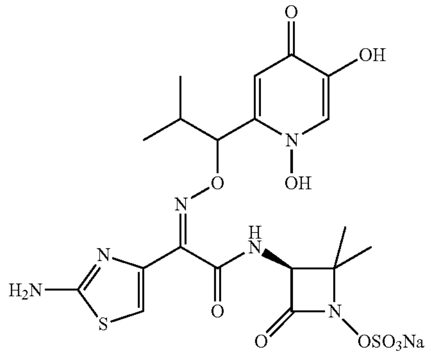

The pharmaceutically acceptable salt of the present invention is a pharmaceutically acceptable salt formed by a monocyclic β-lactam-siderophore conjugate of the formula (I) and an organic base or an inorganic base.

Preferably, the pharmaceutically acceptable salt is a sodium salt, a magnesium salt, a calcium salt, an arginine salt.

The compound of the formula (I) of the present invention has an oximido group which may be a "cis" or a "trans", preferably a "cis" configuration. Accordingly, the compound of the formula (I), an optical isomer thereof or a pharmaceutically acceptable salt thereof of the present invention further includes a cis- or trans-isomer thereof. The optical isomers include its enantiomers, diastereomers, racemates, or mixtures thereof. Further, the compound of the formula (I), optical isomer thereof or pharmaceutically acceptable salt thereof of the present invention may also be present in the form of a solvate such as a hydrate, an alcoholate, a ketone compound or the like, and these solvates are also included within the scope of the invention. Further, the compound of the formula (I), its enantiomer, diastereomer, racemate or a mixture thereof or a pharmaceutically acceptable salt thereof of the present invention may also be present in the form of a tautomer, and these tautomers are also included within the scope of the invention.

Another aspect of the present invention provides a pharmaceutical composition comprising the compound represented by the above formula (I), optical isomer thereof or pharmaceutically acceptable salt thereof as an active ingredient, and a pharmaceutically acceptable excipient.

When the monocyclic β-lactam-siderophore conjugate represented by the formula (I) or a pharmaceutically acceptable salt thereof of the present invention is used for the preparation of an antibacterial agent, it may be used alone, or it may be mixed with the pharmaceutically acceptable excipient (for example, a vehicle, a diluent, and the like) and formulated into a tablet, a capsule, a granule or a syrup for oral administration, or formulated into a liniment or an injection preparation for parenteral administration.

Another aspect of the present invention provides a use of the compounds represented by the above formula (I), optical isomer thereof or pharmaceutically acceptable salt thereof for preparing a medicament for treating an infectious disease caused by bacteria, in particular, including the infectious diseases caused by sensitive and resistant *Pseudomonas aeruginosa, Acinetobacter baumannii, Escherichia coli* and *Klebsiella pneumonia.*

Another aspect of the present invention provides a use of the compounds represented by the above formula (I), optical isomer thereof or pharmaceutically acceptable salt thereof or the pharmaceutical composition as described above, for preparing a medicament for treating an infectious disease caused by bacteria, in particular, including the infectious diseases caused by sensitive and resistant *Pseudomonas aeruginosa, Acinetobacter baumannii, Escherichia coli* and *Klebsiella pneumonia.*

Another aspect of the present invention provides a method for treating an infectious disease caused by bacteria, in particular, including the infectious diseases caused by sensitive and resistant *Pseudomonas aeruginosa, Acinetobacter baumannii, Escherichia coli* and *Klebsiella pneumonia*, comprising the step of administering to a subject the compound represented by the above formula (I), optical isomer thereof or pharmaceutically acceptable salt thereof or the pharmaceutical composition as described above.

Another aspect of the present invention provides a method for preparing said compounds, but the invention is not limited to these specific preparation methods.

The compound of the present invention can be produced by the following method, however, the conditions of the method, for example a reactant, a solvent, an acid, a base, an amount of the compound used, a reaction temperature, reaction time, and the like are not limited to the following description. The compound of the present invention can also be conveniently prepared by optionally combining various synthetic methods described in the specification or known to those skilled in the art.

The compound of the formula (I) of the present invention can be produced according to the method of the reaction scheme (1).

Reaction scheme (1):

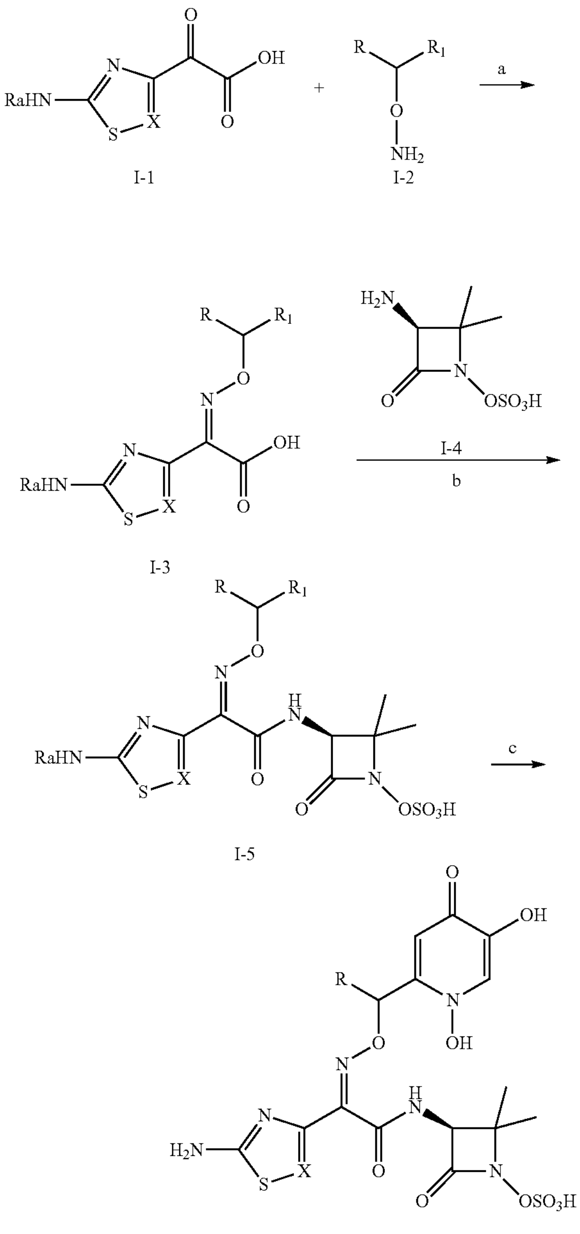

I-1
I-2
I-3
I-5
I in the above reaction scheme (1), X and R are defined as above; $R_a$ is an amino protecting group, the protecting group is selected from the group consisting of: tert-butoxycarbonyl, p-methoxybenzyl, diphenylmethyl, trityl, benzyl, allyl; $R_1$ is

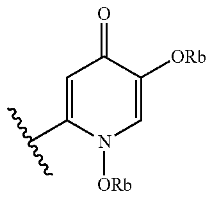

or

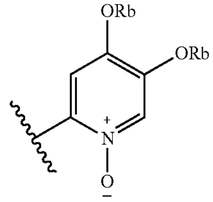

, wherein $R_b$ is a hydroxyl protecting group, the protecting group is selected from the group consisting of: benzhydryl, p-methoxybenzyl or benzyl.

(a) reacting compound I-1 with compound I-2 in a mixed solvent of a polar protic solvent and a non-polar solvent at room temperature for 2 to 6 hours to obtain compound I-3, wherein the polar protic solvent may be methanol or ethanol, and the nonpolar solvent may be a dichloromethane.

(b) reacting compound I-3 with compound I-4 under a condition of a condensing agent and an organic or inorganic base in a polar aprotic solvent as a solvent at room temperature for 4 to 8 hours to obtain compound I-5, wherein the condensing agent may be: 2-(7-azabenzotriazoleyl)-N,N,N',N'-tetramethyluronium hexafluorophosphate (HATU), 1-(3-dimethylaminopropyl)-3-ethylcarbodiimide hydrochloride (EDCI) and 1-hydroxybenzotriazole (HOBT); the organic base may be: triethylamine, diisopropylethylamine; the inorganic base may be sodium hydrogencarbonate, sodium carbonate or potassium hydrogencarbonate; and the polar aprotic solvent may be: dimethyl sulfoxide (DMSO) or N,N-dimethylformamide (DMF).

(c) removing the protecting group of compound I-5 via an acid in a non-polar solvent in the presence of a positive ion trapping agent to obtain compound I, wherein the positive ion trapping agent may be triethylsilane or anisole, and the acid may be trifluoroacetic acid (TFA) or formic acid.

The synthetic method of compound I-1 in the above reaction scheme can refer to the literature (Chemical & Pharmaceutical Bulletin 1990, 38(12), 3476-3479, Bioorg. Med. Chem. 15 (2007) 6716-6732); the synthetic method of compound I-4 may refer to the literature (WO 2008/116813 A2, WO 2013/110643 A1); the synthetic method of the key intermediate I-2 may be selected from one of the following methods:

Method I:

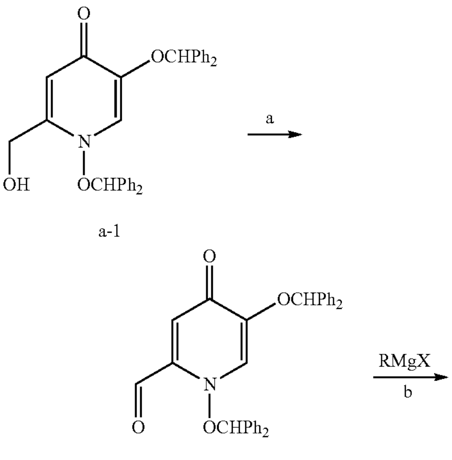

a-1
a-2

-continued

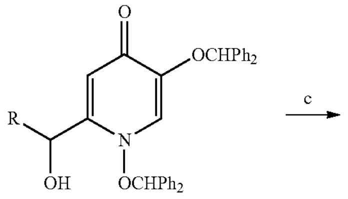

a-3

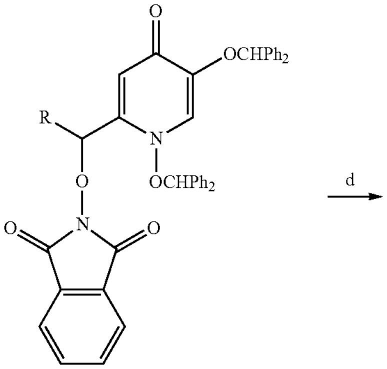

a-4

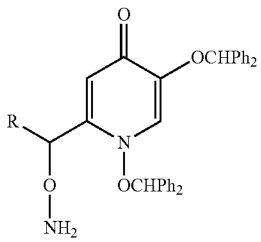

a-5 wherein R is a $C_{1-4}$ linear alkyl group or a $C_{1-4}$ alkenyl group or a $C_{3-4}$ cycloalkyl group;

(a) oxidizing compound a-1 with an oxidizing agent in a non-polar solvent for 4 to 8 hours to obtain compound a-2, wherein the non-polar solvent may be dichloromethane, and the oxidizing agent may be a mixture of sulfur trioxide pyridine and dimethyl sulfoxide or a mixture of oxalyl chloride and dimethyl sulfoxide;

(b) reacting compound a-2 with a metal Grignard reagent RMgX in a non-polar solvent at a low temperature of −10 to −20° C. for 4 to 6 hours to obtain compound a-3, wherein the metal Grignard reagent may be RMgBr or RMgCl, and the non-polar solvent may be tetrahydrofuran;

(c) subjecting to Mitsunobu reaction of compound a-3 and N-hydroxyphthalimide in a non-polar solvent to obtain compound a-4, wherein the non-polar solvent may be tetrahydrofuran or 1,4-dioxane;

(d) subjecting to hydrazinolysis of compound a-4 with a hydrazine hydrate or aminolysis of compound a-4 with methylamine in a polar protic solvent to obtain a compound a-5, wherein the polar protic solvent may be methanol or ethanol.

The synthetic method of the compound a-1 in the above reaction scheme can refer to the document U.S. Pat. No. 4,883,879A.

Method II:

Method I

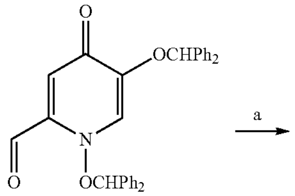

a-2

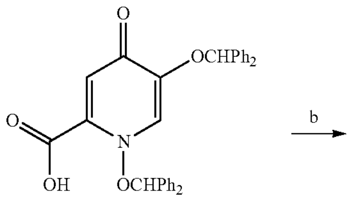

b-1

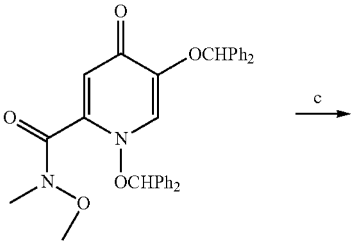

b-2

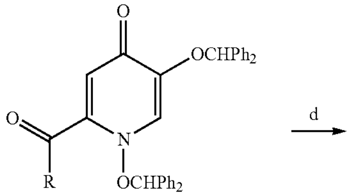

b-3

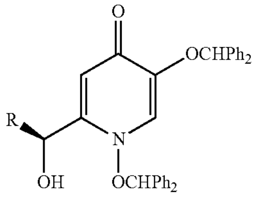

b-4 or

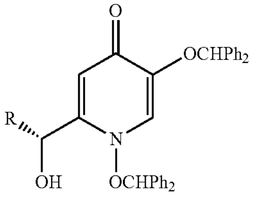

b-5

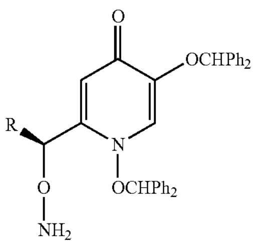

b-6 or

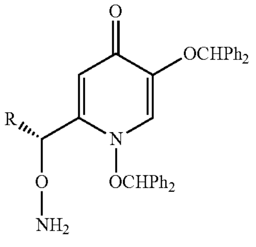

b-7 wherein R is a $C_{1-4}$ linear alkyl group or a $C_{1-4}$ alkenyl group or a $C_{3-4}$ cycloalkyl group;

(a) oxidizing compound a-2 with an oxidizing agent in a mixed solvent of water and a polar aprotic solvent to obtain compound b-1, wherein the polar aprotic solvent may be acetonitrile, acetone or 1,4-dioxane, and the oxidizing agent may be sodium chlorite;

(b) reacting compound b-1 with N-methyl-N-methoxyamine hydrochloride under a condition of a condensing agent and an organic or inorganic base in a polar aprotic solvent as a solvent at room temperature for 4 to 8 hours to obtain compound b-2, wherein the condensing agent may be: a mixture of 2-(7-azabenzotriazoleyl)-N,N,N',N'-tetramethyluronium hexafluorophosphate (HATU) or 1-(3-dimethylaminopropyl)-3-ethylcarbodiimide hydrochloride (EDCI) and 1-hydroxybenzotriazole (HOBT), the organic base may be: triethylamine or diisopropylethylamine, the inorganic base may be sodium hydrogencarbonate, sodium carbonate or potassium hydrogencarbonate, and the polar aprotic solvent may be: dimethyl sulfoxide or N,N-dimethylformamide;

(c) reacting compound b-2 with a metal Grignard reagent RMgX in a non-polar solvent at a low temperature (~10 to −20° C.) for 4 to 6 hours to obtain compound b-3, wherein the metal Grignard reagent may be RMgBr or RMgCl, and the non-polar solvent may be tetrahydrofuran or diethyl ether;

(d) reacting compound b-3 by the action of a transition metal catalyst, a ligand and a hydrogen source in a polar solvent under Ar protection to obtain compound b-4 or b-5, wherein the transition metal catalyst may be dichlorobis(4-methylisopropylphenyl)ruthenium (II) or dichloro(pentamethylcyclopentadienyl)rhodium (III) dimer, the ligand may be (1R,2R)-(−)—N-(p-methylbenzenesulfonyl)-1,2-diphenylethylenediamine or (1S,2S)-(−)-N-(p-methylbenzenesulfonyl)-1,2-diphenylethylenediamine, the hydrogen source may be sodium formate or ammonium formate, and the polar solvent may be N,N-dimethylformamide;

(e) subjecting compound b-4 or b-5 to the method described in the Method I to obtain compound b-6 or b-7.

Method III:

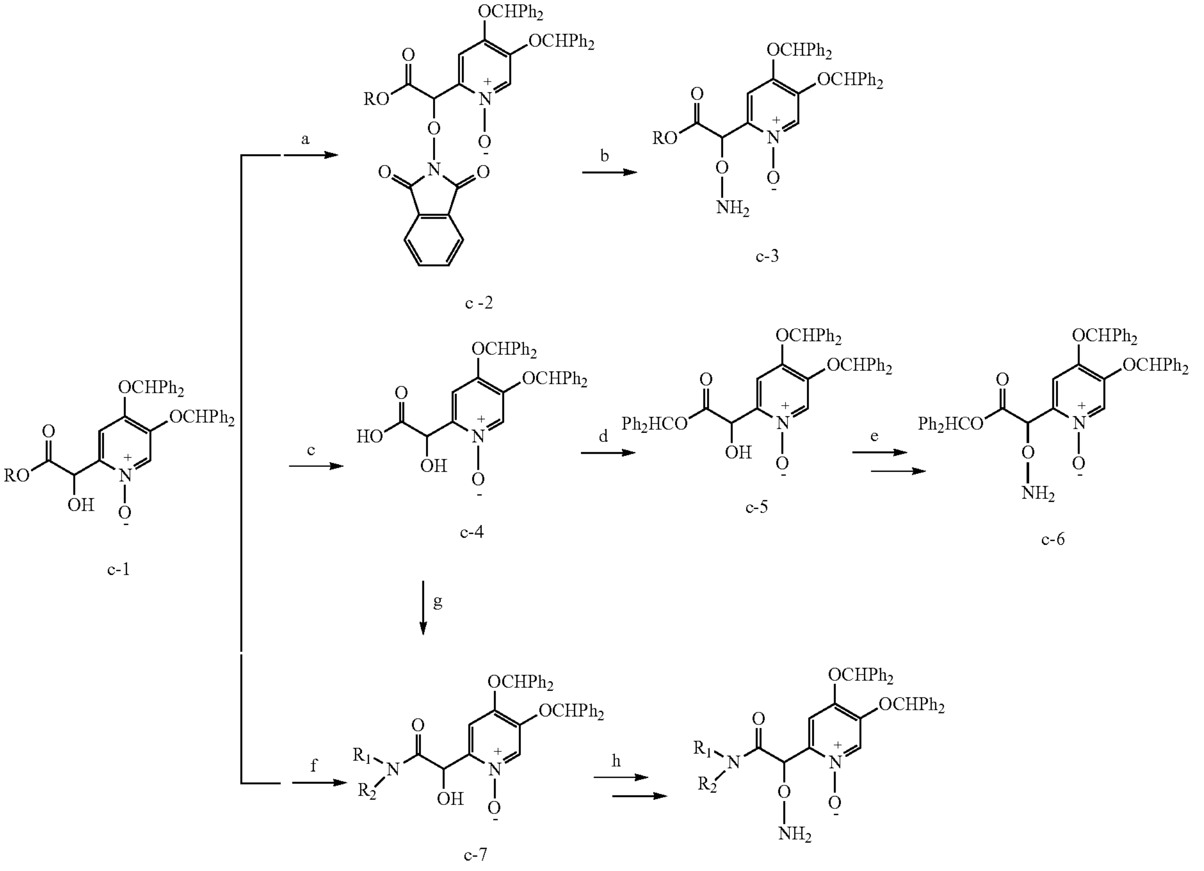

c-1 c-2 c-3 c-4 c-5 c-6 c-7 c-8 wherein R is a $C_{1-6}$ linear alkyl group, a $C_{3-6}$ branched alkyl group or a $C_{3-6}$ cycloalkyl group; and $R_1$ and $R_2$ are each independently: a hydrogen; or a $C_{1-6}$ linear alkyl group, a $C_{3-6}$; branched alkyl group or a $C_{3-6}$ cycloalkyl group;

(a) subjecting to Mitsunobu reaction of compound c-1 and N-hydroxyphthalimide in a non-polar solvent to obtain compound c-2, wherein the non-polar solvent may be tetrahydrofuran or 1,4-dioxane;

(b) subjecting to hydrazinolysis of compound c-2 with hydrazine hydrate or aminolysis of compound c-2 with methylamine in a polar protic solvent to obtain a compound c-3, wherein the polar protic solvent may be methanol or ethanol;

(c) reacting compound c-1 in a mixed polar and non-polar solvents in the presence of an inorganic base at 0° C. to room temperature to obtain a compound c-4, wherein the inorganic base may be sodium hydroxide or lithium hydroxide, the polar solvent may be water or methanol, and the non-polar solvent may be tetrahydrofuran;

(d) reacting compound c-4 with diphenyldiazomethane in a mixed polar and non-polar solvents to obtain compound c-5, wherein the polar solvent may be methanol or ethanol, and the non-polar solvent may be dichloromethane, ethyl acetate or tetrahydrofuran;

(e) subjecting compound c-5 to the above steps a and b to obtain compound c-6;

(f) subjecting to aminolysis of compound c-1 with $HNR_1R_2$ in a polar protic solvent or a non-polar solvent to obtain compound c-7, wherein the polar protic solvent may be a methanol, the non-polar solvent may be tetrahydrofuran;

(g) reacting compound c-4 with amine $HNR_1R_2$ in a polar solvent in the presence of a condensing agent and an organic base at room temperature to obtain a compound c-7, wherein the condensing agent may be 2-(7-azabenzotriazoleyl)-N,N,N',N'-tetramethyluronium hexafluorophosphate (HATU) or 1-hydroxybenzotriazole (HOBT), the organic base may be triethylamine or diisopropyl ethylamine, and the polar solvent may be dichloromethane;

(h) subjecting compound c-7 to the above steps a and b to obtain compound c-8.

The synthetic method of the starting material c-1 in the above reaction scheme is as follows:

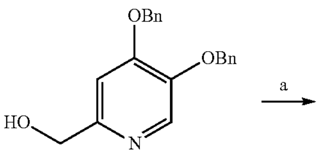

c-9

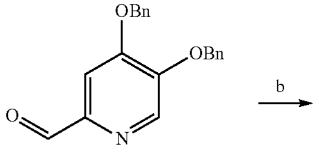

c-10

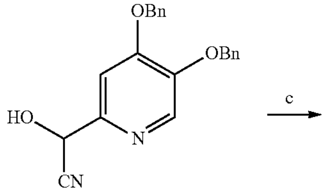

c-11

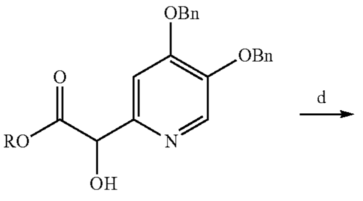

c-12

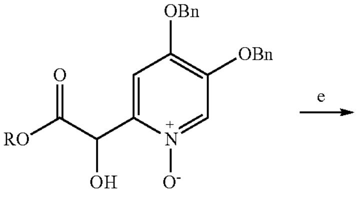

c-13

-continued

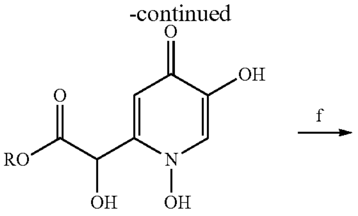

c-14

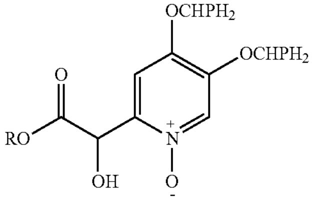

c-1 wherein R is a $C_{1-6}$ linear alkyl group, a $C_{3-6}$ branched alkyl group or a $C_{3-6}$ cycloalkyl group;

(a) oxidizing compound c-9 with an oxidizing agent in a non-polar solvent for 4 to 8 hours to obtain compound c-10, wherein the non-polar solvent may be dichloromethane, and the oxidizing agent may be a mixture of sulfur trioxide pyridine and dimethyl sulfoxide or a mixture of oxalyl chloride and dimethyl sulfoxide;

(b) reacting compound c-10 with sodium cyanide in a mixed solvent of water and a non-polar solvent to obtain compound c-11, wherein the non-polar solvent may be tetrahydrofuran or 1,4-dioxane;

(c) reacting compound c-11 with hydrochloric acid in a polar protic solvent to obtain compound c-12, wherein the polar protic solvent may be alcohol ROH;

(d) oxidizing compound c-12 with an oxidizing agent in a non-polar solvent to obtain compound c-13, wherein the non-polar solvent may be dichloromethane, the oxidizing agent may be m-chloroperoxybenzoic acid (mCPBA) or hydrogen peroxide;

(e) subjecting to deprotecting the benzyl protecting group of compound c-13 in a non-polar solvent under the action of a Lewis acid to obtain compound c-14, wherein the non-polar solvent may be dichloromethane, and the Lewis acid may be boron trichloride or boron tribromide;

(f) reacting compound c-14 with diphenyldiazomethane in a mixed polar and non-polar solvents to obtain compound c-1, wherein the polar solvent may be methanol or ethanol, the non-polar solvent may be dichloromethane, ethyl acetate or tetrahydrofuran.

The synthetic method of the compound c-9 in the above scheme can refer to the literature (WO2012073138A1).

Method IV:

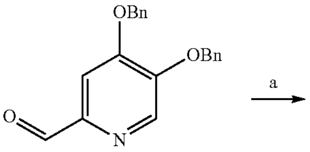

c-10

-continued

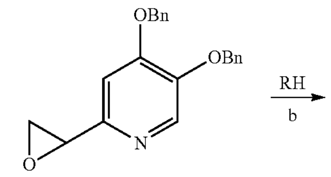

d-1

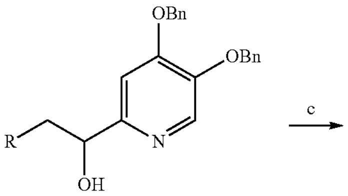

d-2

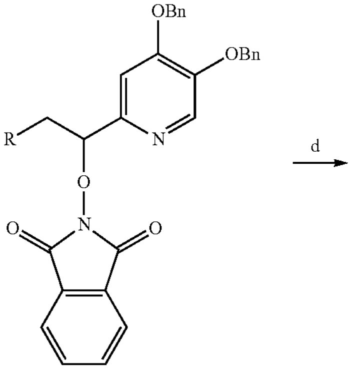

d-3

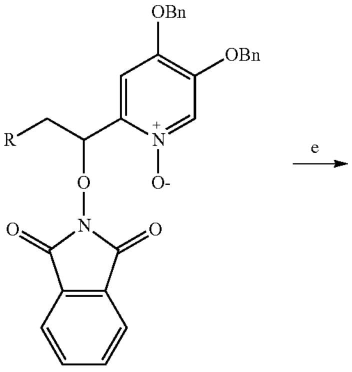

d-4

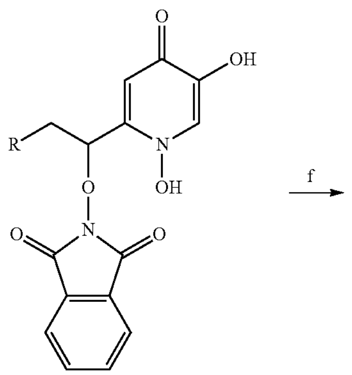

d-5

-continued

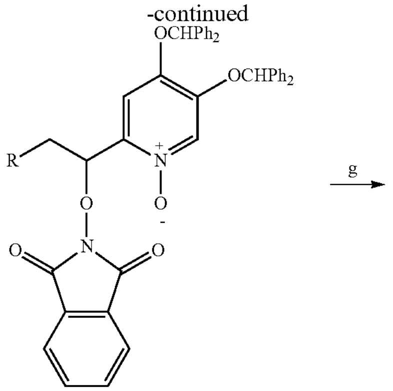

d-6

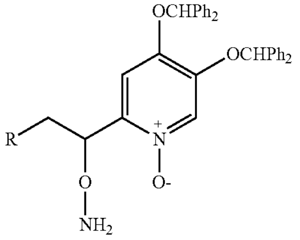

d-7 in the above scheme, R is a hydroxyl group, an amino group, —$OR_1$, —$NR_2R_3$; —$R_1$ is a $C_{1-6}$ linear alkyl group, a $C_{3-6}$ branched alkyl group or a $C_{3-6}$ cycloalkyl group; and $R_2$ and $R_3$ are each independently: a hydrogen or a $C_{1-6}$ linear alkyl group, a $C_{3-6}$ branched alkyl group or a $C_{3-6}$ cycloalkyl group;

(a) reacting compound c-10 with trimethylsulfoxonium iodide or trimethylsulfoxonium iodide under the action of strong alkali in a polar aprotic solvent to obtain compound d-1, wherein the polar aprotic solvent may be dimethyl sulfoxide or N,N-dimethylformamide, and the strong alkali may be sodium hydride or potassium hydride;

(b) reacting compound d-1 with RH in a non-polar solvent under a strong alkali to obtain compound d-2, wherein the non-polar solvent may be tetrahydrofuran, and the strong alkali may be sodium hydride, sodium hydroxide or Potassium hydroxide.

(c) subjecting to Mitsunobu reaction of compound d-2 and N-hydroxyphthalimide in a non-polar solvent to obtain compound d-3, wherein the non-polar solvent may be tetrahydrofuran or 1,4-dioxane;

(d) oxidizing compound d-3 with an oxidizing agent in a non-polar solvent to obtain compound d-4, wherein the non-polar solvent may be dichloromethane, and the oxidizing agent may be m-chloroperoxybenzoic acid or hydrogen peroxide;

(e) subjecting to deprotecting the benzyl protecting group of compound d-4 under the action of a Lewis acid in a non-polar solvent to obtain compound d-5, wherein the non-polar solvent may be dichloromethane, and the Lewis acid is boron trichloride or boron tribromide;

(f) reacting compound d-5 with diphenyldiazomethane in a mixed polar and non-polar solvent to obtain compound d-6, wherein the polar solvent may be methanol or ethanol, and the non-polar solvent may be dichloromethane, ethyl acetate or tetrahydrofuran;

(g) subjecting to hydrazinolysis of compound d-6 with hydrazine hydrate or aminolysis of compound d-6 with methylamine in a polar protic solvent to obtain a compound d-7, wherein the polar protic solvent is methanol or ethanol;

Method V:

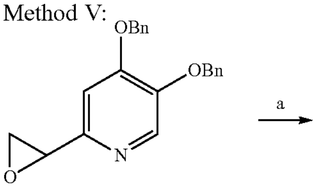

d-1

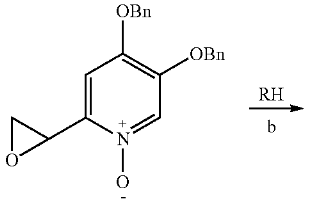

d-8

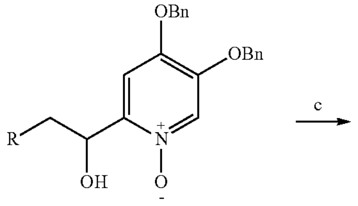

d-9

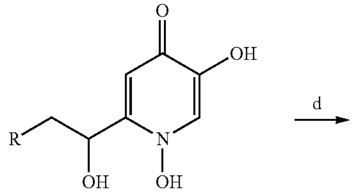

d-10

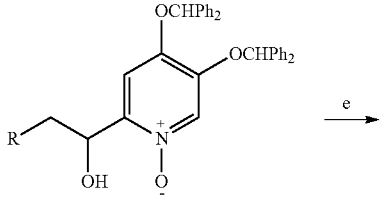

d-11

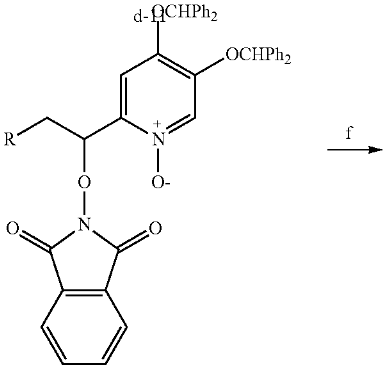

d-12

-continued

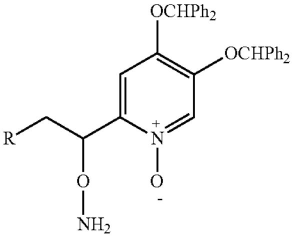

d-13 in the above scheme, R is a hydroxyl group, an amino group, $—OR_1$, $—SR_1$, $—NR_2R_3$; $R_1$ is a $C_{1-6}$ linear alkyl group, a $C_{3-6}$ branched alkyl group or a $C_{3-6}$ cycloalkyl group; and $R_2$ and $R_3$ are each independently: a hydrogen or a $C_{1-6}$ linear alkyl group, a $C_{3-6}$ branched alkyl group or a $C_{3-6}$ cycloalkyl group;

(a) oxidizing compound d-1 with an oxidizing agent in a non-polar solvent to obtain compound d-8, wherein the non-polar solvent may be dichloromethane, and the oxidizing agent may be m-chloroperoxybenzoic acid or hydrogen peroxide;

(b) reacting compound d-8 with RH in a non-polar solvent under a strong alkali to obtain compound d-9, wherein the non-polar solvent may be tetrahydrofuran, and the strong alkali may be sodium hydride, sodium hydroxide or potassium hydroxide;

(c) subjecting to deprotecting the benzyl protecting group of compound d-9 in a non-polar solvent under the action of a Lewis acid to obtain compound d-10, wherein the non-polar solvent may be dichloromethane, and the Lewis acid may be boron trichloride or boron tribromide;

(d) reacting compound d-10 with diphenyldiazomethane in a mixed polar and non-polar solvents to obtain compound d-11, wherein the polar solvent may be methanol or ethanol, and the non-polar solvent may be dichloromethane, ethyl acetate or tetrahydrofuran;

(e) subjecting to Mitsunobu reaction of compound d-11 and N-hydroxyphthalimide in a non-polar solvent to obtain compound d-12, wherein the non-polar solvent may be tetrahydrofuran or 1,4-dioxane;

(f) subjecting to hydrazinolysis of compound d-12 with hydrazine hydrate or aminolysis of compound d-12 with methylamine in a polar protic solvent to obtain a compound d-13, wherein the polar protic solvent may be methanol or ethanol.

Method VI:

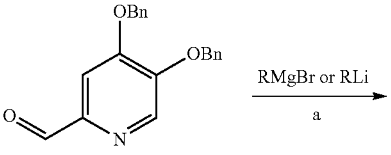

c-10

-continued

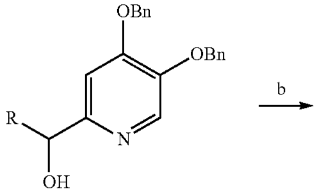

e-1

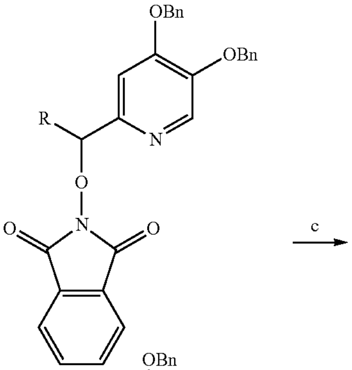

e-2

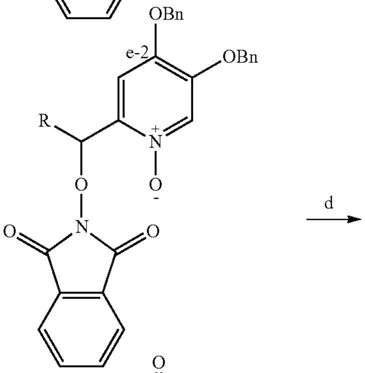

e-3

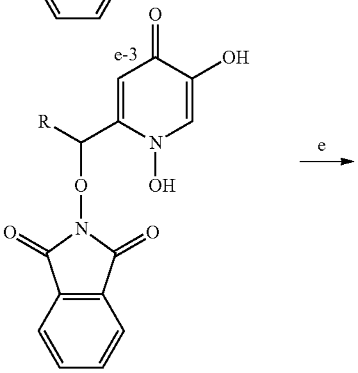

e-4

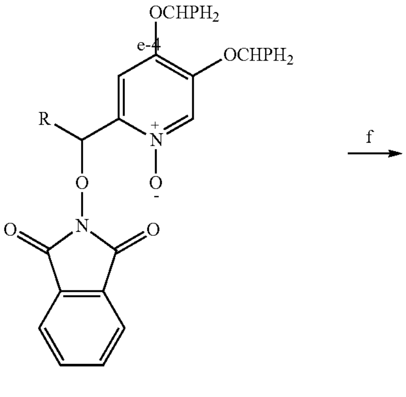

e-5

-continued

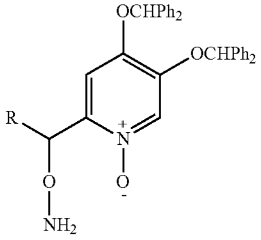

e-6 in the above scheme R is a $C_{1-6}$ linear alkyl group a $C_{3-6}$ branched alkyl group a $C_{3-6}$ cycloalkyl group, a substituted or unsubstituted phenyl group, or a substituted or unsubstituted 5- or 6-membered heteroaryl ring group having 1 to 4 hetero atoms independently selected from the group consisting of N, S and O;

(a) reacting compound c-10 with a Grignard reagent RMgBr or an organolithium reagent RLi in a non-polar solvent to obtain a compound e-1, wherein the non-polar solvent may be tetrahydrofuran or methyltetrahydrofuran;

(b) subjecting to Mitsunobu reaction of compound e-1 and N-hydroxyphthalimide in a non-polar solvent to obtain compound e-2, wherein the non-polar solvent may be tetrahydrofuran or 1,4-dioxane;

(c) oxidizing compound e-2 with an oxidizing agent in a non-polar solvent obtain compound e-3, wherein the non-polar solvent may be dichloromethane, and the oxidizing agent may be m-chloroperoxybenzoic acid or hydrogen peroxide;

(d) subjecting to deprotecting the benzyl protecting group of compound e-3 in a non-polar solvent under the action of a Lewis acid to obtain compound e-4, wherein the non-polar solvent may be dichloromethane, and the Lewis acid may be boron trichloride or boron tribromide;

(e) reacting compound e-4 with diphenyldiazomethane in a mixed polar and non-polar solvents to obtain compound e-5, wherein the polar solvent may be methanol or ethanol, and the non-polar solvent may be dichloromethane, ethyl acetate or tetrahydrofuran;

(f) subjecting to hydrazinolysis of compound e-5 with hydrazine hydrate or aminolysis of compound e-5 with methylamine in a polar protic solvent to obtain a compound e-6, wherein the polar protic solvent may be methanol or ethanol.

Method VII:

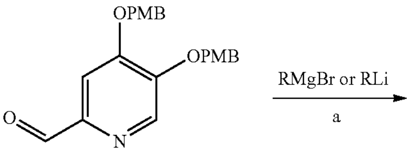

f-1

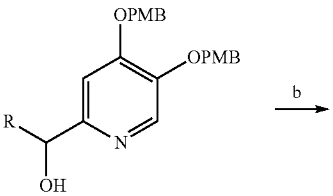

f-2

-continued

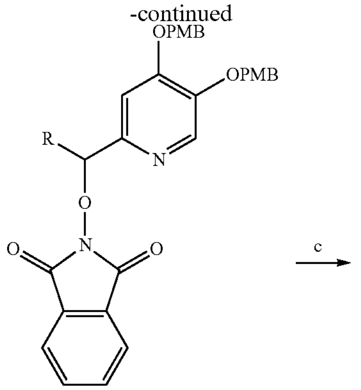

f-3

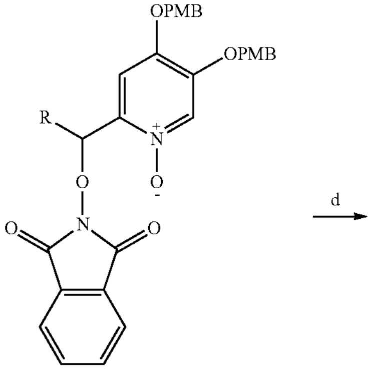

f-4

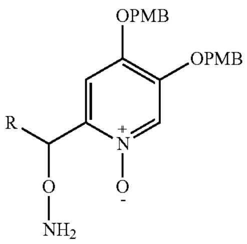

f-5 in the above scheme, R is a $C_{1-6}$ linear alkyl group, a $C_3$-6 branched alkyl group, a $C_{3-6}$ cycloalkyl group, a substituted or unsubstituted phenyl group, or a substituted or unsubstituted 5- or 6-membered heteroaryl ring group having 1 to 4 hetero atoms independently selected from the group consisting of N, S and O.

The synthetic method of compound f-1 can refer to the method of compound c-10.

(a) reacting compound f-1 with a Grignard reagent RMgBr or an organolithium reagent RLi in a non-polar solvent to obtain a compound f-2, wherein the non-polar solvent may be tetrahydrofuran or methyltetrahydrofuran;

(b) subjecting to Mitsunobu reaction of compound f-2 and N-hydroxyphthalimide in a non-polar solvent to obtain compound f-3, wherein the non-polar solvent may be tetrahydrofuran or 1,4-dioxane;

(c) oxidizing compound f-3 with an oxidizing agent in a non-polar solvent obtain compound f-4, wherein the non-polar solvent may be dichloromethane, and the oxidizing agent may be m-chloroperoxybenzoic acid or hydrogen peroxide;

(d) subjecting to hydrazinolysis of compound f-4 with hydrazine hydrate or aminolysis of compound f-4 with methylamine in a polar protic solvent to obtain a compound f-5, wherein the polar protic solvent may be methanol or ethanol.

Method VIII:

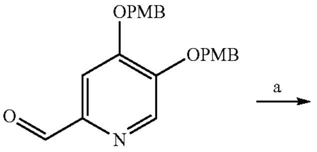

f-1

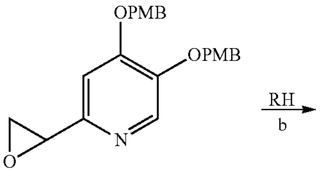

f-6

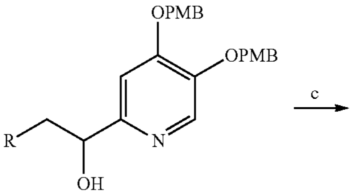

f-7

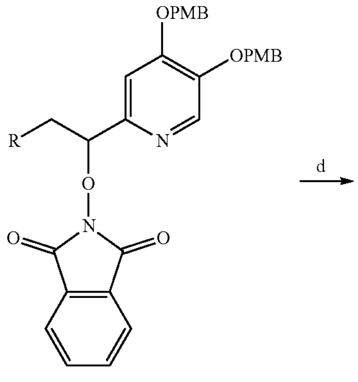

f-8

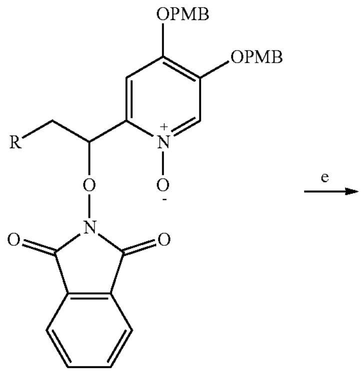

f-9

-continued

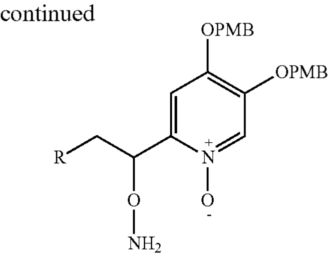

f-10 in the above scheme, R is a hydroxyl group, an amino group, —$OR_1$, —$NR_2R_3$; $R_1$ is a $C_{1-6}$ linear alkyl group, a $C_{3-6}$ branched alkyl group or a $C_{3-6}$ cycloalkyl group; and $R_2$ and $R_3$ are each independently: a hydrogen or a $C_{1-6}$ linear alkyl group, a $C_{3-6}$ branched alkyl group or a $C_{3-6}$ cycloalkyl group;

(a) reacting compound f-1 with trimethylsulfoxonium iodide or trimethylsulfoxonium iodide under the action of strong alkali in a polar aprotic solvent to obtain compound f-6, wherein the polar aprotic solvent may be dimethyl sulfoxide or N,N-dimethylformamide, and the strong alkali may be sodium hydride or potassium hydride;

(b) reacting compound f-6 with RH in a non-polar solvent under a strong alkali to obtain compound f-7, wherein the non-polar solvent may be tetrahydrofuran, and the strong alkali may be sodium hydride, sodium hydroxide or potassium hydroxide.

(c) subjecting to Mitsunobu reaction of compound f-7 and N-hydroxyphthalimide in a non-polar solvent to obtain compound f-8, wherein the non-polar solvent may be tetrahydrofuran or 1,4-dioxane;

(d) oxidizing compound f-8 with an oxidizing agent in a non-polar solvent to obtain compound f-9, wherein the non-polar solvent may be dichloromethane, and the oxidizing agent may be m-chloroperoxybenzoic acid or hydrogen peroxide;

(e) subjecting to hydrazinolysis of compound f-9 with hydrazine hydrate or aminolysis of compound d-6 with methylamine in a polar protic solvent to obtain a compound f-10, wherein the polar protic solvent may be methanol or ethanol.

Method IX:

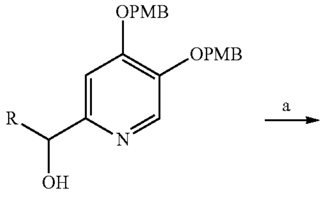

f-2

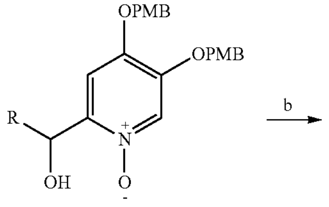

g-1

-continued

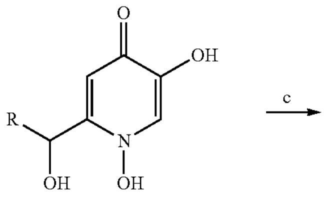

g-2

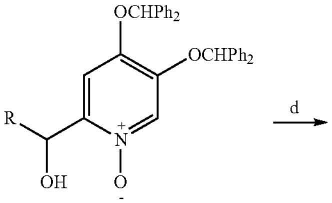

g-3

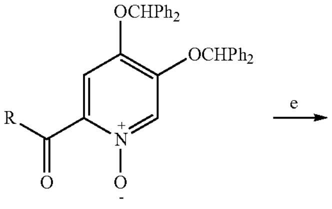

g-4

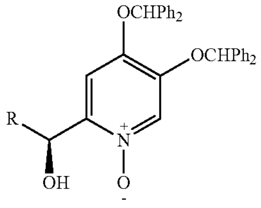

g-5 or

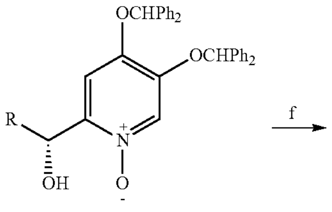

g-6

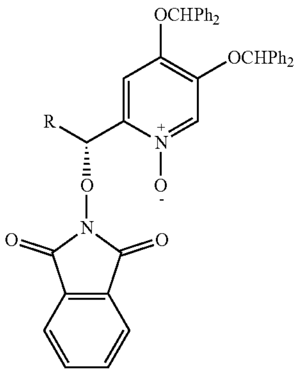

g-7 or

-continued

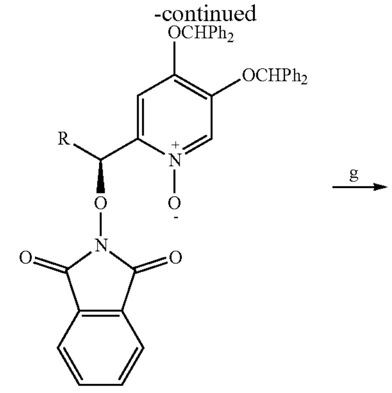

g-8

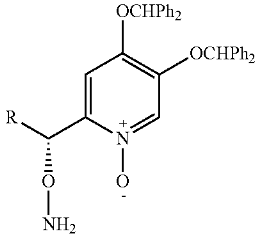

or g-9

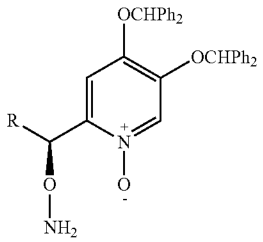

g-10 wherein R is a $C_{1-6}$ linear alkyl group, a $C_{3-6}$ alkenyl group, a $C_{3-6}$ cycloalkyl group, a substituted or unsubstituted phenyl group, or a substituted or unsubstituted 5- or 6-membered heteroaryl ring group having 1 to 4 hetero atoms independently selected from the group consisting of N, S and O;

(a) oxidizing compound f-2 with an oxidizing agent in a non-polar solvent to obtain compound g-1, wherein the non-polar solvent may be dichloromethane, and the oxidizing agent may be m-chloroperoxybenzoic acid or hydrogen peroxide;

(b) subjecting to deprotecting the benzyl protecting group of compound g-1 in a non-polar solvent under the action of a Lewis acid to obtain compound g-2, wherein the non-polar solvent may be dichloromethane, and the Lewis acid may be boron trichloride or boron tribromide;

(c) reacting compound g-2 with diphenyldiazomethane in a mixed polar and non-polar solvents to obtain compound g-3, wherein the polar solvent may be methanol or ethanol; and the non-polar solvent may be dichloromethane, ethyl acetate or tetrahydrofuran;

(d) oxidizing compound g-3 with an oxidizing agent in a non-polar solvent for 4 to 8 hours to obtain compound g-4, wherein the non-polar solvent may be dichloromethane, and the oxidizing agent may be a mixture of sulfur trioxide pyridine and dimethyl sulfoxide or a mixture of oxalyl chloride and dimethyl sulfoxide;

(e) reacting compound g-4 by the action of a transition metal catalyst, a ligand and a hydrogen source in a polar solvent under Ar protection to obtain compound g-5 or g-6, wherein the transition metal catalyst may be dichlorobis(4-methylisopropylphenyl)ruthenium (II) or dichloro(pentamethylcyclopentadienyl)rhodium (III) dimer, the ligand may be (1R,2R)-(−)—N-(p-methylbenzenesulfonyl)-1,2-diphenylethylenediamine or (1S,2S)-(−)-N-(p-methylbenzenesulfonyl)-1,2-diphenylethylenediamine, the hydrogen source may be sodium formate or ammonium formate, and the polar solvent may be N,N-dimethylformamide;

(f) subjecting to Mitsunobu reaction of compound g-5 or g-6 and N-hydroxyphthalimide in a non-polar solvent to obtain compound g-7 or g-8, wherein the non-polar solvent may be tetrahydrofuran or 1,4-dioxane;

(g) subjecting to hydrazinolysis of compound g-7 or g-8 with hydrazine hydrate or aminolysis of compound g-7 or g-8 with methylamine in a polar protic solvent to obtain a compound g-9 or g-10, wherein the polar protic solvent may be methanol or ethanol.

Method X:

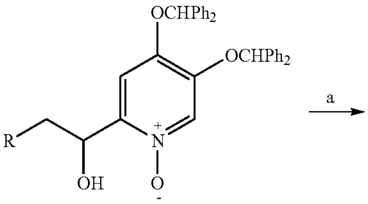

d-11

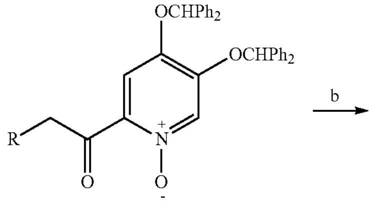

g-11

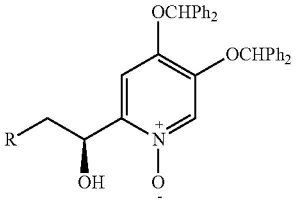

or g-12

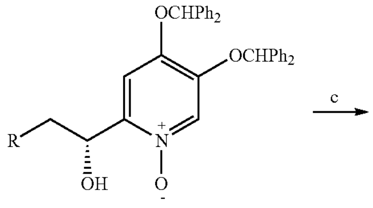

g-13

-continued

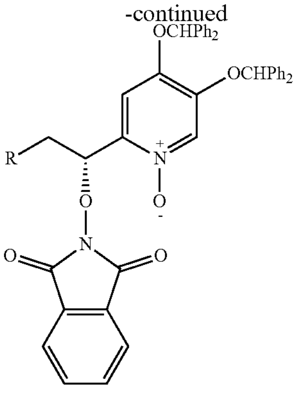

or g-14

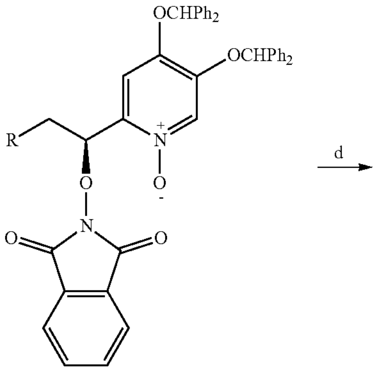

g-15

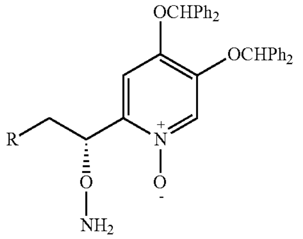

or g-16

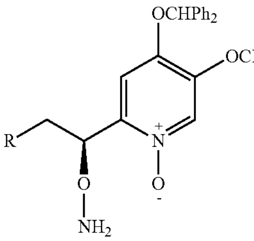

g-17 in the above scheme, R is —$OR_1$, —$SR_1$, —$NR_2R_3$; $R_1$ is a $C_{1-6}$ linear alkyl group, a $C_{3-6}$ branched alkyl group or a $C_{3-6}$ cycloalkyl group; and $R_2$ and $R_3$ are each independently: a hydrogen, a $C_{1-6}$ linear alkyl group, a $C_{3-6}$ branched alkyl group or a $C_{3-6}$ cycloalkyl group;

(a) oxidizing compound d-11 with an oxidizing agent in a non-polar solvent for 4 to 8 hours to obtain compound g-11, wherein the non-polar solvent may be dichloromethane, and the oxidizing agent may be a mixture of sulfur trioxide pyridine and dimethyl sulfoxide or a mixture of oxalyl chloride and dimethyl sulfoxide;

(b) reacting compound g-11 by the action of a transition metal catalyst, a ligand and a hydrogen source in a polar solvent under Ar protection to obtain compound g-12 or g-13, wherein the transition metal catalyst may be dichlorobis(4-methylisopropylphenyl)ruthenium (II) or dichloro (pentamethylcyclopentadienyl)rhodium (III) dimer, the ligand may be (1R,2R)-(−)—N-(p-methylbenzenesulfonyl)-1,2-diphenylethylenediamine or (1S,2S)-(−)-N-(p-methylbenzenesulfonyl)-1,2-diphenylethylenediamine, the hydrogen source may be sodium formate or ammonium formate, and the polar solvent is N,N-dimethylformamide;

(c) subjecting to Mitsunobu reaction of compound g-12 or g-13 and N-hydroxyphthalimide in a non-polar solvent to obtain compound g-14 or g-15, wherein the non-polar solvent may be tetrahydrofuran or 1,4-dioxane;

(d) subjecting to hydrazinolysis of compound g-14 or g-15 with hydrazine hydrate or aminolysis of compound g-14 or g-15 with methylamine in a polar protic solvent to obtain a compound g-16 or g-17, wherein the polar protic solvent may be methanol or ethanol.

DETAILED DESCRIPTION

The inventor synthesized a series of compounds through extensive studies. By performing the antibacterial activity screening and pharmacokinetic screening, the inventor firstly discovered that the compounds of the following formula (I) possess potent antibacterial activity and good harmacokinetic properties. In particular, these compounds are suitable as the drug for anti-infective treatment. Based on these studies, the inventor completed the present invention.

The invention is further illustrated by the following examples, but these examples are not intended to limit the invention. In all the examples, $^1$H-NMR was recorded on a Varian Mercury 300 NMR spectrometer or Varian Mercury 400 NMR spectrometer with chemical shifts expressed in δ (ppm); low resolution mass spectrometry was determined by a Finnigan MAT95 mass spectrometer; For column chromatography, silica of 200-300 mesh was used.

Preparation of Intermediates

Preparation 1

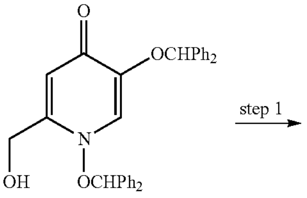

a-1

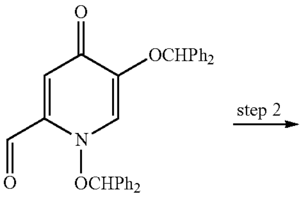

a-2

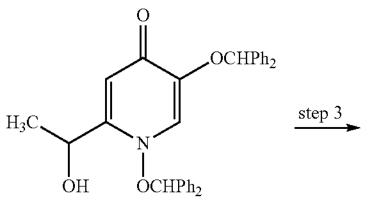

a-3-1

-continued

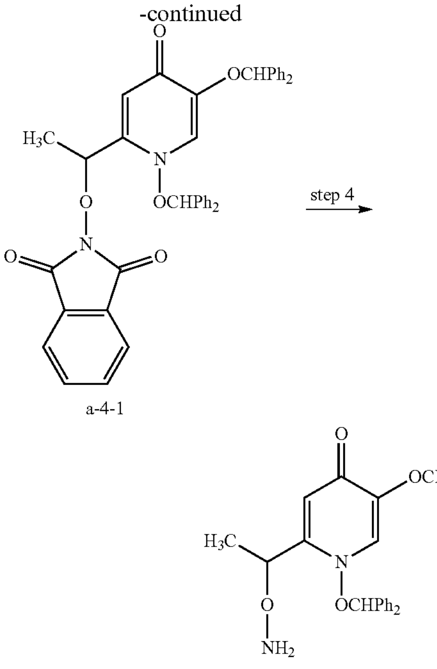

a-4-1 a-5-1

Step 1: Preparation of a-2

Compound a-1 [obtained according to document U.S. Pat. No. 4,883,879A] (15.0 g, 30.64 mmol) was dissolved in a mixed solvent of 210 mL of dichloromethane and 70 mL of dimethyl sulfoxide, 27 mL of triethylamine was added thereto, and the mixture was cooled to 0° C. in an ice water bath. Sulfur trioxide pyridine (24.4 g, 153.20 mmol) was added in three batches and the reaction was carried out at low temperature for 6 hours. After the reaction was completed as monitored by TLC, the resultant was treated under reduced pressure to evaporate dichloromethane, then ethyl acetate (200 mL) was added thereto, the mixture was washed with water (50 mL×5), and saturated brine, dried over anhydrous sodium sulfate, filtered and concentrated. The residue was purified by using column chromatography (dichloromethane:methanol=50:1 to 20:1) to give a white solid compound a-2 (12.0 g, yield: 80.3%).

$^1$H NMR (400 MHz, chloroform-d) δ 9.55 (s, 1H), 7.42-7.30 (m, 16H), 7.13-7.08 (m, 5H), 6.65 (s, 1H), 6.42 (s, 1H), 5.80 (s, 1H).

MS (ESI): m/z 487 [M]$^+$.

Step 2: Preparation of a-3-1

Compound a-2 (1.66 g, 3.40 mmol) was dissolved in 20 mL of dry tetrahydrofuran, and cooled to −20° C. Methyl magnesium bromide (3.4 mL, 10.20 mmol) was added dropwise at low temperature. Thereafter, the reaction was carried out at room temperature for 3 h. After the raw materials disappeared as monitored by TLC, 5 mL of a saturated aqueous solution of ammonium chloride was added dropwise in an ice bath, and the resultant was extracted with ethyl acetate (20 mL×3), washed with saturated brine, dried over anhydrous sodium sulfate, filtered and concentrated under reduced pressure. The residue was purified by using column chromatography (petroleum ether: ethyl acetate=1:1 to 1:4) to give a white solid compound a-3-1 (1.56 g, yield: 91.1%).

$^1$H NMR (400 MHz, chloroform-d) δ 7.54-7.11 (m, 20H), 6.67 (s, 1H), 6.56 (s, 1H), 6.01 (s, 1H), 5.94 (s, 1H), 4.75 (q, J=6.5 Hz, 1H), 1.36 (d, J=6.5 Hz, 3H).

MS(ESI): m/z 504.0, [M+H]$^+$.

Step 3: Preparation of a-4-1

Compound a-3-1 (1.2 g, 2.38 mmol) was dissolved in dry tetrahydrofuran (20 mL). N-hydroxyphthalimide (0.47 g, 2.86 mmol) and triphenylphosphine (0.94 g, 3.58) were sequentially added, and the mixture was cooled to 0° C. in an ice bath. Diethyl azodicarboxylate (0.56 mL, 3.58 mmol) was dissolved in 5 mL of dry tetrahydrofuran, which was slowly added dropwise to the above reaction solution. Thereafter, the ice bath was removed and the temperature was returned to room temperature, the reaction was carried out for 30 min. After the reaction was completed as monitored by TLC, 20 mL of water and 20 mL of saturated sodium bicarbonate solution were added, and the resultant was extracted with ethyl acetate (30×2), washed with saturated brine, dried over anhydrous sodium sulfate, filtered and concentrated under reduced pressure. The residue was purified by using column chromatography (petroleum ether: ethyl acetate=2:1 to 1:2) to give a white solid compound a-4-1 (1.03 g, yield: 66.6%).

$^1$H NMR (400 MHz, chloroform-d) δ 7.84 (dd, J=5.4, 3.2 Hz, 2H), 7.78 (dd, J=5.4, 3.2 Hz, 2H), 7.48-7.30 (m, 20H), 6.82 (s, 1H), 6.44 (s, 1H), 6.36 (s, 1H), 5.98 (s, 1H), 5.28 (q, J=6.8 Hz, 1H), 1.41 (d, J=6.8 Hz, 3H).

MS(ESI): m/z 649.0, [M+H]$^+$.

Step 4: Preparation of a-5-1

Compound a-4-1 (1.03 g, 1.59 mmol) was dissolved in 20 mL of methanol, and 85% hydrazine hydrate (0.15 mL, 2.38 mL) was added thereto. The mixture was reacted at room temperature for 20 min. After the reaction was completed as monitored by TLC, the methanol was evaporated under reduced pressure. 50 mL of ethyl acetate, 20 mL of water and 10 mL of saturated sodium bicarbonate solution were added to separate an organic layer. The aqueous phase was extracted with ethyl acetate (50 mL) once and combined with the organic layer. The resultant was washed with saturated brine, dried over anhydrous sodium sulfate, filtered and concentrated under reduced pressure. The residue was purified by using column chromatography (dichloromethane:methanol=50:1 to 25:1) to give a white solid compound a-5-1 (800 mg, yield 97.1%).

$^1$H NMR (400 MHz, chloroform-d) δ 7.51-7.21 (m, 20H), 6.60 (s, 1H), 6.47 (s, 1H), 6.15 (s, 1H), 5.79 (s, 1H), 5.39 (s, 2H), 4.73 (q, J=6.6 Hz, 1H), 1.28 (d, J=6.6 Hz, 3H).

MS(ESI): m/z 519.1, [M+H]$^+$.

Preparation 2

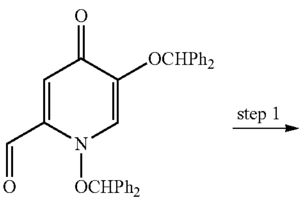

a-2

-continued

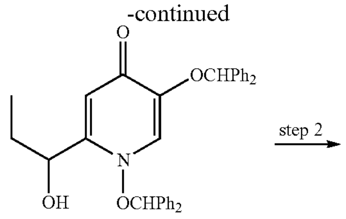

a-3-2

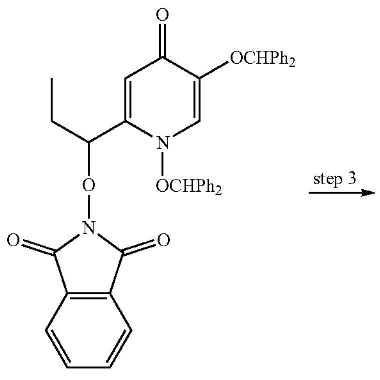

a-4-2

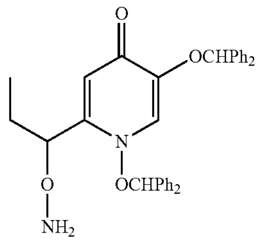

a-5-2

Step 1: Preparation of a-3-2

According to a method similar to that in step 2 of Preparation 1, a white solid compound a-3-2 (720 mg, yield 67.8%.) was prepared from compound a-2 (1.0 g, 2.05 mmol) and 1M of ethylmagnesium bromide (10 mL, 10 mmol).

$^1$H NMR (400 MHz, DMSO-d6) δ 7.48 (s, 1H), 7.45-7.20 (m, 20H), 6.32 (s, 1H), 6.27 (s, 1H), 6.05 (s, 1H), 5.36 (d, J=6.0 Hz, 1H), 4.26 (dt, J=6.7, 6.0 Hz, 1H), 1.43-1.33 (m, 2H), 0.70 (t, J=7.3 Hz, 3H).

MS(ESI): m/z 518.1, $[M+H]^+$.

Step 2: Preparation of a-4-2

According to a method similar to that in step 3 of Preparation 1, a white solid compound a-4-2 (160 mg, yield 61.9%) was prepared from compound a-3-2 (200 mg, 0.39 mmol), N-hydroxyphthalimide (78 mg, 0.46 mmol), triphenylphosphine (262.3 mg, 0.97 mmol) and diethyl azodicarboxylate (0.15 mL, 0.97 mmol).

$^1$H NMR (400 MHz, chloroform-d) δ 7.77-7.68 (m, 4H), 7.36-7.12 (m, 20H), 6.72 (s, 1H), 6.37 (s, 1H), 6.28 (s, 1H), 5.87 (s, 1H), 4.89 (t, J=7.1 Hz, 1H), 1.61-1.40 (m, 2H), 0.86 (t, J=7.4 Hz, 3H).

MS(ESI): m/z 663.2, $[M+H]^+$.

Step 3: Preparation of a-5-2

According to a method similar to that in step 4 of Preparation 1, 110 mg of a white solid compound a-5-2 crude product was prepared from compound a-4-2 (160 mg, 0.24 mmol), 85% hydrazine hydrate (0.03 mL, 0.48 mmol), the crude product was directly used for the next reaction.

MS (ESI): m/z 533.2, $[M+H]^+$

Preparation 3

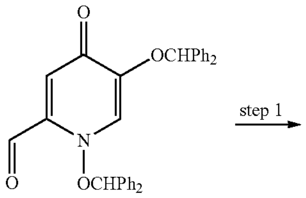

a-2

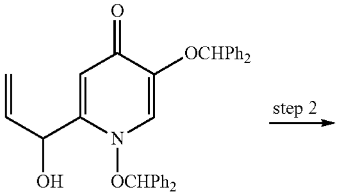

a-3-3

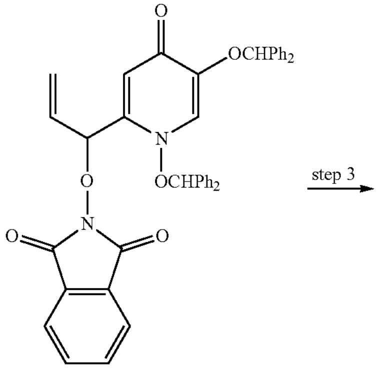

a-4-3

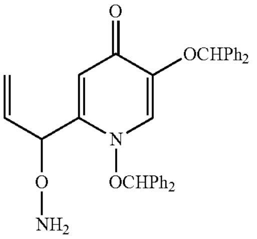

a-5-3

Step 1: Preparation of a-3-3

According to a method similar to that in step 2 of Preparation 1, a white solid compound a-3-3 (800 mg, yield 75.7%.) was prepared from compound a-2 (1.0 g, 2.05 mmol), 1M of vinyl magnesium bromide (10 mL, 10 mmol).

$^1$H NMR (400 MHz, DMSO-d6) δ 7.58 (s, 1H), 7.45-7.17 (m, 20H), 6.35 (s, 1H), 6.32 (s, 1H), 5.93 (s, 1H), 5.78 (d, J=6.0 Hz, 1H), 5.58 (ddd, J=17.1, 10.3, 4.9 Hz, 1H), 5.15-5.11 (m, 1H), 5.11-5.06 (m, 1H), 4.85 (t, J=5.5 Hz, 1H).

MS(ESI): m/z 516.2, $[M+H]^+$.

Step 2: Preparation of a-4-3

According to a method similar to that in step 3 of Preparation 1, a white solid compound a-4-3 (661 mg, yield 64.5%) was prepared from compound a-3-3 (800 mg, 1.55 mmol), N-hydroxyphthalimide (304 mg, 1.9 mmol), triphenylphosphine (839 mg, 3.2 mmol) and diethyl azodicarboxylate (0.5 mL, 3.2 mmol).

$^1$H NMR (400 MHz, chloroform-d) δ 7.83-7.73 (m, 4H), 7.40-7.22 (m, 20H), 6.77 (s, 1H), 6.58 (s, 1H), 6.28 (s, 1H), 5.96 (dd, J=10.2, 8.0 Hz, 1H), 5.92 (s, 1H), 5.55 (d, J=8.0 Hz, 1H), 5.29 (dd, J=17.2, 10.2 Hz, 1H), 5.10 (d, J=17.2 Hz, 1H).

MS(ESI): m/z 661.2, $[M+H]^+$.

Step 3: Preparation of a-5-3

According to a method similar to that in step 4 of Preparation 1, a white solid compound a-5-3 crude product (476 mg) was prepared from compound a-4-3 (660 mg, 1 mmol), 85% hydrazine hydrate (0.12 mL, 2 mmol), the crude product was directly used for the next reaction.

MS (ESI): m/z 531.2, $[M+H]^+$.

Preparation 4

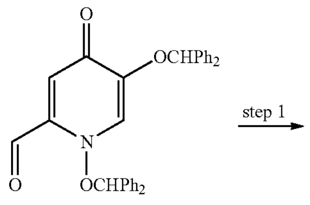

a-2

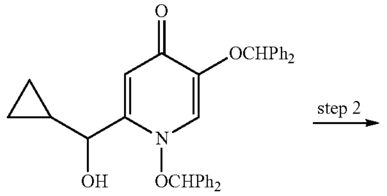

a-3-4

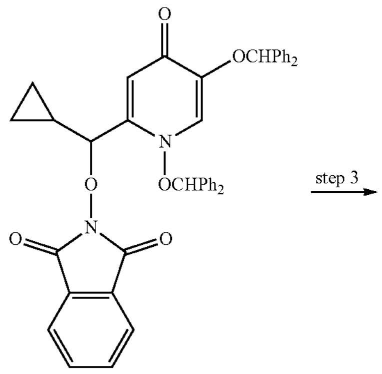

a-4-4

-continued

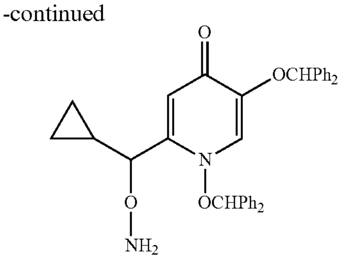

a-5-4

Step 1: Preparation of a-3-4

According to the method in step 2 of Preparation 1, a white solid compound a-3-4 (477 mg, yield 73.2%) was prepared from compound a-2 (600 mg, 1.23 mmol), 0.5M of cyclopropyl magnesium bromide (9.6 mL, 4.8 mmol).

$^1$H NMR (400 MHz, DMSO-d6) δ 7.56 (s, 1H), 7.43-7.12 (m, 20H), 6.33 (s, 1H), 6.28 (s, 1H), 6.11 (s, 1H), 5.43 (d, J=6.2 Hz, 1H), 3.92 (t, J=6.2 Hz, 1H), 0.94-0.83 (m, 1H), 0.39-0.31 (m, 1H), 0.30-0.23 (m, 1H), 0.22-0.15 (m, 1H), −0.03-−0.12 (m, 1H).

MS(ESI): m/z 530.2, $[M+H]^+$.

Step 2: Preparation of a-4-4

According to a method similar to that in step 3 of Preparation 1, a pale yellow solid compound a-4-4 (290 mg, yield 47.7%) was prepared from compound a-3-4 (477 mg, 0.9 mmol), N-hydroxyphthalimide (440 mg, 2.7 mmol), triphenylphosphine (708 mg, 2.7 mmol) and diisopropyl azodicarboxylate (0.54 mL, 2.7 mmol).

$^1$H NMR (400 MHz, chloroform-d) δ 7.84-7.74 (m, 4H), 7.42-7.19 (m, 20H), 6.81 (s, 1H), 6.54 (s, 1H), 6.42 (s, 1H), 5.91 (s, 1H), 4.22 (d, J=9.7 Hz, 1H), 0.95-0.82 (m, 1H), 0.72-0.61 (m, 1H), 0.54-0.41 (m, 2H), −0.11-−0.22 (m, 1H).

MS(ESI): m/z 675.1, $[M+H]^+$.

Step 3: Preparation of a-5-4

According to a method similar to that in step 4 of Preparation 1, 200 mg of a white solid compound a-5-4 crude product was prepared from compound a-4-4 (270 mg, 0.4 mmol), 85% hydrazine hydrate (0.05 mL, 0.8 mmol), the crude product was directly used for the next reaction.

MS (ESI): m/z 545.1, $[M+H]^+$.

Preparation 5

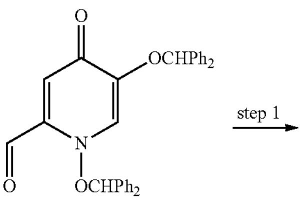

a-2

-continued

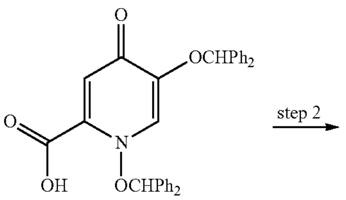

b-1

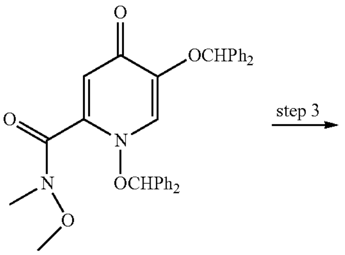

b-2

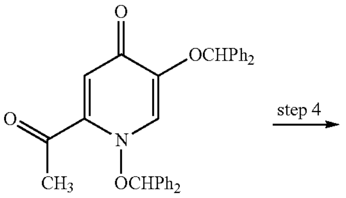

b-3

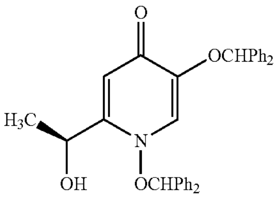

b-4 or

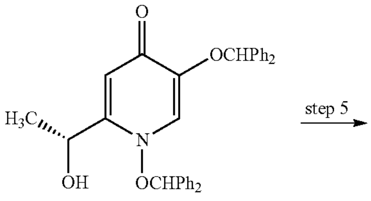

b-5

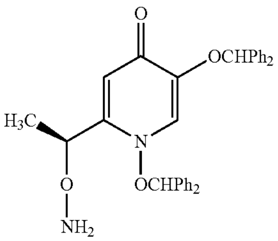

b-6 or

-continued

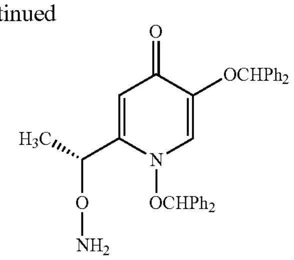

b-7

Step 1: Preparation of b-1

Compound a-2 (3.5 g, 7.18 mmol) was dissolved in 50 mL of acetonitrile, and 40 mL of an aqueous solution of potassium dihydrogen phosphate (9.6 g, 71.8 mmol) and catechol (4.0 g, 35.9 mmol) were added and the mixed solution was stirred at room temperature for 5 min. The mixture was cooled to 0° C. in an ice-bath, and 20 mL of aqueous solution of sodium chlorite (1.9 g, 21.5 mmol) was added thereto, and the mixture was slowly returned to room temperature and reacted for 3 hours. The reaction was completed as monitored by TLC. After adding 100 mL of water, the reaction solution became clear, and the pH of the solution was adjusted to 3 to 5 with a 2N aqueous hydrochloric acid solution, and a white solid was precipitated. The solution was stirred for 10 min, filtered, and dried at 40° C. in vacuo to give compound b-1 (3.5 g, yield: 96.8%).

$^1$H NMR (400 MHz, chloroform-d) δ 11.32 (s, 1H), 7.46-7.20 (m, 20H), 6.54 (s, 1H), 6.34 (s, 1H), 6.01 (s, 1H), 5.52 (s, 1H).

MS (ESI): m/z 503.9, $[M+H]^+$.

Step 2: Preparation of b-2

2-(7-azobenzotriazole)-tetramethyluronium hexafluorophosphate (2.23 g, 5.96 mmol) was suspended in dry dichloromethane (30 mL), and triethylamine (2.8 mL, 19.9 mmol) was added thereto. The mixture was cooled to −20 to −25° C. Compound b-1 (2.0 g, 3.97 mmol) was added at low temperature and reacted therewith for 1 hour, then N-methyl-N-methoxyamine hydrochloride (1.2 g, 11.9 mmol) was added, and reacted therewith at low temperature for 8 hours, the reaction was completed monitored by TLC. After adding 30 mL of water, the resultant was extracted with dichloromethane (30 mL×3), washed with brine, dried over anhydrous sodium sulfate, filtered and concentrated. The residue was purified by using column chromatography (ethyl acetate) to give a white solid compound b-2 (1.33 g, yield 61.3%).

$^1$H NMR (400 MHz, chloroform-d) δ 7.44-7.16 (m, 20H), 6.56 (s, 1H), 6.38 (s, 1H), 6.15 (s, 1H), 5.85 (s, 1H), 3.58 (s, 3H), 3.08 (s, 3H).

MS (ESI): m/z 547.0, $[M+H]^+$.

Step 3: Preparation of b-3

Compound b-2 (1.3 g, 2.38 mmol) was dissolved in dry tetrahydrofuran (30 mL), and the solution was slowly added dropwise to 3 M of a solution of methylmagnesium bromide (4 mL, 12 mmol) in tetrahydrofuran at a temperature of −20 to −25° C. The mixture was reacted for 4 h at low temperature. After the reaction was completed as monitored by TLC, the reaction was quenched with a saturated aqueous solution of ammonium chloride in an ice bath. The resultant was extracted with ethyl acetate (30 mL×2), washed with saturated saline, dried over anhydrous sodium sulfate, filtered, and concentrated. The residue was purified by using column chromatography (petroleum ether:ethyl acetate=1:1 to 1:2) to give a white solid compound b-3 (1.05 g, yield 88%).

$^{1}$H NMR (400 MHz, chloroform-d) δ 7.50-7.08 (m, 20H), 7.01 (s, 1H), 6.52 (s, 1H), 6.26 (s, 1H), 5.84 (s, 1H), 2.16 (s, 3H).

MS(ESI): m/z 501.9, $[M+H]^+$.

Step 4: Preparation of b-4

Under argon atmosphere protection, dichlorobis(4-methylisopropylphenyl)ruthenium (II) (18 mg, 0.03 mmol) and (1S,2S)-(−)-N-(p-methylbenzenesulfonyl)-1,2-diphenylethylenediamine (22 mg, 0.06 mmol) were dissolved in dry N,N-dimethylformamide (5 mL), and triethylamine (6.19 mg) was added thereto and the mixture was stirred at room temperature for 1 hour. At the same time, formic acid (0.4 mL) and triethylamine (0.54 mL) were mixed, and 15 mL of a solution of b-3 (900 mg, 1.8 mmol) in methyl tert-butyl ether was added thereto and stirred. The above ruthenium catalyst complex was added dropwise to the reaction solution of the substrate b-3 at room temperature, and the reaction was carried out overnight. After the reaction was completed as monitored by TLC, the resultant was extracted with ethyl acetate (50 mL), washed with saturated brine, dried over anhydrous sodium sulfate, filtered and concentrated. The residue was purified by using column chromatography (petroleum ether:ethyl acetate=1:1 to 1:4) to give a white solid compound b-4 (700 mg, yield: 77.3%).

$^{1}$H NMR (400 MHz, chloroform-d) δ 7.45-7.09 (m, 20H), 6.61 (s, 1H), 6.60 (s, 1H), 5.97 (s, 1H), 5.94 (s, 1H), 5.05 (s, 1H), 4.77 (q, J=6.4 Hz, 1H), 1.35 (d, J=6.4 Hz, 3H).

MS (ESI): m/z 504.1, $[M+H]^+$.

Preparation of b-5

According to the preparation method of the above compound b-4, a white solid compound b-5 (850 mg, yield 76.8%) was prepared from compound b-3 (1.1 g, 2.2 mmol), dichlorobis(4-methylisopropylphenyl)ruthenium (II) (22 mg, 0.036 mmol) and (1R,2R)-(−)—N-(p-methylbenzenesulfonyl)-1,2-diphenylethylenediamine (26.4 mg, 0.072 mmol).

$^{1}$H NMR (400 MHz, chloroform-d) δ 7.49-7.10 (m, 20H), 6.61 (s, 1H), 6.60 (s, 1H), 5.95 (s, 1H), 5.94 (s, 1H), 5.05 (s, 1H), 4.76 (d, J=6.4 Hz, 1H), 1.35 (d, J=6.4 Hz, 3H).

MS (ESI): m/z 504.1, $[M+H]^+$.

Step 5: Preparation of b-6

According to the methods similar to that in steps 3 and 4 of Preparation 1, a light grey solid compound b-6 (489 mg, yield in two steps 94.7%) was prepared from compound b-5 (500 mg, 0.99 mmol).

$^{1}$H NMR (400 MHz, DMSO-d6) δ 7.46-7.17 (m, 21H), 6.33 (s, 1H), 6.23 (s, 1H), 6.09 (s, 2H), 6.01 (s, 1H), 4.53 (q, J=6.5 Hz, 1H), 1.00 (d, J=6.5 Hz, 3H).

MS (ESI): m/z 519.1, $[M+H]^+$.

Preparation of b-7

According to the methods similar to that in steps 3 and 4 of Preparation 1, a light grey solid compound b-7 (320 mg, yield in two steps 61.7%) was prepared from compound b-4 (500 mg, 0.99 mmol).

$^{1}$H NMR (400 MHz, DMSO-d6) δ 7.46-7.17 (m, 21H), 6.33 (s, 1H), 6.23 (s, 1H), 6.09 (s, 2H), 6.01 (s, 1H), 4.53 (q, J=6.5 Hz, 1H), 1.00 (d, J=6.5 Hz, 3H).

MS (ESI): m/z 519.1, $[M+H]^+$.

Preparation 6

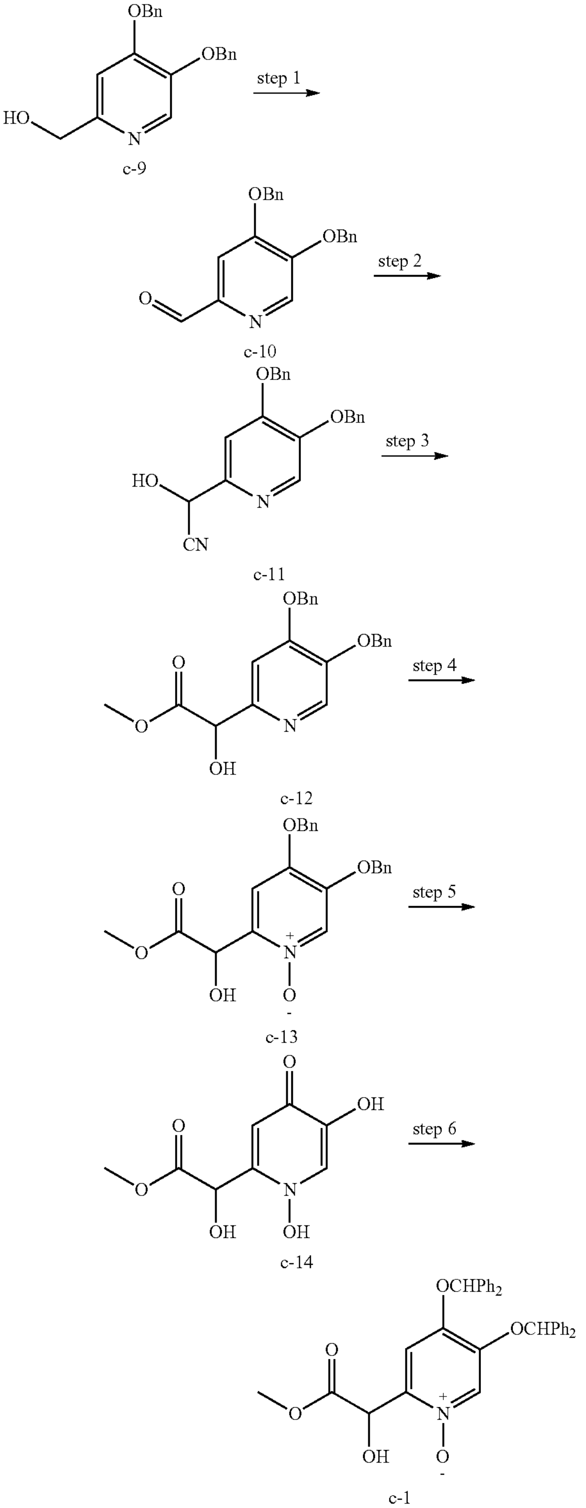

c-9 c-10 c-11 c-12 c-13 c-14 c-1

Step 1: Preparation of c-10

Compound c-9 [obtained according to the document WO2012/073138A1] (27 g, 84 mmol) was dissolved in 300 mL of dichloromethane, 100 mL of dimethyl sulfoxide and triethylamine (46 mL, 335 mmol) were added thereto and the mixture was cooled to 0° C. Sulfur trioxide pyridine (33.3 g, 210 mmol) was added in three batches, and reaction solution was slowly return to room temperature, and reacted for 2 hours. After the reaction was completed as monitored by TLC, dichloromethane was evaporated and removed under reduced pressure, the resultant was added with ethyl acetate 300 mL, washed with 1M diluted aqueous hydrochloric acid (20 mL×5), washed with saturated sodium bicarbonate (20 mL) and saturated brine, dried over anhydrous sodium sulfate, filtered, concentrated to precipitate a solid, which was further slurried in a solution of petroleum ether:ethyl acetate=4:1, and the resultant was filtered and dried to give a white solid compound c-10 (25.5 g, yield 95%).

$^1$H NMR (400 MHz, chloroform-d) δ 9.90 (s, 1H), 8.31 (s, 1H), 7.57 (s, 1H), 7.49-7.31 (m, 10H), 5.32 (s, 2H), 5.27 (s, 2H).

MS (EI): m/z 319, $[M]^+$.

Step 2: Preparation of c-11

The compound c-10 (31.8 g, 99.6 mmol) was dissolved in 120 mL of tetrahydrofuran, and 350 mL of water was added thereto, and the reactant was in a suspended state. Sodium hydrogen sulfite (15.5 g, 149.4 mmol) was added, and the reaction solution changed from clear to turbid, and was stirred for 1 h in an ice bath. Sodium cyanide (7.89 g, 159.4 mmol) was added thereto at 0° C., and reacted therewith at low temperature overnight to precipitate a solid, which was filtered, washed with water, dried by pressing and airing, and dried at 45° C. in vacuo to give a pale yellow solid compound c-11 (33 g, yield 95.6%).

$^1$H NMR (400 MHz, chloroform-d) δ 8.14 (s, 1H), 7.50-7.34 (m, 10H), 7.06 (s, 1H), 5.48 (s, 1H), 5.27 (s, 2H), 5.24 (s, 2H).

Step 3: Preparation of c-12

The compound c-11 (14.1 g, 40.7 mmol) was dissolved in 150 mL of a dry solution of 2M methanol in hydrochloric acid, and reacted at room temperature for 10 hours. After the starting material disappeared as monitored by TLC, methanol was evaporated under reduced pressure, and the residue was added with saturated aqueous sodium bicarbonate solution (50 mL), extracted with ethyl acetate (100 mL×2), washed with saturated brine, dried over anhydrous sodium sulfate, filtered and concentrated. The residue was purified by using column chromatography (petroleum ether:ethyl acetate=4:1 to 2:1) to give a pale light solid compound c-12 (14.5 g, yield: 93.9%).

$^1$H NMR (400 MHz, chloroform-d) δ 8.14 (s, 1H), 7.50-7.28 (m, 10H), 7.08 (s, 1H), 5.26 (s, 2H), 5.23 (s, 1H), 5.21 (s, 2H), 3.73 (s, 3H).

MS(ESI): m/z 380.1, $[M+H]^+$.

Step 4: Preparation of c-13

Compound c-12 (5.1 g, 13.4 mmol) was dissolved in 100 mL of dichloromethane, and cooled to 0° C. m-chloroperoxybenzoic acid (5.5 g, 26.8 mmol) was added thereto, and the reaction solution was slowly returned to room temperature and reacted for 1 to 2 hours, After the raw materials disappeared as monitored by TLC, the reaction solution was added with 50 mL of water, 20 mL of a saturated sodium bicarbonate solution and 50 mL of dichloromethane, and a dichloromethane phase was separated, which was washed with a saturated aqueous solution of sodium thiosulfate (50 mL), and washed with saturated brine, dried over sodium sulfate, filtered and concentrated. The residue was purified by using column chromatography (dichloromethane:methanol=50:1 to 20:1) to give a white solid compound c-13 (3.79 g, 71.5%).

$^1$H NMR (400 MHz, chloroform-d) δ 7.96 (s, 1H), 7.46-7.35 (m, 10H), 6.96 (s, 1H), 5.25 (q, J=12.0 Hz, 2H), 5.16 (s, 2H), 5.14 (s, 1H), 3.78 (s, 3H).

MS (ESI): m/z 396.2, $[M+H]^+$.

Step 5: Preparation of c-14

Compound c-13 (2.5 g, 6.32 mmol) was dissolved in dry dichloromethane (20 mL), cooled to −10° C. 1 M solution of boron trichloride in n-hexane (19 mL, 19 mmol) was slowly added dropwise thereto at low temperature, and the reaction was carried out for 3 h at the low temperature. After the starting material disappeared as monitored by TLC, 5 mL of methanol was slowly added dropwise to quench the reaction in an ice bath. After stirring for 10 min, the solvent was evaporated under reduced pressure to give the crude product of c-14, which was directly used for the next reaction.

MS (ESI): m/z 216.5, $[M+H]^+$.

Step 6: Preparation of c-1

The crude product of the above c-14 was dissolved in 20 mL of methanol. 20 mL of a solution of diphenyldiazomethane (6.13 g, 31.6 mmol) in dichloromethane was slowly added dropwise in an ice bath, and the reaction was carried out at room temperature for 3 hours. After the starting material disappeared as monitored by TLC, the resultant was concentrated under reduced pressure. The residue was purified by using column chromatography (dichloromethane: methanol=50:1 to 20:1) to give a white solid compound c-1 (1.84 g, 53.2%).

$^1$H NMR (400 MHz, chloroform-d) δ 7.82 (s, 1H), 7.46-7.28 (m, 20H), 6.78 (s, 1H), 6.30 (s, 1H), 6.19 (s, 1H), 4.93 (s, 1H), 3.68 (s, 3H).

MS (ESI): m/z 548.1, $[M+H]^+$.

Preparation 7

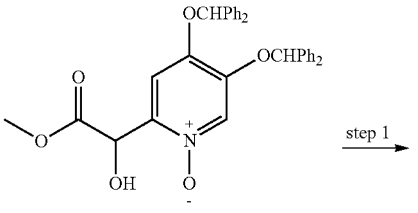

c-1

-continued

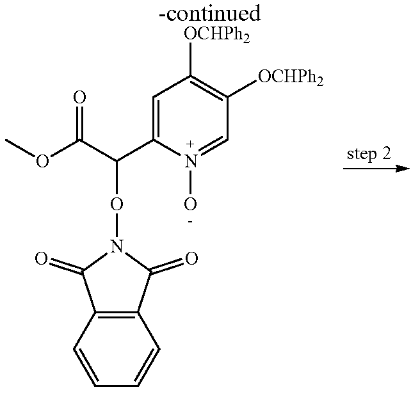

c-2

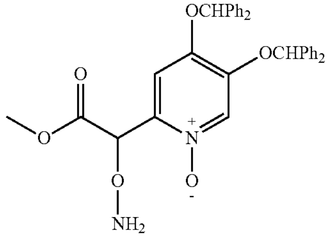

c-3

Step 1: Preparation of c-2

According to the method in step 3 of Preparation 1, a pale yellow solid compound c-2 (1.5 mg, yield 66.5%) was prepared from compound c-1 (1.79 g, 3.26 mmol), N-hydroxyphthalimide (1.60 g, 9.8 mmol), triphenylphosphine (2.58 g, 9.8 mmol) and diisopropyl azodicarboxylate (1.6 mL, 9.8 mmol).

$^1$H NMR (400 MHz, chloroform-d) δ 7.84 (s, 1H), 7.84-7.74 (m, 4H), 7.52-7.26 (m, 21H), 6.50 (s, 1H), 6.21 (s, 1H), 6.09 (s, 1H), 3.72 (s, 3H).

MS (ESI): m/z 693.4, $[M+H]^+$.

Step 2: Preparation of c-3

According to the method in step 4 of Preparation 1, 324 mg of a white solid compound c-3 crude product was prepared from compound c-2 (500 mg, 0.72 mmol), 85% hydrazine hydrate (0.04 mL, 0.72 mmol), the crude product was directly used for the next reaction.

MS (ESI): m/z 563.2, $[M+H]^+$

Preparation 8

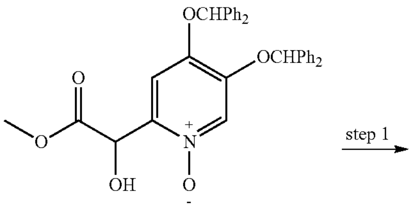

c-1

-continued

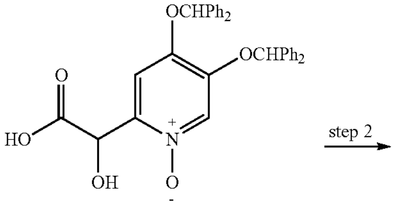

c-4

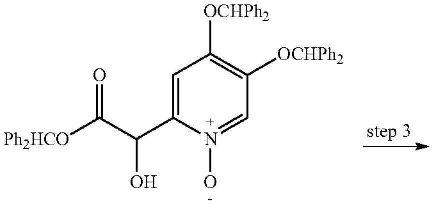

c-5

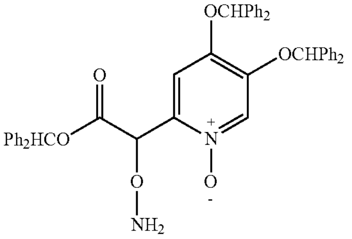

c-6

Step 1: Preparation of c-4

Compound c-1 (2.0 g, 3.65 mmol) was dissolved in 25 mL of tetrahydrofuran, and 25 mL of water was added thereto. Lithium hydroxide (306 mg, 7.3 mmol) was added in an ice bath, and the mixture was returned to room temperature and reacted for 1 hour. After the starting material disappeared as monitored by TLC, the reaction solution was adjusted to pH 5 with 1 M of diluted hydrochloric acid, extracted with ethyl acetate (50 mL×3), and washed with saturated brine, dried over anhydrous sodium sulfate, filtered, concentrated to obtain a pale yellow solid compound c-4, which was directly used for the next reaction without purification.

MS (ESI): m/z 532, $[M-H]^-$.

Step 2: Preparation of c-5

The crude product of the above c-4 was dissolved in 30 mL of methanol, 10 mL of a solution of diphenyldiazomethane (2.12 g, 10.95 mmol) in ethyl acetate was slowly added dropwise in an ice bath, and the reaction was carried out at room temperature for 3 hours. After the starting material disappeared as monitored by TLC, the reaction solution was concentrated under reduced pressure. The residue was purified by using column chromatography (dichloromethane: methanol=50:1 to 20:1) to give a white solid compound c-5 (2.15 g, yield in two steps 84.3%).

$^1$H NMR (400 MHz, chloroform-d) δ 7.80 (s, 1H), 7.52-7.02 (m, 30H), 6.88 (s, 1H), 6.76 (s, 1H), 6.22 (s, 1H), 6.17 (s, 1H), 4.94 (s, 1H).

MS (ESI): m/z 700.1, $[M+H]^+$.

Step 3: Preparation of c-6

According to the methods similar to that in steps 3 and 4 of Preparation 1, a white solid compound c-6 (540 mg, crude product was directly used for the next reaction) was prepared from the above c-5 (2.15 g, 3.08 mmol), N-hydroxyphthalimide (1.51 g, 9.23 mmol), triphenylphosphine (2.42 g, 9.23 mmol) and diisopropyl azodicarboxylate (1.5 mL, 9.23 mmol) and 85% hydrazine hydrate (0.17 mL, 2.84 mmol).

Preparation 9

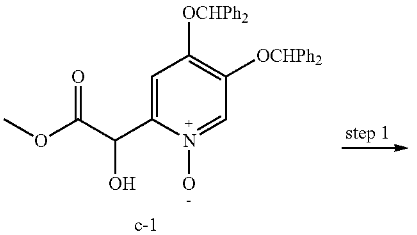

c-1

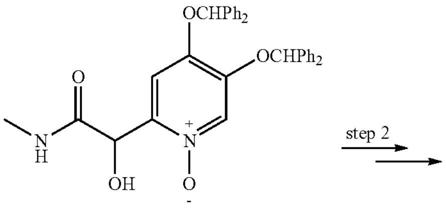

c-7

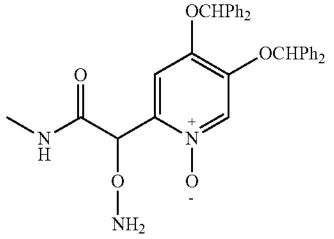

c-8

Step 1: Preparation of c-7

Compound c-1 (930 mg, 1.70 mmol) was dissolved in 10 mL of methanol, a solution of methylamine in methanol (4.5 mL, 34.0 mmol) was added dropwise thereto at room temperature, and the reaction was carried out for 1 hour. After the starting material disappeared as monitored by TLC, the resultant was extracted with ethyl acetate (50 mL×2), washed with saturated brine, dried over anhydrous sodium sulfate, filtered and concentrated. The residue was purified by using column chromatography (petroleum ether: ethyl acetate=1:1 to 1:2) to give a white solid compound c-7 (553 mg, yield: 59.6%).

$^1$H NMR (400 MHz, chloroform-d) δ 9.35 (d, J=4.8 Hz, 1H), 7.79 (s, 1H), 7.47-7.27 (m, 20H), 7.12 (s, 1H), 6.33 (s, 1H), 6.19 (s, 1H), 5.45 (d, J=4.1 Hz, 1H), 4.91 (d, J=4.1 Hz, 1H), 2.75 (d, J=4.8 Hz, 3H).

MS (ESI): m/z 547.1, [M+H]$^+$.

Step 2: Preparation of c-8

According to the methods similar to that in steps 3 and 4 of Preparation 1, a white solid compound c-8 (400 mg, crude product was directly used for the next reaction) was prepared from the above c-7 (535 mg, 0.98 mmol), N-hydroxyphthalimide (480 mg, 2.94 mmol), triphenylphosphine (769 mg, 2.94 mmol) and diisopropyl azodicarboxylate (0.58 mL, 2.94 mmol) and 85% hydrazine hydrate (0.17 mL, 2.84 mmol).

Preparation 10

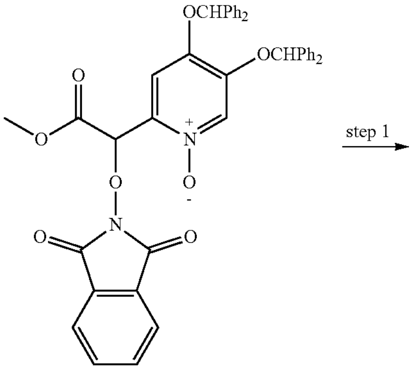

c-2

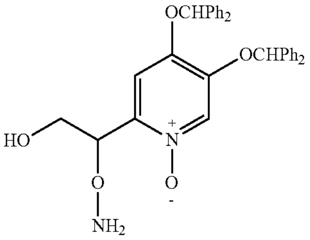

c-15

Step 1: Preparation of c-15

The compound c-2 (400 mg, 0.6 mmol) was dissolved in tetrahydrofuran (20 mL) and cooled to 0° C., and then lithium borohydride (26 mg, 1.2 mmol) was added thereto and reacted therewith for 2 hours. After the starting material disappeared as monitored by TLC, the resultant was extracted with ethyl acetate (30 mL×2), and washed with saturated brine, dried over anhydrous sodium sulfate, filtered and concentrated. The residue was purified by using column chromatography (dichloromethane:methanol=60:1 to 20:1) to give a white solid compound c-15 (173 g, yield: 53.8%).

$^1$H NMR (400 MHz, chloroform-d) δ 7.85 (s, 1H), 7.46-7.27 (m, 20H), 6.79 (s, 1H), 6.33 (s, 1H), 6.19 (s, 1H), 5.20 (t, J=5.6 Hz, 1H), 3.72 (dd, J=14.8, 5.5 Hz, 2H).

MS (ESI): m/z 534.1, [M+H]$^+$.

Preparation 11

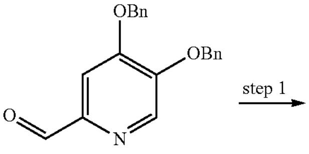

c-10

-continued

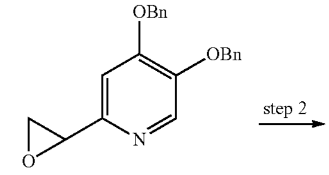

d-1

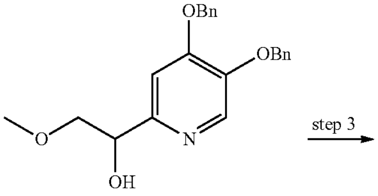

d-2

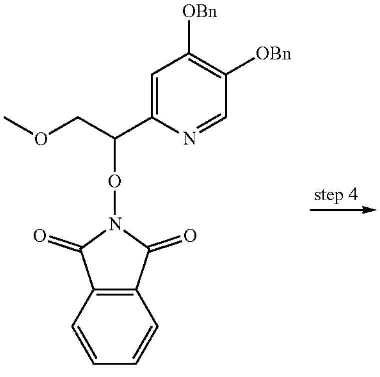

d-3

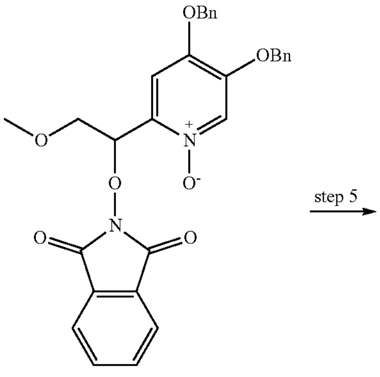

d-4

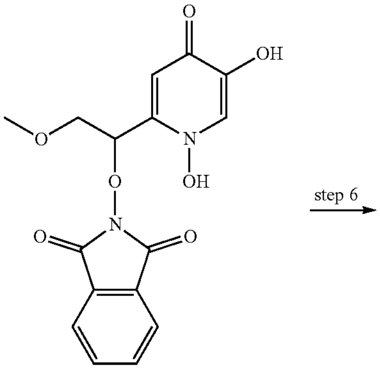

d-5

-continued

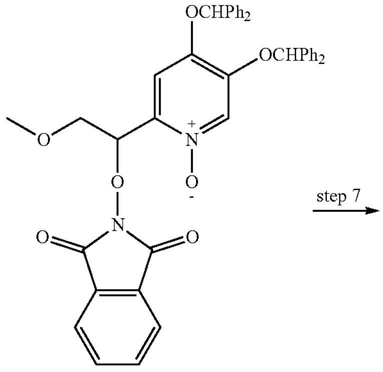

d-6

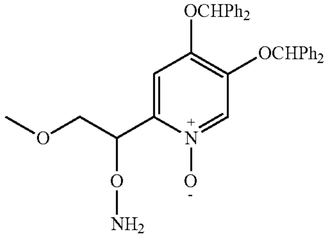

d-7

Step 1: Preparation of d-1

Trimethylsulfoxonium iodide (2.42 g, 11 mmol) was dissolved in 20 mL of dry dimethyl sulfoxide, 10 mL of tetrahydrofuran was added. 60% sodium hydride (440 mg, 11 mmol) was added under ice bath and the mixture was stirred for 1 hour. Compound c-10 (3.2 g, 10 mmol) was dissolved in dry dimethyl sulfoxide (20 mL), and slowly added dropwise to the above reaction solution in an ice bath. Thereafter, the reaction solution was slowly warmed to room temperature, and reacted for 2 h. After the raw materials disappeared as monitored by TLC, the reaction was quenched by adding 10 mL water in an ice bath, and the resultant was extracted with ethyl acetate (50 mL×3), and washed with saturated brine, dried over anhydrous sodium sulfate, filtered and concentrated. The residue was purified by using column chromatography (petroleum ether:ethyl acetate=5:1 to 2:1) to give a white solid compound d-1 (1.89 g, 56.7%).

$^{1}$H NMR (400 MHz, chloroform-d) δ 8.12 (s, 1H), 7.46-7.29 (m, 10H), 6.78 (s, 1H), 5.20 (s, 2H), 5.18 (s, 2H), 3.91 (dd, J=4.2, 2.5 Hz, 1H), 3.11 (dd, J=5.7, 4.2 Hz, 1H), 2.78 (dd, J=5.7, 2.5 Hz, 1H).

MS (ESI): m/z 334.1, $[M+H]^+$.

Step 2: Preparation of d-2

The compound d-1 (500 mg, 1.5 mmol) was dissolved in 10 mL of methanol, a solution of 5 M sodium methoxide in methanol (3 mL, 15 mmol) was added dropwise at room temperature and the reaction was carried out overnight. After the raw materials disappeared as monitored by TLC, the reaction solution was added with 10 mL of water, extracted with ethyl acetate (50 mL×2), and washed with saturated brine, dried over anhydrous sodium sulfate, filtered and concentrated. The residue was purified by using column chromatography (dichloromethane:methanol=50:1 to 20:1) to give a white solid compound d-2 (494 mg, 90.2%).

$^{1}$H NMR (400 MHz, chloroform-d) δ 8.12 (s, 1H), 7.52-7.32 (m, 10H), 7.06 (s, 1H), 5.24 (s, 2H), 5.19 (s, 2H), 4.81 (dd, J=6.6, 4.6 Hz, 1H), 4.08 (s, 1H), 3.62 (dd, J=9.8, 4.6 Hz, 1H), 3.56 (dd, J=9.8, 6.6 Hz, 1H), 3.39 (s, 3H).

MS (ESI): m/z 366.1, $[M+H]^+$.

Step 3: Preparation of d-3

According to the preparation method in step 3 of Preparation 1, a pale yellow solid compound d-3 (170 mg, 81.2%) was prepared from compound d-2 (150 mg, 0.41 mmol), N-hydroxyphthalimide (80 mg, 0.49 mmol), triphenylphosphine (160 mg, 0.62 mmol) and diethyl azodicarboxylate (0.09 mL, 0.62 mmol).

$^{1}$H NMR (400 MHz, chloroform-d) δ 8.11 (s, 1H), 7.80 (dd, J=5.5, 3.1 Hz, 2H), 7.73 (dd, J=5.5, 3.1 Hz, 2H), 7.60 (s, 1H), 7.57-7.31 (m, 10H), 5.58 (dd, J=6.9, 3.2 Hz, 1H), 5.36 (s, 2H), 5.18 (s, 2H), 3.97 (dd, J=11.5, 6.9 Hz, 1H), 3.89 (dd, J=11.5, 3.2 Hz, 1H), 3.41 (s, 3H).

MS (ESI): m/z 511.1, $[M+H]^+$.

Step 4: Preparation of d-4

Compound d-3 (1.1 g, 2.15 mmol) was dissolved in dichloromethane (50 mL), and cooled to 0° C. m-chloroperoxybenzoic acid (880 mg, 4.31 mmol) was added thereto and the reaction system was slowly returned to room temperature and reacted for 1 to 2 hours. After the raw materials disappeared as monitored by TLC, the reaction solution was added with 50 mL of water, 20 mL of saturated sodium bicarbonate solution and 50 mL of dichloromethane, and a dichloromethane phase was separated, which was further washed with 50 mL of a saturated aqueous solution of sodium thiosulfate, and washed with saturated brine, dried over anhydrous sodium sulfate, filtered and concentrated. The residue was purified by using column chromatography (dichloromethane:methanol=50:1 to 20:1) to give a white solid compound d-4 (1.01 g, yield 89.2%).

$^{1}$H NMR (400 MHz, chloroform-d) δ 7.95 (s, 1H), 7.81-7.72 (m, 5H), 7.57-7.30 (m, 10H), 6.21 (dd, J=5.0, 2.5 Hz, 1H), 5.41 (s, 2H), 5.09 (s, 2H), 3.99 (dd, J=11.7, 2.5 Hz, 1H), 3.93 (dd, J=11.7, 5.0 Hz, 1H), 3.41 (s, 3H).

MS (ESI): m/z 527.2, $[M+H]^+$.

Step 5: Preparation of d-5

According to the method in step 5 of Preparation 6, compound d-4 (1.01 g, 1.92 mmol) was removed of its protection group by reacting with boron trichloride (4.6 mL, 4.6 mmol) to give the title compound d-5 (1.07 g, crude, directly used for the next reaction).

Step 6: Preparation of d-6

According to the method in step 6 of Preparation 6, a white solid compound d-6 (700 mg, yield in two steps: 53.7%) was prepared from the above crude d-5 (1.07 g) and diphenyldiazomethane (1.86 g, 9.6 mmol).

$^{1}$H NMR (400 MHz, chloroform-d) δ 7.81 (dd, J=5.4, 3.2 Hz, 2H), 7.79 (s, 1H), 7.77 (s, 1H), 7.74 (dd, J=5.5, 3.1 Hz, 2H), 7.65-7.56 (m, 4H), 7.48-7.30 (m, 16H), 6.74 (s, 1H), 6.18 (s, 1H), 6.18-6.16 (m, 1H), 3.86 (dd, J=11.9, 2.3 Hz, 1H), 3.74 (dd, J=11.9, 5.4 Hz, 1H), 3.30 (s, 3H).

MS (ESI): m/z 679.1, $[M+H]^+$.

Step 7: Preparation of d-7

According to a method similar to that in step 4 of Preparation 1, a white solid compound d-7 (400 mg, crude, directly used for the next reaction) was prepared from compound d-6 (700 mg, 1.03 mmol) and 85% hydrazine hydrate (0.07 mL, 1.13 mmol).

Preparation 12

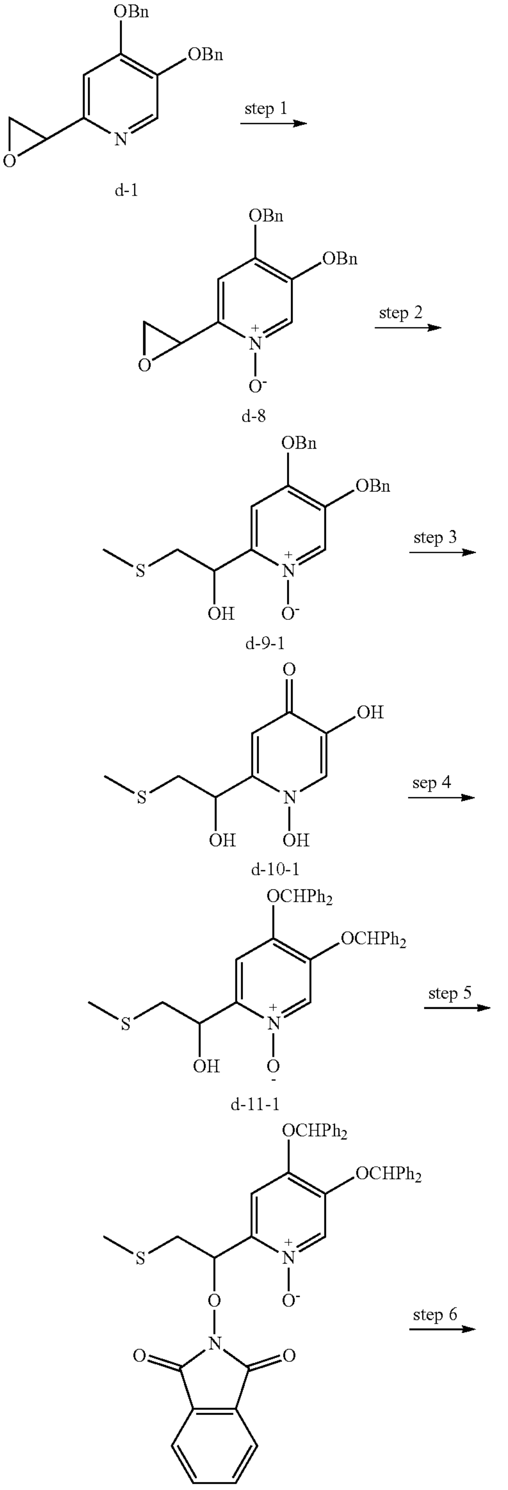

d-12-1

-continued

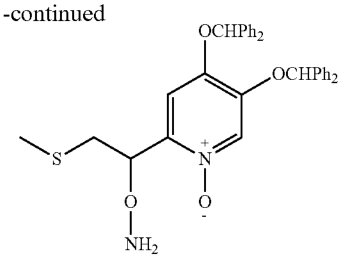

d-13-1

Step 1: Preparation of d-8

According to a method similar to that in step 4 of Preparation 13, a white solid compound d-8 (3.2 g, 80.3%) was prepared from compound d-1 (3.8 g, 11.4 mmol) and m-chloroperoxybenzoic acid (7.05 g, 34.2 mmol).

$^1$H NMR (400 MHz, chloroform-d) δ 7.94 (s, 1H), 7.45-7.32 (m, 10H), 6.73 (s, 1H), 5.21-5.13 (m, 2H), 5.12 (s, 2H), 4.48 (dd, J=4.2, 2.4 Hz, 1H), 3.25 (dd, J=5.6, 4.2 Hz, 1H), 2.62 (dd, J=5.6, 2.4 Hz, 1H).

MS (ESI): m/z 350.1, [M+H]$^+$.

Step 2: Preparation of d-9-1

The compound d-8 (3.0 g, 8.58 mmol) was dissolved in 20 mL of dioxane, a 20% aqueous sodium thiomethoxide solution (14.9 mL, 42.9 mmol) was added thereto, and the reaction was carried out overnight at room temperature to precipitate a white solid. After the raw materials disappeared as monitored by TLC, the reaction solution was filtered, and the white solid was rinsed with water (10 mL), and then rinsed with 5 mL of petroleum ether and dried at 50° C. in vacuo for 10 hours to give a white solid compound d-9-1 (1.43 g, 41.9%).

$^1$H NMR (400 MHz, chloroform-d) δ 7.86 (s, 1H), 7.46-7.33 (m, 10H), 6.88 (s, 1H), 5.93 (d, J=7.4 Hz, 1H), 5.22 (s, 2H), 5.12 (s, 2H), 4.83 (q, J=7.0 Hz, 1H), 3.21 (dd, J=13.7, 7.0 Hz, 1H), 2.85 (dd, J=13.7, 6.5 Hz, 1H), 2.01 (s, 3H).

MS (ESI): m/z 398.0, [M+H]$^+$.

Step 3: Preparation of d-10-1

According to the method in step 5 of Preparation 6, compound d-9-1 (7.2 g, 18.11 mmol) was removed of its protection group by reacting with boron trichloride (45.3 mL, 45.3 mmol) to give the title compound d-10-1 (8.5 g, crude, directly used for the next reaction).

Step 4: Preparation of d-11-1

According to the method in step 6 of Preparation 6, a white solid compound d-11-1 (4.3 g, yield in two steps 43.2%) was prepared from the above crude d-10-1 (8.5 g) and diphenyldiazomethane (21.1 g, 108.7 mmol).

$^1$H NMR (400 MHz, chloroform-d) δ 7.77 (s, 1H), 7.45-7.28 (m, 20H), 6.82 (s, 1H), 6.31 (s, 1H), 6.20 (s, 1H), 5.96 (s, 1H), 4.69 (t, J=6.5 Hz, 1H), 3.04 (dd, J=13.8, 6.9 Hz, 1H), 2.76 (dd, J=13.7, 5.9 Hz, 1H), 1.83 (s, 3H).

MS (ESI): m/z 550.0, [M+H]$^+$.

Step 5: Preparation of d-12-1

According to the preparation method in step 3 of Preparation 1, a pale yellow solid compound d-12-1 (366 mg, 59.9%) was prepared from compound d-11-1 (484 mg, 0.88 mmol), N-hydroxyphthalimide (215 mg, 1.32 mmol), triphenylphosphine (461 mg, 1.76 mmol) and diisopropyl azodicarboxylate (0.27 mL, 1.76 mmol).

$^1$H NMR (400 MHz, chloroform-d) δ 7.82 (s, 1H), 7.81-7.77 (m, 3H), 7.76-7.70 (m, 2H), 7.63-7.27 (m, 20H), 6.73 (s, 1H), 6.18 (s, 1H), 6.14 (dd, J=5.8, 3.5 Hz, 1H), 3.16 (dd, J=14.9, 3.5 Hz, 1H), 2.90 (dd, J=14.9, 5.8 Hz, 1H), 1.88 (s, 3H).

MS (ESI): m/z 695.1, [M+H]$^+$.

Step 6: Preparation of d-13-1

According to a method similar to that in step 4 of Preparation 1, a white solid compound d-13-1 (206 mg, 69.1%) was prepared from compound d-12-1 (366 mg, 0.53 mmol) and 85% hydrazine hydrate (0.04 mL, 0.53 mmol).

$^1$H NMR (400 MHz, chloroform-d) δ 7.81 (s, 1H), 7.49-7.27 (m, 20H), 6.80 (s, 1H), 6.32 (s, 1H), 6.19 (s, 1H), 5.20 (dd, J=7.3, 3.1 Hz, 1H), 5.06 (s, 2H), 2.95 (dd, J=14.2, 3.1 Hz, 1H), 2.62 (dd, J=14.2, 7.3 Hz, 1H), 2.01 (s, 3H).

MS (ESI): m/z 565.1, [M+H]$^+$.

Preparation 13

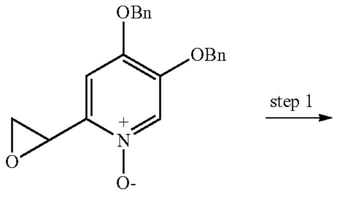

d-8

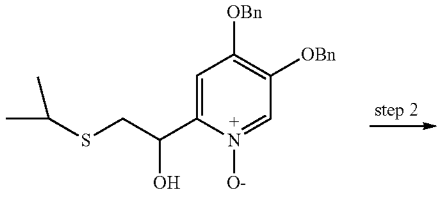

d-9-2

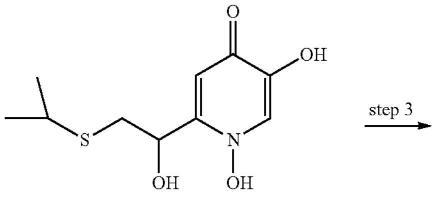

d-10-2

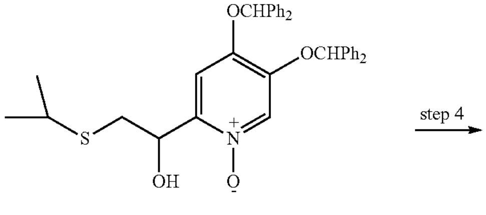

d-11-2

-continued

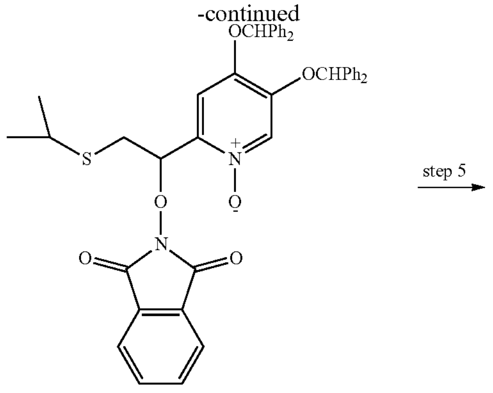

d-12-2

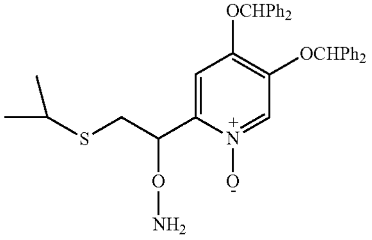

d-13-2

Step 1: Preparation of d-9-2

Isopropyl mercaptan (2.66 mL, 28.6 mmol) was dissolved in 20 mL of dioxane, and cooled to 0° C. in an ice bath. 60% sodium hydride (1.14 g, 28.6 mmol) was added at low temperature and the reaction was carried out for 30 min. The compound d-8 (2.0 g, 5.72 mmol) was dissolved in 10 mL of dioxane, and the solution was added dropwise to the above reaction solution, the reaction was carried out for 1 hour. Water (20 mL) was added to the reaction system to precipitate a white solid. After the reaction was continued for 30 min, the starting material disappeared as monitored by TLC, then the reaction solution was filtered, the filter cake was rinsed with water and petroleum ether, and dried at 55° C. to give white solid compound d-9-2 (1.3 g, 53.4%).

$^1$H NMR (400 MHz, chloroform-d) δ 7.88 (s, 1H), 7.48-7.32 (m, 10H), 6.90 (s, 1H), 5.89 (d, J=6.9 Hz, 1H), 5.23 (s, 2H), 5.14 (s, 2H), 4.85 (q, J=6.7 Hz, 1H), 3.32 (dd, J=13.5, 6.9 Hz, 1H), 2.95-2.83 (m, 2H), 1.26 (d, J=6.7 Hz, 3H), 1.24 (d, J=6.7 Hz, 3H).

MS (ESI): m/z 426.1, [M+H]$^+$.

Step 2: Preparation of d-10-2

According to the method in step 5 of Preparation 6, compound d-9-2 (2.17 g, 5.1 mmol) was removed of its protection group by reacting with boron trichloride (12.7 mL, 12.7 mmol) to give the title compound d-10-2 (2.5 g, crude, directly used for the next reaction).

Step 3: Preparation of d-11-2

According to the method in step 6 of Preparation 6, a white solid compound d-11-2 (1.03 g, yield in two steps: 34.9%) was prepared from the above crude d-10-2 (2.5 g) and diphenyldiazomethane (5.94 g, 30.6 mmol).

$^1$H NMR (400 MHz, chloroform-d) δ 7.77 (s, 1H), 7.47-7.28 (m, 20H), 6.81 (s, 1H), 6.30 (s, 1H), 6.18 (s, 1H), 4.68 (t, J=6.8 Hz, 1H), 3.13 (dd, J=13.6, 7.1 Hz, 1H), 2.83-2.71 (m, 2H), 1.16 (d, J=6.7 Hz, 3H), 1.14 (d, J=6.8 Hz, 3H).

MS (ESI): m/z 578.1, [M+H]$^+$.

Step 4: Preparation of d-12-2

Compound d-11-2 (1.03 g, 1.78 mmol) was dissolved in dry tetrahydrofuran (20 ml), N-hydroxyphthalimide (873 mg, 5.35 mmol) and tributylphosphine (1.2 mL, 5.35 mmol) were added thereto with stirring, and the solution was cooled to −15 to −10° C. Diisopropyl azodicarboxylate (0.66 mL, 5.35 mmol) was dissolved in 5 mL of dry tetrahydrofuran, and the solution obtained was slowly added dropwise to the above reaction solution at a low temperature, which was allowed to react overnight. After the starting material disappeared as monitored by TLC, the reaction solution was warmed to room temperature, extracted with 100 mL of ethyl acetate, and then washed sequentially with a saturated aqueous solution of sodium bicarbonate (20 mL×3), water (20 mL×2) and 20 mL of a saturated aqueous sodium chloride solution, dried over anhydrous sodium sulfate, filtered and concentrated. The residue was purified by using column chromatography (petroleum ether:ethyl acetate=1:2 to 1:4) to give a pale yellow solid compound d-12-2 (641 mg, 49.7%).

$^1$H NMR (400 MHz, chloroform-d) δ 7.81-7.76 (m, 3H), 7.75-7.71 (m, 3H), 7.63-7.28 (m, 20H), 6.73 (s, 1H), 6.15 (s, 1H), 6.09 (dd, J=6.2, 3.5 Hz, 1H), 3.25 (dd, J=14.7, 3.6 Hz, 1H), 2.92-2.81 (m, 2H), 1.13 (d, J=6.7 Hz, 3H), 1.08 (d, J=6.7 Hz, 3H).

MS (ESI): m/z 723.2, [M+H]$^+$.

Step 4: Preparation of d-13-2

According to a method similar to that in step 4 of Preparation 1, a white solid compound d-13-2 (314 mg, 66.0%) was prepared from compound d-12-2 (580 mg, 0.81 mmol) and 85% hydrazine hydrate (0.06 mL, 0.81 mmol).

$^1$H NMR (400 MHz, chloroform-d) δ 7.82 (s, 1H), 7.48-7.27 (m, 20H), 6.78 (s, 1H), 6.31 (s, 1H), 6.18 (s, 1H), 5.14 (dd, J=7.8, 3.1 Hz, 1H), 5.04 (s, 2H), 3.05 (dd, J=14.0, 3.1 Hz, 1H), 2.88 (h, J=6.6 Hz, 1H), 2.61 (dd, J=14.0, 7.8 Hz, 1H), 1.21 (d, J=6.7 Hz, 3H), 1.17 (d, J=6.7 Hz, 3H).

MS (ESI): m/z 593.2, [M+H]$^+$.

Preparation 14

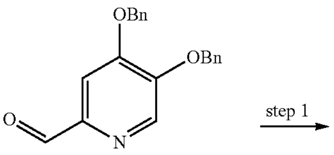

c-10

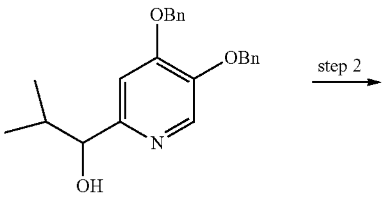

e-1

-continued

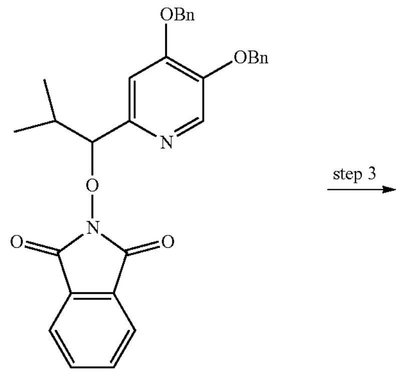

e-2

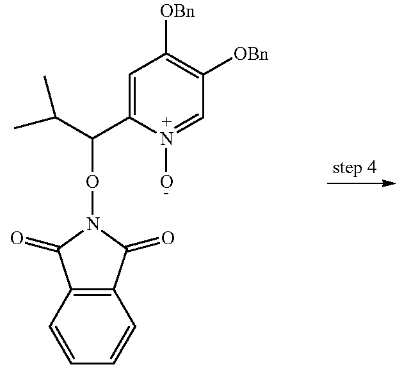

e-3

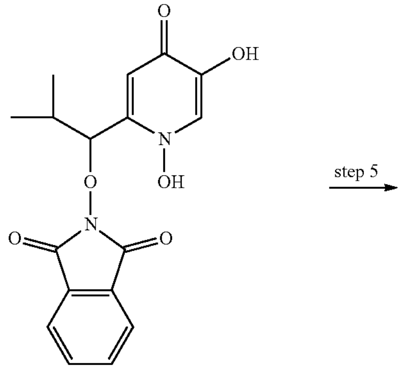

e-4

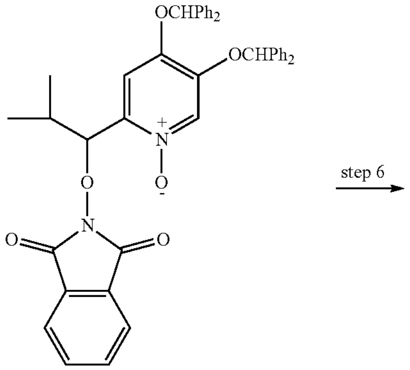

e-5

-continued

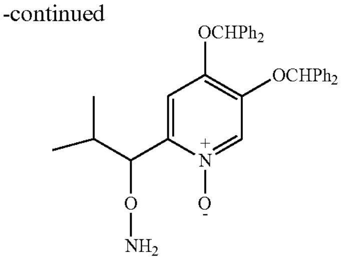

e-6

Step 1: Preparation of e-1

Compound c-10 (320 mg, 1 mmol) was dissolved in dry tetrahydrofuran (10 mL), cooled to −20° C., and isopropyl magnesium bromide (2 mL, 2 mmol) was added dropwise at low temperature. Thereafter, the mixture was warmed to room temperature and reacted for 3 h, then the raw materials disappeared as monitored by TLC. Under ice bath, 5 mL of a saturated aqueous solution of ammonium chloride was added dropwise, and the resultant was extracted with ethyl acetate (10 mL×3), washed with saturated brine, dried over anhydrous sodium sulfate, filtered and concentrated under reduced pressure. The residue was purified by using column chromatography (petroleum ether:ethyl acetate=2:1 to 1:1) to give a white solid compound e-1 (223 mg, yield: 61.4%).

$^1$H NMR (400 MHz, chloroform-d) δ 8.09 (s, 1H), 7.46-7.30 (m, 10H), 6.75 (s, 1H), 5.21 (s, 2H), 5.18 (s, 2H), 4.40 (d, J=4.3 Hz, 1H), 3.98 (s, 1H), 1.97-1.84 (m, 1H), 0.93 (d, J=6.8 Hz, 3H), 0.72 (d, J=6.8 Hz, 3H).

MS (ESI): m/z 364.2, $[M+H]^+$.

Step 2: Preparation of e-2

According to the preparation method in step 3 of Preparation 1, a pale yellow solid compound e-2 (1.0 g, 57.6%) was prepared from compound e-1 (1.24 g, 3.41 mmol), N-hydroxyphthalimide (836 mg, 5.12 mmol), triphenylphosphine (2.22 mg, 8.52 mmol) and diethyl azodicarboxylate (1.2 mL, 8.52 mmol).

$^1$H NMR (400 MHz, chloroform-d) δ 8.02 (s, 1H), 7.72 (dd, J=5.4, 3.2 Hz, 2H), 7.67 (dd, J=5.4, 3.2 Hz, 2H), 7.52 (d, J=7.5 Hz, 2H), 7.48 (s, 1H), 7.43-7.27 (m, 8H), 5.37 (s, 2H), 5.13 (s, 2H), 5.09 (d, J=7.3 Hz, 1H), 2.27-2.14 (m, 1H), 1.15 (d, J=6.8 Hz, 3H), 0.83 (d, J=6.8 Hz, 3H).

MS (ESI): m/z 509.3, $[M+H]^+$.

Step 3: Preparation of e-3

According to the preparation method in step 4 of Preparation 13, a white solid compound e-3 (0.53 g, 52.9%) was prepared from compound e-2 (1.1 g, 2.16 mmol) and m-chloroperoxybenzoic acid (1.1 g, 5.41 mmol).

$^1$H NMR (400 MHz, chloroform-d) δ 7.85 (s, 1H), 7.75 (dd, J=5.7, 3.0 Hz, 2H), 7.70 (dd, J=5.7, 3.0 Hz, 2H), 7.62 (s, 1H), 7.54 (d, J=7.2 Hz, 2H), 7.44-7.31 (m, 8H), 5.99 (d, J=5.2 Hz, 1H), 5.45 (s, 2H), 5.08 (s, 2H), 2.34-2.19 (m, 1H), 1.17 (d, J=6.9 Hz, 3H), 0.98 (d, J=6.9 Hz, 3H).

MS (ESI): m/z 525.1, $[M+H]^+$.

Step 4: Preparation of e-4

According to the method in step 5 of Preparation 6, compound e-3 (820 mg, 1.56 mmol) was removed of its protection group by reacting with boron trichloride (3.9 mL, 3.9 mmol) to give the title compound e-4 (880 mg, crude, directly used for the next reaction).

Step 5: Preparation of e-5

According to the preparation method in step 6 of Preparation 6, a white solid compound e-5 (650 mg, yield in two steps: 61.6%) was prepared from the above crude e-4 (880 mg) and diphenyldiazomethane (1.51 g, 7.8 mmol).

$^1$H NMR (400 MHz, chloroform-d) δ 7.75 (dd, J=5.6, 3.1 Hz, 2H), 7.73 (s, 1H), 7.70 (dd, J=5.6, 3.1 Hz, 2H), 7.59 (s, 1H), 7.59-7.55 (m, 4H), 7.46-7.27 (m, 16H), 6.72 (s, 1H), 6.15 (s, 1H), 5.88 (d, J=6.8 Hz, 1H), 2.11 (h, J=6.9 Hz, 1H), 1.08 (d, J=6.9 Hz, 3H), 0.64 (d, J=6.9 Hz, 3H).

MS (ESI): m/z 677.3, $[M+H]^+$.

Step 6: Preparation of e-6

According to a method similar to that in step 4 of Preparation 1, a white solid compound e-6 (210 mg, crude, directly used for the next reaction) was prepared from compound e-5 (340 mg, 0.50 mmol) and 85% hydrazine hydrate (0.04 mL, 0.60 mmol).

Preparation 15

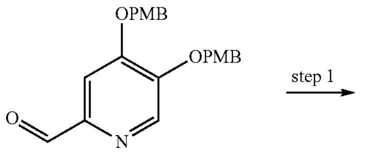

f-1

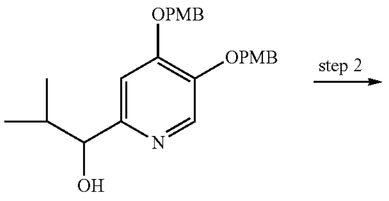

f-2

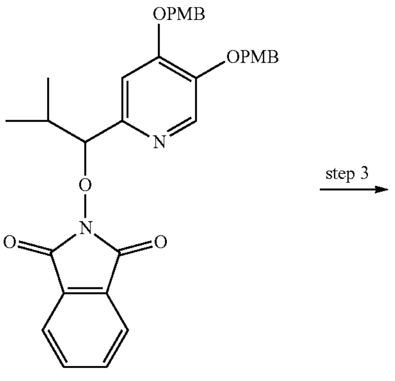

f-3

-continued

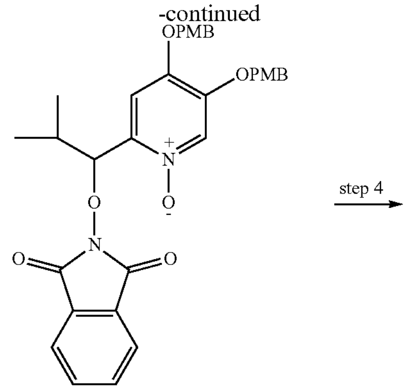

f-4

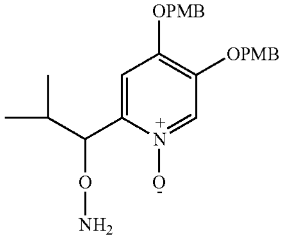

f-5

Step 1: Preparation of f-2

Compound f-1 (1.5 g, 3.95 mmol) was dissolved in dry tetrahydrofuran (20 mL), cooled to −20° C., and a solution of 2.0 M isopropyl magnesium bromide in tetrahydrofuran (5.9 mL, 11.8 mmol) was added dropwise at low temperature. Thereafter, the mixture was warmed to room temperature and reacted for 3 h, then the raw materials disappeared as monitored by TLC. Under ice bath, 5 mL of a saturated aqueous solution of ammonium chloride was added dropwise, and the resultant was extracted with ethyl acetate (30 mL×2), and washed with saturated brine, dried over anhydrous sodium sulfate, filtered and concentrated under reduced pressure. The residue was purified by using column chromatography (petroleum ether:ethyl acetate=2:1 to 1:1) to give a white solid compound f-2 (1.24 g, yield: 74.1%).

$^1$H NMR (400 MHz, chloroform-d) δ 8.07 (s, 1H), 7.33 (t, J=8.9 Hz, 4H), 6.91 (d, J=8.6 Hz, 2H), 6.87 (d, J=8.6 Hz, 2H), 6.76 (s, 1H), 5.12 (s, 2H), 5.08 (s, 2H), 3.82 (s, 3H), 3.80 (s, 3H), 1.98-1.86 (m, 1H), 0.95 (d, J=6.8 Hz, 3H), 0.74 (d, J=6.8 Hz, 3H).

MS (ESI): m/z 424.1, $[M+H]^+$.

Step 2: Preparation of f-3

According to the preparation method in step 3 of Preparation 1, a pale yellow solid compound f-3 (785 mg, 47.6%) was prepared from compound f-2 (1.23 g, 2.9 mmol), N-hydroxyphthalimide (0.71 g, 4.4 mmol), triphenylphosphine (1.52 g, 5.8 mmol) and diethyl azodicarboxylate (0.9 mL, 5.8 mmol).

$^1$H NMR (400 MHz, chloroform-d) δ 8.01 (s, 1H), 7.77-7.73 (m, 2H), 7.71-7.67 (m, 2H), 7.50 (s, 1H), 7.46 (d, J=8.6 Hz, 2H), 7.31 (d, J=8.6 Hz, 2H), 6.94 (d, J=8.6 Hz, 2H), 6.86 (d, J=8.6 Hz, 2H), 5.34 (d, J=11.7 Hz, 1H), 5.25 (d, J=11.6 Hz, 1H), 5.11 (d, J=7.4 Hz, 1H), 5.07 (d, J=11.5 Hz, 1H), 5.05 (d, J=11.5 Hz, 1H), 3.84 (s, 3H), 3.80 (s, 3H), 2.29-2.18 (m, 1H), 1.18 (d, J=6.7 Hz, 3H), 0.86 (d, J=6.9 Hz, 3H).

MS (ESI): m/z 569.1, $[M+H]^+$.

Step 3: Preparation of f-4

According to the preparation method in step 4 of Preparation 13, a white solid compound f-4 (680 mg, 86.1%) was prepared from compound f-3 (770 mg, 1.35 mmol) and m-chloroperoxybenzoic acid (934 mg, 4.05 mmol).

$^1H$ NMR (400 MHz, chloroform-d) δ 7.83 (s, 1H), 7.78-7.74 (m, 2H), 7.72-7.69 (m, 2H), 7.61 (s, 1H), 7.46 (d, J=8.6 Hz, 2H), 7.29 (d, J=8.6 Hz, 2H), 6.93 (d, J=8.7 Hz, 2H), 6.87 (d, J=8.6 Hz, 2H), 6.00 (d, J=5.3 Hz, 1H), 5.41 (d, J=11.7 Hz, 1H), 5.29 (d, J=11.7 Hz, 1H), 5.00 (d, J=11.5 Hz, 1H), 4.98 (d, J=11.5 Hz, 1H), 3.82 (s, 3H), 3.79 (s, 3H), 2.35-2.23 (m, 1H), 1.18 (d, J=6.9 Hz, 3H), 1.01 (d, J=6.9 Hz, 3H).

MS (ESI): m/z 585.2, $[M+H]^+$.

Step 4: Preparation of f-5

According to a method similar to that in step 4 of Preparation 1, a white solid compound f-5 (450 mg, 85.3%) was prepared from compound f-4 (680 mg, 1.16 mmol) and 85% hydrazine hydrate (0.08 mL, 1.16 mmol).

$^1H$ NMR (400 MHz, chloroform-d) δ 7.92 (s, 1H), 7.32 (d, J=8.6 Hz, 4H), 6.89 (dd, J=8.8, 2.3 Hz, 4H), 6.79 (s, 1H), 5.18 (s, 2H), 5.17-5.10 (m, 2H), 5.08 (d, J=5.1 Hz, 1H), 5.01 (s, 2H), 3.80 (s, 3H), 3.79 (s, 3H), 2.17-2.04 (m, 1H), 0.98 (d, J=6.9 Hz, 3H), 0.82 (d, J=6.9 Hz, 3H).

MS (ESI): m/z 455.0, $[M+H]^+$.

Preparation 16

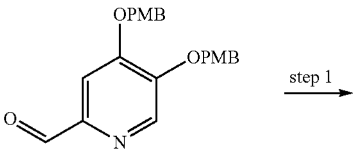

f-1

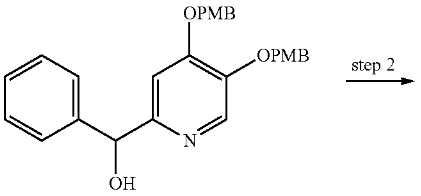

f-2-1

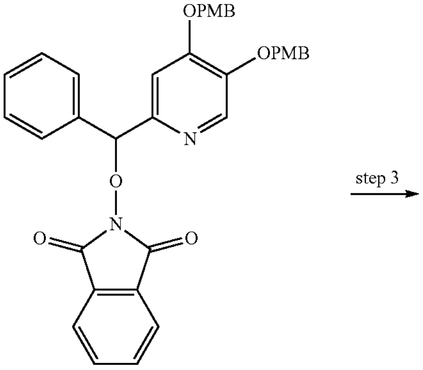

f-3-1

-continued

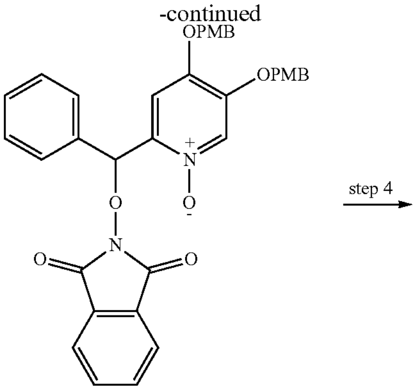

f-4-1

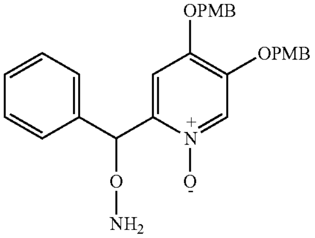

f-5-1

Step 1: Preparation of f-2-1

Compound f-1 (3.5 g, 9.2 mmol) was dissolved in dry tetrahydrofuran (20 mL), cooled to −20° C., and phenylmagnesium chloride (14 mL, 28 mmol) was added dropwise at low temperature. Thereafter, the mixture was warmed to room temperature and reacted for 3 h, then the raw materials disappeared as monitored by TLC. Under ice bath, 5 mL of a saturated aqueous solution of ammonium chloride was added dropwise, and the resultant was extracted with ethyl acetate (30 mL×2), and washed with saturated brine, dried over anhydrous sodium sulfate, filtered and concentrated under reduced pressure. The residue was purified by using column chromatography (petroleum ether:ethyl acetate=2:1 to 1:1) to give a white solid compound f-2-1 (3.85 g, yield: 91.4%).

$^1H$ NMR (400 MHz, chloroform-d) δ 8.08 (s, 1H), 7.37-7.30 (m, 5H), 7.31-7.19 (m, 4H), 6.90-6.83 (m, 4H), 6.65 (s, 1H), 5.60 (s, 1H), 5.07 (s, 2H), 5.04-4.96 (m, 2H), 3.81 (s, 3H), 3.81 (s, 3H).

MS (ESI): m/z 458.1, $[M+H]^+$.

Step 2: Preparation of f-3-1

According to the preparation method in step 3 of Preparation 1, a pale yellow solid compound f-3-1 (4.07 g, 80.4%) was prepared from compound f-2-1 (3.85 g, 8.4 mmol), N-hydroxyphthalimide (1.65 g, 10.1 mmol), triphenylphosphine (3.27 g, 12.6 mmol) and diethyl azodicarboxylate (1.8 mL, 12.6 mmol).

$^1H$ NMR (400 MHz, chloroform-d) δ 8.03 (s, 1H), 7.76 (dd, J=5.6, 3.0 Hz, 2H), 7.70 (dd, J=5.6, 3.0 Hz, 2H), 7.45-7.40 (m, 4H), 7.32-7.28 (m, 5H), 6.93 (d, J=8.7 Hz, 2H), 6.84 (d, J=8.7 Hz, 2H), 6.47 (s, 1H), 5.36-5.22 (m, 2H), 5.05 (s, 2H), 3.83 (s, 3H), 3.78 (s, 3H).

MS (ESI): m/z 603.1, $[M+H]^+$.

Step 3: Preparation of f-4-1

According to the preparation method in step 4 of Preparation 11, a white solid compound f-4-1 (3.7 g, 88.5%) was prepared from compound f-3-1 (4.07 g, 6.75 mmol) and m-chloroperoxybenzoic acid (4.13 g, 20.26 mmol).

$^1$H NMR (400 MHz, chloroform-d) δ 7.86 (s, 1H), 7.84 (s, 1H), 7.78 (dd, J=5.5, 3.1 Hz, 2H), 7.71 (dd, J=5.5, 3.1 Hz, 2H), 7.47-7.41 (m, 4H), 7.33-7.26 (m, 5H), 7.07 (s, 1H), 6.94 (d, J=8.7 Hz, 2H), 6.86 (d, J=8.7 Hz, 2H), 5.45-5.29 (m, 2H), 4.98 (s, 2H), 3.83 (s, 3H), 3.78 (s, 3H).

MS (ESI): m/z 619.2, $[M+H]^+$.

Step 4: Preparation of f-5-1

According to a method similar to that in step 4 of Preparation 1, a white solid compound f-5-1 (230 mg, crude, directly used for the next reaction) was prepared from compound f-4-1 (530 mg, 0.86 mmol) and 85% hydrazine hydrate (0.07 mL, 1.03 mmol).

MS (ESI): m/z 489.1, $[M+H]^+$.

Preparation 17

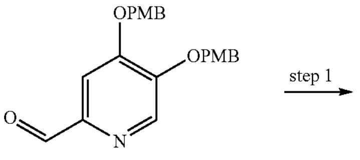

f-1

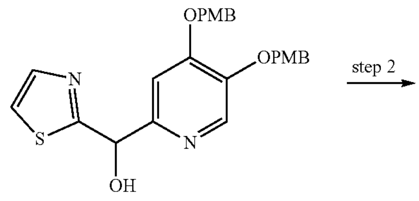

f-2-2

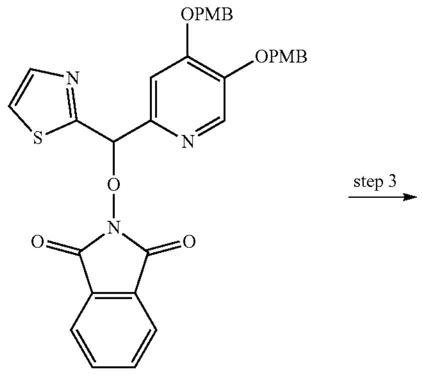

f-3-2

-continued

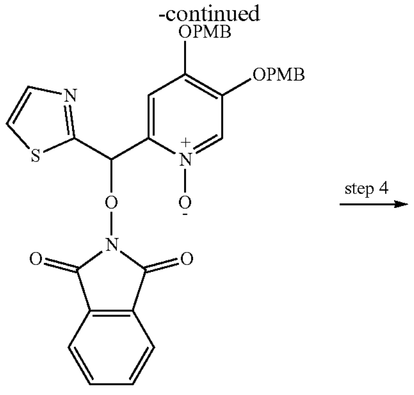

f-4-2

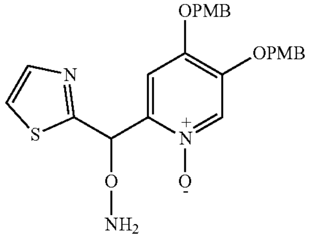

f-5-2

Step 1: Preparation of f-2-2

Compound f-1 (2.5 g, 6.59 mmol) was dissolved in dry tetrahydrofuran (20 mL), and added with 2-bromothiazole (3.6 mL, 39.53 mL), and the mixture was cooled to −78° C. a solution of 2.4 M n-butyllithium in n-hexane (2.7 mL, 6.48 mmol) was slowly added dropwise at low temperature. Thereafter, the mixture was reacted for 1 h, then the starting material disappeared as monitored by TLC. Under ice bath, 5 mL of a saturated aqueous solution of ammonium chloride was added dropwise, and the resultant was extracted with ethyl acetate (30 mL×3), and washed with saturated brine, dried over anhydrous sodium sulfate, filtered and concentrated under reduced pressure. The residue was purified by using column chromatography (petroleum ether:ethyl acetate=1:1 to 1:2) to give a pale yellow oily compound f-2-2 (1.68 g, yield 54.9%).

$^1$H NMR (400 MHz, chloroform-d) δ 8.05 (s, 1H), 7.74 (d, J=3.3 Hz, 1H), 7.34 (d, J=8.6 Hz, 2H), 7.30 (d, J=8.6 Hz, 2H), 7.27 (d, J=3.3 Hz, 1H), 7.24 (s, 1H), 6.88 (t, J=8.7 Hz, 4H), 5.96 (s, 1H), 5.11 (s, 2H), 5.07 (s, 2H), 3.81 (s, 3H), 3.80 (s, 3H).

MS (ESI): m/z 465.1, $[M+H]^+$.

Step 2: Preparation of f-3-2

According to the preparation method in step 3 of Preparation 1, a pale yellow solid compound f-3-2 (0.8 g, 36.3%) was prepared from compound f-2-2 (1.68 g, 3.61 mmol), N-hydroxyphthalimide (1.77 g, 10.85 mmol), triphenylphosphine (4.69 g, 18.05 mmol) and diethyl azodicarboxylate (2.6 mL, 18.05 mmol).

$^1$H NMR (400 MHz, chloroform-d) δ 8.13 (s, 1H), 7.77 (dd, J=5.6, 3.0 Hz, 2H), 7.74 (d, J=3.2 Hz, 1H), 7.71 (dd, J=5.6, 3.0 Hz, 3H), 7.61 (s, 1H), 7.44 (d, J=3.0 Hz, 1H), 7.41 (d, J=8.6 Hz, 2H), 7.30 (d, J=8.6 Hz, 2H), 6.91 (d, J=8.6 Hz, 2H), 6.85 (d, J=8.6 Hz, 2H), 6.62 (s, 1H), 5.24 (d, J=11.5 Hz, 1H), 5.21 (d, J=11.5 Hz, 1H), 5.08 (s, 2H), 3.82 (s, 3H), 3.78 (s, 3H).

MS (ESI): m/z 610.1, $[M+H]^+$.

Step 3: Preparation of f-4-2

According to the preparation method in step 4 of Preparation 13, a white solid compound f-4-2 (328 mg, 40.0%) was prepared from compound f-3-2 (800 mg, 1.31 mmol) and m-chloroperoxybenzoic acid (825 mg, 3.93 mmol).

$^1$H NMR (400 MHz, chloroform-d) δ 7.88 (s, 1H), 7.87 (s, 1H), 7.82 (dd, J=5.5, 3.1 Hz, 1H), 7.80 (d, J=3.2 Hz, 1H), 7.75 (dd, J=5.5, 3.1 Hz, 1H), 7.46 (d, J=3.2 Hz, 1H), 7.43 (d, J=8.6 Hz, 1H), 7.29-7.26 (m, 3H), 6.93 (d, J=8.6 Hz, 1H), 6.86 (d, J=8.6 Hz, 1H), 5.37-5.22 (m, 1H), 5.01 (s, 1H), 3.83 (s, 3H), 3.79 (s, 3H).

MS (ESI): m/z 626.0, $[M+H]^+$.

Step 4: Preparation of f-5-2

According to a method similar to that in step 4 of Preparation 1, a white solid compound f-5-2 (176 mg, 65.4%) was prepared from compound f-4-2 (340 mg, 0.54 mmol) and 85% hydrazine hydrate (0.04 mL, 0.60 mmol).

$^1$H NMR (400 MHz, chloroform-d) δ 7.92 (s, 1H), 7.77 (d, J=3.3 Hz, 1H), 7.33 (d, J=3.3 Hz, 1H), 7.32-7.27 (m, 4H), 7.07 (s, 1H), 6.90-6.86 (m, 4H), 6.57 (s, 1H), 5.73 (s, 2H), 5.14 (d, J=11.6 Hz, 1H), 5.08 (d, J=11.6 Hz, 1H), 5.01 (s, 2H), 3.80 (s, 3H), 3.79 (s, 3H).

MS (ESI): m/z 496.1, $[M+H]^+$.

Preparation 18

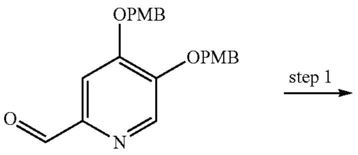

f-1

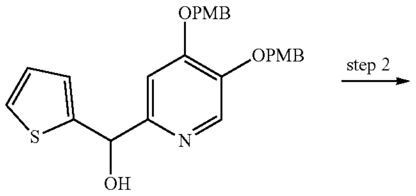

f-2-3

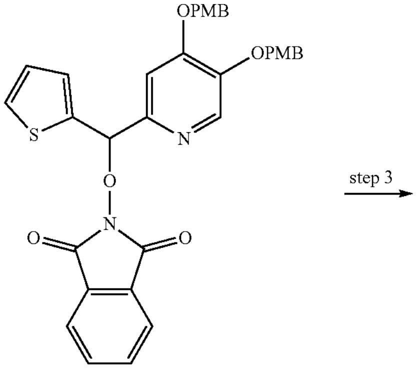

f-3-3

-continued

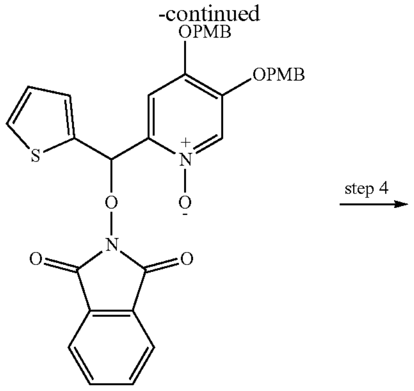

f-4-3

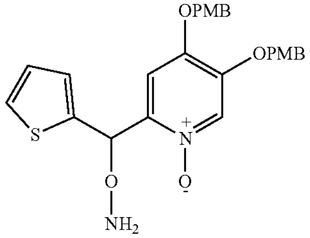

f-5-3

Step 1: Preparation of f-2-3

The thiophene (2.1 mL, 26.3 mmol) was dissolved in 10 mL of dry tetrahydrofuran, cooled to −78° C. A solution of 2.4 M n-butyllithium in n-hexane (3.3 mL, 7.92 mmol) was slowly added dropwise at low temperature, and the mixture was reacted at low temperature for 30 min. Then, 10 mL of a solution of j-1 (1.0 g, 2.63 mmol) in tetrahydrofuran was slowly added dropwise. Thereafter, the mixture was reacted for 3 hours, then the starting material disappeared as monitored by TLC. Under ice bath, 5 mL of a saturated aqueous solution of ammonium chloride was added dropwise, and the resultant was extracted with ethyl acetate (30 mL×2), and washed with saturated brine, dried over anhydrous sodium sulfate, filtered and concentrated under reduced pressure. The residue was purified by using column chromatography (petroleum ether:ethyl acetate=2:1 to 1:1) to give a pale yellow oily compound f-2-3 (0.99 g, yield 81.2%).

$^1$H NMR (400 MHz, chloroform-d) δ 8.08 (s, 1H), 7.32 (d, J=8.8 Hz, 1H), 7.28 (d, J=8.8 Hz, 2H), 7.24 (dd, J=4.5, 1.8 Hz, 1H), 6.95-6.92 (m, 2H), 6.91-6.85 (m, 4H), 6.81 (s, 1H), 5.88 (s, 1H), 5.08 (s, 2H), 5.05 (s, 2H), 3.81 (s, 3H), 3.80 (s, 3H).

MS (ESI): m/z 464.1, $[M+H]^+$.

Step 2: Preparation of f-3-3

According to the preparation method in step 3 of Preparation 1, a yellow compound f-3-3 (2.0 g, 47.6%) was prepared from compound f-2-3 (3.2 g, 6.9 mmol), N-hydroxyphthalimide (3.3 g, 20.7 mmol), triphenylphosphine (5.34 g, 20.7 mmol) and diethyl azodicarboxylate (4.1 mL, 20.7 mmol).

$^1$H NMR (400 MHz, chloroform-d) δ 8.07 (s, 1H), 7.78-7.75 (m, 2H), 7.72 (s, 1H), 7.72-7.69 (m, 2H), 7.44 (d, J=8.7 Hz, 2H), 7.35 (dd, J=5.1, 1.2 Hz, 1H), 7.30 (d, J=8.8 Hz, 2H), 6.99 (ddd, J=3.6, 1.3, 0.7 Hz, 1H), 6.93 (d, J=8.8 Hz, 2H), 6.93-6.90 (m, 1H), 6.85 (d, J=8.8 Hz, 2H), 6.63 (d, J=0.7 Hz, 1H), 5.33 (d, J=11.7 Hz, 1H), 5.26 (d, J=11.7 Hz, 1H), 5.07 (s, 2H), 3.83 (s, 3H), 3.79 (s, 3H).

MS (ESI): m/z 609.1, $[M+H]^+$.

Step 3: Preparation of f-4-3

According to the preparation method in step 4 of Preparation 11, a white solid compound f-4-3 (1.38 g, 67.4%) was prepared from compound f-3-3 (2.0 g, 3.28 mmol) and m-chloroperoxybenzoic acid (2.3 g, 9.8 mmol).

$^1$H NMR (400 MHz, chloroform-d) δ 7.86-7.85 (m, 2H), 7.81-7.78 (m, 2H), 7.76-7.71 (m, 2H), 7.46 (d, J=8.6 Hz, 2H), 7.35 (dd, J=5.1, 1.2 Hz, 1H), 7.31-7.27 (m, 3H), 7.08-7.05 (m, 1H), 6.96-6.92 (m, 3H), 6.87 (d, J=8.6 Hz, 2H), 5.39 (d, J=11.6 Hz, 1H), 5.30 (d, J=11.6 Hz, 1H), 5.00 (s, 2H), 3.83 (s, 3H), 3.79 (s, 3H).

MS (ESI): m/z 625.1, $[M+H]^+$.

Step 4: Preparation of f-5-3

According to a method similar to that in step 4 of Preparation 1, a white solid compound f-5-3 (0.98 g, 82.5%) was prepared from compound f-4-3 (1.5 g, 2.45 mmol) and 85% hydrazine hydrate (0.18 mL, 2.57 mmol).

$^1$H NMR (400 MHz, chloroform-d) δ 7.93 (s, 1H), 7.35-7.31 (m, 4H), 7.29 (dd, J=5.1, 0.9 Hz, 1H), 7.05 (dt, J=3.6, 0.9 Hz, 1H), 7.02 (s, 1H), 6.96 (dd, J=5.1, 3.5 Hz, 1H), 6.93-6.89 (m, 4H), 6.52 (s, 1H), 5.52 (s, 2H), 5.16 (s, 2H), 5.03 (s, 2H), 3.83 (s, 6H).

MS (ESI): m/z 495.1, $[M+H]^+$.

Preparation 19

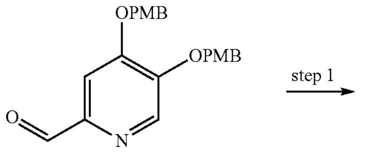

f-1

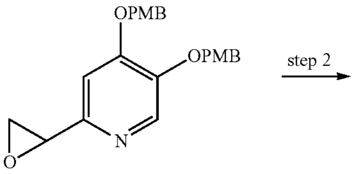

f-6

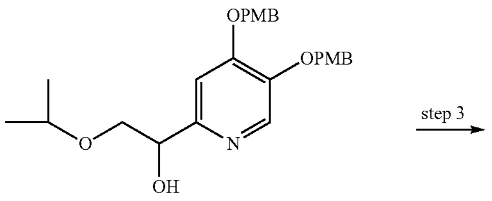

f-7-1

-continued

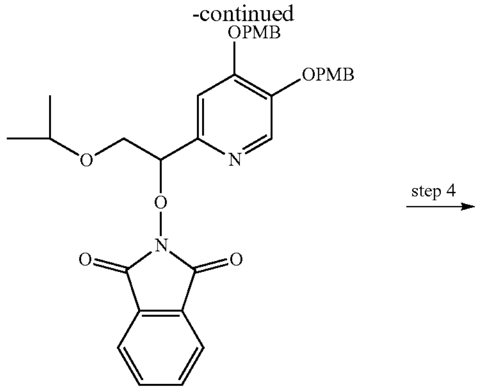

f-8-1

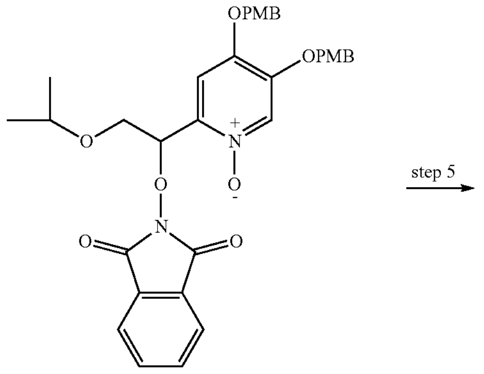

f-9-1

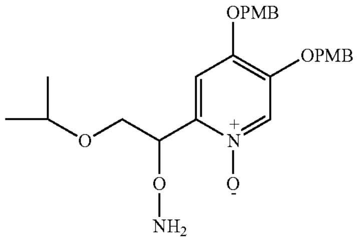

f-10-1

Step 1: Preparation of f-6

According to a method similar to that in step 1 of Preparation 11, a white solid compound f-6 (4.7 g, 45.3%) was prepared from compound f-1 (10 g, 26.4 mmol) and trimethylsulfoxonium iodide (6.4 g, 29.0 mmol), 60% sodium hydride (1.16 g, 29.0 mmol).

$^1$H NMR (400 MHz, chloroform-d) δ 8.09 (s, 1H), 7.34 (d, J=8.6 Hz, 2H), 7.30 (d, J=8.5 Hz, 2H), 6.91 (d, J=8.7 Hz, 2H), 6.86 (d, J=8.7 Hz, 2H), 5.10 (s, 2H), 5.07 (s, 2H), 3.91 (dd, J=4.1, 2.5 Hz, 1H), 3.81 (s, 3H), 3.79 (s, 3H), 3.11 (dd, J=5.6, 4.1 Hz, 1H), 2.79 (dd, J=5.7, 2.5 Hz, 1H).

MS (ESI): m/z 394.1, $[M+H]^+$.

Step 2: Preparation of f-7-1

Isopropanol (2.9 mL, 38 mmol) was dissolved in dry tetrahydrofuran (30 mL), cooled to 0° C., and then 60% sodium hydride (1.5 g, 38 mmol) was added thereto and reacted for 30 min. Compound f-6 (1.5 g, 3.8 mmol) was dissolved in 10 mL of dry tetrahydrofuran, and the solution was slowly added dropwise to the above reaction solution.

The reaction solution was raised to 50° C. and reacted for 8 h, then the starting material disappeared as monitored by TLC. 30 mL of water was added under ice bath to quench the reaction, and the resultant was extracted with ethyl acetate (50 mL×2), and washed with saturated brine, dried over anhydrous sodium sulfate, filtered and concentrated. The residue was purified by using column chromatography (petroleum ether:ethyl acetate=2:1 to 1:1) to give a pale yellow oil f-7-1 (880 mg, 51.1%).

$^{1}$H NMR (400 MHz, chloroform-d) δ 8.07 (s, 1H), 7.35 (d, J=8.6 Hz, 2H), 7.31 (d, J=8.6 Hz, 2H), 7.08 (s, 1H), 6.91 (d, J=8.6 Hz, 2H), 6.86 (d, J=8.6 Hz, 2H), 5.12 (s, 2H), 5.07 (s, 2H), 4.75 (dd, J=7.2, 4.7 Hz, 1H), 3.89 (s, 1H), 3.81 (s, 3H), 3.79 (s, 3H), 3.66-3.57 (m, 2H), 3.51 (dd, J=9.5, 7.3 Hz, 1H), 1.15 (d, J=2.1 Hz, 3H), 1.14 (d, J=2.1 Hz, 3H).

MS (ESI): m/z 454.1, [M+H]$^+$.

Step 3: Preparation of f-8-1

According to the preparation method in step 3 of Preparation 1, a yellow compound f-8-1 (1.0 g, 86.1%) was prepared from compound f-7-1 (880 mg, 1.94 mmol), N-hydroxyphthalimide (475 mg, 2.91 mmol), triphenylphosphine (756 mg, 2.91 mmol) and diisopropyl azodicarboxylate (0.36 mL, 2.91 mmol).

$^{1}$H NMR (400 MHz, chloroform-d) δ 8.06 (s, 1H), 7.80-7.77 (m, 2H), 7.72-7.69 (m, 2H), 7.53 (s, 1H), 7.43 (d, J=8.7 Hz, 2H), 7.29 (d, J=8.7 Hz, 2H), 6.92 (d, J=8.6 Hz, 2H), 6.84 (d, J=8.6 Hz, 2H), 5.54 (dd, J=6.6, 3.4 Hz, 1H), 5.31-5.17 (m, 2H), 5.06 (s, 2H), 3.99-3.89 (m, 2H), 3.82 (s, 3H), 3.78 (s, 3H), 3.60 (p, J=6.1 Hz, 1H), 1.06 (d, J=6.1 Hz, 3H), 1.00 (d, J=6.1 Hz, 3H).

MS (ESI): m/z 599.1, [M+H]$^+$.

Step 4: Preparation of f-9-1

According to the preparation method in step 4 of Preparation 11, a white solid compound f-9-1 (900 mg, 87.6%) was prepared from compound f-8-1 (1.0 g, 1.67 mmol) and m-chloroperoxybenzoic acid (1.03 g, 5.01 mmol).

$^{1}$H NMR (400 MHz, chloroform-d) δ 7.84 (s, 1H), 7.81-7.77 (m, 2H), 7.75 (s, 1H), 7.74-7.71 (m, 2H), 7.46 (d, J=8.6 Hz, 2H), 7.28 (d, J=8.6 Hz, 1H), 6.93 (d, J=8.6 Hz, 2H), 6.86 (d, J=8.6 Hz, 2H), 6.16 (dd, J=5.2, 2.3 Hz, 1H), 5.40-5.24 (m, 2H), 5.07-4.95 (m, 2H), 4.12-4.06 (m, 1H), 3.88 (dd, J=12.0, 5.3 Hz, 1H), 3.82 (s, 3H), 3.79 (s, 3H), 3.73-3.62 (m, 1H), 1.15 (d, J=6.1 Hz, 3H), 1.01 (d, J=6.1 Hz, 3H).

MS (ESI): m/z 615.1, [M+H]$^+$.

Step 5: Preparation of f-10-1

According to a method similar to that in step 4 of Preparation 1, a white solid compound f-10-1 (590 mg, 83.4%) was prepared from compound f-9-1 (900 mg, 1.46 mmol) and 85% hydrazine hydrate (0.10 mL, 1.61 mmol).

$^{1}$H NMR (400 MHz, chloroform-d) δ 7.90 (s, 1H), 7.35-7.29 (m, 4H), 6.92 (s, 1H), 6.91-6.87 (m, 4H), 5.41 (s, 2H), 5.34 (dd, J=5.8, 2.4 Hz, 1H), 5.19-5.07 (m, 2H), 5.02 (s, 2H), 3.84 (dd, J=11.1, 2.4 Hz, 1H), 3.80 (s, 3H), 3.79 (s, 3H), 3.61-3.53 (m, 2H), 1.15 (d, J=6.1 Hz, 3H), 1.04 (d, J=6.1 Hz, 3H).

MS (ESI): m/z 485.0, [M+H]$^+$.

Preparation 20

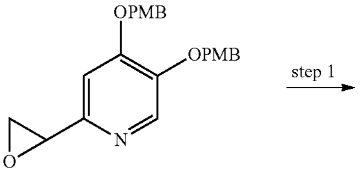

f-6

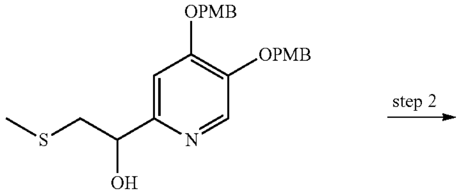

f-7-2

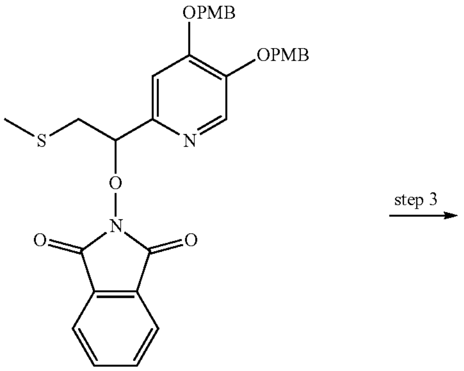

f-8-2

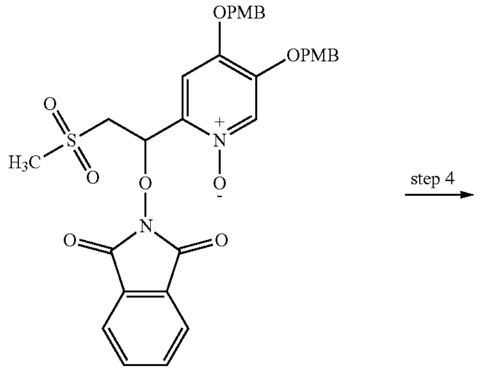

f-9-2

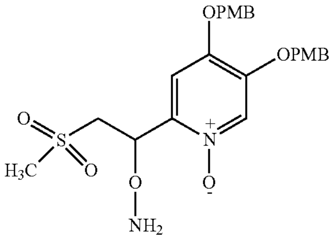

f-10-2

Step 1: Preparation of f-7-2

The compound f-6 (1.64 g, 4.17 mmol) was dissolved in methanol (30 mL), and a 20% aqueous sodium thiomethoxide solution (14 mL, 41.7 mmol) was added thereto, and the mixture was reacted at room temperature for 1 h, then the starting material disappeared as monitored by TLC. The reaction solution was extracted with ethyl acetate (100 mL) and water (20 mL) and the aqueous layer was further extracted with 50 mL of ethyl acetate. The organic phase was combined, washed 5 times with water (20 mL) and saturated brine (20 mL), dried over anhydrous sodium sulfate, filtered and concentrated. The residue was purified by using column chromatography (petroleum ether:ethyl acetate=2:1 to 1:1) to give an anhydrous oil (1.15 g, 62.5).

$^1$H NMR (400 MHz, chloroform-d) δ 8.07 (s, 1H), 7.35 (d, J=8.6 Hz, 2H), 7.30 (d, J=8.6 Hz, 2H), 7.04 (s, 1H), 6.91 (d, J=8.6 Hz, 2H), 6.86 (d, J=8.6 Hz, 2H), 5.13 (s, 2H), 5.07 (s, 2H), 4.74 (dd, J=7.7, 4.5 Hz, 1H), 3.81 (s, 3H), 3.79 (s, 3H), 2.92 (dd, J=13.8, 4.5 Hz, 1H), 2.73 (dd, J=13.8, 7.7 Hz, 1H), 2.04 (s, 3H).

MS (ESI): m/z 442.1, $[M+H]^+$.

Step 2: Preparation of f-8-2

According to the preparation method in step 3 of Preparation 1, a yellow oil f-8-2 (1.2 g, 83.8%) was prepared from compound f-7-2 (1.08 g, 2.44 mmol), N-hydroxyphthalimide (517 mg, 3.17 mmol), triphenylphosphine (1.28 g, 4.88 mmol) and diisopropyl azodicarboxylate (0.75 mL, 4.88 mmol).

$^1$H NMR (400 MHz, chloroform-d) δ 8.06 (s, 1H), 7.76 (dd, J=5.7, 3.0 Hz, 3H), 7.70 (dd, J=5.7, 3.0 Hz, 2H), 7.51 (s, 1H), 7.42 (d, J=8.7 Hz, 2H), 7.29 (d, J=8.7 Hz, 2H), 6.91 (d, J=8.7 Hz, 2H), 6.84 (d, J=8.7 Hz, 2H), 5.50 (s, 1H), 5.22 (s, 2H), 5.05 (s, 2H), 3.82 (s, 3H), 3.78 (s, 3H), 3.19-3.07 (m, 2H), 2.06 (s, 3H).

MS (ESI): m/z 587.0, $[M+H]^+$.

Step 3: Preparation of f-9-2

According to the preparation method in step 4 of Preparation 11, a white solid compound f-9-2 (810 mg, 62.5%) was prepared from compound f-8-2 (1.2 g, 2.04 mmol) and m-chloroperoxybenzoic acid (2.6 g, 12.3 mmol).

$^1$H NMR (400 MHz, chloroform-d) δ 7.88 (s, 1H), 7.83-7.80 (m, 2H), 7.78-7.75 (m, 2H), 7.69 (s, 1H), 7.42 (d, J=8.6 Hz, 2H), 7.28 (d, J=8.6 Hz, 2H), 6.92 (d, J=8.6 Hz, 2H), 6.87 (d, J=8.6 Hz, 2H), 6.29 (dd, J=5.9, 4.4 Hz, 1H), 5.34-5.20 (m, 2H), 5.07-4.97 (m, 2H), 3.82 (s, 3H), 3.79 (s, 3H), 3.79-3.75 (m, 2H), 3.22 (s, 3H).

MS (ESI): m/z 635.0, $[M+H]^+$.

Step 3: Preparation of f-10-2

According to a method similar to that in step 4 of Preparation 1, a white solid compound f-10-2 (636 mg, 82.5%) was prepared from compound f-9-2 (970 mg, 1.53 mmol) and 85% hydrazine hydrate (0.11 mL, 1.68 mmol).

$^1$H NMR (400 MHz, chloroform-d) δ 7.88 (s, 1H), 7.34 (d, J=8.6 Hz, 2H), 7.30 (d, J=8.6 Hz, 2H), 6.94 (s, 1H), 6.92-6.88 (m, 4H), 5.67 (s, 2H), 5.45 (dd, J=8.6, 2.4 Hz, 1H), 5.20 (d, J=11.8 Hz, 1H), 5.11 (d, J=11.8 Hz, 1H), 5.03 (s, 2H), 3.80 (s, 6H), 3.73 (dd, J=14.9, 2.4 Hz, 1H), 3.26 (dd, J=14.8, 8.6 Hz, 1H), 3.05 (s, 3H).

MS (ESI): m/z 505.1, $[M+H]^+$.

Preparation 21

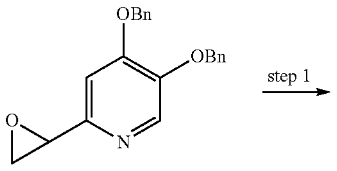

d-1

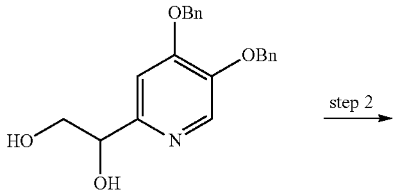

k-1

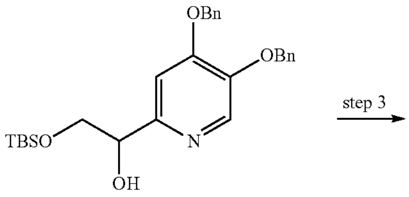

k-2

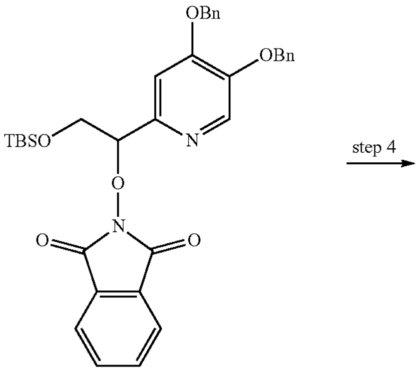

k-3

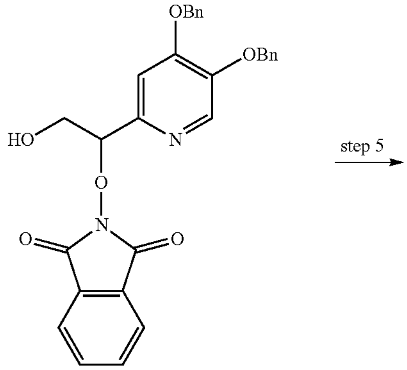

k-4

-continued

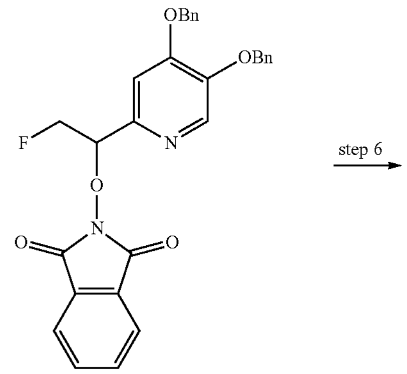

k-5

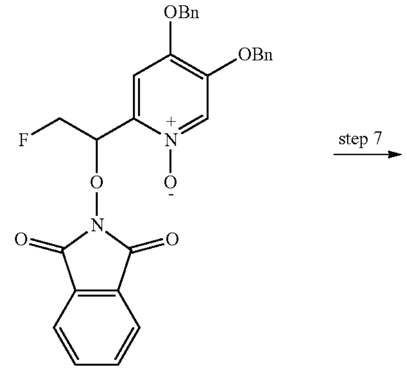

k-6

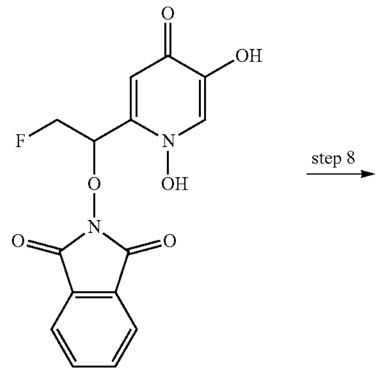

k-7

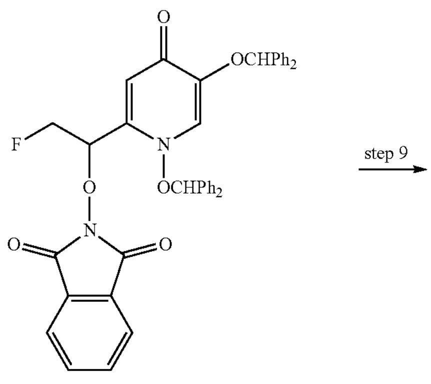

k-8

-continued

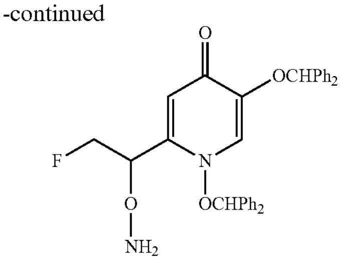

k-9

Step 1: Preparation of k-1

The compound d-1 (6.6 g, 19.8 mmol) was dissolved in 100 mL of dioxane, and 50 mL of a 2 M aqueous sulfuric acid solution was added dropwise at room temperature. Thereafter, the mixture was reacted at 45° C. for 8 hours, then the starting material disappeared as monitored by TLC. The reaction solution was neutralized with 1M sodium hydroxide solution, and the resultant was extracted with ethyl acetate (100 mL×2), washed with saturated brine, dried over anhydrous sodium sulfate, filtered and concentrated under reduced pressure. The residue was purified by using column chromatography (dichloromethane:methanol=50:1 to 20:1) to give an oil k-1 (4.3 g, yield 61.8%).

$^1$H NMR (400 MHz, chloroform-d) δ 8.08 (s, 1H), 7.49-7.32 (m, 10H), 6.95 (s, 1H), 5.23 (s, 2H), 5.18 (s, 2H), 4.71 (dd, J=5.8, 3.9 Hz, 1H), 3.86 (dd, J=11.4, 3.9 Hz, 1H), 3.72 (dd, J=11.4, 5.8 Hz, 1H).

MS (ESI): m/z 352.1, $[M+H]^+$.

Step 2: Preparation of k-2

Compound k-1 (5.0 g, 14.2 mmol) was dissolved in dichloromethane (80 mL), and added with imidazole (1.45 g, 21.3 mmol). Then tert-butyldimethylsilyl chloride (2.27 g, 14.9 mmoL) was added in an ice bath. After reacting for 15 min in the ice bath, the ice bath was removed. The resultant was warmed to room temperature and reacted for 1 hour to precipitate a solid, then the starting material disappeared as monitored by TLC. 50 mL of water was added, and the aqueous layer was separated, which was extracted with dichloromethane (40 mL×2). The methylene chloride phase was combined, washed with saturated brine, dried over anhydrous sodium sulfate, filtered and concentrated under reduced pressure. The residue was purified by using column chromatography (petroleum ether:ethyl acetate=10:1 to 5:1) to give a gel compound k-2 (5.9 g, yield: 89.2%).

$^1$H NMR (400 MHz, chloroform-d) δ 8.10 (s, 1H), 7.47-7.29 (m, 10H), 7.08 (s, 1H), 5.21 (s, 2H), 5.17 (s, 2H), 4.66 (t, J=5.8 Hz, 1H), 3.79 (dd, J=10.0, 5.2 Hz, 1H), 3.72 (dd, J=10.0, 6.4 Hz, 1H), 0.87 (s, 9H), 0.01 (s, 3H), −0.01 (s, 3H).

MS (ESI): m/z 466.1, $[M+H]^+$.

Step 3: Preparation of k-3

According to the preparation method in step 3 of Preparation 1, a pale yellow solid compound k-3 (6.4 g, 82.7%) was prepared from compound k-2 (5.9 g, 12.67 mmol), N-hydroxyphthalimide (2.48 g, 15.2 mmol), triphenylphosphine (4.98 g, 19.0 mmol) and diethyl azodicarboxylate (2.99 mL, 19.0 mmol).

$^1$H NMR (400 MHz, chloroform-d) δ 8.09 (s, 1H), 7.77 (dd, J=5.5, 3.1 Hz, 2H), 7.70 (dd, J=5.5, 3.1 Hz, 2H), 7.57

(s, 1H), 7.54-7.28 (m, 10H), 5.44 (dd, J=5.9, 3.3 Hz, 1H), 5.38-5.26 (m, 2H), 5.16 (s, 2H), 4.17 (dd, J=11.8, 3.3 Hz, 1H), 4.10 (dd, J=11.8, 5.9 Hz, 1H), 0.79 (s, 9H), −0.05 (s, 3H), −0.06 (s, 3H).

MS (ESI): m/z 611.2, $[M+H]^+$.

Step 4: Preparation of k-4

Compound k-3 (7.7 g, 12.6 mmol) was dissolved in acetone 60 mL, and added with 30 mL of water. 16 mL of 2M aqueous hydrochloric acid solution was added dropwise at room temperature, and reacted for 1.5 h to precipitate a white solid, then the starting material disappeared as monitored by TLC. The resultant was filtered and the filter cake was sequentially rinsed with 20 mL of water and 10 mL of acetone, and dried at 40° C. in vacuo to give a white solid compound k-4 (5.1 g, 81.5%).

$^1H$ NMR (400 MHz, chloroform-d) δ 8.09 (s, 1H), 7.84 (dd, J=5.5, 3.1 Hz, 2H), 7.77 (dd, J=5.5, 3.1 Hz, 2H), 7.54 (s, 1H), 7.52-7.29 (m, 10H), 5.30 (s, 2H), 5.20 (d, J=4.4 Hz, 1H), 5.18 (s, 2H), 4.16-4.05 (m, 2H), 3.83 (s, 1H).

MS (ESI): m/z 497.0, $[M+H]^+$.

Step 5: Preparation of k-5

The compound k-4 (3.0 g, 6.04 mmol) was dissolved in dichloromethane (40 mL), cooled to 0° C. in an ice bath, and then diethylamine trifluorosulfide (1.7 mL, 12.08 mmol) was added dropwise. Thereafter, the ice bath was removed and the reaction system returned to room temperature. The reaction was carried out for 18 hours, then the starting material disappeared as monitored by TLC. 10 mL of saturated aqueous sodium bicarbonate solution was slowly added dropwise in an ice bath, and then 20 mL of water was added to separate layers. The aqueous phase was extracted with dichloromethane (30 mL), and then the dichloromethane phase was combined, washed with saturated brine, dried over anhydrous sodium sulfate, filtered and concentrated under reduced pressure. The residue was purified by using column chromatography (petroleum ether:ethyl acetate=4:1 to 2:1) to give compound k-5 (1.54 g, 51.1%).

$^1H$ NMR (400 MHz, chloroform-d) δ 8.12 (s, 1H), 7.84 (dd, J=5.6, 3.0 Hz, 2H), 7.76 (dd, J=5.6, 3.0 Hz, 2H), 7.63 (s, 1H), 7.57-7.31 (m, 10H), 5.62 (ddd, J=19.8, 6.0, 2.7 Hz, 1H), 5.40-5.30 (m, 2H), 5.20 (s, 2H), 5.05-4.95 (m, 1H), 4.93-4.83 (m, 1H).

MS (ESI): m/z 499.0, $[M+H]^+$.

Step 6: Preparation of k-6

According to the preparation method in step 4 of Preparation 11, a white solid compound k-6 (1.36 g, 85.6%) was prepared from compound k-5 (1.54 g, 3.09 mmol) and m-chloroperoxybenzoic acid (1.92 g, 9.26 mmol).

$^1H$ NMR (400 MHz, chloroform-d) δ 7.89 (s, 1H), 7.81 (dd, J=5.7, 3.0 Hz, 2H), 7.79 (s, 1H), 7.75 (dd, J=5.6, 3.0 Hz, 2H), 7.55-7.31 (m, 10H), 6.17 (ddd, J=25.4, 3.7, 1.8 Hz, 1H), 5.46-5.30 (m, 2H), 5.10 (d, J=3.3 Hz, 2H), 5.04-4.81 (m, 2H).

MS (ESI): m/z 515.1, $[M+H]^+$.

Step 7: Preparation of k-7

According to the method in step 5 of Preparation 6, compound k-6 (1.36 g, 2.65 mmol) was removed of its protection group by reacting with boron trichloride (7.8 mL, 7.8 mmol) to give the title compound k-7 (1.4 g, crude, directly used for the next reaction).

Step 8: Preparation of k-8

According to the method in step 6 of Preparation 6, a white solid compound k-8 (720 mg, yield in two steps: 40.7%) was prepared from the above crude k-7 (1.4 g) and diphenyldiazomethane (2.56 g, 13.25 mmol).

$^1H$ NMR (400 MHz, chloroform-d) δ 7.83-7.79 (m, 2H), 7.78 (s, 1H), 7.75 (s, 1H), 7.75-7.72 (m, 2H), 7.60-7.28 (m, 20H), 6.69 (s, 1H), 6.16 (s, 1H), 6.10 (ddd, J=24.1, 4.2, 1.9 Hz, 1H), 4.91 (ddd, J=47.6, 10.7, 2.0 Hz, 1H), 4.67 (ddd, J=47.7, 10.7, 4.2 Hz, 1H).

MS (ESI): m/z 667.1, $[M+H]^+$.

Step 9: Preparation of k-9

According to a method similar to that in step 4 of Preparation 1, a white solid compound k-9 (260 mg, 77.6%) was prepared from compound k-8 (416 mg, 0.62 mmol) and 85% hydrazine hydrate (0.04 mL, 0.68 mmol).

$^1H$ NMR (400 MHz, chloroform-d) δ 7.88 (s, 1H), 7.52-7.29 (m, 20H), 6.82 (s, 1H), 6.34 (s, 1H), 6.21 (s, 1H), 5.27 (ddd, J=24.9, 4.6, 2.1 Hz, 1H), 4.72 (ddd, J=47.8, 10.2, 2.1 Hz, 1H), 4.55 (ddd, J=47.8, 10.2, 4.6 Hz, 1H), 1.77 (s, 2H).

MS (ESI): m/z 537.2, $[M+H]^+$.

Preparation 22

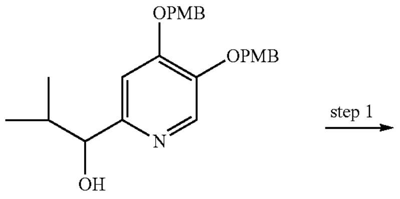

f-2

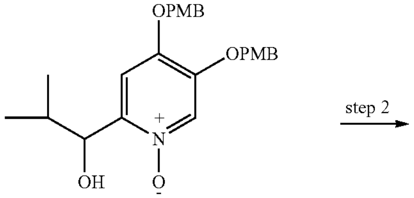

g-1-1

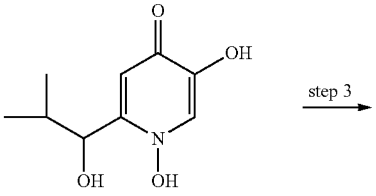

g-2-1

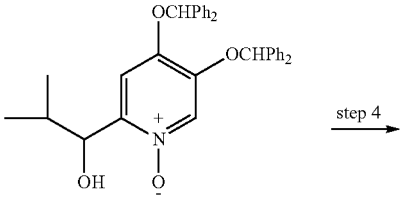

g-3-1

-continued

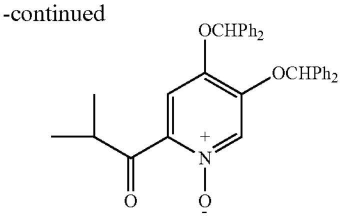

g-4-1

Step 1: Preparation of g-1-1

According to the preparation method in step 4 of Preparation 11, a white solid compound g-1-1 (1.29 g, 82.9%) was prepared from compound f-2 (1.5 g, 3.54 mmol) and m-chloroperoxybenzoic acid (2.4 g, 10.62 mmol).

$^1$H NMR (400 MHz, chloroform-d) δ 7.85 (s, 1H), 7.30 (d, J=8.6 Hz, 4H), 6.90 (dd, J=8.7, 2.2 Hz, 4H), 6.62 (s, 1H), 5.11 (s, 2H), 5.02 (s, 2H), 4.18 (d, J=8.2 Hz, 1H), 3.81 (d, J=0.9 Hz, 6H), 2.41-2.29 (m, 1H), 1.04 (d, J=6.6 Hz, 3H), 0.74 (d, J=6.7 Hz, 3H).

MS (ESI): m/z 440.1, $[M+H]^+$.

Step 2: Preparation of g-2-1

According to the method in step 5 of Preparation 6, compound g-1-1 (6.9 g, 15.7 mmol) was removed of its protection group by reacting with boron trichloride (39 mL, 39.2 mmol) to give the title compound g-2-1 (7.5 g, crude, directly used for the next reaction).

Step 3: Preparation of g-3-1

According to the method in step 6 of Preparation 6, a white solid compound g-3-1 (4.26 g, yield in two steps: 51.0%) was prepared from the above crude g-2-1 (7.5 g) and diphenyldiazomethane (15.2 g, 78.5 mmol).

$^1$H NMR (400 MHz, chloroform-d) δ 7.96 (s, 1H), 7.49-7.24 (m, 20H), 6.63 (s, 1H), 6.33 (s, 1H), 6.24 (s, 1H), 4.23 (t, J=4.5 Hz, 1H), 3.87 (d, J=5.7 Hz, 1H), 1.76-1.65 (m, 1H), 0.76 (d, J=6.8 Hz, 3H), 0.57 (d, J=6.7 Hz, 3H).

MS (ESI): m/z 532.1, $[M+H]^+$.

Step 4: Preparation of g-4-1

The compound g-3-1 (5.5 g, 10.3 mmol) was dissolved in a mixed solvent of dichloromethane 60 mL and dimethyl sulfoxide 60 mL. 11.1 mL of triethylamine was added thereto, and the mixture was cooled to 0° C. in an ice water bath. Sulfur trioxide pyridine (8.3 g, 51.7 mmol) was added in three batches and the mixture was reacted at low temperature for 2 hours. After the reaction was completed as monitored by TLC, dichloromethane was evaporated under reduced pressure, the residue was added with 40 ml of water, extracted with ethyl acetate (50 mL×2), washed with saturated brine, dried over anhydrous sodium sulfate, filtered and concentrated. The residue was purified by using column chromatography (dichloromethane:methanol=50:1 to 20:1) to give a white solid compound g-4-1 (3.58 g, yield 65.3%).

$^1$H NMR (400 MHz, chloroform-d) δ 7.77 (s, 1H), 7.45-7.29 (m, 20H), 7.05 (s, 1H), 6.32 (s, 1H), 6.23 (s, 1H), 3.85 (p, J=6.9 Hz, 1H), 1.06 (d, J=6.9 Hz, 6H).

MS (ESI): m/z 530.2, $[M+H]^+$.

Preparation 23

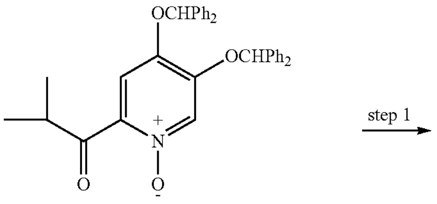

g-4-1

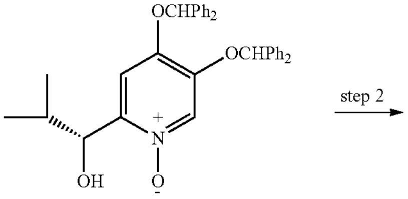

g-6-1

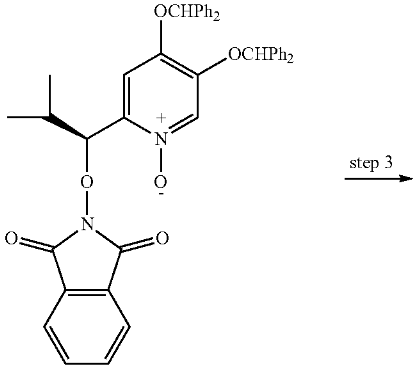

g-8-1

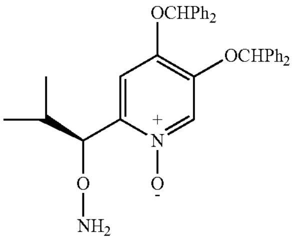

g-10-1

Step 1: Preparation of g-6-1

According to the preparation method for the above compound b-4, a white solid compound g-6-1 (600 mg, Yield 94.0%) was prepared from compound g-4-1 (640 mg, 1.2 mmol), dichlorobis(4-methylisopropylphenyl)phosphonium (II) (21.8 mg, 0.035 mmol) and (1S,2S)-(−)-N-(p-methylbenzenesulfonyl)-1,2-diphenylethylenediamine (25.8 mg, 0.069 mmol).

$^1$H NMR (400 MHz, chloroform-d) δ 7.96 (s, 1H), 7.49-7.24 (m, 20H), 6.63 (s, 1H), 6.33 (s, 1H), 6.24 (s, 1H), 4.23 (t, J=4.5 Hz, 1H), 3.87 (d, J=5.7 Hz, 1H), 1.76-1.65 (m, 1H), 0.76 (d, J=6.8 Hz, 3H), 0.57 (d, J=6.7 Hz, 3H).

MS (ESI): m/z 532.1, $[M+H]^+$.

Step 2: Preparation of g-8-1

Compound g-6-1 (2.75 g, 5.17 mmol) and N-hydroxyphthalimide (844 mg, 5.17 mmol) were dissolved in 100 mL of ultra-dry tetrahydrofuran, and tributylphosphine (1.92 mL, 7.75 mmol) was added thereto. Under argon atmosphere protection, the air inside the reactor was exchanged for three times, and the reaction system was cooled to −15 to −10° C. Then, diisopropyl azodicarboxylate (1.04 mL, 7.75 mmol) was slowly added. After reacting for 8 hours at low temperature, the temperature was returned to room temperature, then the raw materials disappeared as monitored by TLC. 30 mL of water and 20 mL of a saturated sodium bicarbonate solution were added to the reaction solution, which was further extracted with ethyl acetate (50×2), washed with saturated brine, dried over anhydrous sodium sulfate, filtered and concentrated under reduced pressure. The residue was purified by using column chromatography (petroleum ether:ethyl acetate=1:1 to 1:4) to give yellow solid compound g-8-1 (2.5 g, yield 71.4%).

$^1$H NMR (400 MHz, chloroform-d) δ 7.77-7.74 (m, 2H), 7.72 (s, 1H), 7.72-7.68 (m, 2H), 7.59 (s, 1H), 7.58-7.26 (m, 20H), 6.71 (s, 1H), 6.14 (s, 1H), 5.88 (d, J=4.3 Hz, 1H), 2.10 (pd, J=7.0, 4.3 Hz, 1H), 1.07 (d, J=6.9 Hz, 3H), 0.63 (d, J=7.0 Hz, 3H).

MS (ESI): m/z 677.3, $[M+H]^+$.

Step 3: Preparation of g-10-1

According to a method similar to that in step 4 of Preparation 1, a white solid compound g-10-1 (2.36 g, yield 82.5%) was prepared from compound g-8-1 (3.54 g, 5.23 mmol) and 85% hydrazine hydrate (0.34 mL, 5.75 mmol).

$^1$H NMR (400 MHz, chloroform-d) δ 7.84 (s, 1H), 7.48-7.27 (m, 20H), 6.69 (s, 1H), 6.32 (s, 1H), 6.19 (s, 1H), 4.93 (d, J=4.7 Hz, 1H), 1.99 (pd, J=6.9, 4.7 Hz, 1H), 0.92 (d, J=6.9 Hz, 3H), 0.66 (d, J=6.9 Hz, 3H).

MS (ESI): m/z 547.1, $[M+H]^+$.

Preparation 24

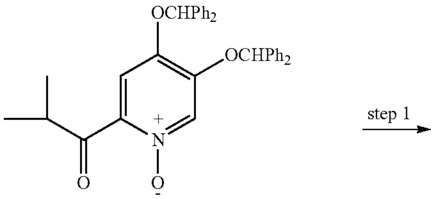

g-4-1

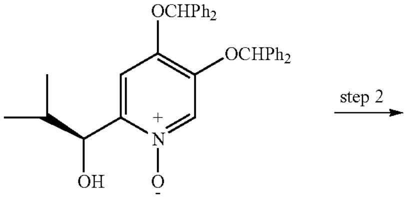

g-5-1

-continued

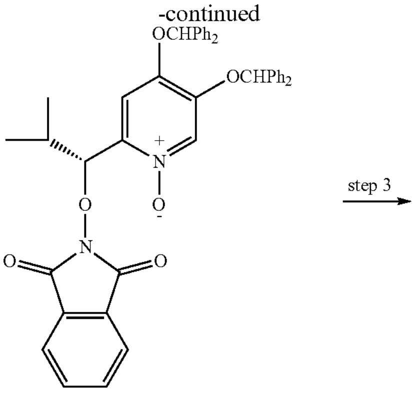

g-7-1

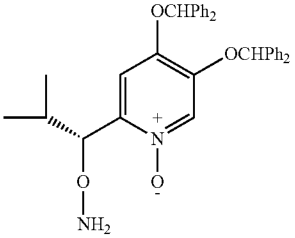

g-9-1

Step 1: Preparation of g-5-1

According to the preparation method for the above compound b-4, a white solid compound g-5-1 (520 mg, 89.8%) was prepared from compound g-4-1 (580 mg, 1.15 mmol), dichlorobis(4-methylisopropylphenyl)phosphonium (II) (21.8 mg, 0.035 mmol) and (1R,2R)-(−)—N-(p-methylbenzenesulfonyl)-1,2-diphenylethylenediamine (25.8 mg, 0.069 mmol).

$^1$H NMR (400 MHz, chloroform-d) δ 7.96 (s, 1H), 7.49-7.24 (m, 20H), 6.63 (s, 1H), 6.33 (s, 1H), 6.24 (s, 1H), 4.23 (t, J=4.5 Hz, 1H), 3.87 (d, J=5.7 Hz, 1H), 1.76-1.65 (m, 1H), 0.76 (d, J=6.8 Hz, 3H), 0.57 (d, J=6.7 Hz, 3H).

Step 2: Preparation of g-7-1

According to a method similar to that in step 2 of Preparation 25, a yellow solid compound g-7-1 (840 mg, 78.6%) was prepared from compound g-5-1 (840 mg, 1.58 mmol), N-hydroxyphthalimide (258 mg, 1.58 mmol), tributylphosphine (0.58 mL, 2.37 mmol) and diisopropyl azodicarboxylate (0.32 mL, 2.37 mmol).

$^1$H NMR (400 MHz, chloroform-d) δ 7.77-7.74 (m, 2H), 7.73 (s, 1H), 7.72-7.69 (m, 2H), 7.59 (s, 1H), 7.58-7.25 (m, 20H), 6.72 (s, 1H), 6.15 (s, 1H), 5.88 (d, J=4.3 Hz, 1H), 2.11 (pd, J=7.0, 4.3 Hz, 1H), 1.08 (d, J=6.9 Hz, 3H), 0.63 (d, J=6.9 Hz, 3H).

MS (ESI): m/z 677.3, $[M+H]^+$.

Step 3: Preparation of g-9-1

According to a method similar to that in step 4 of Preparation 1, a white solid compound g-9-1 (600 mg, yield 88.5%) was prepared from compound g-7-1 (840 mg, 1.24 mmol) and 85% hydrazine hydrate (0.08 mL, 1.36 mmol).

$^1$H NMR (400 MHz, chloroform-d) δ 7.84 (s, 1H), 7.48-7.27 (m, 21H), 6.69 (s, 1H), 6.31 (s, 1H), 6.19 (s, 1H), 4.93

(d, J=4.7 Hz, 1H), 1.99 (pd, J=6.9, 4.7 Hz, 1H), 0.91 (d, J=6.9 Hz, 3H), 0.66 (d, J=6.9 Hz, 3H).

MS (ESI): m/z 547.1, $[M+H]^+$.

Preparation 25

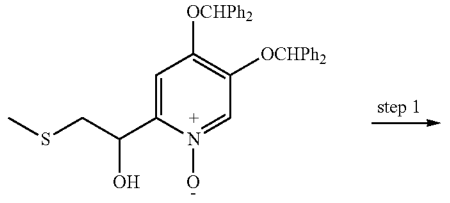

d-11-1

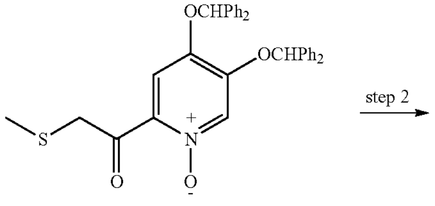

g-11-1

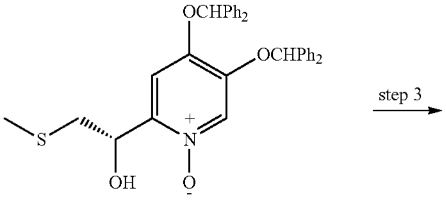

g-13-1

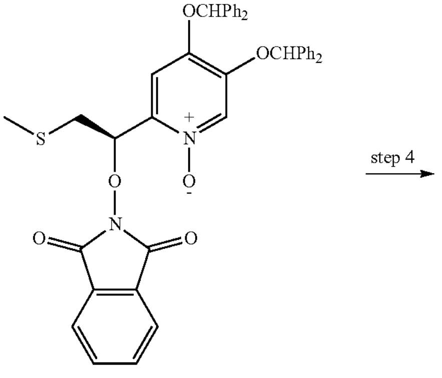

g-15-1

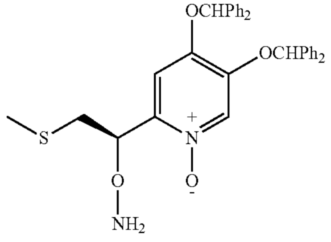

g-17-1

Step 1: Preparation of g-11-1

According to a method similar to that in step 4 of Preparation 22, a yellow solid compound g-11-1 (2.57 g, yield 47.8%) was prepared from compound d-11-1 (5.4 g, 9.8 mmol) and sulphur trioxide pyridine (4.7 g, 29.4 mmol).

$^1$H NMR (400 MHz, chloroform-d) δ 7.77 (s, 1H), 7.48-7.27 (m, 21H), 6.35 (s, 1H), 6.23 (s, 1H), 4.01 (s, 2H), 1.91 (s, 3H).

MS (ESI): m/z 548.1, $[M+H]^+$.

Step 2: Preparation of g-13-1

Under argon atmosphere protection, compound g-11-1 (1.8 g, 3.29 mmol) was dissolved in dry N,N-dimethylformamide (15 mL), then methyl t-butyl ether (10 mL) and (S,S)—N-(p-toluenesulfonyl)-1,2-diphenylmethanediamine (p-isopropylbenzene) ruthenium chloride (II) (62 mg, 0.1 mmol) were sequentially added, during which, the air was exchanged for three times. 1.48 mL of triethylamine and 1.09 mL of formic acid were mixed, and added to the above reaction solution once. After three times of air exchange, the reaction was carried out for 10 hours at room temperature, then the raw materials disappeared as monitored by TLC. The reaction solution was extracted with ethyl acetate (100 mL), washed with saturated brine, dried over anhydrous sodium sulfate, filtered and concentrated. The residue was purified by using column chromatography (petroleum ether: ethyl acetate=1:1 to 1:4) to give a yellow solid compound 1.56 g, which was recrystallized twice with ethyl acetate to give white solid g-13-1 (500 mg, yield 27.7%).

$^1$H NMR (400 MHz, chloroform-d) δ 7.76 (s, 1H), 7.45-7.28 (m, 20H), 6.80 (s, 1H), 6.30 (s, 1H), 6.19 (s, 1H), 5.98 (d, J=7.6 Hz, 1H), 4.73-4.63 (m, 1H), 3.04 (dd, J=13.8, 7.4 Hz, 1H), 2.77 (dd, J=13.8, 6.3 Hz, 1H), 1.82 (s, 3H).

MS (ESI): m/z 550.0, $[M+H]^+$.

Step 3: Preparation of g-15-1

According to a method similar to that in step 2 of Preparation 23, a colorless oil g-15-1 (341 mg, 42.3%) was prepared from compound g-13-1 (640 mg, 1.16 mmol), N-hydroxyphthalimide (1.9 g, 11.6 mmol), tributylphosphine (1.6 mL, 6.96 mmol) and diisopropyl azodicarboxylate (0.86 mL, 6.96 mmol).

$^1$H NMR (400 MHz, chloroform-d) δ 7.81 (s, 1H), 7.81-7.78 (m, 2H), 7.74 (s, 2H), 7.74-7.72 (m, 2H), 7.63-7.27 (m, 20H), 6.73 (s, 1H), 6.17 (s, 1H), 6.13 (dd, J=5.8, 3.5 Hz, 1H), 3.15 (dd, J=14.9, 3.5 Hz, 1H), 2.90 (dd, J=14.9, 5.8 Hz, 1H), 1.88 (s, 3H).

MS (ESI): m/z 695.1, $[M+H]^+$.

Step 4: Preparation of g-17-1

According to a method similar to that in step 4 of Preparation 1, a white solid compound g-17-1 (287 mg, 80.7%) was prepared from compound g-15-1 (439 mg, 0.63 mmol) and 85% hydrazine hydrate (0.05 mL, 0.65 mmol).

$^1$H NMR (400 MHz, chloroform-d) δ 7.81 (s, 1H), 7.49-7.27 (m, 21H), 6.80 (s, 1H), 6.32 (s, 1H), 6.18 (s, 1H), 5.19 (dd, J=7.3, 3.1 Hz, 1H), 5.05 (s, 2H), 2.95 (dd, J=14.2, 3.1 Hz, 1H), 2.62 (dd, J=14.2, 7.3 Hz, 1H), 2.01 (s, 3H).

MS (ESI): m/z 565.1, $[M+H]^+$.

Preparation 26

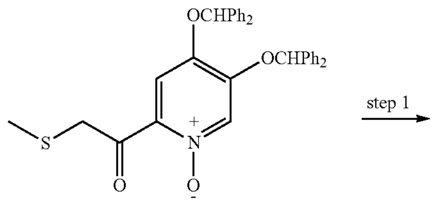

g-11-1

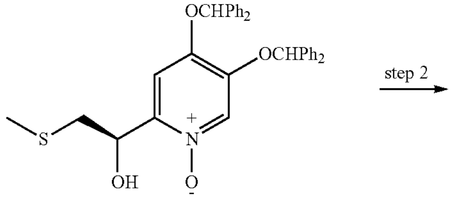

g-12-1

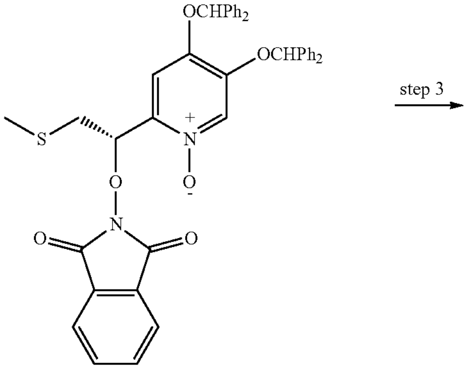

g-14-1

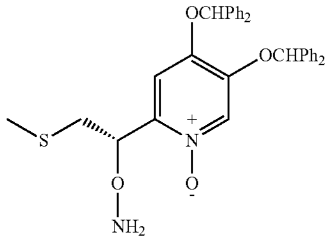

g-16-1

Step 1: Preparation of g-12-1

According to a method similar to that in step 2 of Preparation 25, a white solid g-12-1 (300 mg, yield 23.9%) was prepared from compound g-11-1 (1.25 g, 2.28 mmol) and (R,R)—N-(p-toluenesulfonyl)-1,2-diphenylethanediamine (p-isopropylbenzene) ruthenium chloride (II) (44 mg, 0.07 mmol).

$^1$H NMR (400 MHz, chloroform-d) δ 7.76 (s, 1H), 7.45-7.29 (m, 20H), 6.80 (s, 1H), 6.30 (s, 1H), 6.19 (s, 1H), 5.97 (d, J=7.8 Hz, 1H), 4.72-4.61 (m, 1H), 3.04 (dd, J=13.8, 7.4 Hz, 1H), 2.77 (dd, J=13.8, 6.2 Hz, 1H), 1.83 (s, 3H).

MS (ESI): m/z 550.0, $[M+H]^+$.

Step 2: Preparation of g-14-1

According to a method similar to that in step 2 of Preparation 25, a colorless oil g-14-1 (648 mg, 60.6%) was prepared from compound g-12-1 (848 mg, 1.54 mmol), N-hydroxyphthalimide (2.5 g, 15.4 mmol), tributylphosphine (2.1 mL, 9.24 mmol) and diisopropyl azodicarboxylate (1.1 mL, 9.24 mmol).

$^1$H NMR (400 MHz, chloroform-d) δ 7.82-7.77 (m, 3H), 7.76-7.71 (m, 3H), 7.62-7.27 (m, 20H), 6.73 (s, 1H), 6.16 (s, 1H), 6.13 (dd, J=5.7, 3.5 Hz, 1H), 3.16 (dd, J=14.9, 3.5 Hz, 1H), 2.90 (dd, J=14.9, 5.8 Hz, 1H), 1.88 (s, 3H).

MS (ESI): m/z 695.1, $[M+H]^+$.

Step 3: Preparation of g-16-1

According to a method similar to that in step 4 of Preparation 1, a white solid compound g-16-1 (390 mg, 82.2%) was prepared from compound g-14-1 (583 mg, 0.84 mmol) and 85% hydrazine hydrate (0.06 mL, 0.84 mmol).

$^1$H NMR (400 MHz, chloroform-d) δ 7.81 (s, 1H), 7.47-7.28 (m, 20H), 6.80 (s, 1H), 6.32 (s, 1H), 6.18 (s, 1H), 5.19 (dd, J=7.3, 3.1 Hz, 1H), 5.05 (s, 2H), 2.96 (dd, J=14.2, 3.1 Hz, 1H), 2.62 (dd, J=14.2, 7.3 Hz, 1H), 2.01 (s, 3H).

MS (ESI): m/z 565.1, $[M+H]^+$.

Synthesis of Target Compounds

Example 1: Preparation of (3S)-3-((Z)-2-(2-aminothiazol-4-yl)-2-((1-(1,5-dihydroxy-4-oxo-1,4-dihydropyridin-2-yl)ethoxy)imine)acetamido)-2,2-dimethyl-4-oxoazetidine-1-hydrogen sulfate (Compound 1)

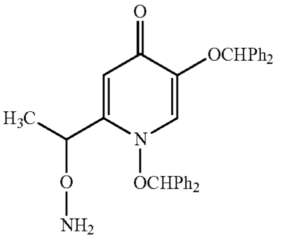

+ a-5-1

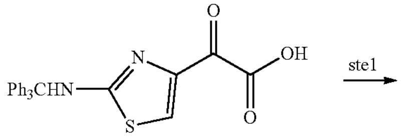

I-1

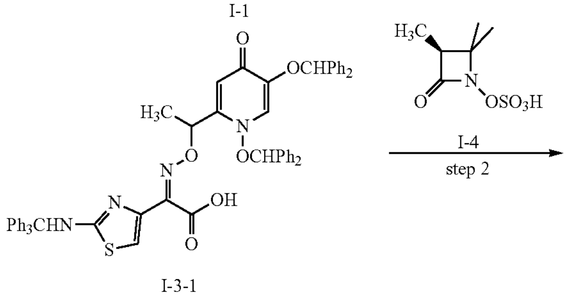

I-3-1

-continued

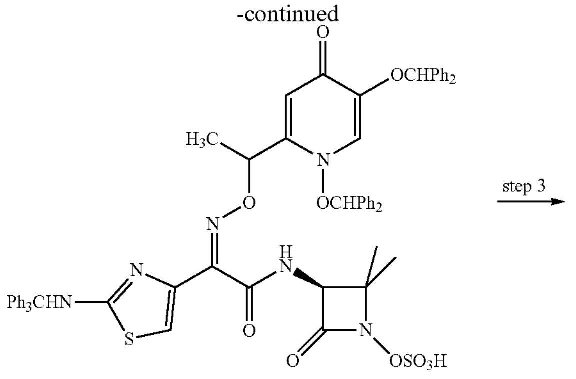

I-5-1

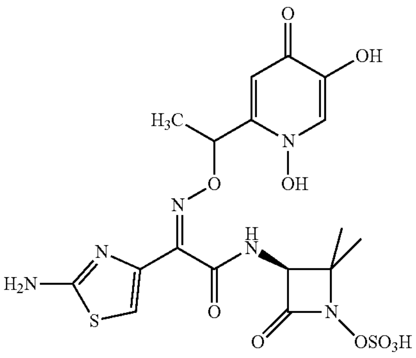

Compound 1

Step 1: Preparation of I-3-1

Compound a-5-1 (800 mg, 1.54 mmol) was dissolved in 30 mL of a mixed solvent of methanol and dichloromethane (volume ratio 1:1), and I-1 (620 mg, 1.46 mmol) was added, and the reaction was carried out at room temperature for 4 hours. After the material a-5-1 disappeared as monitored by TLC, the reaction solution was concentrated. The residue was purified by using column chromatography (dichloromethane:methanol=50:1 to 20:1) to give a pale yellow solid compound I-3-1 (1.12 g, yield 79.3%).

$^1$H NMR (400 MHz, DMSO-d6) δ 8.48 (s, 1H), 7.47-7.17 (m, 35H), 6.68 (s, 1H), 6.49 (s, 1H), 6.13 (s, 1H), 6.11 (s, 1H), 5.04 (q, J=6.6 Hz, 1H), 1.21 (d, J=6.6 Hz, 3H).

MS (ESI): m/z 913.2, [M−H]$^-$.

Step 2: Preparation of I-5-1

Compound I-3-1 (600 mg, 0.66 mmol) and I-4 (207 mg, 0.98 mmol) were dissolved in dimethyl sulfoxide (15 mL) with stirring and 2-(7-azobenzotriazole)-N,N,N',N'-tetramethyluronium hexafluorophosphate (302 mg, 0.79 mmol) and sodium bicarbonate solution (165 mg, 1.97 mmol) were added. The reaction was carried out with stirring at room temperature for 4 hours, then the material I-3-1 disappeared as monitored by TLC. The resultant was added with 30 mL of water, extracted with ethyl acetate (60 mL×2), washed with saturated brine for 5 times, dried over anhydrous sodium sulfate, filtered, concentrated. The residue was purified by using column chromatography (dichloromethane: methanol=50:1 to 20:1) to give a white solid compound I-5-1 (670 mg, yield 92.3%).

$^1$H NMR (400 MHz, DMSO-d6) δ 9.46 (d, J=7.7 Hz, 1H), 8.72 (s, 1/2H), 8.69 (s, 1/2H), 7.72 (s, 1/2H), 7.69 (s, 1/2H), 7.46-7.18 (m, 35H), 6.70 (s, 1/2H), 6.68 (s, 1/2H), 6.39 (s, 1/2H), 6.38 (s, 1/2H), 6.29 (s, 1/2H), 6.16 (s, 1/2H), 5.15-5.01 (m, 1H), 4.50 (d, J=7.8 Hz, 1/2H), 4.46 (d, J=7.5 Hz, 1/2H), 1.40 (s, 3/2H), 1.38 (s, 3/2H), 1.18-1.10 (m, 6H).

MS (ESI): m/z 1105.1, [M−H]$^-$.

Step 3: Preparation of Compound 1

Compound I-5-1 (300 mg, 0.27 mmol) was suspended in 4 mL of dichloromethane, added with triethylsilane (0.14 mL, 0.81 mmol) and cooled to −15 to −20° C. 2 mL of a solution of trifluoroacetic acid (0.95 mL, 13.6 mmol) in dichloromethane was slowly added dropwise at low temperature and the reaction was carried out at low temperature for 7 hours. After the material I-5-1 disappeared as monitored by HPLC, the temperature was slowly warmed to 0° C., and 20 ml of a mixed solution of n-hexane:ethyl acetate=1:2 was added dropwise to the reaction solution to precipitate a solid. After stirring for 20 min, the resultant was filtered fastly, rinsed with ethyl acetate and dried in vacuo to give a white solid compound 1 (117 mg, yield: 81.1%).

$^1$H NMR (400 MHz, DMSO-d6) δ 9.72 (d, J=7.7 Hz, 1/2H), 9.67 (d, J=7.7 Hz, 1/2H), 8.24 (s, 1H), 7.16 (s, 1/2H), 7.01 (s, 1/2H), 6.86 (s, 1/2H), 6.84 (s, 1/2H), 5.67-5.53 (m, 1H), 4.67 (t, J=7.5 Hz, 1H), 1.53-1.43 (m, 6H), 1.32 (s, 3/2H), 1.29 (s, 3/2H).

MS (ESI): m/z 530.9, [M−H]$^-$.

Example 2: Preparation of (3S)-3-((Z)-2-(2-aminothiazol-4-yl)-2-(((S)1-(1,5-dihydroxy-4-oxo-1,4-dihydropyridin-2-yl)ethoxy)imine)acetamido)-2,2-dimethyl-4-oxoazetidine-1-hydrogen sulfate (Compound 2)

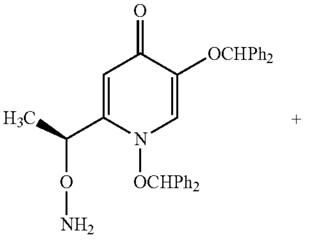

b-6

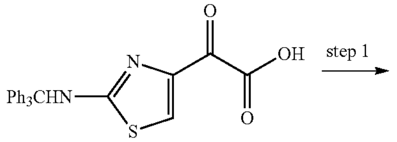

I-1

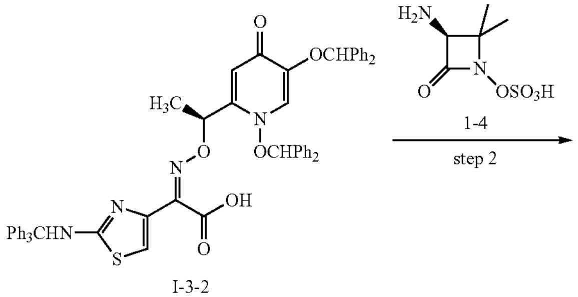

I-3-2

-continued

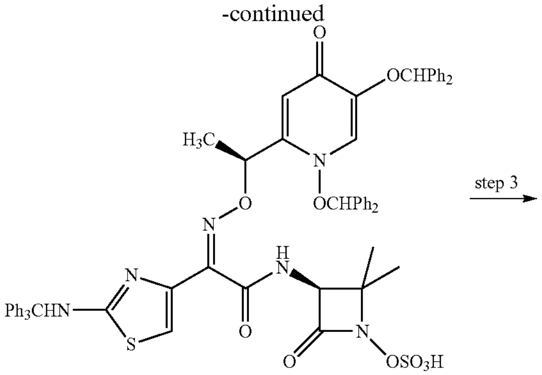

I-5-2

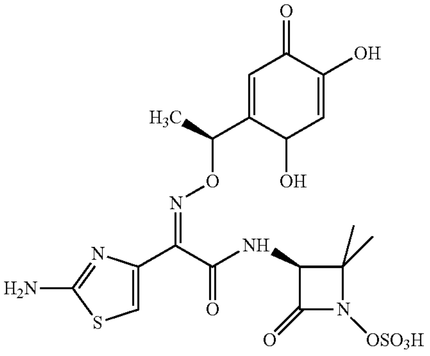

Compound 2

Step 1: Preparation of I-3-2

According to a method similar to that in step 1 of Example 1, a pale yellow solid compound I-3-2 (400 mg, yield 47%) was prepared from compound b-6 (480 mg, 0.92 mmol) and I-1 (373 mg, 0.92 mmol).

$^1$H NMR (400 MHz, DMSO-d6) δ 8.39 (s, 1H), 7.45-7.20 (m, 35H), 6.63 (s, 1H), 6.55 (s, 1H), 6.14 (s, 1H), 6.05 (s, 1H), 5.04 (q, J=6.4 Hz, 1H), 1.21 (d, J=6.4 Hz, 3H).

MS (ESI): m/z 913.2, [M−H]$^-$.

Step 2: Preparation of I-5-2

According to a method similar to that in step 2 of Example 1, a white solid compound I-5-2 (300 mg, yield 61.6%) was prepared from compound I-3-2 (400 mg, 0.44 mmol) and I-4 (126 mg, 0.60 mmol).

$^1$H NMR (400 MHz, DMSO-d6) δ 9.46 (d, J=7.5 Hz, 1H), 8.72 (s, 1H), 7.45 (s, 1H), 7.41-7.19 (m, 35H), 6.69 (s, 1H), 6.33 (s, 1H), 6.22 (s, 1H), 5.98 (s, 1H), 5.06 (q, J=6.6 Hz, 1H), 4.46 (d, J=7.5 Hz, 1H), 1.39 (s, 3H), 1.17 (d, J=6.5 Hz, 3H), 1.13 (s, 3H).

MS (ESI): m/z 1105.1, [M−H]$^-$.

Step 3: Preparation of Compound 2

According to a method similar to that in step 3 of Example 1, a white solid compound 2 (136 mg, yield: 94.6%) was prepared from compound I-5-2 (296 mg, 0.27 mmol) and trifluoroacetic acid (0.95 mL, 13.6 mmol).

$^1$H NMR (400 MHz, Methanol-d4) δ 9.70 (d, J=7.6 Hz, 1H), 8.22 (s, 1H), 6.99 (s, 1H), 6.84 (s, 1H), 5.61 (q, J=6.7 Hz, 1H), 4.66 (d, J=7.5 Hz, 1H), 1.50-1.44 (m, 6H), 1.32 (s, 3H).

MS (ESI): m/z 530.9, [M−H]$^-$.

Example 3: Preparation of (3S)-3-((Z)-2-(2-aminothiazol-4-yl)-2-(((R)1-(1,5-dihydroxy-4-oxo-1,4-(4-dihydropyridin-2-yl)ethoxy)imine)acetamido)-2,2-dimethyl-4-oxoazetidine-1-hydrogen sulfate (Compound 3)

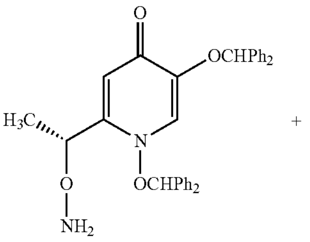

b-7

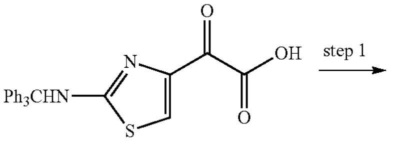

I-1

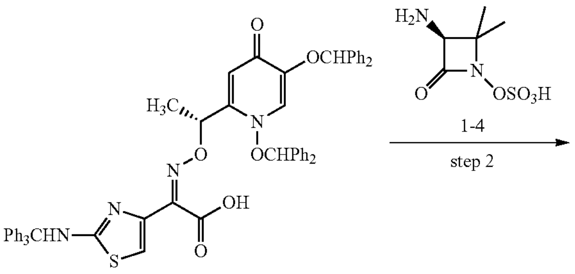

I-3-3

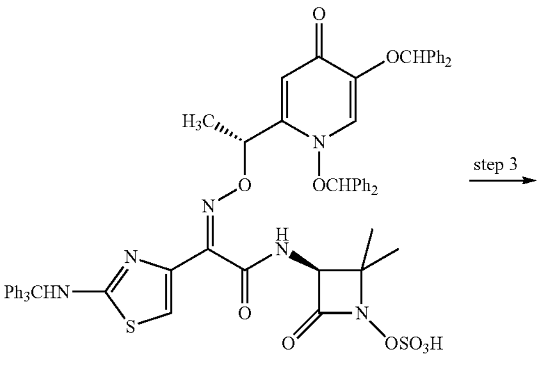

I-5-3

-continued

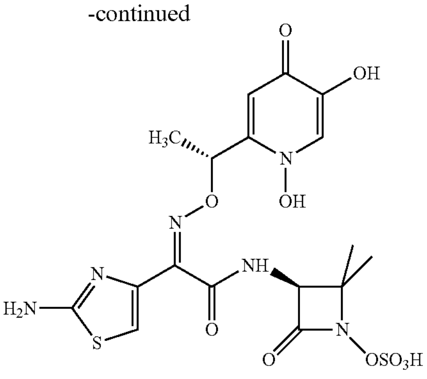

Compound 3

Step 1: Preparation of I-3-3

According to a method similar to that in step 1 of Example 1, a pale yellow solid compound I-3-3 (300 mg, yield 57%) was prepared from compound b-7 (300 mg, 0.58 mmol) and I-1 (240 mg, 0.58 mmol).

$^1$H NMR (400 MHz, DMSO-d6) δ 8.38 (s, 1H), 7.43-7.13 (m, 35H), 6.62 (s, 1H), 6.55 (s, 1H), 6.14 (s, 1H), 6.04 (s, 1H), 5.03 (q, J=6.6 Hz, 1H), 1.21 (d, J=6.6 Hz, 3H).

MS (ESI): m/z 913.2, $[M-H]^-$.

Step 2: Preparation of I-5-3

According to a method similar to that in step 2 of Example 1, a white solid compound I-5-3 (200 mg, yield 56.4%) was prepared from compound I-3-3 (290 mg, 0.32 mmol) and I-4 (100 mg, 0.48 mmol).

$^1$H NMR (400 MHz, DMSO-d6) δ 9.47 (d, J=7.8 Hz, 1H), 8.68 (s, 1H), 7.44 (s, 1H), 7.41-7.19 (m, 35H), 6.68 (s, 1H), 6.33 (s, 1H), 6.21 (s, 1H), 6.10 (s, 1H), 5.00 (q, J=6.6 Hz, 1H), 4.51 (d, J=7.8 Hz, 1H), 1.37 (s, 3H), 1.13 (d, J=6.8 Hz, 3H), 1.11 (s, 3H).

Step 3: Preparation of Compound 3

According to a method similar to that in step 3 of Example 1, a white solid compound 3 (60 mg, yield 83%) was prepared from compound I-5-3 (150 mg, 0.14 mmol) and trifluoroacetic acid (1 mL, 14 mmol).

$^1$H NMR (400 MHz, DMSO-d6) δ 9.64 (d, J=7.7 Hz, 1H), 8.20 (s, 1H), 7.13 (s, 1H), 6.82 (s, 1H), 5.57 (q, J=6.6 Hz, 1H), 4.68 (d, J=7.7 Hz, 1H), 1.51-1.44 (m, 6H), 1.29 (s, 3H).

MS (ESI): m/z 530.9, $[M-H]^-$.

Example 4: (3S)-3-((Z)-2-(2-aminothiazol-4-yl)-2-((1-(1,5-dihydroxy-4-oxo-1,4-dihydropyridin-2-yl)propoxy)imine)acetamido)-2,2-dimethyl-4-oxoazetidine-1-hydrogen sulfate (Compound 4)

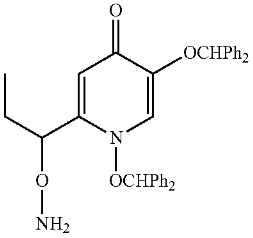

a-5-2

+

-continued

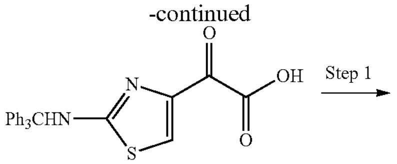

I-1

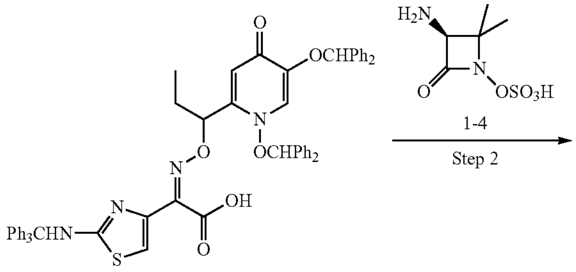

I-3-4

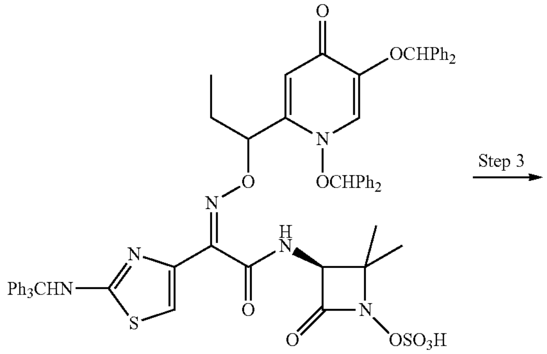

I-5-4

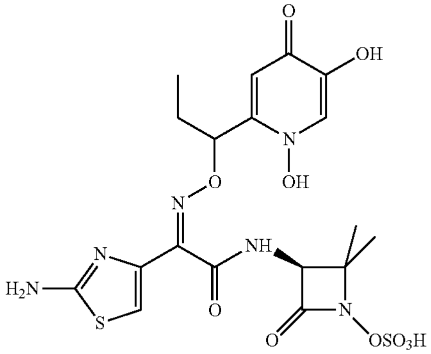

Compound 4

Step 1: Preparation of I-3-4

According to a method similar to that in step 1 of Example 1, a pale yellow solid compound I-3-4 (300 mg, yield 68.8%) was prepared from compound a-5-2 (250 mg, 0.47 mmol) and I-1 (194 mg, 0.47 mmol).

$^1$H NMR (400 MHz, DMSO-d6) δ 8.73 (s, 1H), 7.54 (s, 1H), 7.47-7.18 (m, 35H), 6.81 (s, 1H), 6.29 (s, 1H), 6.27 (s, 1H), 5.93 (s, 1H), 4.81 (m, 1H), 1.33-1.19 (m, 2H), 0.67 (t, J=7.3 Hz, 3H).

MS (ESI): m/z 927.1, $[M-H]^-$.

Step 2: Preparation of I-5-4

According to a method similar to that in step 2 of Example 1, a white solid compound I-5-4 (250 mg, yield 69.7%) was prepared from compound I-3-4 (300 mg, 0.32 mmol) and I-4 (95 mg, 0.45 mmol).

$^1$H NMR (400 MHz, DMSO-d6) δ 9.50 (d, J=7.9 Hz, 1/2H), 9.46 (d, J=7.5 Hz, 1/2H), 8.65 (s, 1/2H), 8.62 (s, 1/2H), 7.43-7.19 (m, 35H), 6.71 (s, 1/2H), 6.69 (s, 1/2H), 6.33 (s, 1H), 6.18 (s, 1/2H), 6.17 (s, 1/2H), 6.07 (s, 1/2H), 5.95 (s, 1/2H), 4.85 (dd, J=8.1, 4.7 Hz, 1/2H), 4.77 (dd, J=8.6, 4.4 Hz, 1/2H), 4.52 (d, J=7.8 Hz, 1/2H), 4.48 (d, J=7.5 Hz, 1/2H), 1.99 (dt, J=13.2, 7.0 Hz, 2H), 1.40 (s, 3/2H), 1.38 (s, 3/2H), 1.17 (s, 3H), 0.67 (t, J=7.3 Hz, 3H).

MS (ESI): m/z 1119.1, [M−H]$^-$.

Step 3: Preparation of Compound 4

According to a method similar to that in step 3 of Example 1, a white solid compound 4 (75 mg, yield 61%) was prepared from compound I-5-4 (250 mg, 0.22 mmol) and trifluoroacetic acid (0.8 mL, 11 mmol).

$^1$H NMR (400 MHz, DMSO-d6) δ 9.70 (d, J=7.7 Hz, 1/2H), 9.65 (d, J=7.7 Hz, 1/2H), 8.21 (d, J=1.8 Hz, 1H), 7.35-7.19 (m, 2H), 7.07 (s, 1/2H), 6.99 (s, 1/2H), 6.83 (s, 1/2H), 6.81 (s, 1/2H), 5.49 (dd, J=7.8, 4.0 Hz, 1/2H), 5.43 (dd, J=8.3, 4.0 Hz, 1/2H), 4.68 (d, J=7.6 Hz, 1H), 1.98-1.85 (m, 1H), 1.80-1.66 (m, 1H), 1.49 (s, 3/2H), 1.47 (s, 3/2H), 1.33 (s, 3/2H), 1.31 (s, 3/2H), 1.01-0.90 (m, 3H).

MS (ESI): m/z 545.0, [M−H]$^-$.

Example 5: Preparation of (3S)-3-((Z)-2-(2-aminothiazol-4-yl)-2-(((1-(1,5-dihydroxy-4-oxo-1,4-dihydropyridin-2-yl)allyl)oxy)imine)acetamido)-2,2-dimethyl-4-oxoazetidine-1-hydrogen sulfate (Compound 5)

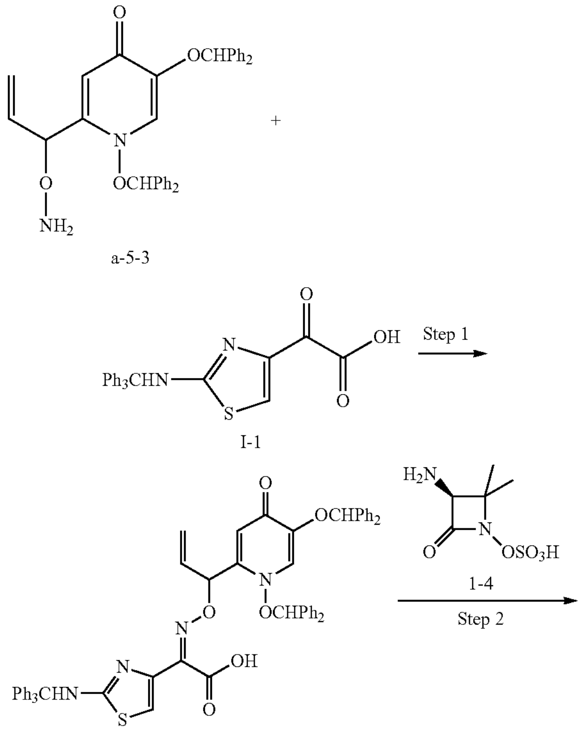

a-5-3

I-1

I-3-5

-continued

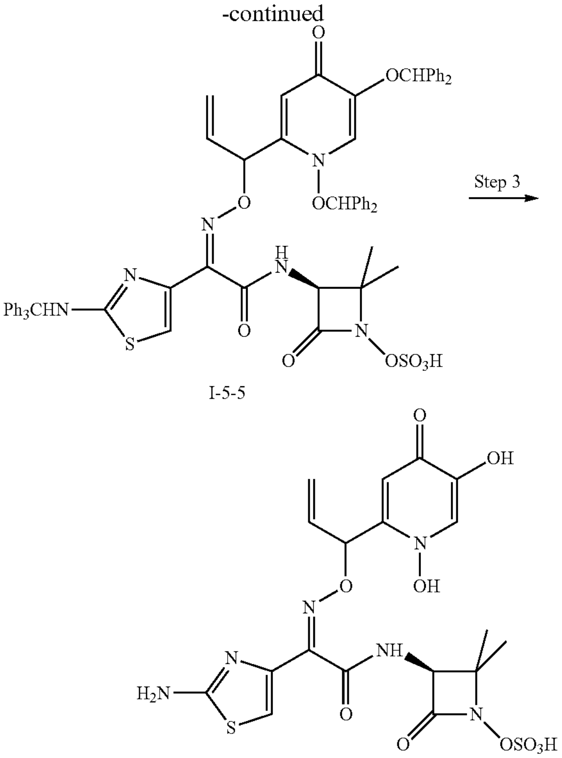

I-5-5

Compound 5

Step 1: Preparation of I-3-5

According to a method similar to that in step 1 of Example 1, a pale yellow solid compound I-3-5 (480 mg, yield 60.9%) was prepared from compound a-5-3 (450 mg, 0.85 mmol) and I-1 (350 mg, 0.85 mmol).

$^1$H NMR (400 MHz, DMSO-d6) δ 8.45 (s, 1H), 7.52-7.15 (m, 35H), 6.66 (s, 1H), 6.52 (s, 1H), 6.11 (s, 1H), 6.04 (s, 1H), 5.68 (t, J=12.6 Hz, 1H), 5.45 (d, J=5.4 Hz, 1H), 5.26-5.14 (m, 2H).

MS (ESI): m/z 925.1, [M−H]$^-$.

Step 2: Preparation of I-5-5

According to a method similar to that in step 2 of Example 1, a white solid compound I-5-5 (300 mg, yield 51.5%) was prepared from compound I-3-5 (480 mg, 0.52 mmol) and 1-4 (163 mg, 0.78 mmol).

$^1$H NMR (400 MHz, DMSO-d6) δ 9.52 (t, J=8.3 Hz, 1H), 8.79 (s, 1/2H), 8.73 (s, 1/2H), 7.53-7.12 (m, 35H), 6.72 (s, 1/2H), 6.70 (s, 1/2H), 6.32 (s, 1/2H), 6.31 (s, 1/2H), 6.22 (s, 1/2H), 6.18 (s, 1/2H), 5.98 (s, 1/2H), 5.92 (s, 1/2H), 5.69 (ddd, J=17.2, 10.7, 5.3 Hz, 1/2H), 5.58 (ddd, J=17.5, 10.7, 5.4 Hz, 1/2H), 5.47 (dt, J=5.4, 1.4 Hz, 1/2H), 5.44-5.41 (m, 1/2H), 5.34-5.08 (m, 2H), 4.52 (d, J=7.9 Hz, 1/2H), 4.48 (d, J=7.5 Hz, 1/2H), 1.37 (s, 3/2H), 1.35 (s, 3/2H), 1.06 (s, 3/2H), 1.03 (s, 3/2H).

MS (ESI): m/z 1117.3, [M−H]$^-$.

Step 3: Preparation of Compound 5

According to a method similar to that in step 3 of Example 1, a white solid compound 5 (100 mg, yield 68%) was prepared from compound I-5-5 (300 mg, 0.27 mmol) and trifluoroacetic acid (1 mL, 13.5 mmol).

$^1H$ NMR (400 MHz, DMSO-d6) δ 9.71 (d, J=7.3 Hz, 1/2H), 9.66 (d, J=8.6 Hz, 1/2H), 8.23 (s, 1H), 7.37-7.25 (m, 1H), 7.09 (s, 1/2H), 6.85 (s, 1/2H), 6.15-5.97 (m, 2H), 5.48-5.32 (m, 2H), 4.67 (t, J=7.6 Hz, 1H), 1.45 (s, 3/2H), 1.27 (s, 3/2H), 1.23 (s, 3H).

MS (ESI): m/z 543.0, $[M-H]^-$.

Example 6: Preparation of (3S)-3-((Z)-2-(2-aminothiazol-4-yl)-2-((cyclopropyl(1,5-dihydroxy-4-oxo-1,4-dihydropyridin-2-yl)methoxy)imine)acetamido)-2,2-dimethyl-4-oxoazetidine-1-hydrogen sulfate (Compound 6)

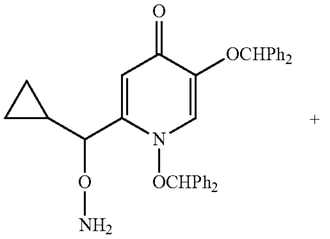

a-5-4

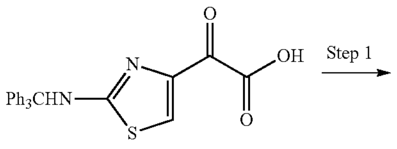

I-1

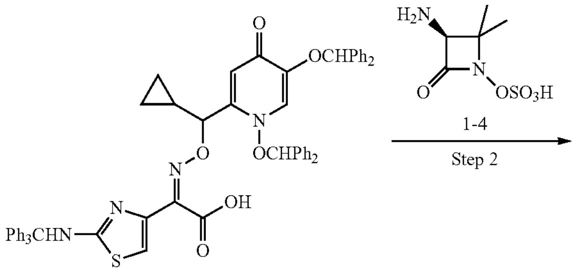

I-3-6

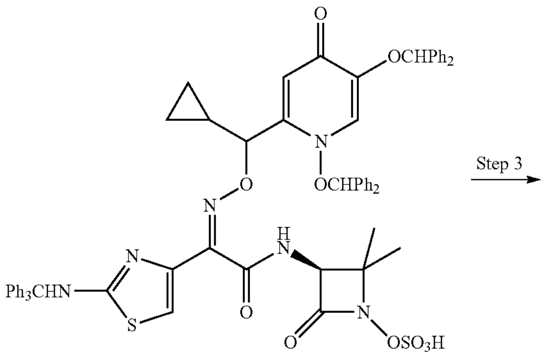

I-5-6

-continued

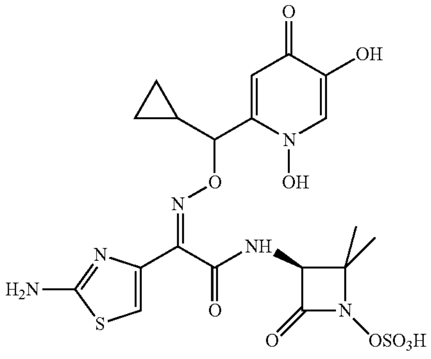

Compound 6

Step 1: Preparation of I-3-6

According to a method similar to that in step 1 of Example 1, a pale yellow solid compound I-3-6 (390 mg, yield 64.7%) was prepared from compound a-5-4 (350 mg, 0.64 mmol) and I-1 (265 mg, 0.64 mmol).

$^1H$ NMR (400 MHz, Methanol-d4) δ 8.20 (s, 1H), 6.67 (s, 1H), 6.63 (s, 1H), 6.24 (s, 1H), 5.98 (s, 1H), 4.40 (d, J=7.9 Hz, 1H), 1.07 (d, J=11.7 Hz, 1H), 0.48 (s, 1H), 0.36 (s, 1H), 0.28 (d, J=8.6 Hz, 1H), 0.03 (s, 1H).

MS (ESI): m/z 939.1, $[M-H]^-$.

Step 2: Preparation of I-5-6

According to a method similar to that in step 2 of Example 1, a white solid compound I-5-6 (340 mg, yield 73.2%) was prepared from compound I-3-6 (390 mg, 0.41 mmol) and I-4 (126 mg, 0.60 mmol).

$^1H$ NMR (400 MHz, DMSO-d6) δ 9.45 (d, J=7.7 Hz, 1H), 8.63 (d, J=3.3 Hz, 1H), 7.43-7.13 (m, 35H), 6.73 (s, 1/2H), 6.70 (s, 1/2H), 6.34 (s, 1/2H), 6.31 (s, 1/2H), 6.20 (s, 1/2H), 6.16 (s, 1/2H), 6.13 (s, 1/2H), 6.12 (s, 1/2H), 4.53 (d, J=7.8 Hz, 1/2H), 4.48 (d, J=7.6 Hz, 1/2H), 4.39 (d, J=8.1 Hz, 1/2H), 4.32 (d, J=7.9 Hz, 1/2H), 1.37 (s, 3H), 1.14 (s, 3/2H), 1.12 (s, 3/2H), 0.90-0.83 (m, 1H), 0.53-0.44 (m, 1H), 0.42-0.32 (m, 1H), 0.30-0.24 (m, 1/2H), 0.23-0.16 (m, 1/2H), −0.04-−0.17 (m, 1H).

MS (ESI): m/z 1131.2, $[M-H]^-$.

Step 3: Preparation of Compound 6

According to a method similar to that in step 3 of Example 1, a white solid compound 6 (70 mg, yield 44.7%) was prepared from compound I-5-6 (323 mg, 0.28 mmol) and trifluoroacetic acid (1.1 mL, 14 mmol).

$^1H$ NMR (400 MHz, DMSO-d6) δ 9.65 (d, J=7.7 Hz, 1H), 8.27-8.19 (m, 1H), 7.04 (d, J=18.5 Hz, 1H), 6.82-6.72 (m, 1H), 5.23-5.11 (m, 1H), 4.66 (t, J=7.0 Hz, 1H), 1.48-1.42 (m, 3H), 1.34 (d, J=19.7 Hz, 3H), 0.88-0.82 (m, 1H), 0.58-0.52 (m, 3H), 0.46 (s, 1H).

MS (ESI): m/z 557.0, $[M-H]^-$.

Example 7: Preparation of (3S)-3-((Z)-2-(2-aminothiazol-4-yl)-2-((1-(1,5-dihydroxy-4-oxo-1,4-dihydropyridin-2-yl)hydroxyethoxy)imine)acetamido)-2,2-dimethyl-4-oxoazetidine-1-hydrogen sulfate (Compound 7)

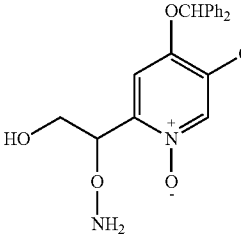

e-1

+

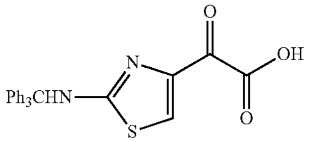

I-1

Step 1

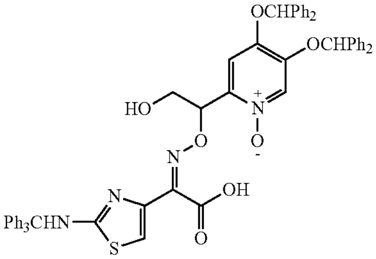

I-3-7

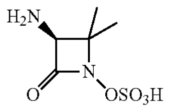

1-4

Step 2

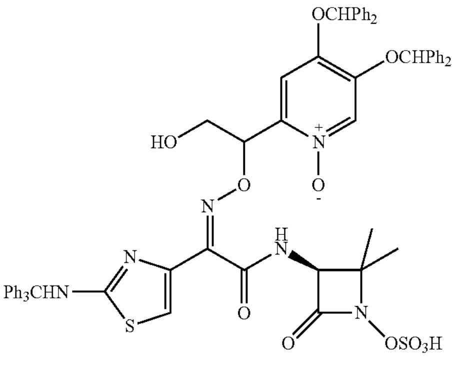

I-5-7

Step 3

-continued

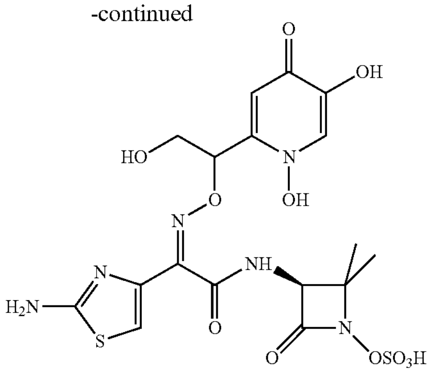

Compound 7

Step 1: Preparation of I-3-7

According to a method similar to that in step 1 of Example 1, a pale yellow solid compound I-3-7 (380 mg, yield 38.1%) was prepared from compound e-1 (570 mg, 1.07 mmol) and I-1 (258 mg, 0.62 mmol).

$^1$H NMR (400 MHz, DMSO-d6) δ 8.67 (s, 1H), 7.92 (s, 1H), 7.62-7.14 (m, 35H), 35H), 7.08-6.97 (m, 1H), 6.78 (s, 1H), 6.61 (s, 1H), 5.39 (dd, J=7.0, 2.6 Hz, 1H), 3.70-3.60 (m, 2H).

MS (ESI): m/z 929.2, $[M-H]^-$.

Step 2: Preparation of I-5-7

According to a method similar to that in step 2 of Example 1, a white solid compound I-5-7 (120 mg, yield 26.1%) was prepared from compound I-3-7 (380 mg, 0.41 mmol) and I-4 (128 mg, 0.61 mmol).

$^1$H NMR (400 MHz, DMSO-d6) δ 9.73 (d, J=7.5 Hz, 1/2H), 9.68 (d, J=7.2 Hz, 1/2H), 8.91 (s, 1/2H), 8.88 (s, 1/2H), 8.02 (s, 1/2H), 8.01 (s, 1/2H), 7.60-7.11 (m, 35H), 6.83 (s, 1/2H), 6.79 (s, 1/2H), 6.78 (s, 1/2H), 6.76 (s, 1/2H), 6.69 (s, 1/2H), 6.67 (s, 1/2H), 5.50-5.45 (m, 1H), 4.69 (t, J=7.7 Hz, 1H), 3.65-3.47 (m, 2H), 1.54 (s, 3/2H), 1.52 (s, 3/2H), 1.35 (s, 3/2H), 1.34 (s, 3/2H).

MS (ESI): m/z 1121.1, $[M-H]^-$.

Step 3: Preparation of Compound 7

According to a method similar to that in step 3 of Example 1, a white solid compound 7 (46 mg, yield 76.3%) was prepared from compound I-5-7 (120 mg, 0.11 mmol) and trifluoroacetic acid (0.4 mL, 5 mmol).

$^1$H NMR (400 MHz, DMSO-d6) δ 9.61 (t, J=7.6 Hz, 1H), 8.24 (s, 1H), 7.13 (s, 1/2H), 7.02 (s, 1/2H), 6.85 (s, 1/2H), 6.84 (s, 1/2H), 5.62-5.55 (m, 1H), 4.68 (dd, J=7.7, 3.4 Hz, 1H), 3.89-3.71 (m, 2H), 1.48 (s, 3/2H), 1.47 (s, 3/2H), 1.33 (s, 3/2H), 1.29 (s, 3/2H).

MS (ESI): m/z 547.0, [M−H]⁻.

Example 8: Preparation of (3S)-3-((Z)-2-(2-aminothiazol-4-yl)-2-((1-(1,5-dihydroxy-4-oxo-1,4-dihydropyridin-2-yl)methoxyethoxy)imine)acetamido)-2,2-dimethyl-4-oxoazetidine-1-hydrogen sulfate (Compound 8)

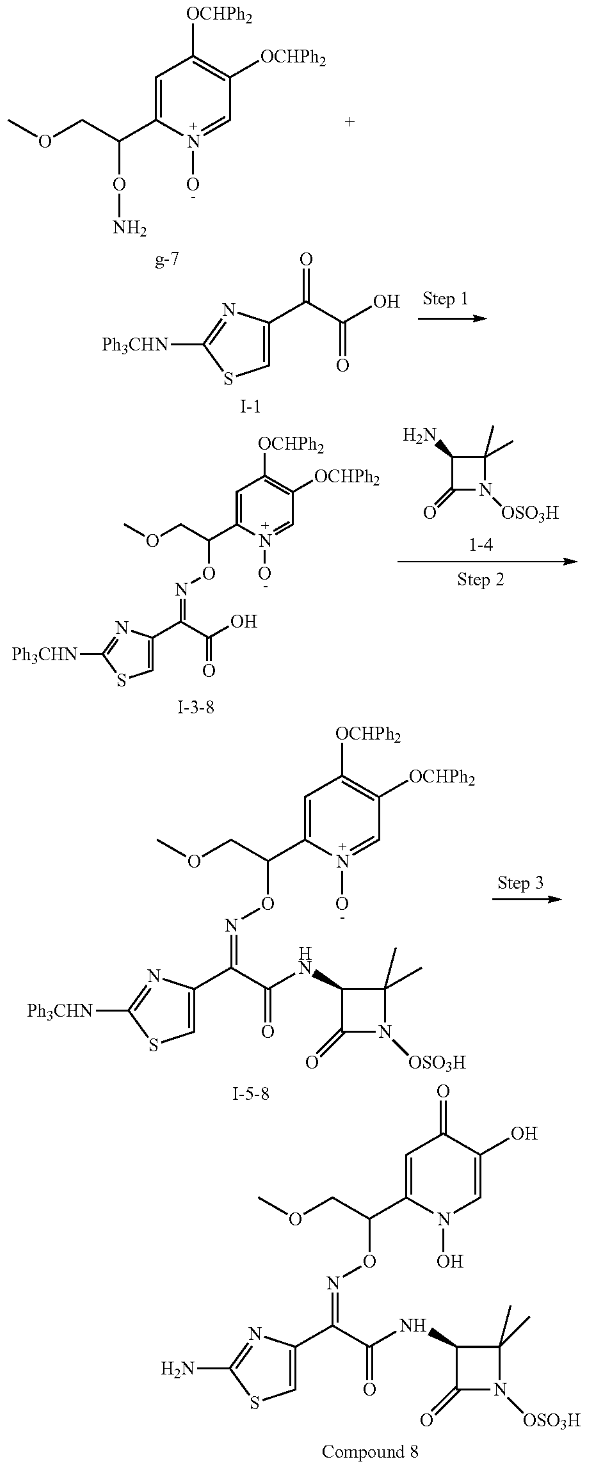

g-7, I-1, I-4, I-3-8, I-5-8, Compound 8

Step 1: Preparation of I-3-8

According to a method similar to that in step 1 of Example 1, a white solid compound I-3-8 (360 mg, yield 65.3%) was prepared from compound g-7 (320 mg, 0.58 mmol) and I-1 (230 mg, 0.55 mmol).

$^1$H NMR (400 MHz, DMSO-d6) δ 8.93 (s, 1H), 8.01 (s, 1H), 7.58-7.05 (m, 35H), 6.93 (s, 1H), 6.69 (s, 1H), 6.57 (s, 1H), 5.52 (d, J=6.3 Hz, 1H), 3.57 (d, J=11.7 Hz, 1H), 3.48 (dd, J=11.7, 6.3 Hz, 1H), 3.14 (s, 3H).

MS (ESI): m/z 943.1, [M−H]⁻.

Step 2: Preparation of I-5-8

According to a method similar to that in step 2 of Example 1, a white solid compound I-5-8 (204 mg, yield 84.6%) was prepared from compound I-3-8 (200 mg, 0.21 mmol) and I-4 (67 mg, 0.31 mmol).

$^1$H NMR (400 MHz, DMSO-d6) δ 9.83 (d, J=7.5 Hz, 1/2H), 9.75 (d, J=7.2 Hz, 1/2H), 8.93 (s, 1/2H), 8.91 (s, 1/2H), 8.03 (s, 1/2H), 8.01 (s, 1/2H), 7.62-7.16 (m, 35H), 6.85 (s, 1/2H), 6.80 (s, 1/2H), 6.79 (s, 1H), 6.71 (s, 1/2H), 6.69 (s, 1/2H), 5.55 (t, J=6.4 Hz, 1H), 5.33 (t, J=4.8 Hz, 1H), 4.73 (d, J=7.5 Hz, 1/2H), 4.66 (d, J=7.2 Hz, 1/2H), 3.08 (d, J=1.7 Hz, 3H), 1.55 (s, 3/2H), 1.52 (s, 3/2H), 1.35 (s, 3/2H), 1.34 (s, 3/2H).

MS (ESI): m/z 1135.0, [M−H]⁻.

Step 3: Preparation of Compound 8

According to a method similar to that in step 3 of Example 1, a white solid compound 8 (80 mg, yield 82.7%) was prepared from compound I-5-8 (196 mg, 0.17 mmol) and trifluoroacetic acid (0.6 mL, 8.6 mmol).

$^1$H NMR (400 MHz, DMSO-d6) δ 9.72 (d, J=7.9 Hz, 1/2H), 9.69 (d, J=8.1 Hz, 1/2H), 8.22 (s, 1H), 7.12 (s, 1/2H), 7.00 (s, 1/2H), 6.85 (s, 1/2H), 6.84 (s, 1/2H), 5.72-5.65 (m, 1H), 4.67 (dd, J=7.7, 2.8 Hz, 1H), 3.76-3.65 (m, 2H), 3.28 (s, 3/2H), 3.23 (s, 3/2H), 1.48 (s, 3/2H), 1.47 (s, 3/2H), 1.34 (s, 3/2H), 1.31 (s, 3/2H).

MS (ESI): m/z 560.9, [M−H]⁻.

Example 9: Preparation of (3S)-3-((Z)-2-(2-aminothiazol-4-yl)-2-((1-(1,5-dihydroxy-4-oxo-1,4-dihydropyridin-2-yl)-2-(methoxy)-2-oxoethoxy)imine) acetamido)-2,2-dimethyl-4-ox oxazetidine-1-hydrogen sulfate (Compound 9)

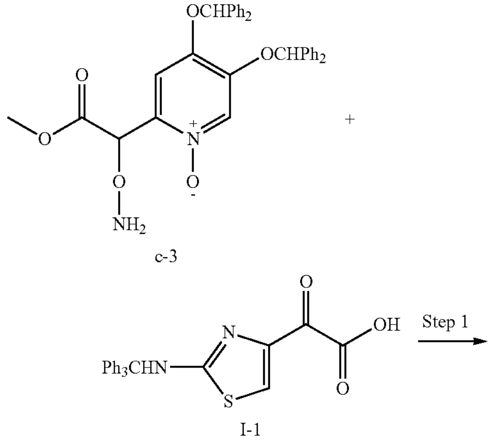

c-3, I-1

-continued

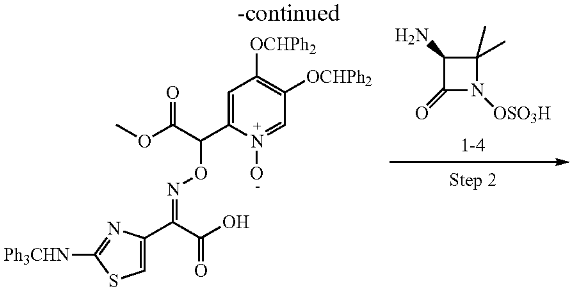

I-3-9

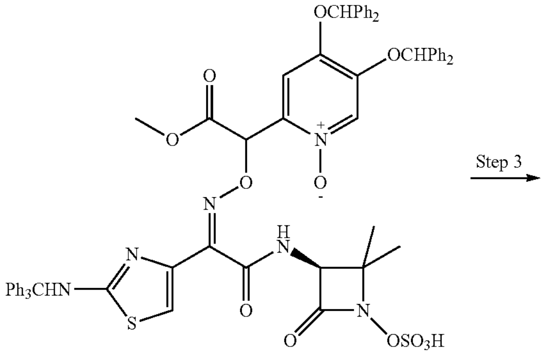

I-5-9

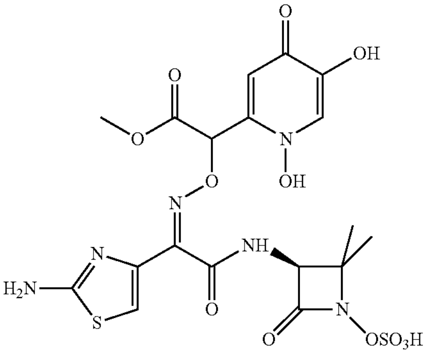

Compound 9

Step 1: Preparation of I-3-9

According to a method similar to that in step 1 of Example 1, a pale yellow solid compound I-3-9 (200 mg, yield 41.3%) was prepared from compound c-3 (286 mg, 0.51 mmol) and I-1 (210 mg, 0.51 mmol).

$^1$H NMR (400 MHz, DMSO-d6) 8.64 (s, 1H), 8.20 (s, 1H), 7.95 (s, 1H), 7.62-7.13 (m, 35H), 6.96 (s, 1H), 6.84 (s, 1H), 6.68 (s, 1H), 5.55 (s, 1H), 3.60 (s, 3H).

MS (ESI): m/z 956.8, $[M-H]^-$.

Step 2: Preparation of I-5-9

According to a method similar to that in step 2 of Example 1, a white solid compound I-5-9 (140 mg, yield 36.4%) was prepared from compound I-3-9 (320 mg, 0.33 mmol) and I-4 (105 mg, 0.50 mmol).

$^1$H NMR (400 MHz, DMSO-d6) δ 9.84 (d, J=7.4 Hz, 1/2H), 9.67 (d, J=7.3 Hz, 1/2H), 8.97 (s, 1/2H), 8.91 (s, 1/2H), 8.05 (s, 1H), 7.62-7.03 (m, 35H), 6.94 (s, 1/2H), 6.86 (s, 1/2H), 6.79-6.64 (m, 2H), 5.73 (s, 1/2H), 5.69 (s, 1/2H), 4.65 (d, J=7.4 Hz, 1/2H), 4.60 (d, J=7.4 Hz, 1/2H), 3.53 (s, 3/2H), 3.52 (s, 3/2H), 1.46 (s, 3/2H), 1.45 (s, 3/2H), 1.19-1.12 (m, 3H).

MS (ESI): m/z 1149.1, $[M-H]^-$.

Step 3: Preparation of Compound 9

According to a method similar to that in step 3 of Example 1, a white solid compound 9 (92 mg, yield 83.9%). was prepared from compound I-5-9 (220 mg, 0.19 mmol) and trifluoroacetic acid (0.67 mL, 9.5 mmol).

$^1$H NMR (500 MHz, DMSO-d6) δ 9.73 (d, J=7.8 Hz, 1/2H), 9.63 (d, J=7.8 Hz, 1/2H), 8.09 (s, 1/2H), 8.08 (s, 1/2H), 7.15 (s, 1/2H), 7.02 (s, 1/2H), 6.91 (s, 1/2H), 6.89 (s, 1/2H), 6.07 (s, 1/2H), 6.05 (s, 1/2H), 4.63 (dd, J=7.8, 4.0 Hz, 1H), 3.70 (s, 3/2H), 3.68 (s, 3/2H), 1.44 (s, 3/2H), 1.42 (s, 3/2H), 1.22 (s, 3/2H), 1.11 (s, 3/2H).

MS (ESI): m/z 574.9, $[M-H]^-$.

Example 10: Preparation of (3S)-3-((Z)-2-(2-aminothiazol-4-yl)-2-((1-(1,5-dihydroxy-4-oxo-1,4-dihydropyridin-2-yl)-2-(hydroxy)-2-oxoethoxy)imine) acetamido)-2,2-dimethyl-4-ox oxazetidine-1-hydrogen sulfate (Compound 10)

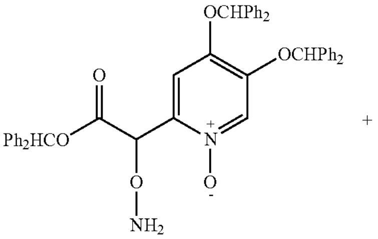

c-6

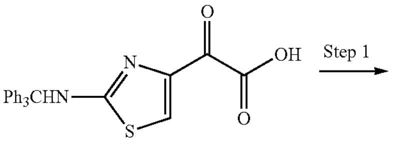

I-1

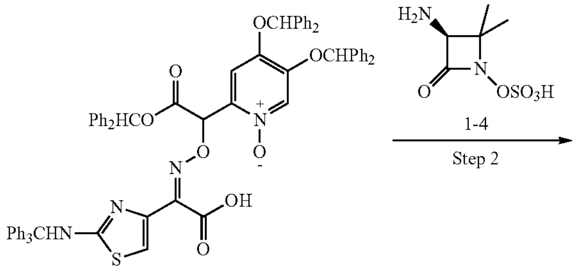

I-3-10

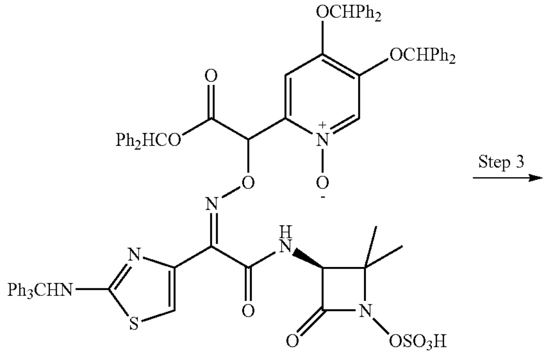

I-5-10

-continued

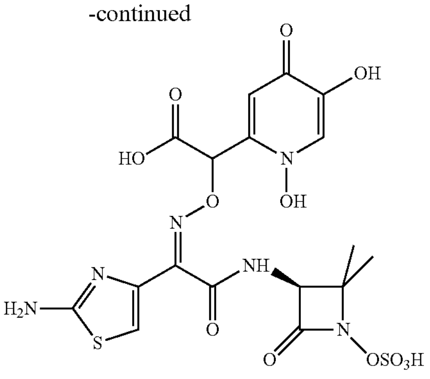

Compound 10

Step 1: Preparation of I-3-10

According to a method similar to that in step 1 of Example 1, a pale yellow solid compound I-3-10 (370 mg, yield 70.1%) was prepared from compound c-6 (340 mg, 0.48 mmol) and I-1 (197 mg, 0.48 mmol).

$^1$H NMR (400 MHz, DMSO-d6) δ 8.63 (s, 1H), 8.24 (s, 1H), 8.03 (s, 1H), 7.60-7.13 (m, 45H), 7.02-6.97 (m, 1H), 6.83 (s, 1H), 6.72 (s, 1H), 6.70 (s, 1H), 5.72 (s, 1H).

MS (ESI): m/z 1109.1, [M−H]$^-$.

Step 2: Preparation of I-5-10

According to a method similar to that in step 2 of Example 1, a white solid compound I-5-10 (321 mg, yield 76.0%) was prepared from compound I-3-10 (360 mg, 0.32 mmol) and I-4 (102 mg, 0.48 mmol).

$^1$H NMR (400 MHz, DMSO-d6) δ 9.80 (d, J=7.5 Hz, 1/2H), 9.73 (d, J=7.2 Hz, 1/2H), 8.96 (s, 1/2H), 8.92 (s, 1/2H), 8.15 (s, 1/2H), 8.11 (s, 1/2H), 7.64-7.09 (m, 35H), 6.91 (s, 1/2H), 6.83 (s, 1/2H), 6.77 (s, 1H), 6.76 (s, 1/2H), 6.73 (s, 1/2H), 6.69 (s, 1/2H), 6.67 (s, 1/2H), 5.86 (s, 1H), 4.63 (d, J=7.5 Hz, 1/2H), 4.56 (d, J=7.2 Hz, 1/2H), 1.37 (s, 3H), 1.07 (s, 3/2H), 1.02 (s, 3/2H).

MS (ESI): m/z 1301.0, [M−H]$^-$.

Step 3: Preparation of Compound 10

According to a method similar to that in step 3 of Example 1, a white solid compound 10 (100 mg, yield: 80.0%) was prepared from compound I-5-10 (290 mg, 0.22 mmol) and trifluoroacetic acid (0.78 mL, 11.1 mmol).

$^1$H NMR (400 MHz, DMSO-d6) δ 9.68 (d, J=7.7 Hz, 1/2H), 9.63 (d, J=7.8 Hz, 1/2H), 8.08 (s, 1H), 7.09 (s, 1/2H), 7.00 (s, 1/2H), 6.88 (s, 1/2H), 6.87 (s, 1/2H), 5.99 (d, J=1.1 Hz, 1H), 4.67 (dd, J=7.8, 5.6 Hz, 1H), 1.46 (s, 3/2H), 1.44 (s, 3/2H), 1.29 (s, 3/2H), 1.20 (s, 3/2H).

MS (ESI): m/z 561.0, [M−H]$^-$.

Example 11: Preparation of (3S)-3-((Z)-2-(2-aminothiazol-4-yl)-2-((1-(1,5-dihydroxy-4-oxo-1,4-dihydropyridin-2-yl)-2-(methylamine)-2-oxoethoxy)imine)acetamido)-2,2-dimethyl-4-oxoazetidine-1-hydrogen sulfate (Compound 11)

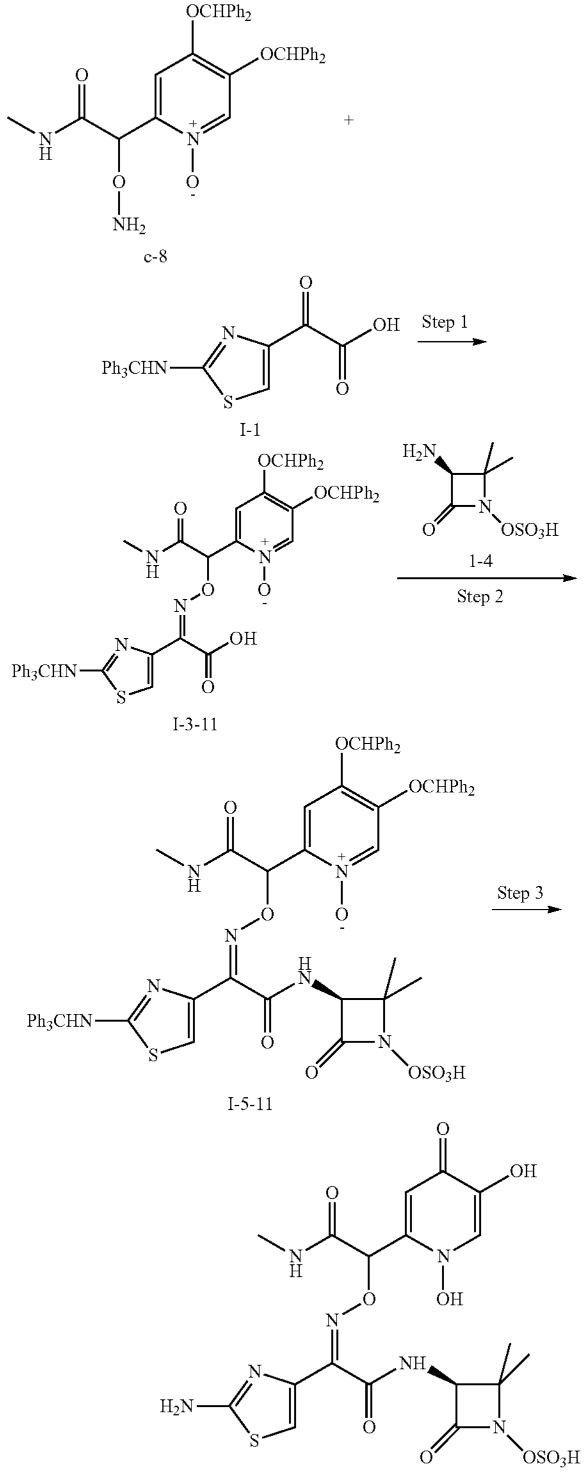

Compound 11

Step 1: Preparation of I-3-11

According to a method similar to that in step 1 of Example 1, a white solid compound I-3-11 (160 mg, yield: 18.7%) was prepared from compound c-8 (500 mg, 0.89 mmol) and I-1 (277 mg, 0.67 mmol).

$^1$H NMR (400 MHz, DMSO-d6) δ 8.70 (s, 1H), 8.65 (s, 1H), 7.95 (s, 1H), 7.72 (s, 1H), 7.46-7.00 (m, 35H), 6.79 (s, 1H), 6.66 (s, 1H), 5.70 (s, 1H), 2.55 (d, J=4.5 Hz, 3H).

MS (ESI): m/z 956.1, $[M-H]^-$.

Step 2: Preparation of I-5-11

According to a method similar to that in step 2 of Example 1, a white solid compound I-5-11 (120 mg, yield: 62.4%). was prepared from compound I-3-11 (160 mg, 0.17 mmol) and I-4 (53 mg, 0.25 mmol).

$^1$H NMR (400 MHz, DMSO-d6) δ 9.71 (d, J=7.8 Hz, 1/2H), 9.67 (d, J=7.7 Hz, 1/2H), 8.96 (s, 1/2H), 8.92 (s, 1/2H), 8.25 (q, J=4.8 Hz, 1/2H), 8.17 (q, J=4.9 Hz, 1/2H), 8.06 (s, 1/2H), 8.04 (s, 1/2H), 7.59-7.07 (m, 35H), 6.88 (s, 1/2H), 6.84 (s, 1/2H), 6.76 (s, 1/2H), 6.75 (s, 1/2H), 6.73 (s, 1/2H), 6.70 (s, 1/2H), 5.85 (s, 1H), 4.66 (dd, J=7.7, 3.9 Hz, 1H), 2.54 (t, J=4.5 Hz, 3H), 1.46 (s, 3/2H), 1.45 (s, 3/2H), 1.20 (s, 3/2H), 1.15 (s, 3/2H).

MS (ESI): m/z 1148.0, $[M-H]^-$.

Step 3: Preparation of Compound 11

According to a method similar to that in step 3 of Example 1, a white solid compound 11 (43 mg, yield 77.8%) was prepared from compound I-5-11 (110 mg, 0.10 mmol) and trifluoroacetic acid (0.35 mL, 5.0 mmol).

$^1$H NMR (400 MHz, Methanol-d4) δ 9.65 (t, J=8.0 Hz, 1H), 8.37-8.30 (m, 1/2H), 8.17 (s, 3/2H), 7.13 (s, 1/2H), 6.98 (s, 1/2H), 6.92 (s, 1/2H), 6.90 (s, 1/2H), 6.04 (s, 1/2H), 6.02 (s, 1/2H), 4.68 (d, J=7.8 Hz, 1/2H), 4.64 (d, J=8.0 Hz, 1/2H), 2.70 (d, J=4.9 Hz, 3H), 1.45 (s, 3/2H), 1.43 (s, 3/2H), 1.19 (s, 3/2H), 1.17 (s, 3/2H).

MS (ESI): m/z 574.1, $[M-H]^-$.

Example 12: Preparation of (3S)-3-((Z)-2-(2-aminothiazol-4-yl)-2-((1-(1,5-dihydroxy-4-oxo-1,4-dihydropyridin-2-yl)methylisopropyloxy)imine)acetamido)-2,2-dimethyl-4-oxoazetidine-1-hydrogen sulfate (Compound 12)

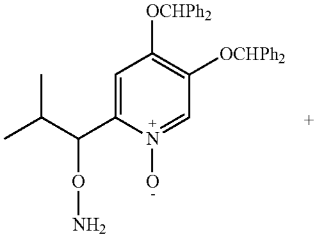

e-6

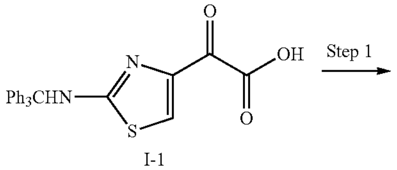

I-1

-continued

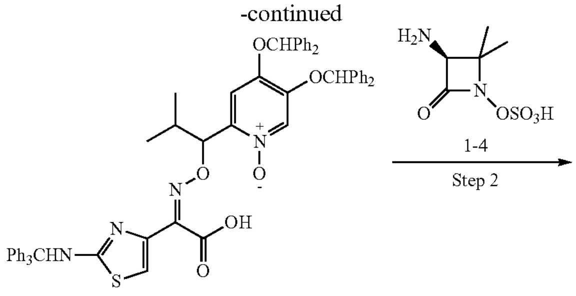

I-3-12

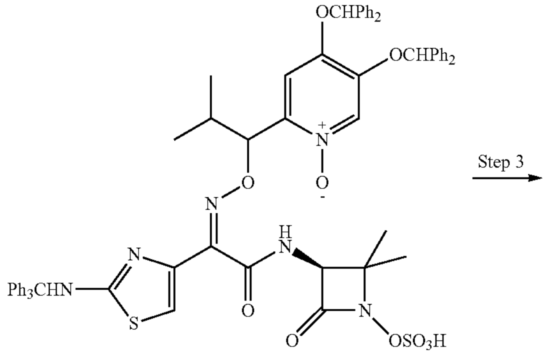

I-5-12

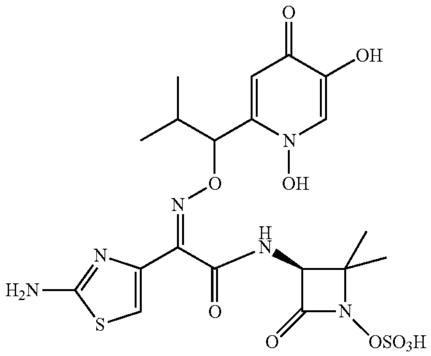

Compound 12

Step 1: Preparation of I-3-12

According to a method similar to that in step 1 of Example 1, a pale yellow solid compound I-3-12 (236 mg, yield: 65.1%) was prepared from compound e-6 (210 mg, 0.38 mmol) and I-1 (144 mg, 0.34 mmol).

$^1$H NMR (400 MHz, DMSO-d6) δ 8.90 (s, 1H), 7.99 (s, 1H), 7.62-7.15 (m, 35H), 6.96 (s, 1H), 6.90 (s, 1H), 6.69 (s, 1H), 6.54 (s, 1H), 5.28 (d, J=3.2 Hz, 1H), 2.12-2.00 (m, 1H), 0.90 (d, J=7.0 Hz, 3H), 0.43 (d, J=7.0 Hz, 3H).

MS (ESI): m/z 941.1, $[M-H]^-$.

Step 2: Preparation of I-5-12

According to a method similar to that in step 2 of Example 1, a white solid compound I-5-12 (294 mg, yield: 94.1%) was prepared from compound I-3-12 (260 mg, 0.27 mmol) and I-4 (87 mg, 0.41 mmol).

$^1$H NMR (400 MHz, DMSO-d6) δ 9.77 (d, J=7.7 Hz, 1/2H), 9.68 (d, J=7.0 Hz, 1/2H), 8.90 (s, 1H), 8.02 (s, 1/2H), 7.99 (s, 1/2H), 7.63-7.16 (m, 35H), 7.04 (s, 1/2H), 6.87 (s, 1/2H), 6.79 (s, 1/2H), 6.77 (s, 1/2H), 6.74 (s, 1/2H), 6.73 (s, 1/2H), 6.72 (s, 1/2H), 6.70 (s, 1/2H), 5.32 (d, J=3.2 Hz,

1/2H), 5.26 (d, J=3.7 Hz, 1/2H), 4.81 (d, J=7.8 Hz, 1/2H), 4.65 (d, J=7.1 Hz, 1/2H), 2.05-1.93 (m, 1H), 1.57 (s, 3/2H), 1.52 (s, 3/2H), 1.37 (s, 3/2H), 1.34 (s, 3/2H), 0.87 (d, J=6.9 Hz, 3/2H), 0.82 (d, J=7.0 Hz, 3/2H), 0.36 (d, J=7.0 Hz, 3/2H), 0.32 (d, J=7.1 Hz, 3/2H).

MS (ESI): m/z 1133.1, $[M-H]^-$.

Step 3: Preparation of Compound 12

According to a method similar to that in step 3 of Example 1, a white solid compound 12 (100 mg, yield 68.9%) was prepared from compound I-5-12 (294 mg, 0.26 mmol) and trifluoroacetic acid (0.9 mL, 12.9 mmol).

$^1$H NMR (500 MHz, DMSO-d6) δ 9.69 (d, J=8.0 Hz, 1/2H), 9.65 (d, J=7.5 Hz, 1/2H), 8.24 (s, 1/2H), 8.23 (s, 1/2H), 7.02 (s, 1/2H), 7.00 (s, 1/2H), 6.83 (s, 1/2H), 6.81 (s, 1/2H), 5.44 (d, J=4.8 Hz, 1/2H), 5.37 (d, J=5.4 Hz, 1/2H), 4.71 (d, J=7.9 Hz, 1/2H), 4.68 (d, J=7.6 Hz, 1/2H), 2.23-2.09 (m, 1H), 1.48 (s, 3/2H), 1.47 (s, 3/2H), 1.35 (s, 3/2H), 1.34 (s, 3/2H), 1.00-0.96 (m, 3H), 0.92-0.85 (m, 3H).

MS (ESI): m/z 559.1, $[M-H]^-$.

Example 13: Preparation of (3S)-3-((Z)-2-(2-aminothiazol-4-yl)-2-((1-(1,5-dihydroxy-4-oxo-1,4-dihydropyridin-2-yl)phenylmethoxy)imine)acetamido)-2,2-dimethyl-4-oxoazetidine-1-hydrogen sulfate (Compound 13)

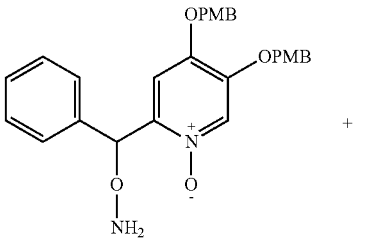

f-5-1

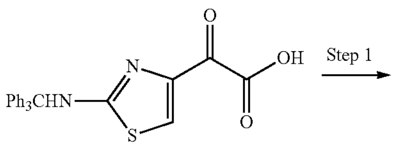

I-1

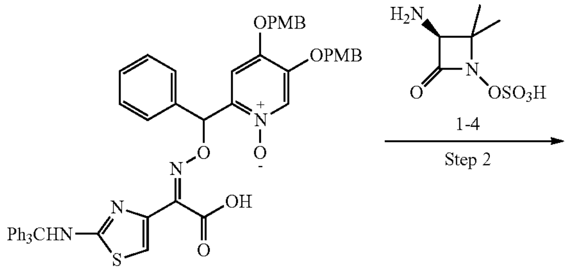

I-3-13

-continued

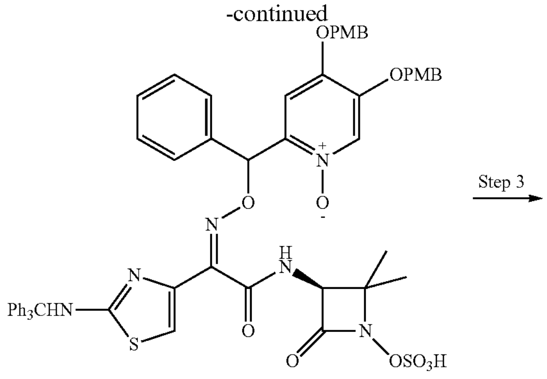

I-5-13

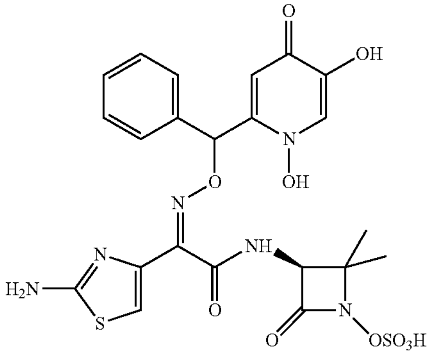

Compound 13

Step 1: Preparation of I-3-13

According to a method similar to that in step 1 of Example 1, a pale yellow solid compound I-3-13 (570 mg, yield: 70.2%) was prepared from compound f-5-1 (448 mg, 0.92 mmol) and I-1 (342 mg, 0.83 mmol).

$^1$H NMR (400 MHz, DMSO-d6) δ 8.89 (s, 1H), 8.07 (s, 1H), 7.41-7.15 (m, 24H), 6.97-6.84 (m, 5H), 6.56 (s, 1H), 5.14 (s, 2H), 5.05 (s, 2H), 3.74 (s, 3H), 3.73 (s, 3H).

MS (ESI): m/z 883.2, $[M-H]^-$.

Step 2: Preparation of I-5-13

According to a method similar to that in step 2 of Example 1, a white solid compound I-5-13 (240 mg, yield: 65.7%) was prepared from compound I-3-13 (300 mg, 0.34 mmol) and I-4 (92.6 mg, 0.44 mmol).

$^1$H NMR (400 MHz, DMSO-d6) δ 9.71 (d, J=7.6 Hz, 1/2H), 9.65 (d, J=8.0 Hz, 1/2H), 8.94 (s, 1/2H), 8.93 (s, 1/2H), 8.07 (s, 1/2H), 8.05 (s, 1/2H), 7.39-7.09 (m, 24H), 6.96 (s, 1H), 6.94 (s, 1H), 6.93 (s, 1/2H), 6.91 (s, 1/2H), 6.88 (s, 1/2H), 6.86 (s, 1/2H), 6.82 (s, 1/2H), 6.78 (s, 1/2H), 6.54 (s, 1H), 5.30-5.17 (m, 2H), 5.10-5.04 (m, 2H), 4.60 (dd, J=7.6, 3.5 Hz, 1H), 3.75-3.73 (m, 6H), 1.40 (s, 3/2H), 1.36 (s, 3/2H), 1.11 (s, 3/2H), 0.88 (s, 3/2H).

MS (ESI): m/z 1075.3, $[M-H]^-$.

Step 3: Preparation of Compound 13

According to a method similar to that in step 3 of Example 1, a white solid compound 13 (100 mg, yield: 80.1%) was prepared from compound I-5-13 (230 mg, 0.21 mmol) and trifluoroacetic acid (1.5 mL, 21 mmol).

$^1$H NMR (400 MHz, DMSO-d6) δ 9.68 (d, J=8.1 Hz, 1/2H), 9.63 (d, J=8.0 Hz, 1/2H), 8.15 (s, 1/2H), 8.14 (s, 1/2H), 7.43-7.31 (m, 5H), 7.20 (s, 1/2H), 7.16 (s, 1/2H), 6.87 (s, 1/2H), 6.84 (s, 1/2H), 6.60 (s, 1/2H), 6.57 (s, 1/2H), 4.62 (dd, J=7.8, 1.6 Hz, 1H), 1.37 (s, 3/2H), 1.34 (s, 3/2H), 1.05 (s, 3/2H), 0.80 (s, 3/2H).

MS (ESI): m/z 593.1, [M−H]⁻.

Example 14: Preparation of (3S)-3-((Z)-2-(2-aminothiazol-4-yl)-2-(((1,5-dihydroxy-4-oxo-1,4-dihydropyridin-2-yl)(thiazol-2-yl)methoxy)imine)acetamido)-2,2-dimethyl-4-oxoazetidine-1-hydrogen sulfate (Compound 14)

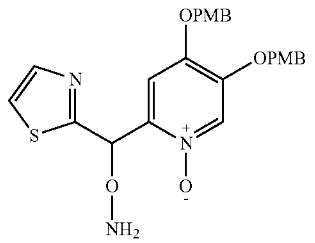

f-5-2

+

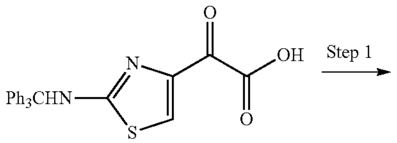

I-1

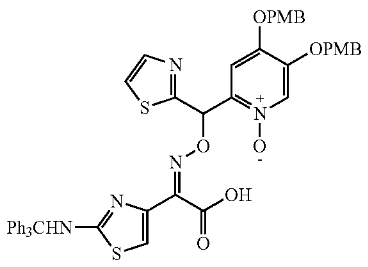

I-3-14

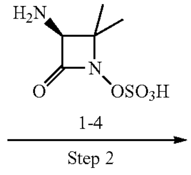

1-4

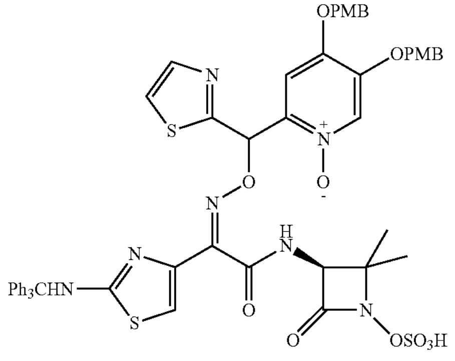

I-5-14

-continued

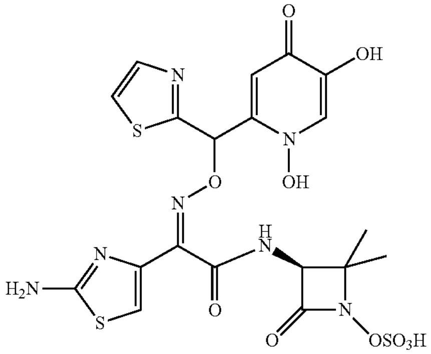

Compound 14

Step 1: Preparation of I-3-14

According to a method similar to that in step 1 of Example 1, a pale yellow solid compound I-3-14 (400 mg, yield 44.8%) was prepared from compound f-5-2 (495 mg, 1.00 mmol) and I-1 (370 mg, 0.90 mmol).

$^1$H NMR (400 MHz, DMSO-d6) δ 8.69 (s, 1H), 8.05 (s, 1H), 7.79-7.74 (m, 1H), 7.42-7.20 (m, 20H), 6.96-6.91 (m, 2H), 6.86-6.80 (m, 2H), 6.75 (s, 1H), 6.70 (s, 1H), 5.35-5.10 (m, 2H), 5.07 (s, 2H), 3.75 (s, 3H), 3.73 (s, 3H).

MS (ESI): m/z 890.1, [M−H]⁻.

Step 2: Preparation of I-5-14

According to a method similar to that in step 2 of Example 1, a white solid compound I-5-14 (230 mg, yield 47.4%) was prepared from compound I-3-14 (400 mg, 0.45 mmol) and I-4 (141 mg, 0.67 mmol).

$^1$H NMR (400 MHz, DMSO-d6) δ 9.73 (t, J=7.0 Hz, 1H), 8.94 (d, J=2.2 Hz, 1H), 8.14 (s, 1/2H), 8.12 (s, 1/2H), 7.82-7.76 (m, 2H), 7.39-7.15 (m, 20H), 6.97-6.92 (m, 2H), 6.92-6.87 (m, 2H), 6.86-6.82 (m, 2H), 5.25-5.05 (m, 4H), 4.57 (d, J=7.6 Hz, 1/2H), 4.54 (d, J=7.6 Hz, 1/2H), 3.74 (s, 3H), 3.72 (s, 3H), 1.35 (s, 3H), 1.07 (s, 3/2H), 0.88 (s, 3/2H).

MS (ESI): m/z 1082.1, [M−H]⁻.

Step 3: Preparation of Compound 14

According to a method similar to that in step 3 of Example 1, a white solid compound 14 (94 mg, yield: 75.5%) was prepared from compound I-5-14 (225 mg, 0.21 mmol) and trifluoroacetic acid (1.5 mL, 21 mmol).

$^1$H NMR (500 MHz, DMSO-d6) δ 9.76-9.69 (m, 1H), 8.18 (s, 1/2H), 8.15 (s, 1/2H), 7.92 (d, J=3.3 Hz, 1/2H), 7.84 (d, J=3.2 Hz, 1/2H), 7.28-7.23 (m, 1/2H), 7.20-7.17 (m, 1/2H), 7.09 (s, 1/2H), 6.99 (s, 1/2H), 6.95 (s, 1/2H), 6.93 (s, 1/2H), 4.63 (d, J=8.0 Hz, 1/2H), 4.61 (d, J=8.0 Hz, 1/2H), 1.46 (s, 3/2H), 1.39 (s, 3/2H), 1.26 (s, 3/2H), 0.91 (s, 3/2H).

MS (ESI): m/z 599.9, $[M-H]^-$.

Example 15: Preparation of (3S)-3-((Z)-2-(2-aminothiazol-4-yl)-2-(((1,5-dihydroxy-4-oxo-1,4-dihydropyridin-2-yl)(thiophen-2-yl)methoxy)imine)acetamido)-2,2-dimethyl-4-oxoazetidine-1-hydrogen sulfate (Compound 15)

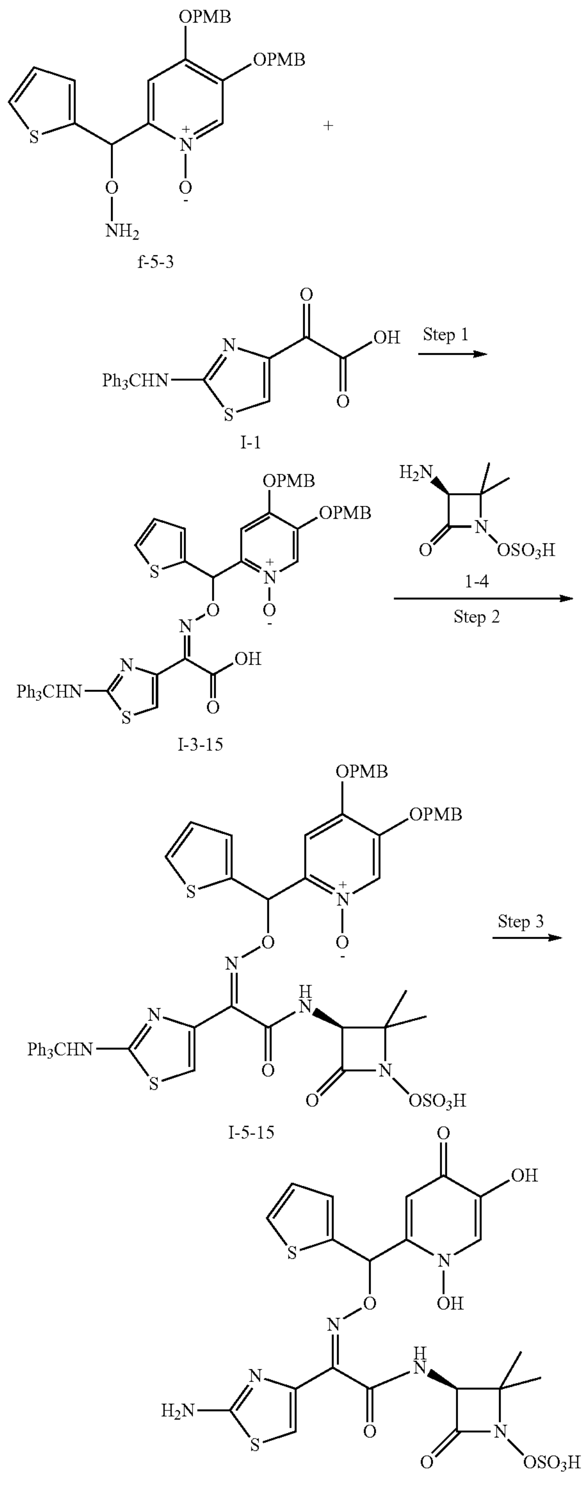

Compound 15

Step 1: Preparation of I-3-15

According to a method similar to that in step 1 of Example 1, a pale yellow solid I-3-15 (474 mg, yield 58.4%) was prepared from compound f-5-3 (450 mg, 0.91 mmol) and I-1 (339 mg, 0.81 mmol).

$^1$H NMR (400 MHz, DMSO-d6) δ 8.90 (s, 1H), 8.12 (s, 1H), 7.54 (dd, J=5.1, 1.3 Hz, 1H), 7.36-7.24 (m, 18H), 7.20 (d, J=8.6 Hz, 2H), 6.99-6.90 (m, 4H), 6.87 (d, J=8.6 Hz, 2H), 6.77 (s, 1H), 5.15-5.04 (m, 4H), 3.75 (s, 3H), 3.73 (s, 3H).

MS (ESI): m/z 889.0, $[M-H]^-$.

Step 2: Preparation of I-5-15

According to a method similar to that in step 2 of Example 1, a white solid compound I-5-15 (500 mg, yield 91.4%) was prepared from compound I-3-15 (450 mg, 0.51 mmol) and I-4 (159 mg, 0.76 mmol).

$^1$H NMR (400 MHz, DMSO-d6) δ 9.72 (d, J=7.7 Hz, 1/2H), 9.69 (d, J=7.7 Hz, 1/2H), 8.95 (s, 1H), 8.13 (s, 1/2H), 8.10 (s, 1/2H), 7.53 (dd, J=5.1, 1.2 Hz, 1/2H), 7.51 (dd, J=5.1, 1.3 Hz, 1/2H), 7.40-7.26 (m, 18H), 7.25-7.21 (m, 2H), 7.11 (s, 1/2H), 6.98-6.93 (m, 2H), 6.92 (s, 1/2H), 6.90 (s, 1/2H), 6.88 (s, 1/2H), 6.87-6.84 (m, 1H), 6.83 (d, J=0.7 Hz, 1/2H), 6.79 (d, J=0.7 Hz, 1/2H), 6.78 (s, 1/2H), 6.75 (d, J=0.8 Hz, 1/2H), 5.29-5.14 (m, 2H), 5.09 (d, J=7.4 Hz, 2H), 4.62 (d, J=7.7 Hz, 1/2H), 4.59 (d, J=7.6 Hz, 1/2H), 3.75 (d, J=1.3 Hz, 3H), 3.74 (d, J=1.1 Hz, 3H), 1.40 (s, 3/2H), 1.39 (s, 3/2H), 1.16 (s, 3/2H), 0.99 (s, 3/2H).

MS (ESI): m/z 1081.1, $[M-H]^-$.

Step 3: Preparation of Compound 15

According to a method similar to that in step 3 of Example 1, a white solid compound 15 (73 mg, yield 43.9%) was prepared from compound I-5-15 (300 mg, 0.28 mmol) and trifluoroacetic acid (2.0 mL, 27.7 mmol).

$^1$H NMR (600 MHz, DMSO-d6) δ 9.70 (d, J=7.7 Hz, 1/2H), 9.66 (d, J=7.9 Hz, 1/2H), 8.15 (s, 1/2H), 8.14 (s, 1/2H), 7.66-7.62 (m, 2H), 7.23 (s, 1/2H), 7.16 (s, 1/2H), 7.12 (d, J=3.5 Hz, 1/2H), 7.09 (d, J=3.6 Hz, 1/2H), 7.05-7.02 (m, 1H), 6.88 (s, 1/2H), 6.86 (s, 1/2H), 6.81 (d, J=1.9 Hz, 1H), 4.65-4.61 (m, 1H), 1.39 (s, 3/2H), 1.37 (s, 3/2H), 1.10 (s, 3/2H), 0.91 (s, 3/2H).

MS (ESI): m/z 599.0, $[M-H]^-$.

Example 16: Preparation of (3S)-3-((Z)-2-(2-aminothiazol-4-yl)-2-((1-(1,5-dihydroxy-4-oxo-1,4-dihydropyridin-2-yl)-2-(methylthio)ethoxy)imine)acetamido)-2,2-dimethyl-4-oxoazetidine-1-hydrogen sulfate (Compound 16)

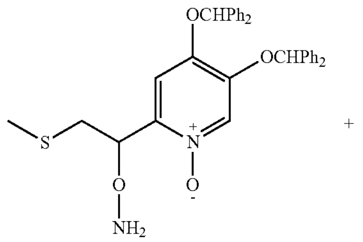

d-13-1

-continued

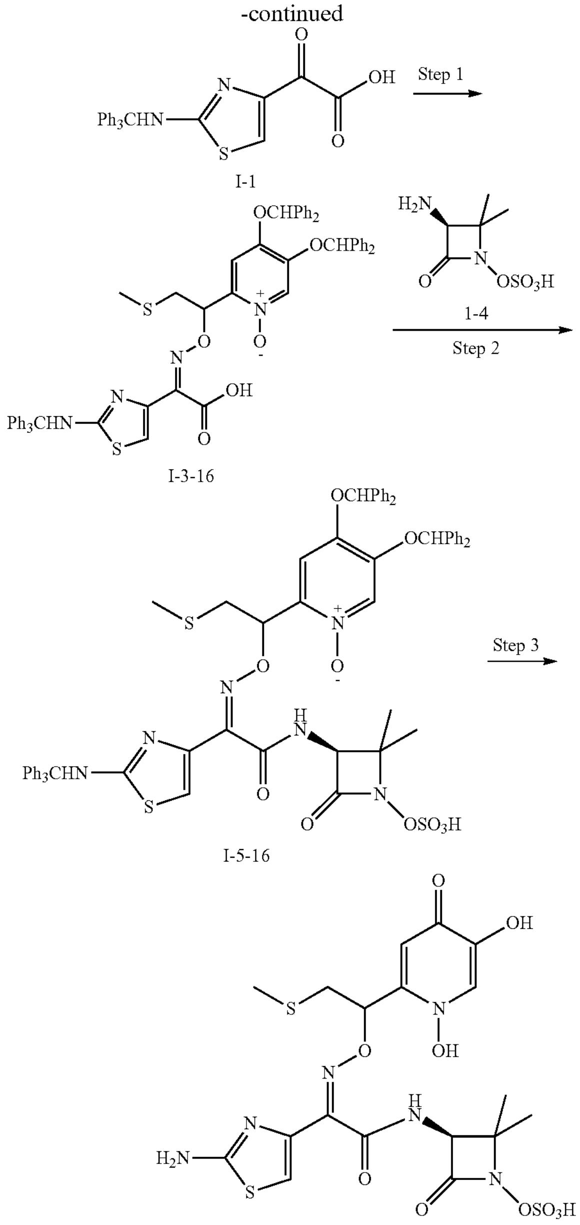

I-1
I-3-16
I-5-16
Compound 16

Step 1: Preparation of I-3-16

According to a method similar to that in step 1 of Example 1, a white solid compound I-3-16 (380 mg, yield 77.1%) was prepared from compound d-13-1 (290 mg, 0.51 mmol) and I-1 (191 mg, 0.46 mmol) $^1$H NMR (400 MHz, DMSO-d6) δ 8.77 (s, 1H), 7.94 (s, 1H), 7.60-7.08 (m, 35H), 7.05 (s, 1H), 6.85 (s, 1H), 6.66 (s, 1H), 5.48 (d, J=7.0 Hz, 1H), 3.00-2.90 (m, 1H), 2.66 (dd, J=14.9, 7.1 Hz, 1H), 1.96 (s, 3H).

MS (ESI): m/z 959.2, [M−H]$^-$.

Step 2: Preparation of I-5-16

According to a method similar to that in step 2 of Example 1, a white solid compound I-5-16 (310 mg, yield: 65.9%) was prepared from compound I-3-16 (380 mg, 0.40 mmol) and I-4 (124 mg, 0.59 mmol).

$^1$H NMR (400 MHz, DMSO-d6) δ 9.81 (d, J=7.8 Hz, 1/2H), 9.78 (d, J=7.7 Hz, 1/2H), 8.92 (s, 1/2H), 8.89 (s, 1/2H), 8.02 (s, 1/2H), 8.01 (s, 1/2H), 7.60-7.18 (m, 35H), 6.83 (s, 1/2H), 6.83 (s, 1/2H), 6.80 (s, 1/2H), 6.77 (s, 1/2H), 6.72-6.70 (m, 1H), 5.57 (td, J=6.8, 3.2 Hz, 1H), 4.76 (d, J=7.7 Hz, 1/2H), 4.65 (d, J=7.7 Hz, 1/2H), 2.84 (ddd, J=15.0, 7.0, 3.2 Hz, 1H), 2.60 (dt, J=14.7, 7.4 Hz, 1H), 1.87 (s, 3/2H), 1.73 (s, 3/2H), 1.54 (s, 3/2H), 1.52 (s, 3/2H), 1.36 (s, 3/2H), 1.32 (s, 3/2H).

MS (ESI): m/z 1151.2, [M−H]$^-$.

Step 3: Preparation of Compound 16

According to a method similar to that in step 3 of Example 1, a white solid compound 16 (140 mg, yield 90.1%) was prepared from compound I-5-16 (285 mg, 0.25 mmol) and trifluoroacetic acid (1.8 mL, 25 mmol).

$^1$H NMR (400 MHz, DMSO-d6) δ 9.71 (dd, J=10.0, 7.7 Hz, 1H), 8.24 (s, 1H), 7.13 (s, 1/2H), 7.12 (s, 1/2H), 6.88 (s, 1/2H), 6.87 (s, 1/2H), 5.79-5.73 (m, 1H), 4.68 (d, J=7.8 Hz, 1/2H), 4.66 (d, J=7.9 Hz, 1/2H), 3.08 (td, J=15.2, 4.1 Hz, 1H), 2.95 (dt, J=14.9, 7.0 Hz, 1H), 2.13 (s, 3/2H), 2.06 (s, 3/2H), 1.47 (d, J=3.4 Hz, 3H), 1.33 (s, 3/2H), 1.30 (s, 3/2H).

MS (ESI): m/z 576.9, [M−H]$^-$.

Example 17: Preparation of (3S)-3-((Z)-2-(2-aminothiazol-4-yl)-2-((1-(1,5-dihydroxy-4-oxo-1,4-dihydropyridin-2-yl)-2-(isopropylthio)ethoxy)imine)acetamido)-2,2-dimethyl-4-oxoazetidine-1-hydrogen sulfate (Compound 17)

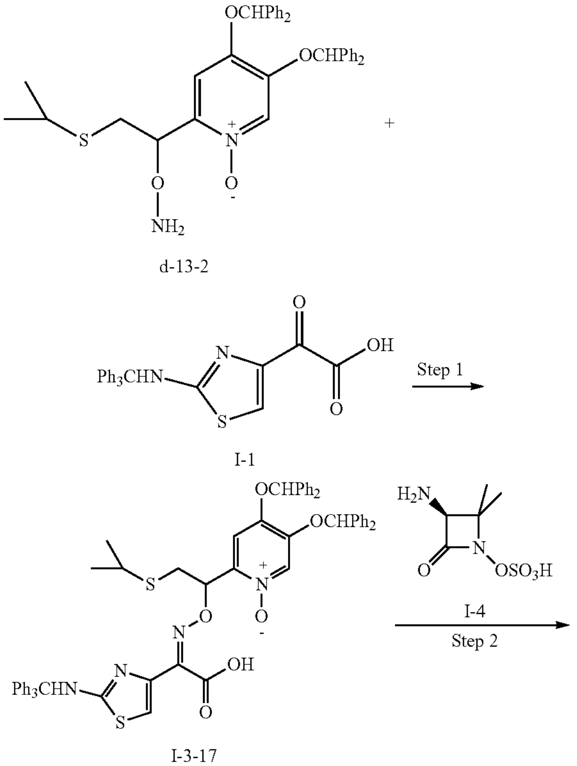

d-13-2
I-1
I-3-17

-continued

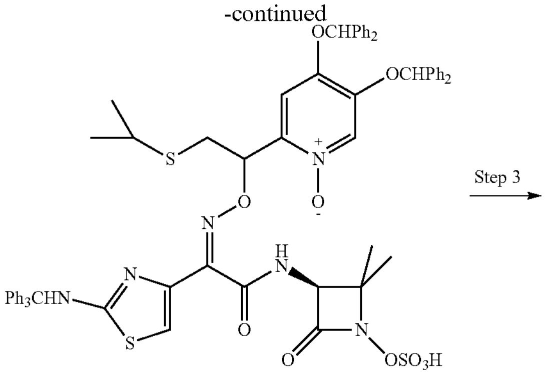

I-5-17

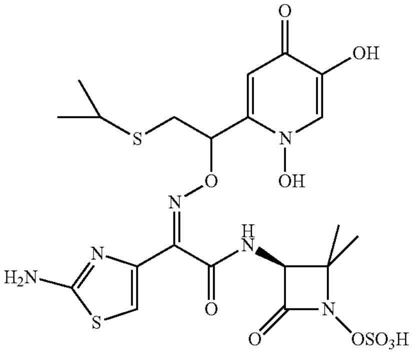

Compound 17

Step 1: Preparation of I-3-17

According to a method similar to that in step 1 of Example 1, a pale yellow solid compound I-3-17 (390 mg, yield 76.7%) was prepared from compound d-13-2 (305 mg, 0.51 mmol) and I-1 (202 mg, 0.49 mmol).

$^1$H NMR (400 MHz, DMSO-d6) δ 8.92 (s, 1H), 8.01 (s, 1H), 7.60-7.03 (m, 35H), 6.93 (s, 1H), 6.70 (s, 1H), 6.57 (s, 1H), 5.48 (dd, J=7.3, 2.9 Hz, 1H), 3.00 (dd, J=14.7, 2.9 Hz, 1H), 2.84 (p, J=6.7 Hz, 1H), 2.69 (dd, J=14.7, 7.3 Hz, 1H), 1.06 (d, J=6.6 Hz, 3H), 1.02 (d, J=6.7 Hz, 3H).

MS (ESI): m/z 987.1, [M−H]$^-$.

Step 2: Preparation of I-5-17

According to a method similar to that in step 2 of Example 1, a pale yellow solid compound I-5-17 (400 mg, yield 92.5%) was prepared from compound I-3-17 (362 mg, 0.37 mmol) and I-4 (115 mg, 0.55 mmol).

$^1$H NMR (400 MHz, DMSO-d6) δ 9.86-9.78 (m, 1H), 8.95 (s, 1/2H), 8.91 (s, 1/2H), 8.04 (s, 1/2H), 8.03 (s, 1/2H), 7.62-7.15 (m, 35H), 6.85 (s, 1/2H), 6.83 (s, 1/2H), 6.81 (s, 1/2H), 6.80 (s, 1/2H), 6.72 (d, J=4.0 Hz, 1H), 5.57-5.47 (m, 1H), 4.76 (d, J=7.7 Hz, 1/2H), 4.61 (d, J=7.7 Hz, 1/2H), 2.93-2.79 (m, 2H), 2.67-2.57 (m, 1H), 1.56 (s, 3/2H), 1.53 (s, 3/2H), 1.38 (s, 3/2H), 1.33 (s, 3/2H), 1.02 (d, J=6.8 Hz, 3/2H), 0.99 (dd, J=6.7, 2.2 Hz, 3H), 0.90 (d, J=6.6 Hz, 3/2H).

MS (ESI): m/z 1179.2, [M−H]$^-$.

Step 3: Preparation of Compound 17

According to a method similar to that in step 3 of Example 1, a white solid compound 17 (160 mg, yield: 90.9%) was prepared from compound I-5-17 (343 mg, 0.29 mmol) and trifluoroacetic acid (2.1 mL, 29 mmol).

$^1$H NMR (600 MHz, DMSO-d6) δ 9.71 (d, J=7.8 Hz, 1/2H), 9.69 (d, J=7.9 Hz, 1/2H), 8.24 (d, J=2.4 Hz, 1H), 7.15 (s, 1/2H), 7.09 (s, 1/2H), 6.88 (s, 1/2H), 6.87 (s, 1/2H), 5.72 (dd, J=6.9, 4.1 Hz, 1/2H), 5.69 (dd, J=7.2, 4.0 Hz, 1/2H), 4.68 (d, J=7.8 Hz, 1/2H), 4.64 (d, J=7.7 Hz, 1/2H), 3.11 (dt, J=14.5, 3.9 Hz, 1H), 3.04-2.85 (m, 2H), 1.48 (s, 3/2H), 1.47 (s, 3/2H), 1.33 (s, 3/2H), 1.31 (s, 3/2H), 1.20-1.16 (m, 9/2H), 1.13 (d, J=6.7 Hz, 3/2H).

MS (ESI): m/z 604.9, [M−H]$^-$.

Example 18: Preparation of (3S)-3-((Z)-2-(2-aminothiazol-4-yl)-2-((1-(1,5-dihydroxy-4-oxo-1,4-dihydropyridin-2-yl)-2-isopropoxyethoxy)imine)acetamido)-2,2-dimethyl-4-oxoazetidine-1-hydrogen sulfate (Compound 18)

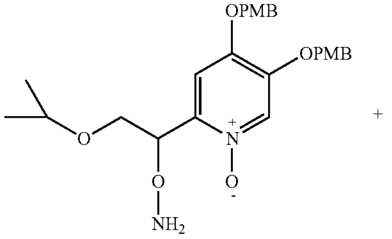

f-10-1

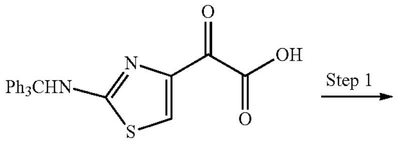

I-1

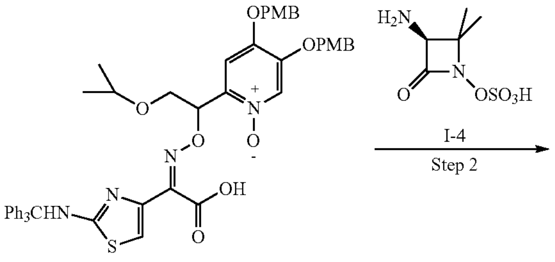

I-3-18

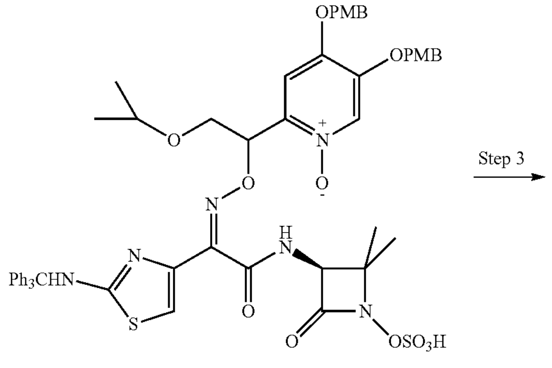

I-5-18

-continued

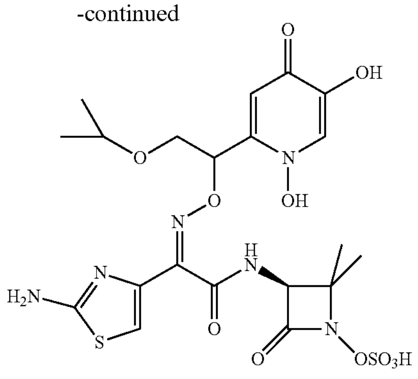

Compound 18

Step 1: Preparation of I-3-18

According to a method similar to that in step 1 of Example 1, a pale yellow solid compound I-3-18 (990 mg, yield 92.1%) was prepared from compound f-10-1 (590 mg, 1.22 mmol) and I-1 (479 mg, 1.16 mmol).

$^1$H NMR (400 MHz, DMSO-d6) δ 8.66 (s, 1H), 8.04 (s, 1H), 7.75 (s, 1H), 7.39-7.18 (m, 19H), 6.92 (d, J=8.7 Hz, 2H), 6.83 (d, J=8.7 Hz, 2H), 6.72 (s, 1H), 5.59-5.53 (m, 1H), 5.28 (d, J=11.8 Hz, 1H), 5.09 (d, J=11.9 Hz, 1H), 5.05 (s, 2H), 3.73 (s, 3H), 3.71 (s, 3H), 3.70-3.63 (m, 1H), 3.62-3.55 (m, 1H), 3.47-3.41 (m, 1H), 1.07 (d, J=6.1 Hz, 3H), 1.00 (d, J=6.0 Hz, 3H).

MS (ESI): m/z 879.1, [M−H]$^-$.

Step 2: Preparation of I-5-18

According to a method similar to that in step 2 of Example 1, a white solid compound I-5-18 (525 mg, yield 88.1%) was prepared from compound I-3-18 (490 mg, 0.56 mmol) and I-4 (175 mg, 0.83 mmol).

$^1$H NMR (400 MHz, DMSO-d6) δ 9.75 (d, J=7.4 Hz, 1/2H), 9.70 (d, J=7.8 Hz, 1/2H), 8.91 (d, J=2.9 Hz, 1H), 8.11 (s, 1/2H), 8.09 (s, 1/2H), 7.37-7.16 (m, 19H), 7.09 (s, 1/2H), 6.99 (s, 1/2H), 6.96-6.91 (m, 2H), 6.89 (d, J=8.7 Hz, 1/2H), 6.85 (d, J=8.7 Hz, 1/2H), 6.80 (d, J=0.7 Hz, 1/2H), 6.74 (d, J=0.7 Hz, 1/2H), 5.67 (dd, J=6.5, 2.1 Hz, 1/2H), 5.62 (dd, J=6.1, 2.3 Hz, 1/2H), 5.25-5.01 (m, 4H), 4.65 (d, J=7.7 Hz, 1/2H), 4.60 (d, J=7.4 Hz, 1/2H), 3.74 (d, J=1.6 Hz, 3H), 3.71 (s, 3H), 3.70-3.61 (m, 1H), 3.58-3.43 (m, 2H), 3.17 (s, 3/2H), 3.16 (s, 3/2H), 1.47 (s, 3/2H), 1.45 (s, 3/2H), 1.33 (s, 3/2H), 1.31 (s, 3/2H), 1.01 (dd, J=6.1, 3.1 Hz, 3H), 0.95 (d, J=6.1 Hz, 3/2H), 0.93 (d, J=6.2 Hz, 3/2H).

MS (ESI): m/z 1071.2, [M−H]$^-$.

Step 3: Preparation of Compound 18

According to a method similar to that in step 3 of Example 1, a white solid compound 18 (153 mg, yield 79.4%) was prepared from compound I-5-18 (350 mg, 0.33 mmol) and trifluoroacetic acid (2.3 mL, 33 mmol).

$^1$H NMR (500 MHz, Methanol-d4) δ 8.12 (s, 1/2H), 8.11 (s, 1/2H), 7.18 (s, 1/2H), 7.17 (s, 1/2H), 7.14 (s, 1/2H), 7.09 (s, 1/2H), 5.96 (dd, J=5.4, 3.0 Hz, 1/2H), 5.89 (t, J=4.6 Hz, 1/2H), 4.87 (s, 1/2H), 4.80 (s, 1/2H), 4.01-3.83 (m, 2H), 3.63 (dp, J=18.5, 6.1 Hz, 1H), 1.63 (s, 3/2H), 1.60 (s, 3/2H), 1.49 (s, 3/2H), 1.39 (s, 3/2H), 1.13 (dd, J=6.1, 2.9 Hz, 3H), 1.10 (d, J=6.1 Hz, 3/2H), 1.08 (d, J=6.1 Hz, 3/2H).

MS (ESI): m/z 588.9, [M−H]$^-$.

Example 19: Preparation of (3S)-3-((Z)-2-(2-aminothiazol-4-yl)-2-((1-(1,5-dihydroxy-4-oxo-1,4-dihydropyridin-2-yl)-2-(methylsulfonyl)ethoxy)imine)acetamido)-2,2-dimethyl-4-oxoazetidine-1-hydrogen sulfate (Compound 19)

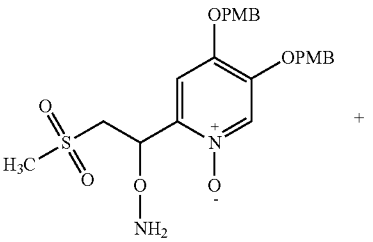

f-10-2

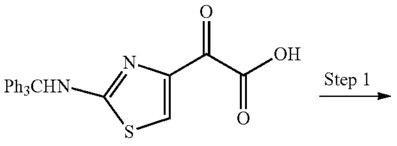

I-1

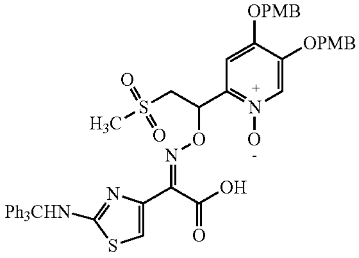

I-3-19

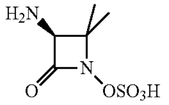

I-4

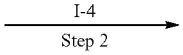

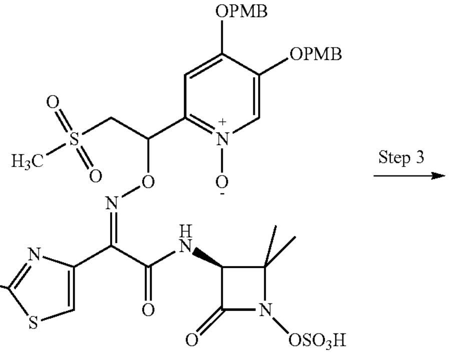

I-5-19

-continued

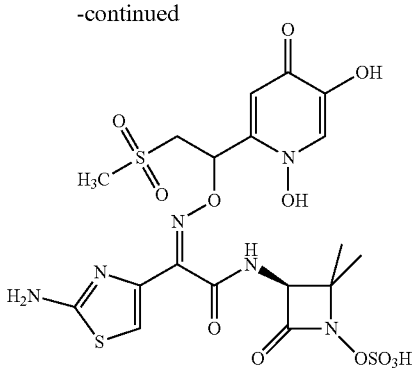

Compound 19

Step 1: Preparation of I-3-19

According to a method similar to that in step 1 of Example 1, a pale yellow solid compound I-3-19 (610 mg, yield 53.7%) was prepared from compound f-10-2 (636 mg, 1.26 mmol) and I-1 (496 mg, 1.19 mmol).

$^1$H NMR (400 MHz, DMSO-d6) δ 8.66 (s, 1H), 8.11 (s, 1H), 7.65 (s, 1H), 7.37-7.34 (m, 2H), 7.33 (s, 1H), 7.32-7.25 (m, 15H), 7.24-7.20 (m, 2H), 6.92 (d, J=8.7 Hz, 2H), 6.79 (d, J=8.7 Hz, 2H), 6.76 (s, 1H), 5.78 (dd, J=9.9, 2.7 Hz, 1H), 5.24-5.03 (m, 4H), 3.74 (s, 3H), 3.70 (s, 3H), 3.67-3.48 (m, 2H), 3.09 (s, 3H).

MS (ESI): m/z 899.0, $[M-H]^-$.

Step 2: Preparation of I-5-19

According to a method similar to that in step 2 of Example 1, a white solid compound I-5-19 (390 mg, yield 68.5%) was prepared from compound I-3-19 (470 mg, 0.52 mmol) and I-4 (165 mg, 0.78 mmol).

$^1$H NMR (400 MHz, DMSO-d6) δ 9.79 (d, J=8.2 Hz, 1/2H), 9.76 (d, J=7.4 Hz, 1/2H), 8.94 (s, 1/2H), 8.92 (s, 1/2H), 8.19 (s, 1/2H), 8.18 (s, 1/2H), 7.39-7.20 (m, 19H), 7.17 (s, 1/2H), 7.05 (s, 1/2H), 6.96-6.91 (m, 2H), 6.89-6.83 (m, 2H), 5.99 (dd, J=8.3, 4.0 Hz, 1/2H), 5.92 (dd, J=10.1, 2.5 Hz, 1/2H), 5.28-4.97 (m, 4H), 4.71 (d, J=8.1 Hz, 1/2H), 4.58 (d, J=7.3 Hz, 1/2H), 3.76-3.70 (m, 6H), 3.68-3.47 (m, 2H), 3.08 (s, 3/2H), 3.05 (s, 3/2H), 1.45 (s, 3/2H), 1.44 (s, 3/2H), 1.30 (s, 3H).

MS (ESI): m/z 1091.1, $[M-H]^-$.

Step 3: Preparation of Compound 19

According to a method similar to that in step 3 of Example 1, a white solid compound 19 (160 mg, yield 77.5%) was prepared from compound I-5-19 (370 mg, 0.34 mmol) and trifluoroacetic acid (2.4 mL, 34 mmol).

$^1$H NMR (500 MHz, DMSO-d6) δ 9.81 (d, J=7.6 Hz, 1/2H), 9.71 (d, J=7.7 Hz, 1/2H), 8.26 (s, 1H), 7.19 (s, 1/2H), 7.07 (s, 1/2H), 6.95 (s, 1/2H), 6.92 (s, 1/2H), 6.05-5.95 (m, 1H), 4.76-4.62 (m, 1H), 3.95-3.79 (m, 1H), 3.71-3.53 (m, 1H), 3.10 (s, 3/2H), 3.07 (s, 3/2H), 1.48 (s, 3/2H), 1.33 (s, 3/2H), 1.17 (t, J=7.1 Hz, 3H).

MS (ESI): m/z 608.9, $[M-H]^-$.

Example 20: Preparation of (3S)-3-((Z)-2-(2-Aminothiazol-4-yl)-2-((1-(1,5-dihydroxy-4-oxo-1,4-dihydropyridin-2-yl)-2-fluoroethoxy)imine)acetamido)-2,2-dimethyl-4-oxoazetidine-1-hydrogen sulfate (Compound 20)

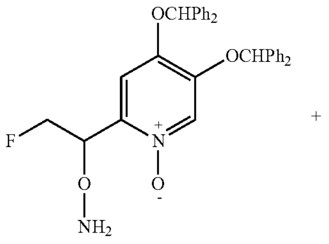

k-9

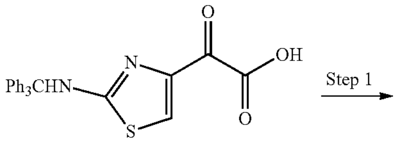

I-1

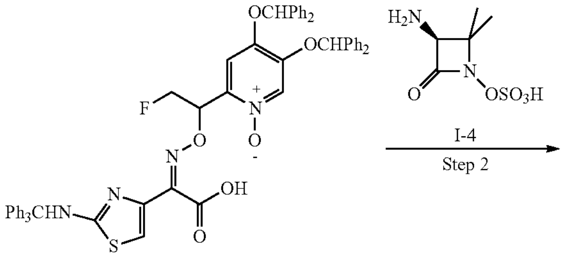

I-3-20

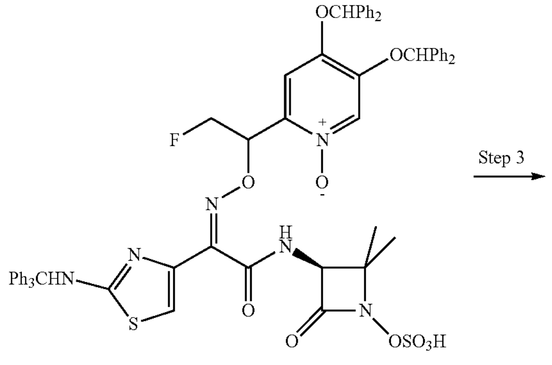

I-5-20

-continued

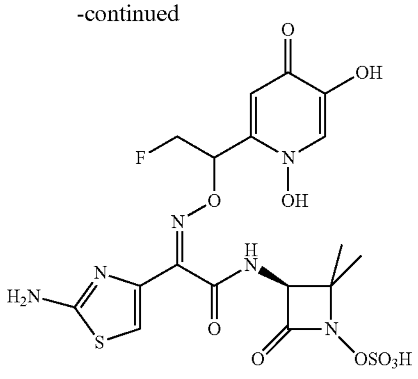

Compound 20

Step 1: Preparation of I-3-20

According to a method similar to that in step 1 of Example 1, a white solid compound I-3-20 (347 mg, yield: 62.4%) was prepared from compound k-9 (320 mg, 0.59 mmol) and I-1 (234 mg, 0.56 mmol).

$^{1}$H NMR (400 MHz, DMSO-d6) δ 8.93 (s, 1H), 8.08 (s, 1H), 7.59-7.01 (m, 35H), 6.96 (s, 1H), 6.71 (s, 1H), 6.58 (s, 1H), 5.66-5.57 (m, 1H), 4.79-4.63 (m, 1H), 4.62-4.45 (m, 1H).

MS (ESI): m/z 931.1, [M−H]$^-$.

Step 2: Preparation of I-5-20

According to a method similar to that in step 2 of Example 1, a white solid compound I-5-20 (200 mg, yield 47.8%) was prepared from compound I-3-20 (347 mg, 0.37 mmol) and I-4 (117 mg, 0.56 mmol).

$^{1}$H NMR (400 MHz, DMSO-d6) δ 9.87 (d, J=7.4 Hz, 1/2H), 9.78 (d, J=7.1 Hz, 1/2H), 8.93 (s, 1/2H), 8.90 (s, 1/2H), 8.09 (s, 1/2H), 8.07 (s, 1/2H), 7.61-7.11 (m, 35H), 6.89 (s, 1/2H), 6.83 (s, 1/2H), 6.80 (s, 1/2H), 6.78 (s, 1/2H), 6.73 (s, 1/2H), 6.71 (s, 1/2H), 5.68-5.62 (m, 1/2H), 5.62-5.56 (m, 1/2H), 4.72 (d, J=7.4 Hz, 1/2H), 4.66 (d, J=7.1 Hz, 1/2H), 4.58-4.25 (m, 2H), 1.54 (s, 3/2H), 1.51 (s, 3/2H), 1.34 (s, 3/2H), 1.32 (s, 3/2H).

MS (ESI): m/z 1123.1, [M−H]$^-$.

Step 3: Preparation of Compound 20

According to a method similar to that in step 3 of Example 1, a white solid compound 20 (80 mg, yield 81.6%) was prepared from compound I-5-20 (200 mg, 0.18 mmol) and trifluoroacetic acid (0.7 mL, 8.89 mmol).

$^{1}$H NMR (500 MHz, DMSO-d6) δ 9.75 (d, J=7.6 Hz, 1/2H), 9.72 (d, J=7.7 Hz, 1/2H), 8.23-8.15 (m, 1H), 7.49 (s, 1/2H), 7.45 (s, 1/2H), 7.12 (s, 1/2H), 6.97 (s, 1/2H), 5.87-5.74 (m, 1H), 5.19-5.08 (m, 1/2H), 5.06-4.99 (m, 1/2H), 4.93-4.82 (m, 1/2H), 4.82-4.73 (m, 1/2H), 4.60 (d, J=7.6 Hz, 1/2H), 4.57 (d, J=7.7 Hz, 1/2H), 1.48 (s, 3/2H), 1.47 (s, 3/2H), 1.32 (s, 3/2H), 1.29 (s, 3/2H).

MS (ESI): m/z 549.0, [M−H]$^-$.

Example 21: Preparation of (3S)-3-((Z)-2-(2-Amino-5-bromothiazol-4-yl)-2-((1-(1,5-dihydroxy-4-oxo-1,4-dihydropyridin-2-yl)ethoxy)imine)acetamido)-2,2-dimethyl-4-oxoazetidine-1-hydrogen sulfate (Compound 21)

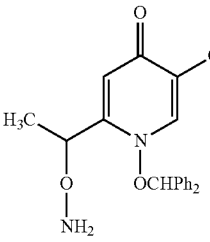

a-5-1

+

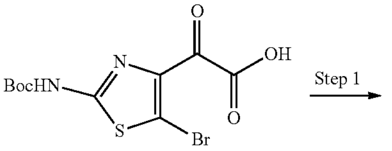

I-1-1

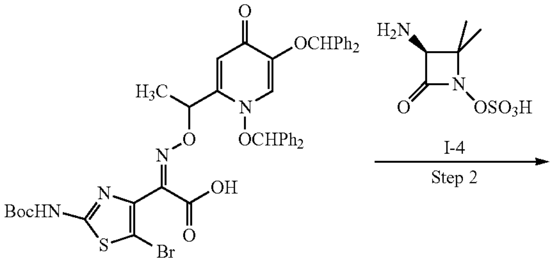

I-3-21

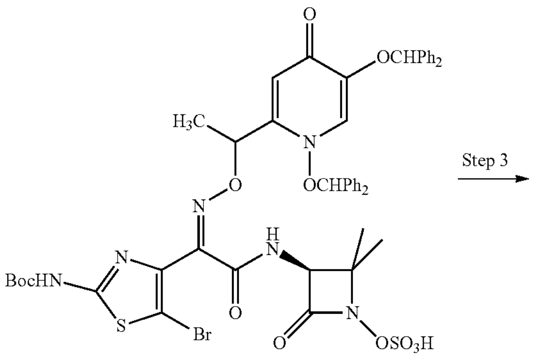

I-5-21

-continued

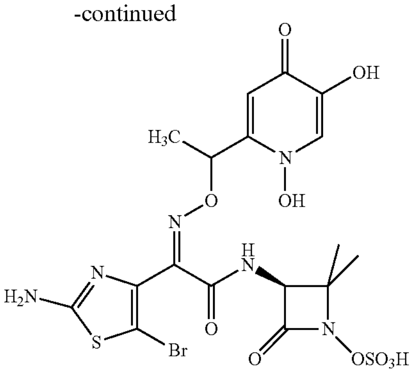

Compound 21

Step 1: Preparation of I-3-21

According to a method similar to that in step 1 of Example 1, a pale yellow solid compound I-3-21 (300 mg, yield 65.2%) was prepared from compound a-5-1 (280 mg, 0.54 mmol) and I-1-1 (190 mg, 0.54 mmol).

$^1$H NMR (400 MHz, DMSO-d6) δ 12.03 (s, 1H), 7.51 (s, 1H), 7.44-7.15 (m, 20H), 6.35 (s, 1H), 6.26 (s, 1H), 6.13 (s, 1H), 5.17 (q, J=6.6 Hz, 6H), 1.47 (s, 9H), 1.21 (d, J=6.6 Hz, 3H).

MS (ESI): m/z 849.0, $[M-H]^-$.

Step 2: Preparation of I-5-21

According to a method similar to that in step 2 of Example 1, a white solid compound I-5-21 (274 mg, yield: 80.7%) was prepared from compound I-3-21 (300 mg, 0.35 mmol) and I-4 (111 mg, 0.53 mmol).

$^1$H NMR (400 MHz, DMSO-d6) δ 12.11 (s, 1/2H), 12.07 (s, 1/2H), 9.59 (dd, J=7.9, 4.4 Hz, 1H), 7.58 (d, J=1.6 Hz, 1H), 7.44-7.06 (m, 20H), 6.31 (d, J=2.2 Hz, 1H), 6.25 (s, 1/2H), 6.24 (s, 1/2H), 6.16 (s, 1/2H), 6.04 (s, 1/2H), 5.21-5.09 (m, 1H), 4.55 (d, J=8.0 Hz, 1/2H), 4.51 (d, J=7.8 Hz, 1/2H), 1.46 (d, J=1.2 Hz, 9H), 1.40 (s, 3/2H), 1.38 (s, 3/2H), 1.18-1.16 (m, 3H), 1.12 (dd, J=6.9, 3.8 Hz, 3H).

MS (ESI): m/z 1041.1, $[M-H]^-$.

Step 3: Preparation of Compound 21

According to a method similar to that in step 3 of Example 1, a white solid compound 21 (82 mg, yield 47.9%) was prepared from compound I-5-21 (270 mg, 0.28 mmol) and trifluoroacetic acid (1.0 mL, 14.0 mmol).

$^1$H NMR (400 MHz, DMSO-d6) δ 9.69 (d, J=7.5 Hz, 1/2H), 9.57 (d, J=7.7 Hz, 1/2H), 8.26 (s, 1/2H), 8.25 (s, 1/2H), 7.23 (s, 1/2H), 7.06 (s, 1/2H), 5.77-5.54 (m, 1H), 4.61 (d, J=7.8 Hz, 1/2H), 4.58 (d, J=7.6 Hz, 1/2H), 1.54 (d, J=6.7 Hz, 3/2H), 1.51 (d, J=6.8 Hz, 3/2H), 1.47 (s, 3/2H), 1.44 (s, 3/2H), 1.33 (s, 3/2H), 1.27 (s, 3/2H).

MS (ESI): m/z 610.0, $[M-H]^-$.

Example 22: Preparation of (3S)-3-((Z)-2-(2-amino-5-chlorothiazol-4-yl)-2-((1-(1,5-dihydroxy-4-oxo-1,4-dihydropyridin-2-yl)ethoxyl)imine)acetamido)-2,2-dimethyl-4-oxoazetidine-1-hydrogen sulfate (Compound 22)

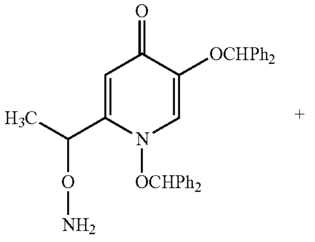

a-5-1

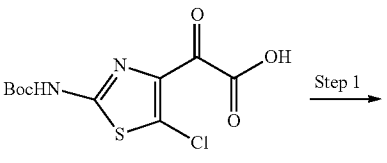

I-1-2

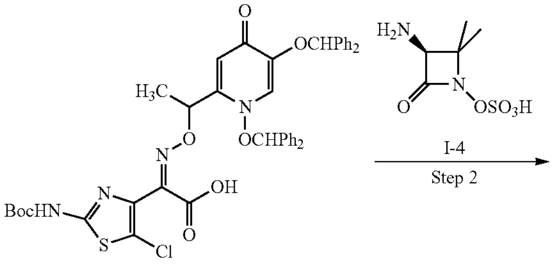

I-3-22

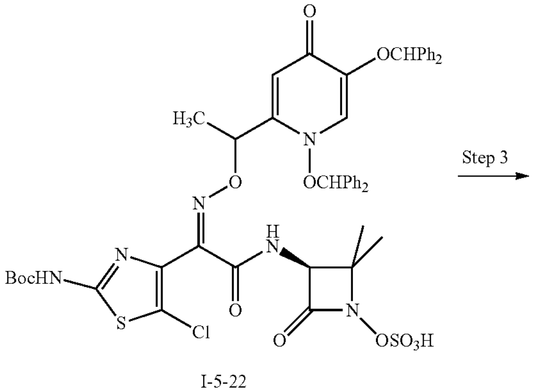

I-5-22

-continued

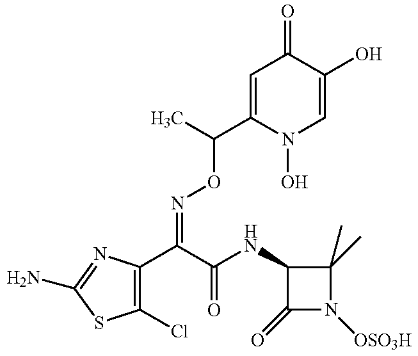

Compound 22

Step 1: Preparation of I-3-22

According to a method similar to that in step 1 of Example 1, a pale yellow solid compound I-3-22 (348 mg, yield 66.3%) was prepared from compound a-5-1 (340 mg, 0.65 mmol) and I-1-2 (191 mg, 0.62 mmol).

$^1H$ NMR (400 MHz, DMSO-d6) δ 12.05 (s, 1H), 7.63 (s, 1H), 7.49-7.08 (m, 20H), 6.33 (s, 1H), 6.28 (s, 1H), 6.05 (s, 1H), 5.19 (q, J=6.6 Hz, 1H), 1.46 (s, 9H), 1.17 (d, J=6.6 Hz, 3H).

MS (ESI): m/z 805.1, $[M-H]^-$.

Step 2: Preparation of I-5-22

According to a method similar to that in step 2 of Example 1, a white solid compound I-5-22 (333 mg, yield 81.6%) was prepared from compound I-3-22 (330 mg, 0.41 mmol) and I-4 (112 mg, 0.53 mmol).

$^1H$ NMR (400 MHz, DMSO-d6) δ 9.60 (dd, J=7.7, 3.2 Hz, 1H), 7.60 (s, 1H), 7.45-7.02 (m, 20H), 6.32 (s, 1H), 6.26 (s, 1/2H), 6.25 (s, 1/2H), 6.15 (s, 1/2H), 6.03 (s, 1/2H), 5.24-5.08 (m, 1H), 4.56 (d, J=8.3 Hz, 1/2H), 4.52 (d, J=7.6 Hz, 1/2H), 1.46 (s, 9H), 1.41 (s, 3/2H), 1.39 (s, 3/2H), 1.18 (s, 3/2H), 1.17 (s, 3/2H), 1.10 (d, J=6.0 Hz, 3/2H), 1.03 (d, J=6.1 Hz, 3/2H).

MS (ESI): m/z 997.1, $[M-H]^-$.

Step 3: Preparation of Compound 22

According to a method similar to that in step 3 of Example 1, a white solid compound 22 (140 mg, yield 77.2%) was prepared from compound I-5-22 (320 mg, 0.32 mmol) and trifluoroacetic acid (2.3 mL, 32.0 mmol).

$^1H$ NMR (400 MHz, DMSO-d6) δ 9.69 (d, J=7.8 Hz, 1/2H), 9.59 (d, J=7.9 Hz, 1/2H), 8.22 (s, 1H), 7.18 (s, 1/2H), 7.01 (s, 1/2H), 5.68-5.58 (m, 1H), 4.61 (d, J=7.8 Hz, 1/2H), 4.58 (d, J=7.9 Hz, 1/2H), 1.50 (t, J=7.0 Hz, 3H), 1.46 (s, 3/2H), 1.44 (s, 3/2H), 1.32 (s, 3/2H), 1.27 (s, 3/2H).

MS (ESI): m/z 565.0, $[M-H]^-$.

Example 23: Preparation of (3S)-3-((Z)-2-(5-amino-1,2,4-thiadiazol-3-yl)-2-((1-(1,5-dihydroxy-4-oxo-1,4-dihydropyridin-2-yl)ethoxy)imine)acetamido)-2,2-dimethyl-4-oxoazetidine-1-hydrogen sulfate (Compound 23)

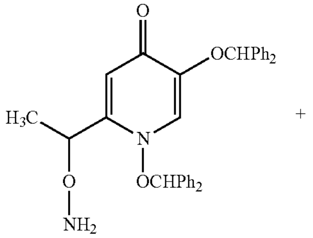

a-5-1

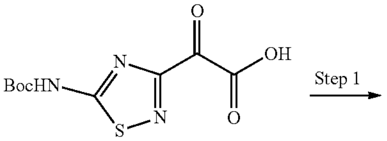

I-1-3

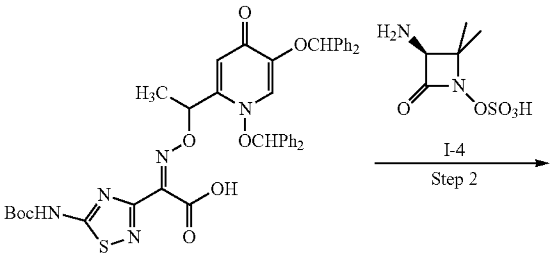

I-3-23

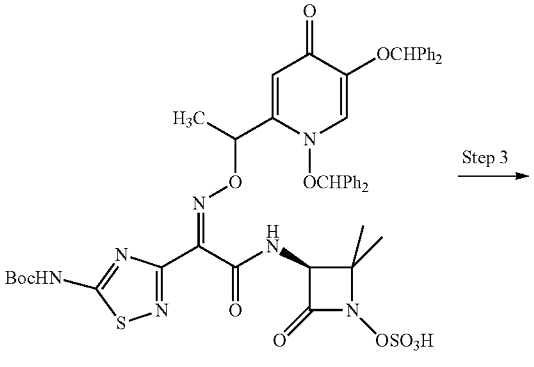

I-5-23

-continued

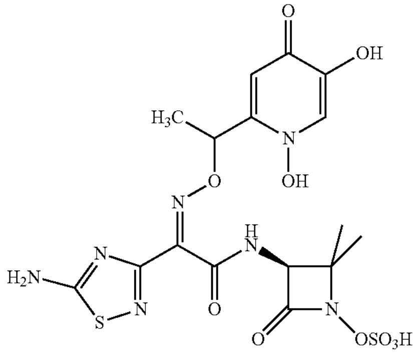

Compound 23

Step 1: Preparation of I-3-23

According to a method similar to that in step 1 of Example 1, a pale yellow solid compound I-3-23 (188 mg, yield 32.4%) was prepared from compound a-5-1 (387 mg, 0.75 mmol) and I-1-3 (136 mg, 0.50 mmol).

$^1$H NMR (400 MHz, DMSO-d6) δ 12.59 (s, 1H), 7.44 (s, 1H), 7.42-7.32 (m, 20H), 6.42 (s, 1H), 6.20 (s, 1H), 6.09 (s, 1H), 5.21 (q, J=6.9 Hz, 1H), 1.50 (s, 9H), 1.24 (d, J=6.9 Hz, 3H).

MS (ESI): m/z 772.1, [M−H]$^-$.

Step 2: Preparation of I-5-23

According to a method similar to that in step 2 of Example 1, a white solid compound I-5-23 (200 mg, yield 87.7%) was prepared from compound I-3-23 (183 mg, 0.24 mmol) and I-4 (74.5 mg, 0.36 mmol).

$^1$H NMR (400 MHz, DMSO-d6) δ 12.61 (s, 1H), 9.62 (d, J=7.7 Hz, 1H), 7.52 (s, 1/2H), 7.47 (s, 1/2H), 7.42-7.11 (m, 20H), 6.31 (s, 1H), 6.23 (s, 1/2H), 6.20 (s, 1/2H), 6.09 (s, 1/2H), 6.00 (s, 1/2H), 5.25-5.08 (m, 1H), 4.57 (d, J=8.0 Hz, 1/2H), 4.54 (d, J=7.7 Hz, 1/2H), 1.46 (s, 9H), 1.38 (s, 3/2H), 1.37 (s, 3/2H), 1.20-1.16 (m, 3H), 1.14 (s, 3/2H), 1.13 (s, 3/2H).

MS (ESI): m/z 964.1, [M−H]$^-$.

Step 3: Preparation of Compound 23

According to a method similar to that in step 3 of Example 1, a white solid compound 23 (89 mg, yield: 80.1%) was prepared from compound I-5-23 (200 mg, 0.21 mmol) and trifluoroacetic acid (1.5 mL, 21.0 mmol).

$^1$H NMR (400 MHz, DMSO-d6) δ 9.68 (d, J=7.6 Hz, 1/2H), 9.64 (d, J=7.7 Hz, 1/2H), 8.00 (s, 1H), 6.96 (s, 1/2H), 6.80 (s, 1/2H), 5.72-5.59 (m, 1H), 4.64 (d, J=7.6 Hz, 1/2H), 4.62 (d, J=7.7 Hz, 1/2H), 1.47 (t, J=3.4 Hz, 3H), 1.45 (s, 3/2H), 1.41 (s, 3/2H), 1.32 (s, 3/2H), 1.29 (s, 3/2H).

MS (ESI): m/z 532.0, [M−H]$^-$.

Example 24: Preparation of (3S)-3-((Z)-2-(2-amino-5-chlorothiazol-4-yl)-2-((1-(1,5-dihydroxy-4-oxo-1,4-dihydropyridin-2-yl)-2-methylpropoxy)imine)acetamido)-2,2-dimethyl-4-oxoazetidine-1-hydrogen sulfate (Compound 24)

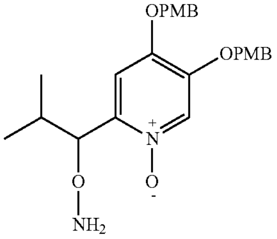

+ f-5

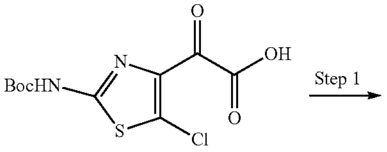

I-1-2

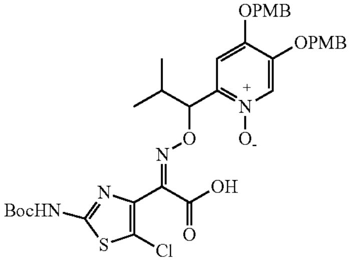

I-3-24

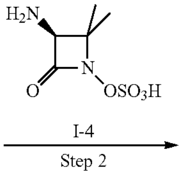

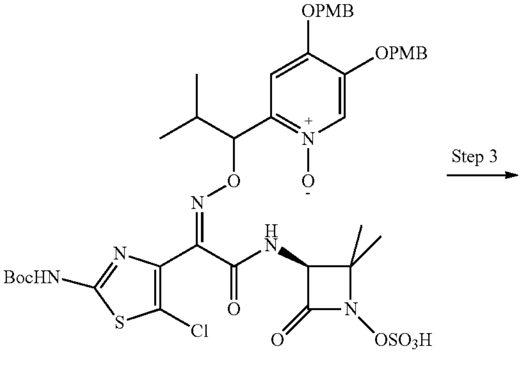

I-5-24

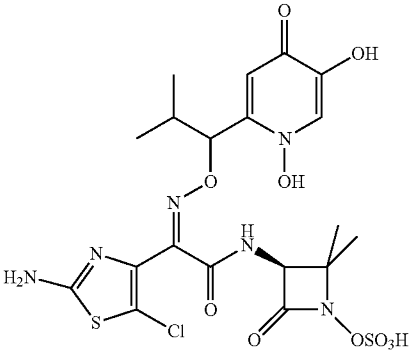

Compound 24

Step 1: Preparation of I-3-24

According to a method similar to that in step 1 of Example 1, a pale yellow solid compound I-3-24 (250 mg, yield 50.9%) was prepared from compound f-5 (300 mg, 0.66 mmol) and I-1-2 (182 mg, 0.59 mmol).

$^1$H NMR (400 MHz, DMSO-d6) δ 11.90 (s, 1H), 7.97 (s, 1H), 7.75 (s, 1H), 7.40 (d, J=8.5 Hz, 2H), 7.29 (d, J=8.6 Hz, 2H), 6.92 (d, J=8.6 Hz, 2H), 6.80 (d, J=8.5 Hz, 2H), 5.39-5.35 (m, 1H), 5.35-5.17 (m, 2H), 5.06-4.96 (m, 2H), 3.74 (s, 3H), 3.69 (s, 3H), 2.36-2.21 (m, 1H), 1.45 (s, 9H), 1.03 (d, J=6.8 Hz, 3H), 0.74 (d, J=6.9 Hz, 3H).

MS (ESI): m/z 741.1, $[M-H]^-$.

Step 2: Preparation of I-5-24

According to a method similar to that in step 2 of Example 1, a white solid compound I-5-24 (368 mg, yield: 86.1%) was prepared from compound I-3-24 (340 mg, 0.46 mmol) and I-4 (144 mg, 0.69 mmol).

$^1$H NMR (400 MHz, DMSO-d6) δ 12.11 (s, 1/2H), 12.05 (s, 1/2H), 9.82 (d, J=7.6 Hz, 1/2H), 9.70 (d, J=8.1 Hz, 1/2H), 8.08 (s, 1/2H), 8.05 (s, 1/2H), 7.35-7.31 (m, 4H), 7.07 (s, 1/2H), 6.97 (s, 1/2H), 6.96-6.92 (m, 2H), 6.84 (d, J=8.7 Hz, 1H), 6.79 (d, J=8.6 Hz, 1H), 5.54 (d, J=4.1 Hz, 1/2H), 5.48 (d, J=4.3 Hz, 1/2H), 5.26-5.13 (m, 2H), 5.12-5.00 (m, 2H), 4.75 (d, J=8.1 Hz, 1/2H), 4.70 (d, J=7.6 Hz, 1/2H), 3.75 (d, J=1.3 Hz, 3H), 3.70 (s, 3/2H), 3.68 (s, 3/2H), 2.31-2.19 (m, 1H), 1.50 (s, 3/2H), 1.47 (s, 3/2H), 1.46 (d, J=1.1 Hz, 9H), 1.39 (s, 3/2H), 1.36 (s, 3/2H), 1.00 (dd, J=7.0, 1.4 Hz, 3H), 0.75 (d, J=6.9 Hz, 3/2H), 0.70 (d, J=7.0 Hz, 3/2H).

MS (ESI): m/z 933.1, $[M-H]^-$.

Step 3: Preparation of Compound 24

According to a method similar to that in step 3 of Example 1, a white solid compound 24 (132 mg, yield 58.2%) was prepared from compound I-5-24 (357 mg, 0.38 mmol) and trifluoroacetic acid (2.8 mL, 38.0 mmol).

$^1$H NMR (600 MHz, DMSO-d6) δ 9.64 (d, J=7.6 Hz, 1/2H), 9.54 (d, J=7.9 Hz, 1/2H), 8.22 (s, 1/2H), 8.21 (s, 1/2H), 7.05 (s, 1/2H), 7.02 (s, 1/2H), 5.45-5.43 (m, 1/2H), 5.37-5.34 (m, 1/2H), 4.64-4.60 (m, 1H), 2.24-2.12 (m, 1H), 1.46 (s, 3/2H), 1.45 (s, 3/2H), 1.34 (s, 3/2H), 1.33 (s, 3/2H), 0.97-0.89 (m, 6H).

MS (ESI): m/z 593.0, $[M-H]^-$.

Example 25: Preparation of (3S)-3-((Z)-2-(5-amino-1,2,4-thiadiazol-3-yl)-2-((1-(1,5-dihydroxy-4-oxo-1,4-dihydropyridin-2-yl)-2-methylpropoxy)imine)acetamido)-2,2-dimethyl-4-oxoazetidine-1-hydrogen sulfate (Compound 25)

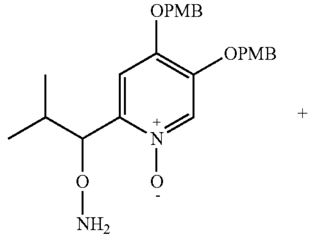

f-5

-continued

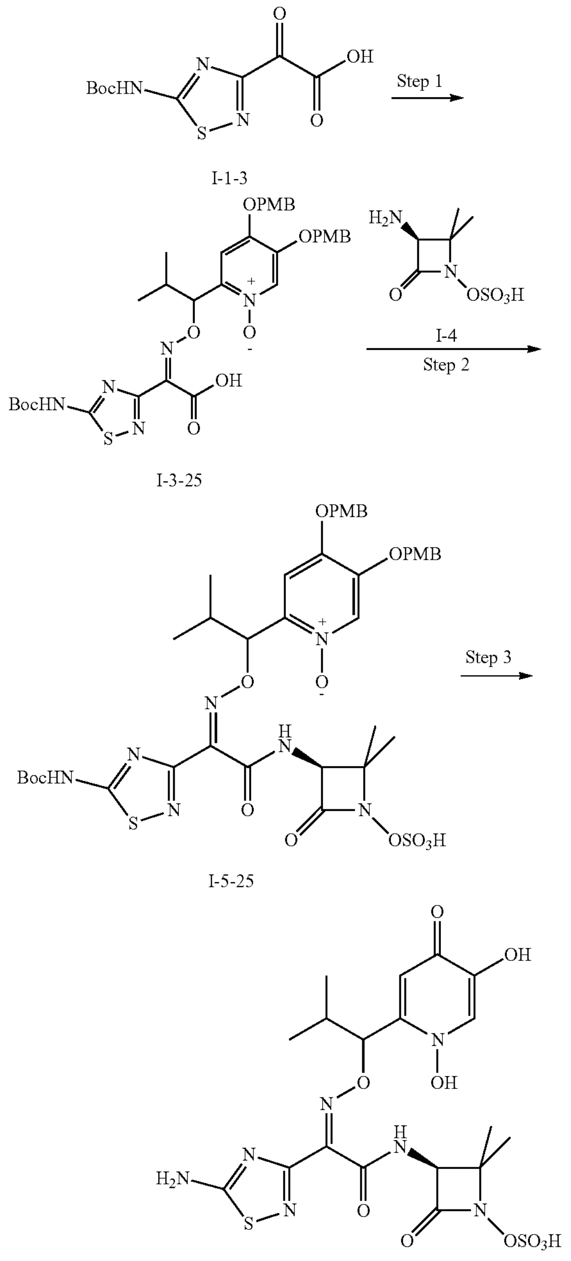

Compound 25

Step 1: Preparation of I-3-25

According to a method similar to that in step 1 of Example 1, a pale yellow solid compound I-3-25 (250 mg, yield 53.3%) was prepared from compound f-5 (300 mg, 0.66 mmol) and I-1-3 (108 mg, 0.40 mmol).

$^1$H NMR (400 MHz, DMSO-d6) δ 12.61 (s, 1H), 8.12 (s, 1H), 7.33 (d, J=8.1 Hz, 2H), 7.26 (d, J=8.0 Hz, 2H), 6.94 (d, J=7.9 Hz, 2H), 6.88 (s, 1H), 6.75 (d, J=8.1 Hz, 2H), 5.58 (s, 1H), 5.19-4.99 (m, 4H), 3.75 (s, 3H), 3.65 (s, 3H), 2.31-2.18 (m, 1H), 1.49 (s, 9H), 1.00 (d, J=6.7 Hz, 3H), 0.78 (d, J=6.7 Hz, 3H).

MS (ESI): m/z 708.1, [M−H]⁻.

Step 2: Preparation of I-5-25

According to a method similar to that in step 2 of Example 1, a white solid compound I-5-25 (385 mg, yield 86.6%) was prepared from compound I-3-25 (350 mg, 0.49 mmol) and I-4 (156 mg, 0.74 mmol).

$^1$H NMR (400 MHz, DMSO-d6) δ 12.59 (s, 1/2H), 12.58 (s, 1/2H), 9.85 (d, J=7.6 Hz, 1/2H), 9.77 (d, J=7.9 Hz, 1/2H), 8.10 (s, 1/2H), 8.08 (s, 1/2H), 7.37-7.27 (m, 4H), 6.98-6.92 (m, 5/2H), 6.86 (s, 1/2H), 6.80 (d, J=8.4 Hz, 1H), 6.74 (d, J=8.4 Hz, 1H), 5.59 (d, J=4.0 Hz, 1/2H), 5.53 (d, J=4.5 Hz, 1/2H), 5.25-5.00 (m, 4H), 4.77-4.74 (m, 1H), 3.75 (d, J=1.4 Hz, 3H), 3.68 (s, 3/2H), 3.67 (s, 3/2H), 2.27-2.12 (m, 1H), 1.51-1.48 (m, 12H), 1.40 (s, 3/2H), 1.38 (s, 3/2H), 0.99 (dd, J=6.9, 3.8 Hz, 3H), 0.76 (d, J=6.9 Hz, 3/2H), 0.71 (d, J=6.9 Hz, 3/2H).

MS (ESI): m/z 900.0, [M−H]⁻.

Step 3: Preparation of Compound 25

According to a method similar to that in step 3 of Example 1, a white solid compound 25 (100 mg, yield 67.7%) was prepared from compound I-5-25 (237 mg, 0.26 mmol) and trifluoroacetic acid (1.9 mL, 26.3 mmol).

$^1$H NMR (500 MHz, DMSO-d6) δ 9.66 (d, J=7.7 Hz, 1/2H), 9.61 (d, J=7.7 Hz, 1/2H), 8.21 (s, 1/2H), 8.20 (s, 1/2H), 8.12 (d, J=8.8 Hz, 2H), 6.97 (d, J=3.9 Hz, 1H), 5.51 (d, J=5.1 Hz, 1/2H), 5.42 (d, J=5.8 Hz, 1/2H), 4.67 (d, J=7.9 Hz, 1/2H), 4.64 (d, J=7.7 Hz, 1/2H), 2.23-2.10 (m, 1H), 1.47 (s, 3/2H), 1.46 (s, 3/2H), 1.34 (s, 3/2H), 1.33 (s, 3/2H), 1.01-0.95 (m, 3H), 0.93-0.86 (m, 3H).

MS (ESI): m/z 560.0, [M−H]⁻.

Example 26: Preparation of (S)-3-((Z)-2-(2-amino-5-chlorothiazol-4-yl)-2-(((S)-1-(1,5-dihydroxy-4-oxo-1,4-dihydropyridin-2-yl)ethoxy)imine)acetamido)-2,2-dimethyl-4-oxoazetidine-1-hydrogen sulfate (Compound 26)

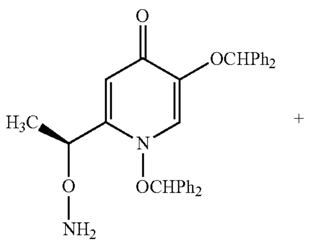

b-6

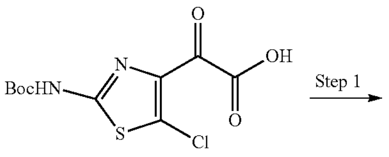

I-1-2

-continued

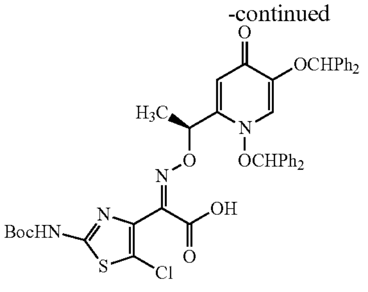

I-3-26

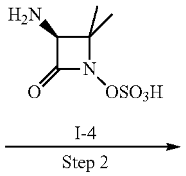

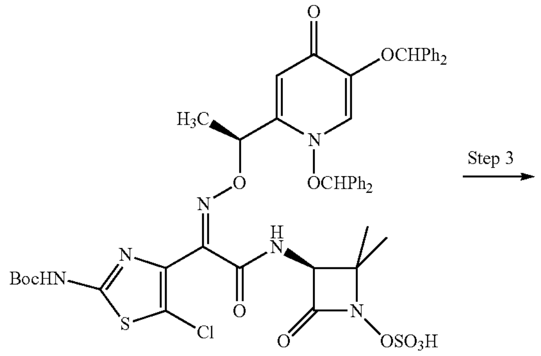

I-5-26

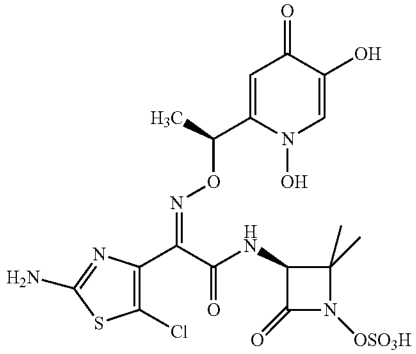

Compound 26

Step 1: Preparation of I-3-26

According to a method similar to that in step 1 of Example 1, a pale yellow solid compound I-3-26 (520 mg, yield 83.7%) was prepared from compound b-6 (400 mg, 0.77 mmol) and I-1-2 (224 mg, 0.73 mmol).

$^1$H NMR (400 MHz, DMSO-d6) δ 12.01 (s, 1H), 7.49 (s, 1H), 7.44-7.14 (m, 20H), 6.36 (s, 1H), 6.25 (s, 1H), 6.13 (s, 1H), 5.16 (q, J=6.6 Hz, 1H), 1.47 (s, 9H), 1.19 (d, J=6.6 Hz, 3H).

MS (ESI): m/z 805.1, [M−H]⁻.

Step 2: Preparation of I-5-26

According to a method similar to that in step 2 of Example 1, a white solid compound I-5-26 (440 mg, yield 68.3%) was prepared from compound I-3-26 (520 mg, 0.64 mmol) and I-4 (203 mg, 0.97 mmol).

$^1$H NMR (400 MHz, DMSO-d6) δ 12.11 (s, 1H), 9.62 (d, J=7.8 Hz, 1H), 7.61 (s, 1H), 7.44-7.26 (m, 20H), 7.11 (s, 1H), 7.10 (s, 1H), 6.33 (s, 1H), 6.27 (s, 1H), 6.04 (s, 1H), 5.18 (q, J=6.6 Hz, 1H), 4.53 (d, J=7.8 Hz, 1H), 1.47 (s, 9H), 1.41 (s, 3H), 1.19 (s, 3H), 1.12 (d, J=6.6 Hz, 3H).

MS (ESI): m/z 997.1, [M−H]⁻.

Step 3: Preparation of Compound 26

According to a method similar to that in step 3 of Example 1, a white solid compound 26 (106 mg, yield 71.9%) was prepared from compound I-5-26 (260 mg, 0.26 mmol) and trifluoroacetic acid (2.0 mL, 26 mmol).

$^{1}$H NMR (600 MHz, DMSO-d6) δ 9.69 (d, J=7.6 Hz, 1H), 8.26 (s, 1H), 7.05 (s, 1H), 5.64 (q, J=6.7 Hz, 1H), 4.58 (d, J=7.6 Hz, 1H), 1.50 (d, J=6.6 Hz, 3H), 1.46 (s, 3H), 1.32 (s, 3H).

MS (ESI): m/z 565.0, [M−H]⁻.

Example 27: Preparation of (S)-3-((Z)-2-(5-amino-1,2,4-thiadiazol-3-yl)-2-(((S)-1-(1, 5-dihydroxy-4-oxo-1,4-dihydropyridin-2-yl)ethoxy)imine)acetamido)-2,2-dimethyl-4-oxoazetidine-1-hydrogen sulfate (Compound 27)

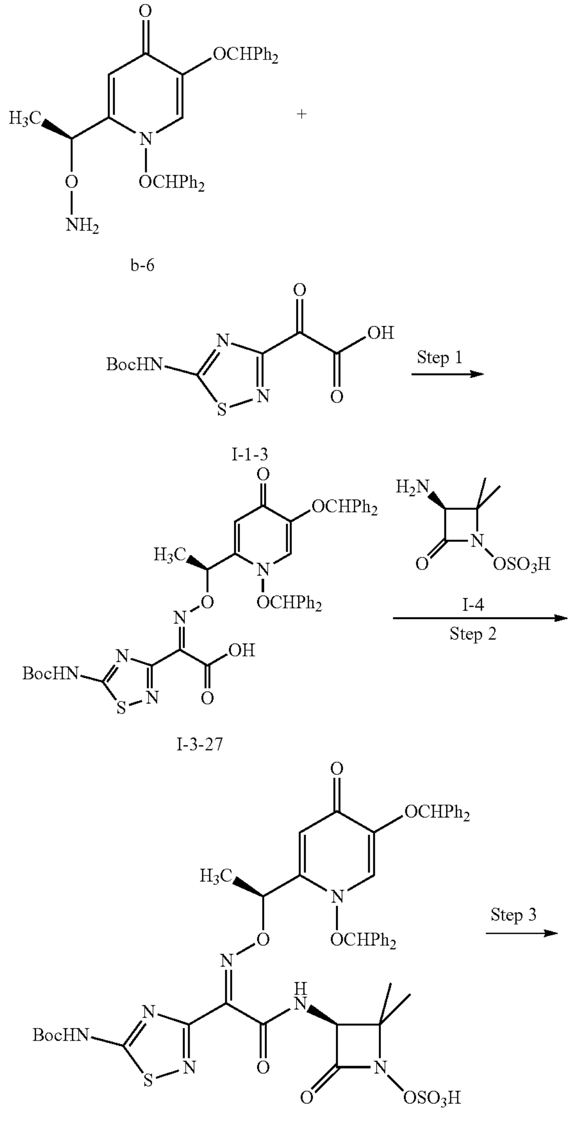

I-5-27

-continued

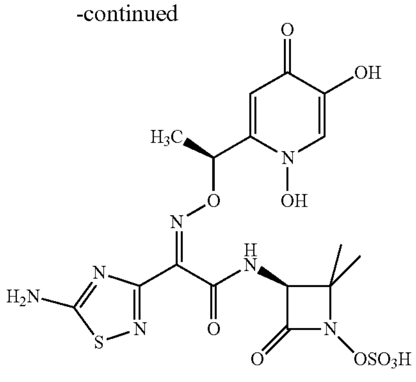

Compound 27

Step 1: Preparation of I-3-27

According to a method similar to that in step 1 of Example 1, a pale yellow solid compound I-3-27 (390 mg, yield 49.4%) was prepared from compound b-6 (527 mg, 1.02 mmol) and I-1-3 (250 mg, 0.91 mmol).

$^{1}$H NMR (400 MHz, DMSO-d6) δ 12.49 (s, 1H), 7.43-7.28 (m, 20H), 7.26 (s, 1H), 6.52 (s, 1H), 6.18 (s, 1H), 6.12 (s, 1H), 5.17 (q, J=6.8 Hz, 1H), 1.50 (s, 9H), 1.25 (d, J=6.8 Hz, 3H).

MS (ESI): m/z 772.1, [M−H]⁻.

Step 2: Preparation of I-5-27

According to a method similar to that in step 2 of Example 1, a white solid compound I-5-27 (300 mg, yield 77.6%) was prepared from compound I-3-27 (310 mg, 0.4 mmol) and I-4 (126 mg, 0.6 mmol).

$^{1}$H NMR (400 MHz, DMSO-d6) δ 12.66 (s, 1H), 9.66 (d, J=7.6 Hz, 1H), 7.51 (s, 1H), 7.44-7.16 (m, 20H), 6.35 (s, 1H), 6.24 (s, 1H), 6.03 (s, 1H), 5.23 (q, J=6.6 Hz, 1H), 4.58 (d, J=7.6 Hz, 1H), 1.50 (s, 9H), 1.42 (s, 3H), 1.21 (d, J=6.6 Hz, 3H), 1.17 (s, 3H).

MS (ESI): m/z 964.1, [M−H]⁻.

Step 3: Preparation of Compound 27

According to a method similar to that in step 3 of Example 1, a white solid compound 27 (116 mg, yield: 65.9%) was prepared from compound I-5-27 (320 mg, 0.33 mmol) and trifluoroacetic acid (2.4 mL, 33.0 mmol).

$^{1}$H NMR (600 MHz, DMSO-d6) δ 9.70 (d, J=7.5 Hz, 1H), 8.25 (s, 1H), 8.15 (s, 2H), 7.00 (s, 1H), 5.69 (q, J=6.5 Hz, 1H), 4.63 (d, J=7.5 Hz, 1H), 1.50 (d, J=6.7 Hz, 3H), 1.47 (s, 3H), 1.32 (s, 3H).

MS (ESI): m/z 532.0, [M−H]⁻.

Example 28: Preparation of (3S)-3-((Z)-2-(2-aminothiazol-4-yl)-2-(((S)-1-(1,5-dihydroxy-4-oxo-1,4-Dihydropyridin-2-yl)-2-methylisopropyloxy)imine) acetamido)-2,2-dimethyl-4-oxoazetidine-1-hydrogen sulfate (Compound 28)

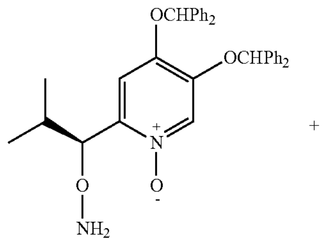

g-10-1

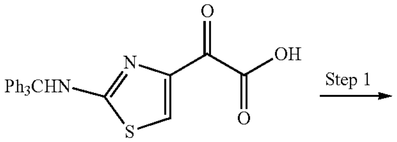

I-1

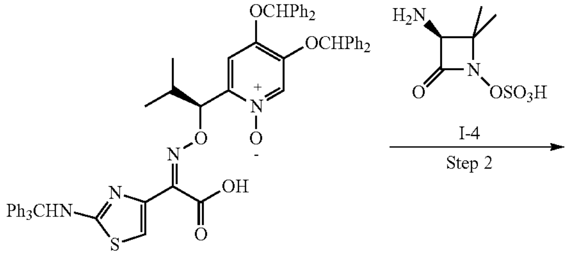

I-3-28

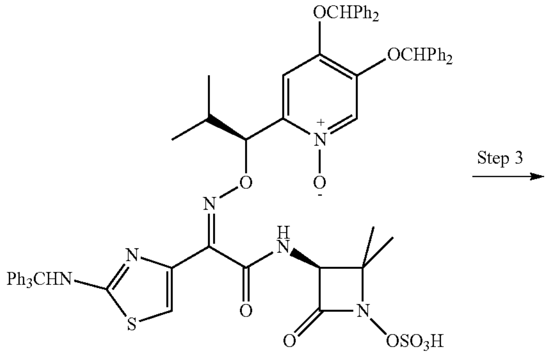

I-5-28

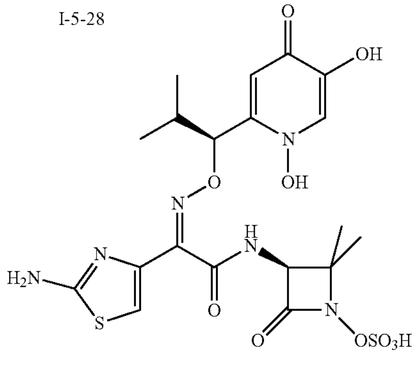

Compound 28

Step 1: Preparation of I-3-28

According to a method similar to that in step 1 of Example 1, a pale yellow solid compound I-3-28 (683 mg, yield: 82.5%) was prepared from compound g-10-1 (480 mg, 0.88 mmol) and I-1 (327 mg, 0.79 mmol).

$^1$H NMR (400 MHz, DMSO-d6) δ 8.90 (s, 1H), 7.99 (s, 1H), 7.62-7.16 (m, 35H), 6.95 (s, 1H), 6.90 (s, 1H), 6.69 (s, 1H), 6.54 (s, 1H), 5.28 (d, J=3.2 Hz, 1H), 2.12-2.00 (m, 1H), 0.90 (d, J=6.8 Hz, 3H), 0.43 (d, J=6.8 Hz, 3H).

MS (ESI): m/z 941.1, [M−H]⁻.

Step 2: Preparation of I-5-28

According to a method similar to that in step 2 of Example 1, a white solid compound I-5-28 (740 mg, yield 93.1%) was prepared from compound I-3-28 (663 mg, 0.70 mmol) and I-4 (221 mg, 1.05 mmol).

$^1$H NMR (400 MHz, DMSO-d6) δ 9.78 (d, J=7.8 Hz, 1H), 8.91 (s, 1H), 8.00 (s, 1H), 7.64-7.17 (m, 35H), 7.05 (s, 1H), 6.79 (s, 1H), 6.77 (s, 1H), 6.71 (s, 1H), 5.32 (d, J=3.3 Hz, 1H), 4.81 (d, J=7.8 Hz, 1H), 2.03-1.90 (m, 1H), 1.57 (s, 3H), 1.35 (s, 3H), 0.88 (d, J=6.9 Hz, 3H), 0.32 (d, J=7.0 Hz, 3H).

MS (ESI): m/z 1133.1, [M−H]⁻.

Step 3: Preparation of Compound 28

According to a method similar to that in step 3 of Example 1, a white solid compound 28 (135 mg, yield 71.9%) was prepared from compound I-5-28 (380 mg, 0.34 mmol) and trifluoroacetic acid (2.4 mL, 33.5 mmol).

$^1$H NMR (500 MHz, DMSO-d6) δ 9.71 (d, J=7.8 Hz, 1H), 8.24 (s, 1H), 7.03 (s, 1H), 6.85 (s, 1H), 5.45 (d, J=5.0 Hz, 1H), 4.71 (d, J=7.8 Hz, 1H), 2.22-2.13 (m, 1H), 1.48 (s, 3H), 1.35 (s, 3H), 0.98 (d, J=6.9 Hz, 3H), 0.88 (d, J=6.8 Hz, 3H).

MS (ESI): m/z 559.1, [M−H]⁻.

Example 29: Preparation of (3S)-3-((Z)-2-(2-amino-5-chlorothiazol-4-yl)-2-(((S)-1-(1,5-dihydroxy-4-oxo-1,4-dihydropyridin-2-yl)-2-methylpropoxy) imine)acetamido)-2,2-dimethyl-4-oxoazetidine-1-hydrogen sulfate (Compound 29)

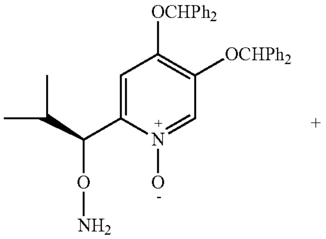

g-10-1

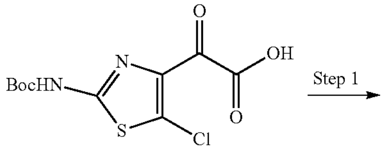

I-1-12

-continued

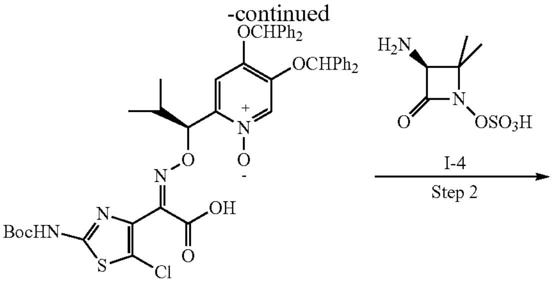

I-3-29

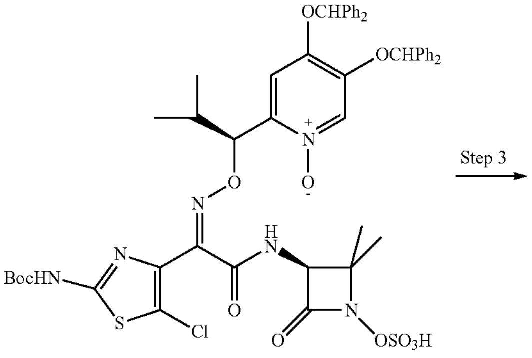

I-5-29

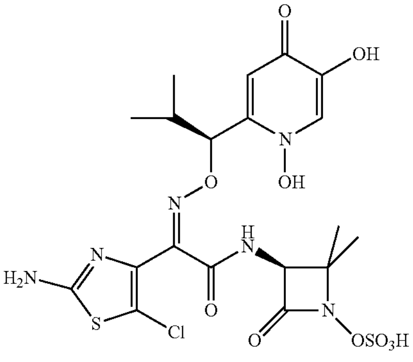

Compound 29

Step 1: Preparation of I-3-29

According to a method similar to that in step 1 of Example 1, a pale yellow solid compound I-3-29 (595 mg, yield 81.9%) was prepared from compound g-10-1 (475 mg, 0.87 mmol) and I-1-2 (239 mg, 0.78 mmol).

$^1H$ NMR (400 MHz, DMSO-d6) δ 12.00 (s, 1H), 7.96 (s, 1H), 7.68-7.16 (m, 22H), 6.68 (s, 1H), 5.31 (d, J=6.3 Hz, 1H), 2.17-2.06 (m, 1H), 1.46 (s, 9H), 0.92 (d, J=6.8 Hz, 3H), 0.47 (d, J=6.8 Hz, 3H).

MS (ESI): m/z 834.1, $[M-H]^-$.

Step 2: Preparation of I-5-29

According to a method similar to that in step 2 of Example 1, a white solid compound I-5-29 (640 mg, yield 89.8%) was prepared from compound I-3-29 (580 mg, 0.69 mmol) and I-4 (219 mg, 1.04 mmol).

$^1H$ NMR (400 MHz, DMSO-d6) δ 12.07 (d, J=3.9 Hz, 1H), 9.90 (d, J=8.0 Hz, 1H), 7.98 (s, 1H), 7.64-7.21 (m, 20H), 7.09 (s, 1H), 6.77 (s, 1H), 6.69 (s, 1H), 5.40 (d, J=3.4 Hz, 1H), 4.87 (d, J=8.0 Hz, 1H), 2.03 (td, J=7.0, 3.6 Hz, 1H), 1.59 (s, 3H), 1.45 (s, 9H), 1.40 (s, 3H), 0.89 (d, J=6.9 Hz, 3H), 0.38 (d, J=7.0 Hz, 3H).

MS (ESI): m/z 1025.1, $[M-H]^-$.

Step 3: Preparation of Compound 29

According to a method similar to that in step 3 of Example 1, a white solid compound 29 (145 mg, yield 81.2%) was prepared from compound I-5-29 (310 mg, 0.30 mmol) and trifluoroacetic acid (2.1 mL, 30 mmol).

$^1H$ NMR (500 MHz, DMSO-d6) δ 9.66 (d, J=7.8 Hz, 1H), 8.25 (s, 1H), 7.05 (s, 1H), 5.44 (d, J=5.8 Hz, 1H), 4.62 (d, J=7.7 Hz, 1H), 2.24-2.11 (m, 1H), 1.46 (s, 3H), 1.35 (s, 3H), 0.95 (d, J=7.0 Hz, 3H), 0.92 (d, J=6.9 Hz, 3H).

MS (ESI): m/z 593.0, $[M-H]^-$.

Example 30: Preparation of (3S)-3-((Z)-2-(5-amino-1,2,4-thiadiazol-3-yl)-2-(((S)-1-(1, 5-dihydroxy-4-oxo-1,4-dihydropyridin-2-yl)-2-methylpropoxy)imine)acetamido)-2,2-dimethyl-4-oxoazetidine-1-hydrogen sulfate (Compound 30)

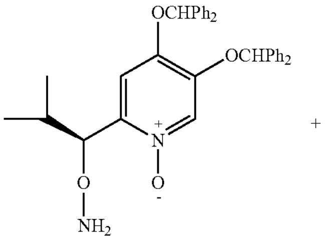

g-10-1

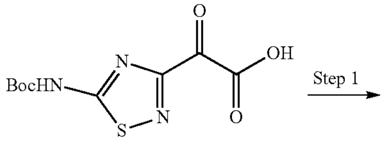

I-1-3

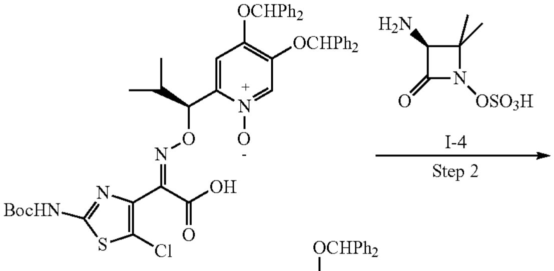

I-3-30

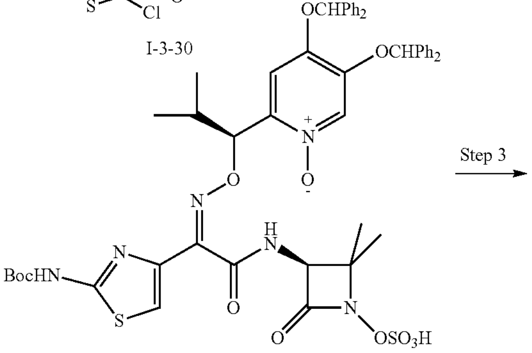

I-5-30

-continued

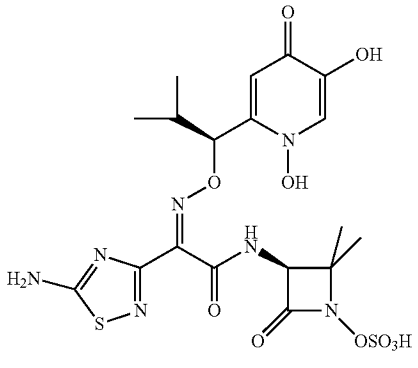

Compound 30

Step 1: Preparation of I-3-30

According to a method similar to that in step 1 of Example 1, a pale yellow solid compound I-3-30 (560 mg, yield 84.9%) was prepared from compound g-10-1 (450 mg, 0.82 mmol) and I-1-3 (224 mg, 0.82 mmol).

$^1$H NMR (400 MHz, DMSO-d6) δ 12.54 (s, 1H), 8.04 (s, 1H), 7.61-7.06 (m, 20H), 6.89 (s, 1H), 6.71 (s, 1H), 6.54 (s, 1H), 5.43 (d, J=3.8 Hz, 1H), 2.14-2.03 (m, 1H), 1.49 (s, 9H), 0.90 (d, J=6.8 Hz, 3H), 0.52 (d, J=6.9 Hz, 3H).

MS (ESI): m/z 800.1, [M−H]$^-$.

Step 2: Preparation of I-5-30

According to a method similar to that in step 2 of Example 1, a white solid compound I-5-30 (545 mg, yield 86.3%) was prepared from compound I-3-30 (510 mg, 0.64 mmol) and I-4 (200 mg, 0.95 mmol).

$^1$H NMR (400 MHz, DMSO-d6) δ 12.52 (s, 1H), 9.92 (d, J=7.7 Hz, 1H), 8.02 (s, 1H), 7.65-7.18 (m, 20H), 6.98 (s, 1H), 6.76 (s, 1H), 6.71 (s, 1H), 5.47 (d, J=3.5 Hz, 1H), 4.90 (d, J=7.7 Hz, 1H), 2.06-1.92 (m, 1H), 1.60 (s, 3H), 1.48 (s, 9H), 1.41 (s, 3H), 0.88 (d, J=6.8 Hz, 3H), 0.38 (d, J=6.9 Hz, 3H).

MS (ESI): m/z 992.1, [M−H]$^-$.

Step 3: Preparation of Compound 30

According to a method similar to that in step 3 of Example 1, a white solid compound 30 (140 mg, yield: 83.1%) was prepared from compound I-5-30 (298 mg, 0.30 mmol) and trifluoroacetic acid (2.1 mL, 30 mmol).

$^1$H NMR (500 MHz, DMSO-d6) δ 9.67 (d, J=7.7 Hz, 1H), 8.26 (s, 1H), 8.12 (s, 2H), 7.02 (s, 1H), 5.51 (d, J=5.2 Hz, 1H), 4.67 (d, J=7.6 Hz, 1H), 2.24-2.11 (m, 1H), 1.48 (s, 3H), 1.35 (s, 3H), 0.99 (d, J=6.7 Hz, 3H), 0.90 (d, J=6.8 Hz, 3H).

MS (ESI): m/z 559.9, [M−H]$^-$.

Example 31: Preparation of (3S)-3-((Z)-2-(2-aminothiazol-4-yl)-2-(((R)-1-(1,5-dihydroxy-4-oxo-1,4-dihydropyridin-2-yl)-2-methylisopropyloxy)imine) acetamido)-2,2-dimethyl-4-oxoazetidine-1-hydrogen sulfate (Compound 31)

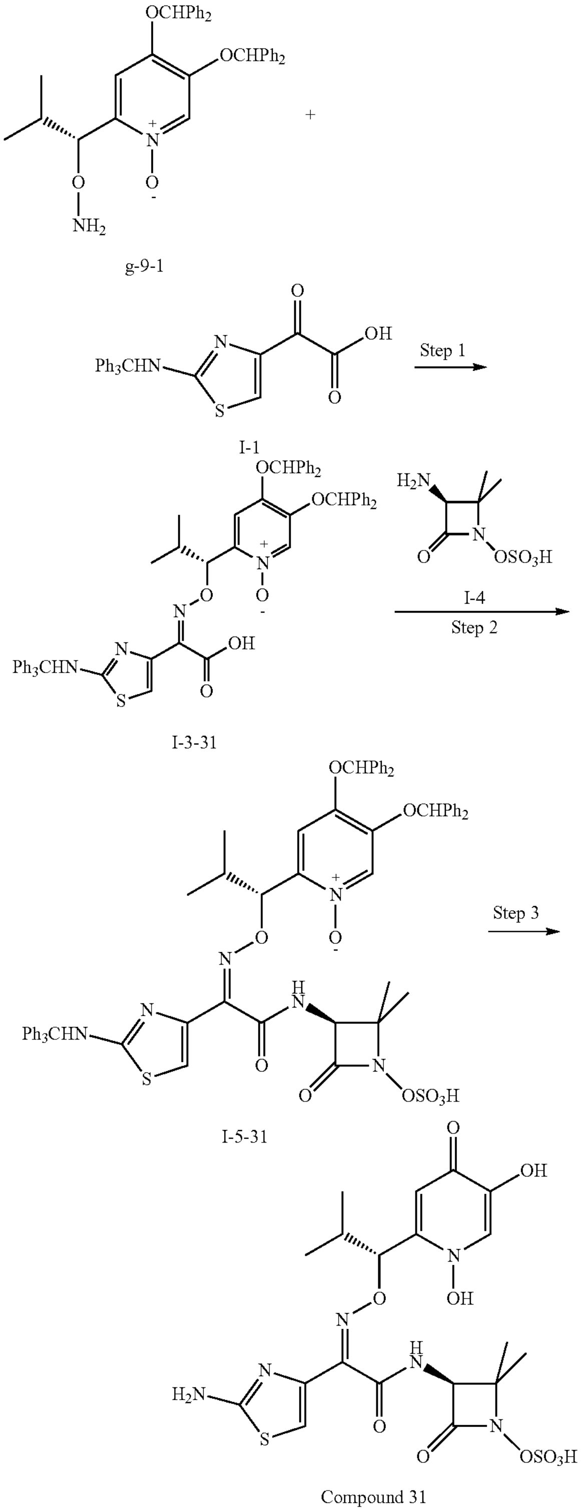

g-9-1

I-1

I-3-31

I-5-31

Compound 31

Step 1: Preparation of I-3-31

According to a method similar to that in step 1 of Example 1, a pale yellow solid compound I-3-31 (500 mg, yield 72.5%) was prepared from compound g-9-1 (400 mg, 0.73 mmol) and I-1 (242 mg, 0.59 mmol).

$^1$H NMR (400 MHz, DMSO-d6) δ 8.90 (s, 1H), 7.99 (s, 1H), 7.62-7.16 (m, 35H), 6.95 (s, 1H), 6.90 (s, 1H), 6.69 (s, 1H), 6.54 (s, 1H), 5.28 (d, J=3.2 Hz, 1H), 2.12-2.00 (m, 1H), 0.90 (d, J=6.8 Hz, 3H), 0.43 (d, J=6.8 Hz, 3H).

MS (ESI): m/z 941.1, $[M-H]^-$.

Step 2: Preparation of I-5-31

According to a method similar to that in step 2 of Example 1, a white solid compound I-5-31 (520 mg, yield 89.9%) was prepared from compound I-3-31 (480 mg, 0.51 mmol) and I-4 (160 mg, 0.76 mmol).

$^1$H NMR (400 MHz, DMSO-d6) δ 9.68 (d, J=7.1 Hz, 1H), 8.91 (s, 1H), 8.03 (s, 1H), 7.63-7.17 (m, 35H), 6.87 (s, 1H), 6.75 (s, 1H), 6.74 (s, 1H), 6.73 (s, 1H), 5.26 (d, J=3.8 Hz, 1H), 4.65 (d, J=7.1 Hz, 1H), 1.94-1.84 (m, 1H), 1.53 (s, 3H), 1.37 (s, 3H), 0.83 (d, J=6.8 Hz, 3H), 0.36 (d, J=6.9 Hz, 3H).

MS (ESI): m/z 1133.1, $[M-H]^-$.

Step 3: Preparation of Compound 31

According to a method similar to that in step 3 of Example 1, a white solid compound 31 (110 mg, yield 60.2%) was prepared from compound I-5-31 (370 mg, 0.33 mmol) and trifluoroacetic acid (2.35 mL, 32.6 mmol).

$^1$H NMR (600 MHz, DMSO-d6) δ 9.68 (d, J=7.8 Hz, 1H), 8.25 (s, 1H), 7.01 (s, 1H), 6.84 (s, 1H), 5.37 (d, J=5.5 Hz, 1H), 4.68 (d, J=7.7 Hz, 1H), 2.22-2.10 (m, J=6.7 Hz, 1H), 1.47 (s, 3H), 1.33 (s, 3H), 0.98 (d, J=6.9 Hz, 3H), 0.90 (d, J=6.8 Hz, 3H).

MS (ESI): m/z 559.1, $[M-H]^-$.

Example 32: Preparation of (3S)-3-((Z)-2-(2-amino-5-chlorothiazol-4-yl)-2-(((R)-1-(1,5-dihydroxy-4-oxo-1,4-dihydropyridin-2-yl)-2-methylpropoxy)imine)acetamido)-2,2-dimethyl-4-oxoazetidine-1-hydrogen sulfate (Compound 32)

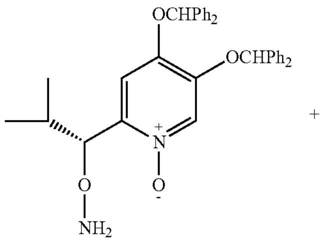

g-9-1

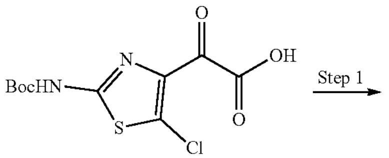

I-1-2

-continued

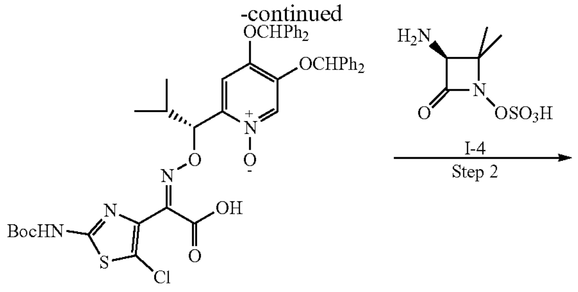

I-3-32

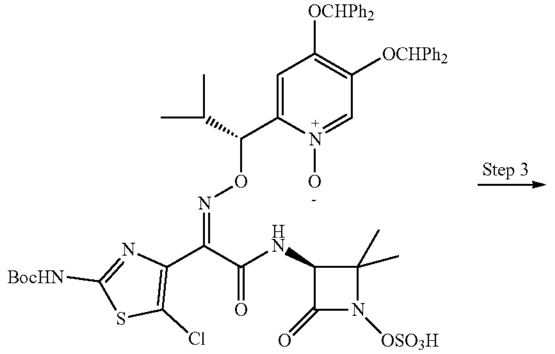

I-5-32

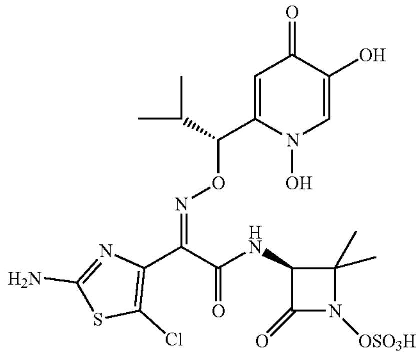

Compound 32

Step 1: Preparation of I-3-32

According to a method similar to that in step 1 of Example 1, a pale yellow solid compound I-3-32 (510 mg, yield 80.6%) was prepared from compound g-9-1 (415 mg, 0.76 mmol) and I-1-2 (209 mg, 0.68 mmol).

$^1$H NMR (400 MHz, DMSO-d6) δ 11.92 (s, 1H), 7.88 (s, 1H), 7.67-7.19 (m, 22H), 6.64 (s, 1H), 5.23 (s, 1H), 2.12 (s, 1H), 1.45 (s, 9H), 0.96 (d, J=6.9 Hz, 3H), 0.47 (d, J=7.0 Hz, 3H).

MS (ESI): m/z 834.1, $[M-H]^-$.

Step 2: Preparation of I-5-32

According to a method similar to that in step 2 of Example 1, a white solid compound I-5-32 (567 mg, yield: 90.1%) was prepared from compound I-3-32 (510 mg, 0.61 mmol) and I-4 (192 mg, 0.92 mmol).

$^1$H NMR (400 MHz, DMSO-d6) δ 12.03 (s, 1H), 9.79 (d, J=7.7 Hz, 1H), 8.01 (s, 1H), 7.62-7.19 (m, 22H), 6.94 (s, 1H), 6.74 (s, 1H), 6.72 (s, 1H), 5.33 (d, J=4.2 Hz, 1H), 4.73

(d, J=7.7 Hz, 1H), 1.98-1.90 (m, 1H), 1.54 (s, 3H), 1.45 (s, 9H), 1.42 (s, 3H), 0.82 (d, J=6.8 Hz, 3H), 0.45 (d, J=6.9 Hz, 3H).

MS (ESI): m/z 1025.1, $[M-H]^-$.

Step 3: Preparation of Compound 32

According to a method similar to that in step 3 of Example 1, a white solid compound 32 (130 mg, yield: 68.3%) was prepared from compound I-5-32 (330 mg, 0.32 mmol) and trifluoroacetic acid (2.4 mL, 32 mmol).

$^1H$ NMR (500 MHz, DMSO-d6) δ 9.56 (d, J=7.9 Hz, 1H), 8.26 (s, 1H), 7.07 (s, 1H), 5.35 (d, J=6.4 Hz, 1H), 4.62 (d, J=7.9 Hz, 1H), 2.18 (dp, J=13.6, 6.9, 6.4 Hz, 1H), 1.45 (s, 3H), 1.33 (s, 3H), 0.94 (t, J=6.3 Hz, 6H).

MS (ESI): m/z 593.0, $[M-H]^-$.

Example 33: Preparation of (3S)-3-((Z)-2-(5-amino-1,2,4-thiadiazol-3-yl)-2-(((R)-1-(1, 5-dihydroxy-4-oxo-1,4-dihydropyridin-2-yl)-2-methylpropoxy) imine)acetamido)-2,2-dimethyl-4-oxoazetidine-1-hydrogen sulfate (Compound 33)

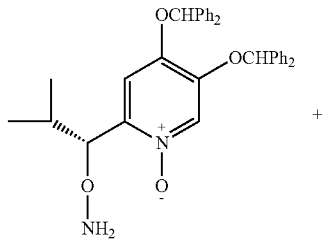

g-9-1

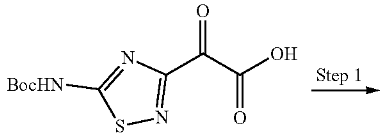

I-1-3

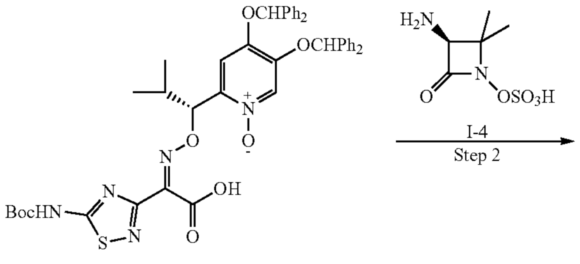

I-3-33

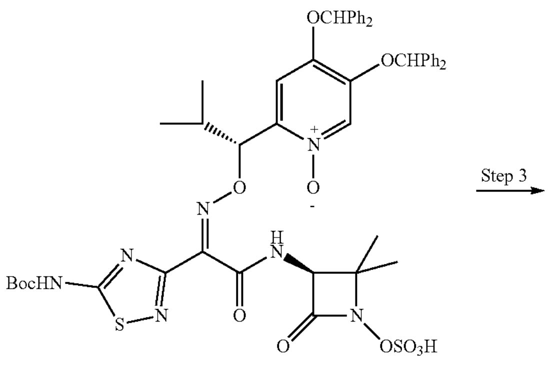

I-5-33

-continued

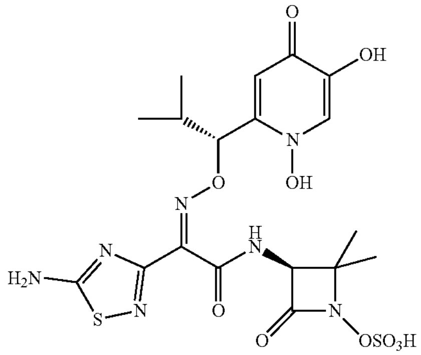

Compound 33

Step 1: Preparation of I-3-33

According to a method similar to that in step 1 of Example 1, a pale yellow solid compound I-3-33 (533 mg, yield 75.8%) was prepared from compound g-9-1 (480 mg, 0.88 mmol) and I-1-3 (240 mg, 0.88 mmol).

$^1H$ NMR (400 MHz, DMSO-d6) δ 12.54 (s, 1H), 8.04 (s, 1H), 7.61-7.06 (m, 20H), 6.89 (s, 1H), 6.71 (s, 1H), 6.54 (s, 1H), 5.43 (d, J=3.8 Hz, 1H), 2.14-2.02 (m, 1H), 1.49 (s, 9H), 0.90 (d, J=6.8 Hz, 3H), 0.52 (d, J=6.9 Hz, 3H).

MS (ESI): m/z 800.1, $[M-H]^-$.

Step 2: Preparation of I-5-33

According to a method similar to that in step 2 of Example 1, a white solid compound I-5-33 (520 mg, yield 81.8%) was prepared from compound I-3-33 (513 mg, 0.64 mmol) and I-4 (202 mg, 0.96 mmol).

$^1H$ NMR (400 MHz, DMSO-d6) δ 12.52 (s, 1H), 9.84 (d, J=7.2 Hz, 1H), 8.04 (s, 1H), 7.64-7.19 (m, 20H), 6.88 (s, 1H), 6.73 (s, 1H), 6.72 (s, 1H), 5.40 (d, J=4.3 Hz, 1H), 4.73 (d, J=7.2 Hz, 1H), 2.04-1.84 (m, 1H), 1.56 (s, 3H), 1.49 (s, 9H), 1.45 (s, 3H), 0.82 (d, J=6.9 Hz, 3H), 0.45 (d, J=6.9 Hz, 3H).

MS (ESI): m/z 992.1, $[M-H]^-$.

Step 3: Preparation of Compound 33

According to a method similar to that in step 3 of Example 1, a white solid compound 33 (100 mg, yield: 67.9%) was prepared from compound I-5-33 (260 mg, 0.26 mmol) and trifluoroacetic acid (1.8 mL, 26.2 mmol).

$^1H$ NMR (500 MHz, DMSO-d6) δ 9.62 (d, J=7.7 Hz, 1H), 8.26 (s, 1H), 8.10 (s, 2H), 7.02 (s, 1H), 5.42 (d, J=5.8 Hz, 1H), 4.64 (d, J=7.6 Hz, 1H), 2.16 (h, J=6.8 Hz, 1H), 1.46 (s, 3H), 1.33 (s, 3H), 0.98 (d, J=6.9 Hz, 3H), 0.92 (d, J=6.7 Hz, 3H).

MS (ESI): m/z 559.9, [M−H]⁻.

Example 34: Preparation of (3S)-3-((Z)-2-(2-aminothiazol-4-yl)-2-(((R)-1-(1,5-dihydroxy-4-oxo-1,4-dihydropyridin-2-yl)-2-(methylthio)ethoxy)imine) acetamido)-2,2-dimethyl-4-oxoazetidine-1-hydrogen sulfate (Compound 34)

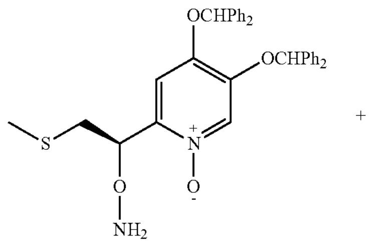

g-17-1

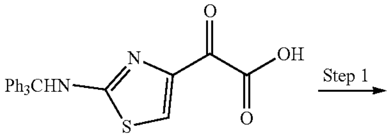

I-1

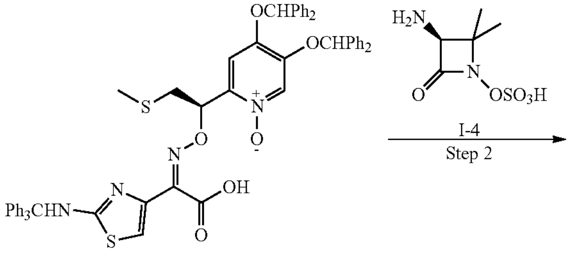

I-3-34

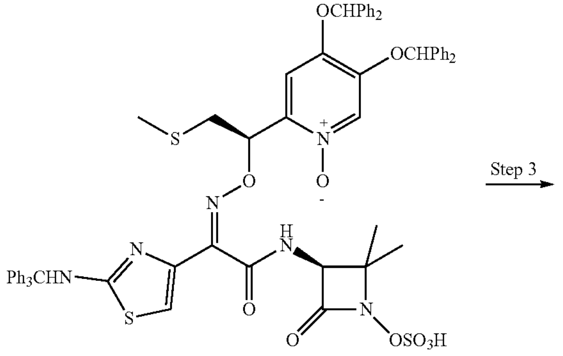

I-5-34

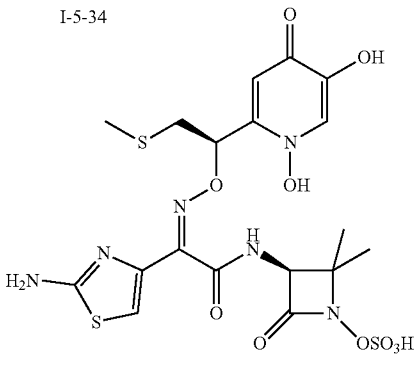

Compound 34

Step 1: Preparation of I-3-34

According to a method similar to that in step 1 of Example 1, a white solid compound I-3-34 (371 mg, yield 76.0%) was prepared from compound g-17-1 (287 mg, 0.51 mmol) and I-1 (200 mg, 0.48 mmol).

$^1$H NMR (400 MHz, DMSO-d6) δ 8.89 (s, 1H), 7.97 (s, 1H), 7.60-7.04 (m, 35H), 6.92 (s, 1H), 6.66 (s, 1H), 6.57 (s, 1H), 5.53 (dd, J=6.6, 3.0 Hz, 1H), 2.96 (dd, J=14.8, 3.0 Hz, 1H), 2.71 (dd, J=14.8, 6.7 Hz, 1H), 1.91 (s, 3H).

MS (ESI): m/z 959.2, [M−H]⁻.

Step 2: Preparation of I-5-34

According to a method similar to that in step 2 of Example 1, a pale yellow solid compound I-5-34 (335 mg, yield: 83.3%) was prepared from compound I-3-34 (336 mg, 0.35 mmol) and I-4 (110 mg, 0.52 mmol).

$^1$H NMR (400 MHz, DMSO-d6) δ 9.82 (d, J=7.7 Hz, 1H), 8.94 (s, 1H), 8.02 (s, 1H), 7.66-7.05 (m, 35H), 6.84 (s, 1H), 6.83 (s, 1H), 6.72 (s, 1H), 5.59 (dd, J=6.6, 3.0 Hz, 1H), 4.76 (d, J=7.7 Hz, 1H), 2.85 (dd, J=14.6, 3.0 Hz, 1H), 2.61 (dd, J=14.6, 6.6 Hz, 1H), 1.73 (s, 3H), 1.55 (s, 3H), 1.33 (s, 3H).

MS (ESI): m/z 1151.2, [M−H]⁻.

Step 3: Preparation of Compound 34

According to a method similar to that in step 3 of Example 1, a white solid compound 34 (118 mg, yield: 87.2%) was prepared from compound I-5-34 (270 mg, 0.23 mmol) and trifluoroacetic acid (1.7 mL, 23 mmol).

$^1$H NMR (400 MHz, DMSO-d6) δ 9.72 (d, J=7.9 Hz, 1H), 8.24 (s, 1H), 7.12 (s, 1H), 6.89 (s, 1H), 5.77 (dd, J=6.4, 3.9 Hz, 1H), 4.69 (d, J=7.8 Hz, 1H), 3.12-3.03 (m, 1H), 2.96 (dd, J=14.6, 6.5 Hz, 1H), 2.06 (s, 3H), 1.47 (s, 3H), 1.32 (s, 3H).

MS (ESI): m/z 576.9, [M−H]⁻.

Example 35: Preparation of (3S)-3-((Z)-2-(2-aminothiazol-4-yl)-2-(((S)-1-(1,5-dihydroxy-4-oxo-1,4-dihydropyridin-2-yl)-2-(methylthio)ethoxy)imine) acetamido)-2,2-dimethyl-4-oxoazetidine-1-hydrogen sulfate (Compound 35)

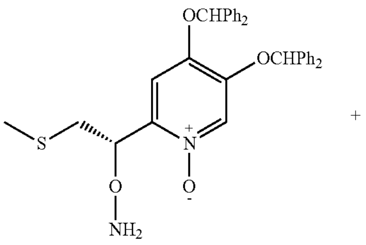

g-16-1

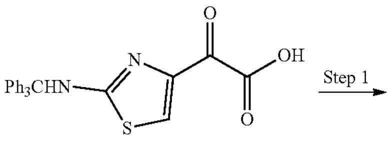

I-1

-continued

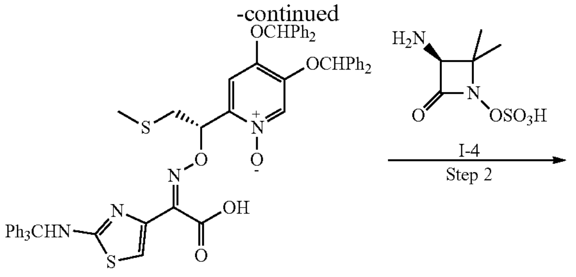

I-3-35

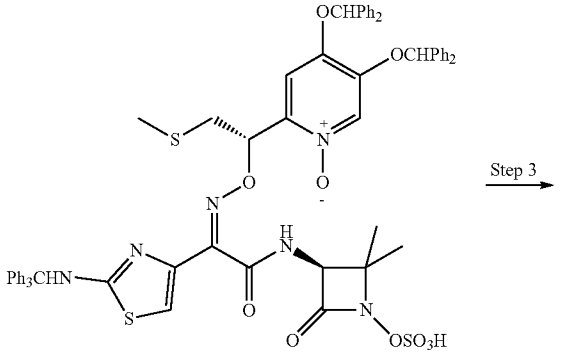

I-5-35

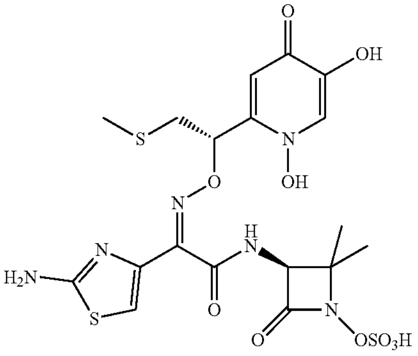

Compound 35

Step 1: Preparation of I-3-35

According to a method similar to that in step 1 of Example 1, a yellow solid compound I-3-35 (522 mg, yield: 85.3%) was prepared from compound g-16-1 (360 mg, 0.64 mmol) and I-1 (264 mg, 0.64 mmol).

$^1$H NMR (400 MHz, DMSO-d6) δ 8.93 (s, 1H), 8.00 (s, 1H), 7.63-7.05 (m, 35H), 6.94 (s, 1H), 6.70 (s, 1H), 6.57 (s, 1H), 5.54 (d, J=6.5 Hz, 1H), 2.97 (d, J=14.3 Hz, 1H), 2.71 (dd, J=14.9, 6.9 Hz, 1H), 1.93 (s, 3H).

MS (ESI): m/z 959.2, [M−H]$^-$.

Step 2: Preparation of I-5-35

According to a method similar to that in step 2 of Example 1, a pale yellow solid compound I-5-35 (505 mg, yield 91.7%) was prepared from compound I-3-35 (460 mg, 0.48 mmol) and I-4 (151 mg, 0.72 mmol).

$^1$H NMR (400 MHz, DMSO-d6) δ 9.79 (d, J=7.3 Hz, 1H), 8.90 (s, 1H), 8.02 (s, 1H), 7.63-7.18 (m, 35H), 6.80 (s, 1H), 6.77 (s, 1H), 6.71 (s, 1H), 5.56 (dd, J=6.8, 3.2 Hz, 1H), 4.65 (d, J=7.3 Hz, 1H), 2.82 (dd, J=14.8, 3.2 Hz, 1H), 2.58 (dd, J=14.8, 6.8 Hz, 1H), 1.86 (s, 3H), 1.51 (s, 3H), 1.35 (s, 3H).

MS (ESI): m/z 1151.2, [M−H]$^-$.

Step 3: Preparation of Compound 35

According to a method similar to that in step 3 of Example 1, a white solid compound 35 (109 mg, yield: 71.4%) was prepared from compound I-5-35 (304 mg, 0.26 mmol) and trifluoroacetic acid (1.9 mL, 26 mmol).

$^1$H NMR (600 MHz, DMSO-d6) δ 9.73 (d, J=7.8 Hz, 1H), 8.24 (s, 1H), 7.13 (s, 1H), 6.87 (d, J=1.3 Hz, 1H), 5.75 (dd, J=6.7, 4.1 Hz, 1H), 4.66 (d, J=7.8 Hz, 1H), 3.10 (dd, J=14.9, 4.1 Hz, 1H), 2.94 (dd, J=14.9, 6.8 Hz, 1H), 2.13 (s, 3H), 1.47 (s, 3H), 1.30 (s, 3H).

MS (ESI): m/z 576.9, [M−H]$^-$.

Example 36: Preparation of (3S)-3-((Z)-2-(2-aminothiazol-4-yl)-2-((1-(1,5-dihydroxy-4-oxo-1,4-dihydropyridin-2-yl)methylisopropyloxy)imine)acetamido)-2,2-dimethyl-4-oxoazetidine-1-sodium sulfate (Compound 36)

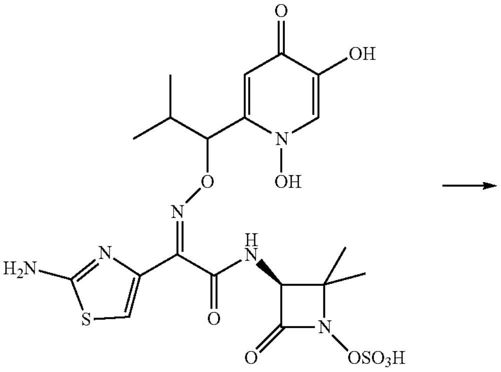

Compound 12

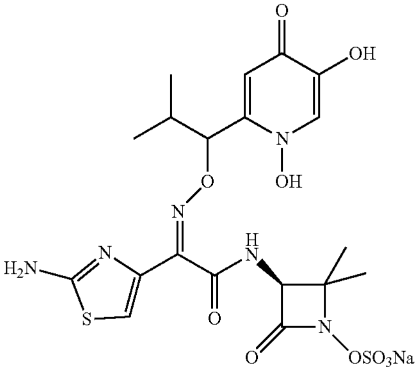

Compound 36

Compound 12 (100 mg, 0.18 mmol) was dissolved in water (10 mL), and 2 mL of an aqueous solution of sodium bicarbonate (15 mg, 0.18 mmol) was slowly added dropwise in an ice bath. After reacting for 10 min, the mixture was frozen at −70° C. and lyophilized to give compound 36 (99.6 mg, yield 95%) $^1$H NMR (500 MHz, DMSO-d6) δ 9.72 (d, J=7.9 Hz, 1/2H), 9.63 (d, J=7.5 Hz, 1/2H), 8.22 (s, 1/2H), 8.21 (s, 1/2H), 7.01 (s, 1/2H), 6.99 (s, 1/2H), 6.81 (s, 1/2H), 6.79 (s, 1/2H), 5.46 (d, J=4.8 Hz, 1/2H), 5.39 (d, J=5.4 Hz, 1/2H), 4.68 (d, J=7.9 Hz, 1/2H), 4.66 (d, J=7.6 Hz, 1/2H), 2.21-2.07 (m, 1H), 1.48 (s, 3/2H), 1.47 (s, 3/2H), 1.35 (s, 3/2H), 1.34 (s, 3/2H), 1.00-0.96 (m, 3H), 0.94-0.83 (m, 3H).

MS (ESI): m/z 559.1, $[M-Na]^-$.

Test Example 1: Experiments for Assaying the In Vitro Activity of Preferred Compounds Against Multidrug-Resistant Negative Bacteria 1.1 Test Strains and Culture Method Thereof 1.1.1 Test Strains The clinical isolated strains selected for in vitro antibacterial activity screening are shown in the following Table 1:

TABLE 1

Clinical isolated strains selected for in vitro antibacterial activity screening

| Name of the Strain | Number |
|---|---|
| *Escherichia coli* (ESBLs) | 4 |
| Multi-drug resistant *Klebsiella pneumoniae* (KPC2) | 4 |
| Multidrug-resistant *Acinetobacter baumannii* (integron I, OXA23) | 4 |
| Multidrug-resistant *Pseudomonas aeruginosa* (integrator I, IMP4) | 4 |

Supplier of the strains: all of the above strains were provided by Sichuan Primed Shines Bio-tech Co., Ltd. A single colony was isolated by streaking on agar plates for each strain prior to the experiment, and the cells freshly cultured at 37° C. overnight were appropriately diluted for the experiment.

Strain for quality control: *Escherichia coli* ATCC35218, purchased from National Center of Clinical Laboratory.

1.1.2 Medium and Culture Condition:

Medium: MH liquid medium (OXOID).

Culture condition: cells were incubated at 35-37° C. for 16-18 h.

1.2 Test Method for Antibacterial Activity In Vitro

The broth microdilution method recommended by Clinical and Laboratory Standards Institute (CLSI), Performance Standards for Antimicrobial Susceptibility Testing; Twenty-Third Informational Supplement, M02-All, M07-A9 and M11-A8, 2013 was used to determine the MIC value of each test sample against each test strain in the normal MH medium and iron-deficient MH medium.

1.2.1 MIC in Normal MH Medium

After diluting each sample to different concentrations with normal MH medium, 100 μl of each test sample solution at different concentrations was separately aspirated onto a 96-well sterile polystyrene plate. Drug solutions were added to the 1st to 10th well with the final concentrations of 16, 8, 4, 2, 1, 0.5, 0.25, 0.125, 0.06, and 0.03 mg/L in each well, respectively. The 11th well, as a blank control, was not added with drugs and bacteria. The 12th well, as a bacterial growth control, was added with bacteria but no drug.

The test bacterial liquid was adjusted to a bacterial suspension of 0.5 Mcfarland standard with physiological saline, and diluted with MH broth at 1:100, and then added to the drug solution so that a final concentration of the bacterial liquid was approximately $10^4$ CFU/ml; 100 μl of the bacterial liquid was further added to each of the above wells (the total volume in each well is 200 μl), which was sealed and placed in a 35-37° C. incubator for 18-20 h for testing the result. The $OD_{600}$ value was measured by a microplate reader, Minimal Inhibitory Concentration (MIC) of a drug is the lowest concentration of the drug which prevents growth of bacteria in the wells. 1.2.2 MIC in iron-deficient MH medium In the preliminary experiment, the optimum concentration of 2,2'-bipyridine (BPL) in the medium was determined to be 16 mg/L in the preparation of iron-deficient environment; such concentration (the MH medium containing 16 mg/L 2,2'-bipyridine (BPL)) did not affect the growth of each test bacteria. BPL was added to the normal MH medium to obtain a final concentration of 16 mg/L; According to the method in Section 1.2.1, 100 μl of each test sample solution at different concentrations was aspirated to the 1st to 10th well in a 96-well sterile polystyrene plate to obtain the final drug concentrations of 16, 8, 4, 2, 1, 0.5, 0.25, 0.125, 0.06, and 0.03 mg/L, respectively. Then, 100 μl of the test bacterial liquid was added to each well (200 μl per well), and the final concentration of the bacterial liquid was approximately $10^4$ CFU/ml. After sealing, it was placed in a 35-37° C. incubator for 18-20 hours for testing the result. The $OD_{600}$ value was measured by a microplate reader, Minimal Inhibitory Concentration (MIC) of a drug is the lowest concentration of the drug which prevents growth of bacteria in the wells.

1.3 Test Results of the In Vitro Activity of the Compounds of the Present Invention Against Multidrug-Resistant Negative Bacteria As the positive control groups, BAL30072, aztreonam, meropenem and ceftizoxime sodium were used. Among them, aztreonam is a marketed drug of monocyclic β-lactams, which is only effective against Gram-negative bacteria; meropenem is a marketed drug of carbapenems; ceftizoxime sodium is a marketed drug of the third-generation cephalosporins; BAL30072 is a monocyclic β-lactam-iron carrier conjugate in clinical phase I.

TABLE 2

Antibacterial activity MIC of the compounds of the present invention under normal MH medium condition (unit: mg/L)

| Compound | *Escherichia coli* ATCC 35218 | *Escherichia coli* (4 strains) | *Klebsiella pneumoniae* (4 strains) | *Acinetobacter baumarmii* (4 strains) | *Pseudomonas aeruginosa* (4 strains) |
|---|---|---|---|---|---|
| Compound 12 | <0.03 | 0.03-0.25 | 0.5-1 | 2 | 0.25-2 |
| Compound 16 | <0.03 | 0.125-0.5 | 0.5-1 | 1-2 | 0.25-2 |
| Compound 22 | <0.03 | 0.06-0.5 | 1 | 2 | 0.5-2 |
| Compound 26 | <0.03 | 0.25-1 | 1-4 | 1 | 0.5-1 |
| Compound 29 | <0.03 | 1-2 | 1-4 | 1-2 | 0.25-2 |

TABLE 2-continued

Antibacterial activity MIC of the compounds of the present invention under normal MH medium condition (unit: mg/L)

| Compound | *Escherichia coli* ATCC 35218 | *Escherichia coli* (4 strains) | *Klebsiella pneumoniae* (4 strains) | *Acinetobacter baumarmii* (4 strains) | *Pseudomonas aeruginosa* (4 strains) |
|---|---|---|---|---|---|
| BAL-30072 | 0.125 | 1 | ≥64 | 2-4 | 2 |
| aztreonam | 0.5 | 0.5-32 | >64 | >64 | 4-32 |
| meropenem | 0.125 | 0.25-32 | 32-64 | 64 | 32-64 |
| ceftizoxime sodium | 0.25 | 0.5-2 | 32-64 | 32-64 | >64 |

It can be seen from the data in Table 2 that under normal conditions, the compounds of the present invention have potent anti-negative bacteria activity in vitro, which is significantly better than the activity of the positive control drugs BAL-30072, aztreonam, meropenem and ceftizoxime sodium. More importantly, the antibacterial spectrum of the compounds of the invention covers the four most important multi-drug resistant Gram-negative bacteria, i.e., *Escherichia coli, Klebsiella pneumoniae, Acinetobacter baumannii* and *Pseudomonas aeruginosa.*

The compounds of the present invention also have potent antibacterial activity against multidrug-resistant *Klebsiella pneumoniae* (KPC2) which is resistant to BAL-30072, aztreonam, meropenem, and ceftizoxime sodium.

Compared to the positive control compound BAL30072, the compounds of the present invention have significantly more potent antibacterial activity against *Escherichia coli* and *Klebsiella pneumoniae*, for example:

The Example compound 12 is 4-32 times more effective than BAL30072 in its inhibitory activity against *Escherichia coli*; and 64-128 times more effective than BAL30072 in its inhibitory activity against *Klebsiella pneumoniae.*

The Example compound 16 is 2-8 times more effective than BAL30072 in its inhibitory activity against *Escherichia coli*; and 64-128 times more effective than BAL30072 in its inhibitory activity against *Klebsiella pneumoniae.*

The Example compound 22 is 4-16 times more effective than BAL30072 in its inhibitory activity against *Escherichia coli*; and 64 times more effective than BAL30072 in its inhibitory activity against *Klebsiella pneumoniae.*

TABLE 3

Antibacterial activity MIC of the compounds of the present invention under iron-deficient MH medium condition (unit: mg/L)

| Compound | *Escherichia coli* ATCC 35218 | *Escherichia coli* (4 strains) | *Klebsiella pneumoniae* (4 strains) | *Acinetobacter baumannii* (4 strains) | *Pseudomonas aeruginosa* (4 strains) |
|---|---|---|---|---|---|
| Compound 12 | <0.03 | 0.03-0.25 | 0.25-0.5 | 0.5-1 | 0.25-1 |
| Compound 16 | <0.03 | 0.06-0.25 | 0.5-1 | 0.5-1 | 0.125-1 |
| Compound 22 | <0.03 | 0.06-0.25 | 1 | 1 | 0.5-1 |
| Compound 24 | <0.03 | 0.06-0.25 | 0.125-0.5 | 1-2 | 0.25-2 |
| Compound 26 | <0.03 | 0.03-0.25 | 0.5-4 | 0.5-1 | 0.25-1 |
| Compound 28 | <0.03 | 0.125-0.25 | 1 | 1-2 | 0.125-1 |
| Compound 29 | <0.03 | 0.125-1 | 0.25-0.5 | 0.5-1 | 0.06-1 |
| BAL-30072 | 0.06 | 0.25-1 | ≥64 | 1-2 | 1-2 |

The 2,2'-bipyridine is used to simulate the real environment in the body by chelating the iron in the normal medium to create an iron-deficient environment, and bacteria is stimulated to secret a large amount of iron carrier to compete with 2,2'-bipyridine for iron in the substrate, which stimulates a unique iron-producing pathway of bacteria, facilitating the antibacterial action of iron-antibiotic conjugates. On the other hand, in humans or animals, free iron is bonded to transferrin, causing that a very low concentration of free iron could be used by bacteria, while iron-deficient medium supplemented with 2,2'-bipyridine exactly simulates the low iron environment in the body, thus, iron-deficient medium condition is considered to better reflect the antibacterial effects of the compounds.

The data in Table 3 shows that the in vitro anti-negative bacteria activity of the compounds of the present invention is further improved under iron-deficient condition as compared with normal condition, demonstrating the mechanism by which the iron carrier-antibiotic conjugate exerts an antibacterial effect.

Compared with the positive control compound BAL30072, the compounds of the present invention have significantly more superior effect against the four most important multidrug-resistant Gram-negative bacteria, i.e., *Escherichia coli, Klebsiella pneumoniae, Acinetobacter baumannii* and *Pseudomonas aeruginosa.*

The Example compound 12 is 128-256 times more effective than BAL30072 in the inhibitory activity against *Klebsiella pneumonia.*

The Example compound 16 is 64-128 times more effective than BAL30072 in the inhibitory activity against *Klebsiella pneumonia.*

The Example compound 22 is 64 times more effective than BAL30072 in the inhibitory activity against *Klebsiella pneumonia.*

The Example compound 24 is 128-512 times more effective than BAL30072 in the inhibitory activity against *Klebsiella pneumonia.*

The Example compound 26 is 16-128 times more effective than BAL30072 in the inhibitory activity against *Klebsiella pneumonia.*

The Example compound 28 is 64 times more effective than BAL30072 in the inhibitory activity against *Klebsiella pneumonia*.

The Example compound 29 is 128-256 times more effective than BAL30072 in the inhibitory activity against *Klebsiella pneumonia*.

In summary, compared with the existing drugs aztreonam, meropenem, ceftizoxime sodium and BAL30072, the compounds of the present invention have significantly more superior antibacterial activity in vitro against Gram-negative bacteria (including multidrug-resistant negative bacteria), thus they have more potent antibacterial activity and broader antibacterial spectrum. The compounds of the present invention also have potent antibacterial activity against multi-drug resistant *Klebsiella pneumoniae* (KPC2) which is resistant to BAL-30072, aztreonam, meropenem, and ceftizoxime sodium.

Test Example 2 Pharmacokinetic Test of the Compounds of the Present Invention in Rats 2.1 Test Scheme 2.1.1 Test drug: BAL30072, Example Compound 12.

2.1.2 Test animals: 6 SD rats, male, weight: 200-220 g.

2.1.3 Drug Preparation: an appropriate amount of the sample was weighed and prepared into a 0.2 mg/mL solution with water for injection.

2.1.4 Administration of the drug: 6 SD rats, male, weight: 200-220 g, were randomly divided into two groups, 3 rats in each group. After fasted for 12 h, the rats were administered intravenously with BAL30072 and Example Compound 14. The intravenous dose was 1.0 mg/kg, and the intravenous volume was 5 mL/kg.

2.2 Time Point for Blood Collection and Sample Processing

Intravenous administration: 2 min, 5 min, 15 min, 30 min, 45 min, 1 h, 1.5 h and 3 h after administration. At the above set time points, 0.3 ml of venous blood was taken from the posterior venous plexus of the rat eye, placed in a heparinized tube, centrifuged at 11,000 rpm for 5 min, then the plasma was separated and stored in a refrigerator at −20° C. All of the rats were fed 2 hours after administration.

2.3 Sample Testing and Data Analysis

The concentration of BAL30072 and Example Compound 12 in plasma of the rats was determined by LC/MS/MS method.

After administration, the pharmacokinetic parameters were calculated using a non-compartmental model of WinNonlin 5.3 software (Pharsight, USA).

2.4 Results of the Pharmacokinetic Parameters

TABLE 4

Pharmacokinetic parameters of the compounds of the invention

| Example | Area Under the Curve $AUC_{0-4}$ (ng · h/mL) | Residence Time MRT (h) | Half-life $T_{1/2}$ (h) | Clearance CL (L/h/kg) | Apparent Distribution Volume Vss (L/kg) |
|---|---|---|---|---|---|
| BAL30072 | 1714 ± 306 | 0.25 ± 0.02 | 0.27 ± 0.04 | 0.59 ± 0.09 | 0.14 ± 0.01 |
| Compound 12 | 1730 ± 697 | 0.51 ± 0.18 | 0.45 ± 0.11 | 0.66 ± 0.33 | 0.30 ± 0.03 |

The disadvantage of the compounds of the present invention is that the half-life is too short, which will be disadvantageous for the drug's efficacy, thus intravenous drip administration is generally recommended. The data in Table 4 shows that the area under the curve $AUC_{0-t}$ of the compounds of the present invention is slightly better than that of BAL30072, and the half-life, $T_{1/2}$ 0.45±0.11 h, is significantly longer than that of BAL30072. In summary, the compounds of the present invention have superior metabolic properties than BAL30072, and each metabolic parameter thereof is ideal.

Test Example 3 Test for the In Vivo Efficacy of the Compounds of the Present Invention Against Gram-Negative Bacteria in Mice 3.1 Test strains: Clinically isolated pathogenic *Escherichia coli* ECO-14-4 (ESBLs), supplied by Sichuan Primed Shines Bio-tech Co., Ltd.

3.2 Test animals: Kunming mice, age: 4 to 5 weeks, weight: 18 to 22 g, half male, half female, SPF grade.

3.3 Test methods: Mice were randomly divided into several groups, 5 mice for each group, half male and half female, and 5 doses for each test drug: 1.25, 2.5, 5, 10 and 20 mg/kg. The mice were intraperitoneally injected with 0.5 mL of 5.0×10 CFU/mL bacterial suspension for each mouse, and subcutaneously injected with the drug at the designed dose 0.5 h and 4 h after infection. The subcutaneous injection volume was 0.2 ml/20 g mouse weight; the number of deaths in mice was observed and recorded for 7 consecutive days. According to the number of deaths in mice, the half effective dose $ED_{50}$ was calculated according to the Bliss method using the DAS 1.0 software, edited by Sun Ruiyuan et al.

3.4 Test Results

TABLE 5

In vivo efficacy of Compound 12 on mice systemically infected with clinically isolated pathogenic *Escherichia coli* ECO-14-4 (ESBLs)

| Compound | $ED_{50}$ (mg/kg) Subcutaneous injection |
|---|---|
| Compound 12 | 3.37 |
| BAL30072 | 4.19 |

It can be seen from Table 5 that for the mice model systemically infected with the clinically isolated pathogenic *Escherichia coli* ECO-14-4 (ESBLs), the half effective dose $ED_{50}$ of compound 12 of the present invention is lower than that of the control drug BAL30072, and it is proved that that compound 12 of the present invention has a very good therapeutic effect on the mice systemically infected with the clinically isolated pathogenic *Escherichia coli*, its in vivo activity is better than that of the control drug BAL30072, and thus it is more effective.

Test Example 4 Test for In Vivo Efficacy of the Compounds of the Present Invention Against Multidrug-Resistant Gram-Negative Bacteria in Mice 4.1 Test strains: clinically isolated pathogenic multidrug-resistant *Klebsiella pneumoniae* KR15-4 (KPC2), provided by Sichuan Primed Shines Bio-tech Co., Ltd.

4.2 Test animals: Kunming mice, age: 4 to 5 weeks, weight: 18 to 22 g, half male, half female, SPF grade.

4.3 Test methods: Mice were randomly divided into several groups, 5 mice for each group, half male and half female, and 4 doses for each test drug: 12.5, 25, 50 and 100 mg/kg. The mice were intraperitoneally injected with 0.5 mL of $3.0\times10^6$ CFU/mL bacterial suspension for each mouse, and subcutaneously injected with the drug at the designed dose 0.5 h and 4 h after infection. The subcutaneous injection volume was 0.2 ml/20 g mouse weight; the number of deaths in mice was observed and recorded for 7 consecutive days. According to the number of deaths in mice, the half effective dose $ED_{50}$ was calculated according to the Bliss method using the DAS 1.0 software, edited by Sun Ruiyuan et al.

4.4 Test Results

TABLE 7

In vivo efficacy of Compound 12 on mice systemically infected with clinically isolated pathogenic multidrug-resistant *Klebsiella pneumoniae* KR15-4 (KPC2)

| Compound | $ED_{50}$ (mg/kg) Subcutaneous injection |
|---|---|
| Compound12 | 10.20 |
| BAL30072 | >100 |
| Meropenem | >100 |
| Aztreonam | >100 |

It can be seen from Table 7 that, compound 12 of the present invention exhibits potent protective effect in vivo for the mice model systemically infected with clinically isolated pathogenic multidrug-resistant *Klebsiella pneumoniae* KR15-4 (KPC2), and half effective dose $ED_{50}$ via subcutaneous injection was 10.20 mg/kg, while the marketed drugs meropenem and aztreonam and the control compound BAL30072 show no in vivo protective effects in the dose range, and their $ED_{50}$ values were greater than 100 mg/kg, indicating that compound 12 of the present invention has a very good therapeutic effect on the mice systemically infected with clinically isolated pathogenic multidrug-resistant *Klebsiella pneumoniae* KR15-4 (KPC2), thus the effect thereof is significantly better than those of the existing drugs, meropenem and aztreonam and the control compound BAL30072, it is further proved that compound 12 of the invention has a significant advantage in the treatment of infection caused by multidrug-resistant Gram-negative bacteria.

In summary, the compounds of the present invention have a novel chemical structure, and their activities against Gram-negative bacteria in vivo and in vitro are significantly better than those of the drugs aztreonam, meropenem and ceftizoxime sodium, and they also show good antibacterial activity against the meropenem-resistant bacteria, meanwhile, those compounds also have ideal pharmacokinetic properties. Therefore, the compounds of the present invention can be used as a medicament for treating infectious diseases caused by Gram-negative bacteria, particularly infectious diseases caused by drug-resistant Gram-negative bacteria.

What claimed is:

1. A monocyclic β-lactam-siderophore conjugate represented by formula (I), an optical isomer thereof or a pharmaceutically acceptable salt thereof:

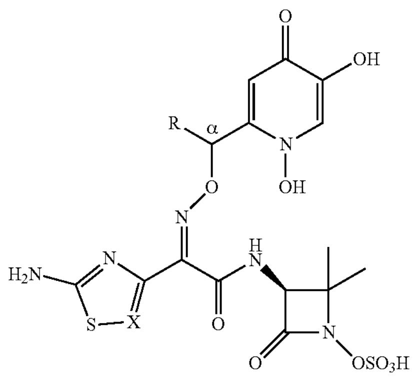

(I)

wherein X=CY or N, Y is H or a halogen;

R is (1) a carboxyl group, —$COOR_1$ or —$CONR_2R_3$;

(2) an unsubstituted $C_{1-6}$ linear alkyl group, an unsubstituted $C_{3-6}$ branched alkyl group, a $C_{3-6}$ cycloalkyl group or an unsubstituted $C_{2-7}$ alkenyl group;

(3) a substituted $C_{1-4}$ linear alkyl group or $C_{3-6}$ branched alkyl group, wherein the substituent is a hydroxyl group, an amino group, a cyano group, —$OR_1$, —$SR_1$, —$S(O_2)R_1$, —$NR_2R_3$, and a halogen;

(4) a substituted or unsubstituted phenyl group, wherein the substituent in the substituted phenyl group is 1 to 3 substituents independently selected from the group consisting of a hydroxyl group, a cyano group, —$R_1$, —$OR_1$, —$NR_2R_3$ and a halogen; or (5) a substituted or unsubstituted 5- or 6-membered heteroaryl ring group having 1 to 4 hetero atoms independently selected from the group consisting of N, S and O, wherein the substituent in the 5- or 6-membered heteroaryl ring group is independently selected from the group consisting of a hydroxyl group, a cyano group, —$R_1$, —$OR_1$, —$NR_2R_3$, and a halogen;

$R_1$ is a $C_{1-6}$ linear alkyl group, a $C_{3-6}$ branched alkyl group or a $C_{3-6}$ cycloalkyl group;

$R_2$ and $R_3$ are each independently a hydrogen, a $C_{1-6}$ linear alkyl group, a $C_{3-6}$ branched alkyl group or a $C_{3-6}$ cycloalkyl group;

the halogen is F, Cl, Br or I; preferably F, Cl or Br;

a stereo configuration of an alpha carbon may be of S type or R type or (R, S) type.

2. The monocyclic β-lactam-siderophore conjugate, optical isomer thereof or pharmaceutically acceptable salt thereof according to claim 1, wherein Y is H, Cl or Br.

3. The monocyclic β-lactam-siderophore conjugate, optical isomer thereof or pharmaceutically acceptable salt thereof according to claim 1, wherein when R is a substituted $C_{1-4}$ linear alkyl group or $C_{3-6}$ branched alkyl group, the substituent is a hydroxyl group, —$OR_1$, —$SR_1$, —$S(O_2)R_1$.

4. The monocyclic β-lactam-siderophore conjugate, optical isomer thereof or pharmaceutically acceptable salt thereof according to claim 1, wherein R is selected from the group consisting of a methyl group, an ethyl group, a propyl group, a butyl group, an isopropyl group, an isobutyl group, a cyclopropyl group and a vinyl group; a monosubstituted $C_{1-4}$ linear alkyl group and $C_{3-6}$ branched alkyl group, wherein the substituent is selected from the group consisting of a hydroxyl group, —$OR_1$, —$SR_1$ and —$S(O_2)R_1$; a phenyl group; a substituted or unsubstituted 5- or 6-membered heteroaryl ring group having 1 to 2 heteroatoms independently selected from the group consisting of N, S and O, wherein the substituent in the 5- or 6-membered heteroaryl ring group is independently selected from the group consisting of a hydroxyl group, a cyano group, —$R_1$, —$OR_1$, —$NR_2R_3$, and a halogen.

5. The monocyclic β-lactam-siderophore conjugate, optical isomer thereof or pharmaceutically acceptable salt thereof according to claim 1, wherein $R_1$ is a methyl group, an ethyl group, a propyl group, an isopropyl group, a n-butyl group, an isobutyl group, a sec-butyl group, a tert-butyl group or a cyclopropyl group; $R_2$ and $R_3$ are each independently a hydrogen, a methyl group, an ethyl group, a propyl group, an isopropyl group, a n-butyl group, an isobutyl group, a sec-butyl group, a tert-butyl group or a cyclopropyl group.

6. The monocyclic β-lactam-siderophore conjugate, optical isomer thereof or pharmaceutically acceptable salt thereof according to claim 1, wherein $R_1$ is a methyl group, an ethyl group, a propyl group, an isopropyl group; $R_2$ and $R_3$ are each independently a hydrogen, a methyl group, an ethyl group, a propyl group, an isopropyl group.

7. The monocyclic β-lactam-siderophore conjugate, optical isomer thereof or pharmaceutically acceptable salt thereof according to claim 1, wherein the representative compound of formula (I) is one of the following compounds:

compound 1

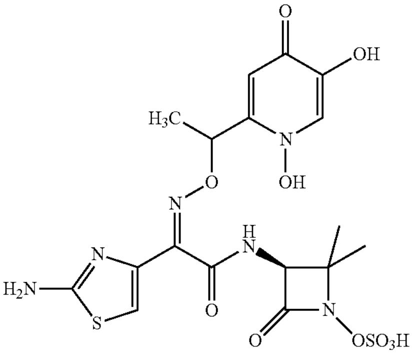

compound 2

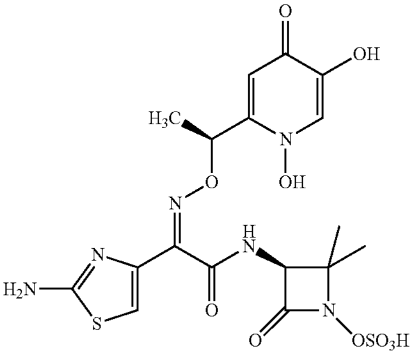

-continued compound 3

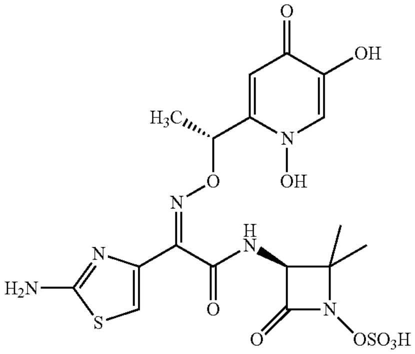

compound 4

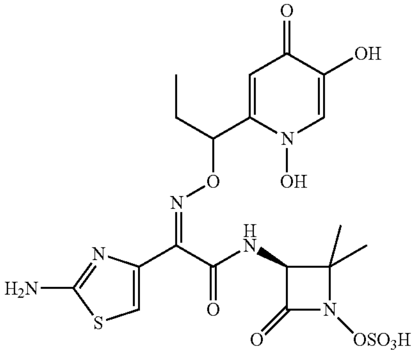

compound 5

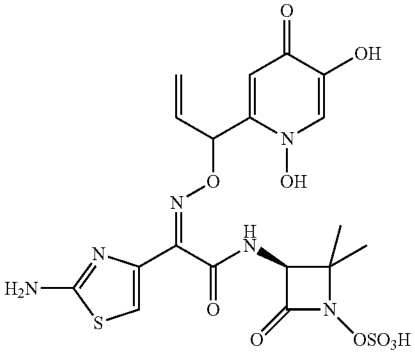

compound 6

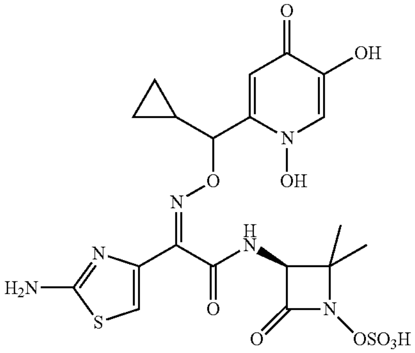

-continued
compound 7
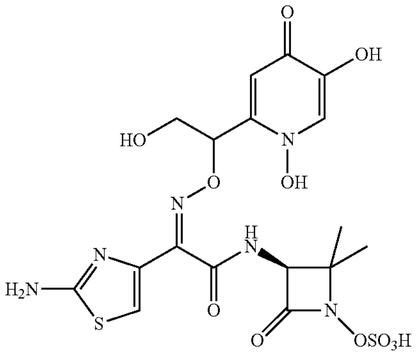
compound 8
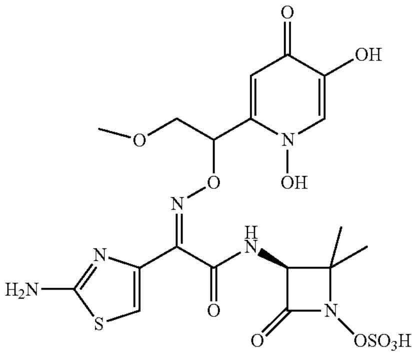
compound 9
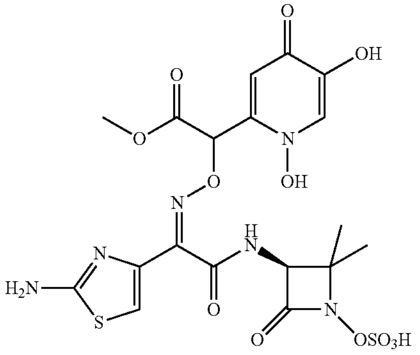
compound 10
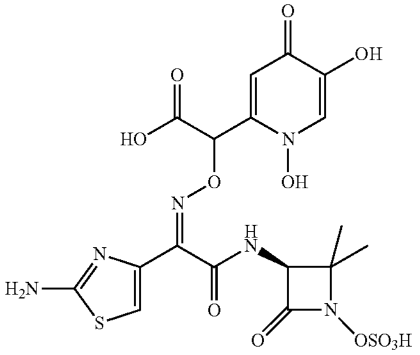
-continued
compound 11
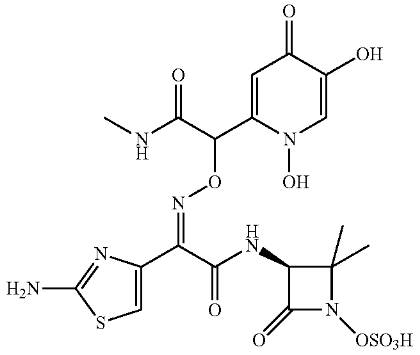
compound 12
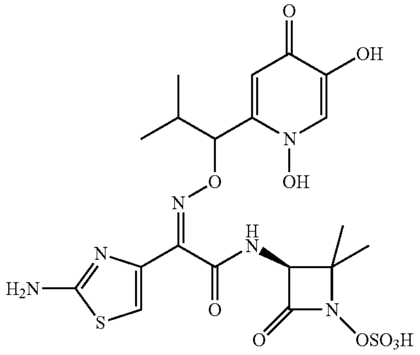
compound 13
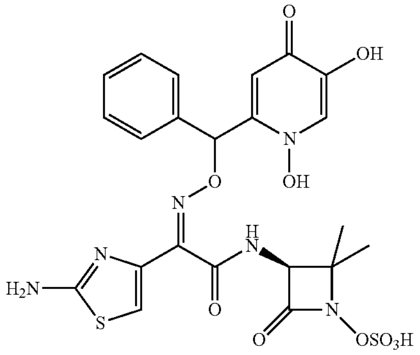
compound 14
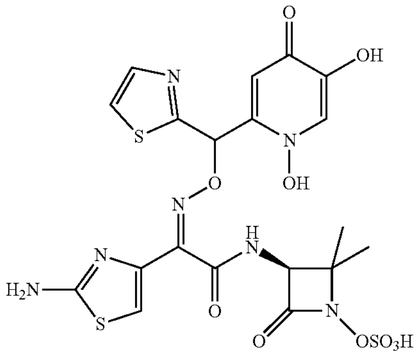

compound 15
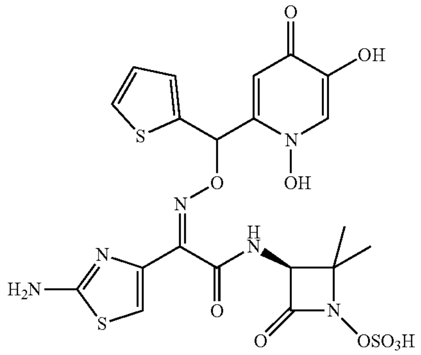
compound 16
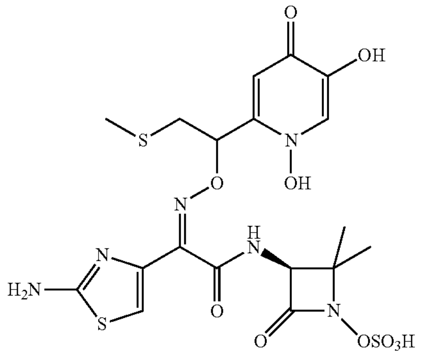
compound 17
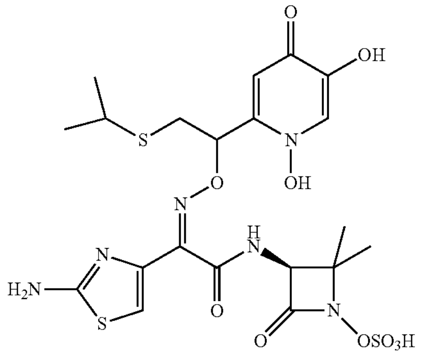
compound 18
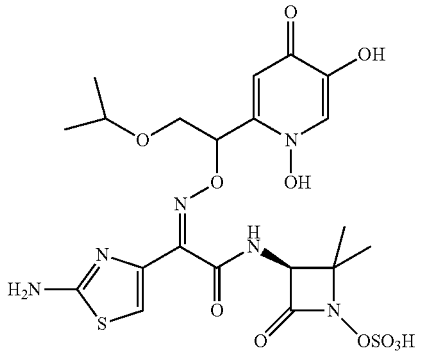
compound 19
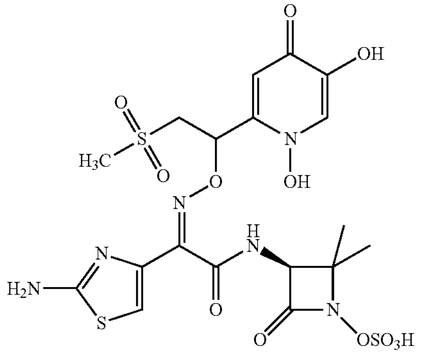
compound 20
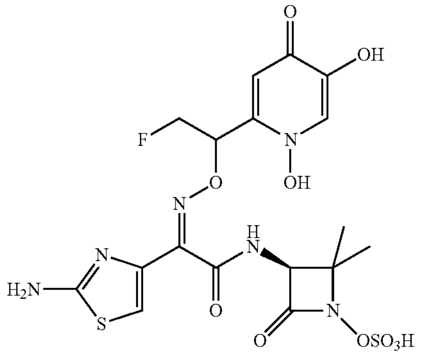
compound 21
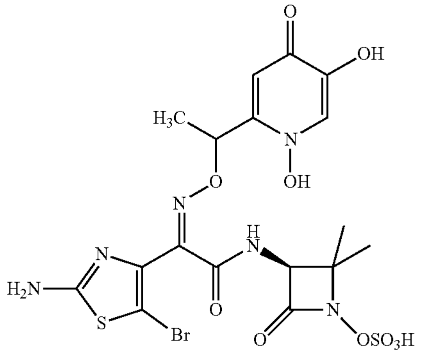
compound 22
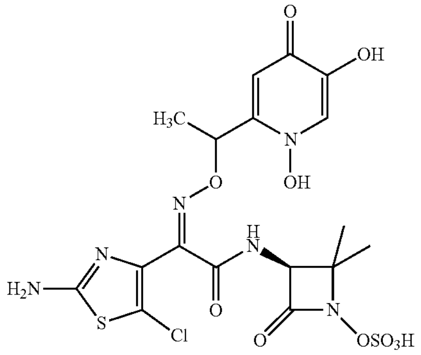

-continued
compound 23
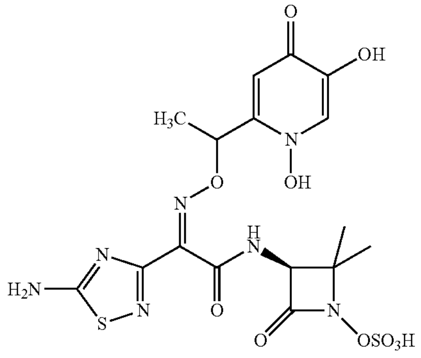
compound 24
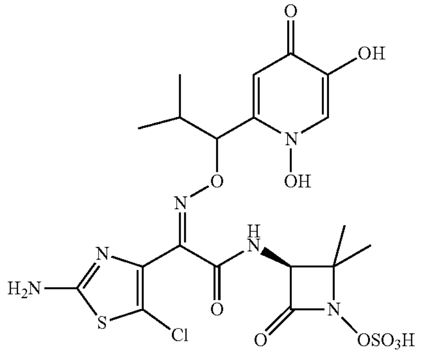
compound 25
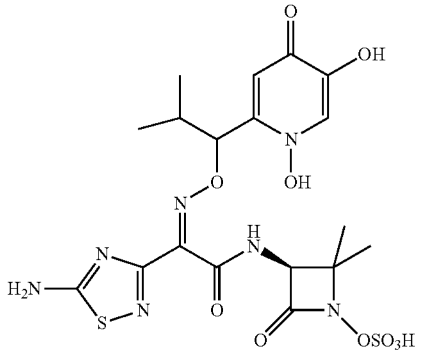
compound 26
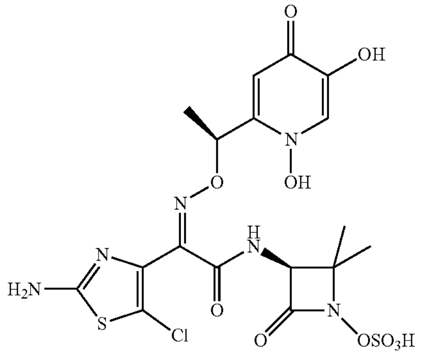
-continued
compound 27
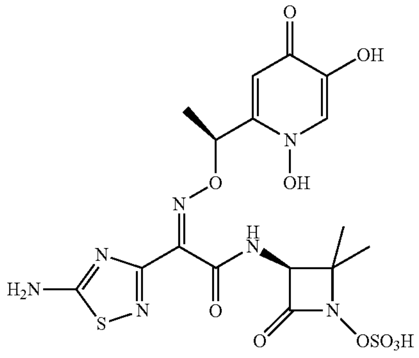
compound 28
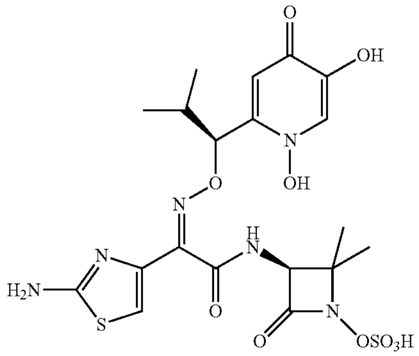
compound 29
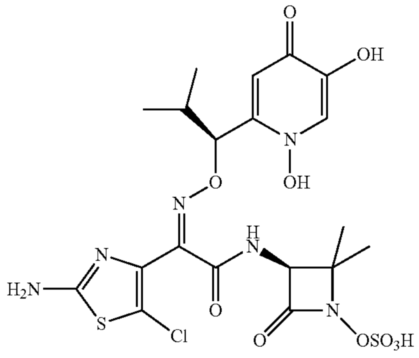
compound 30
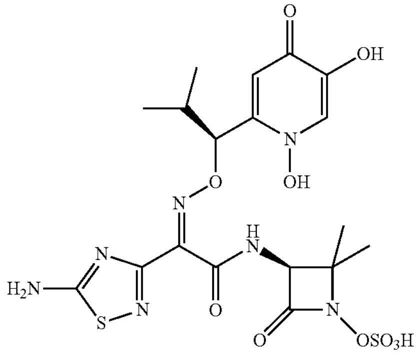

-continued compound 31

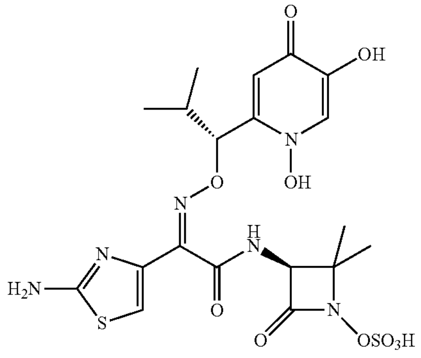

compound 32

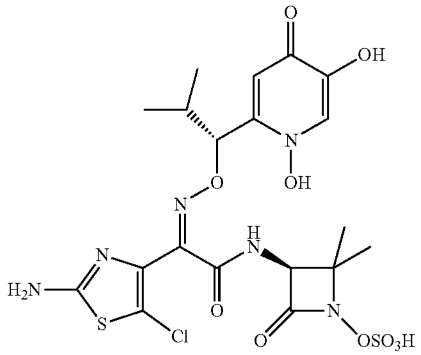

compound 33

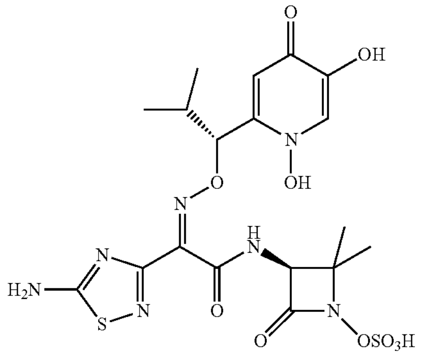

compound 34

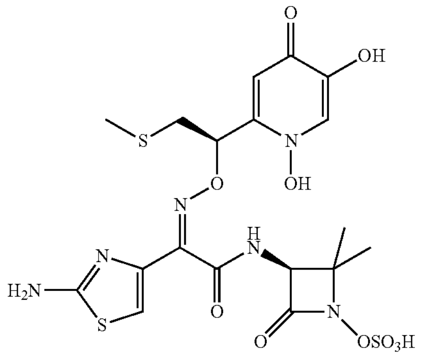

-continued compound 35

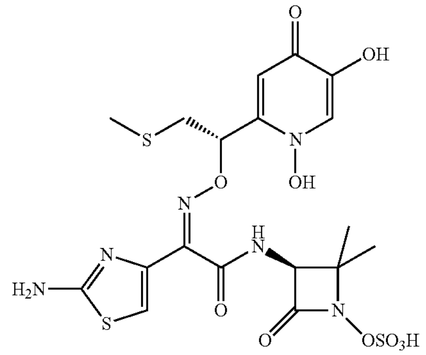

compound 36

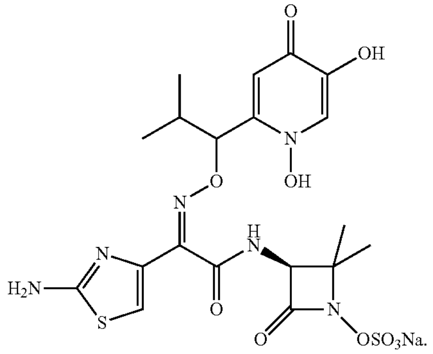

8. A pharmaceutical composition comprising the monocyclic β-lactam-siderophore conjugate, optical isomer thereof or pharmaceutically acceptable salt thereof according to claim 1 as an active ingredient, and a pharmaceutically acceptable excipient.

9. Use of the monocyclic β-lactam-siderophore conjugate, optical isomer thereof or pharmaceutically acceptable salt thereof according to claim 1 for preparing a medicament for treating an infectious disease caused by bacteria, in particular, including the infectious diseases caused by sensitive and resistant *Pseudomonas aeruginosa, Acinetobacter baumannii, Escherichia coli* and *Klebsiella pneumonia.*

10. A method for preparing the monocyclic β-lactam-siderophore conjugate, optical isomer thereof or pharmaceutically acceptable salt thereof according to claim 1, comprising steps as shown in the following reaction scheme (1):

reaction scheme (1):

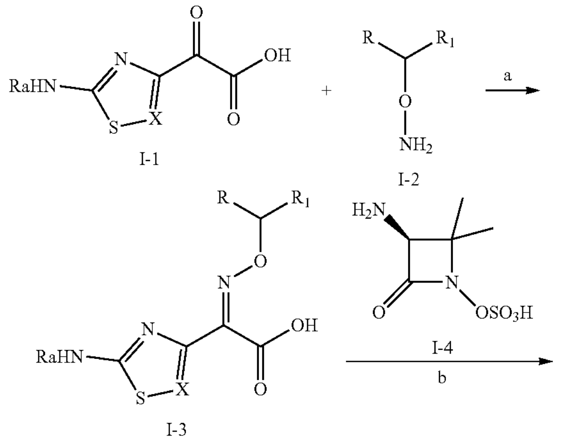

-continued

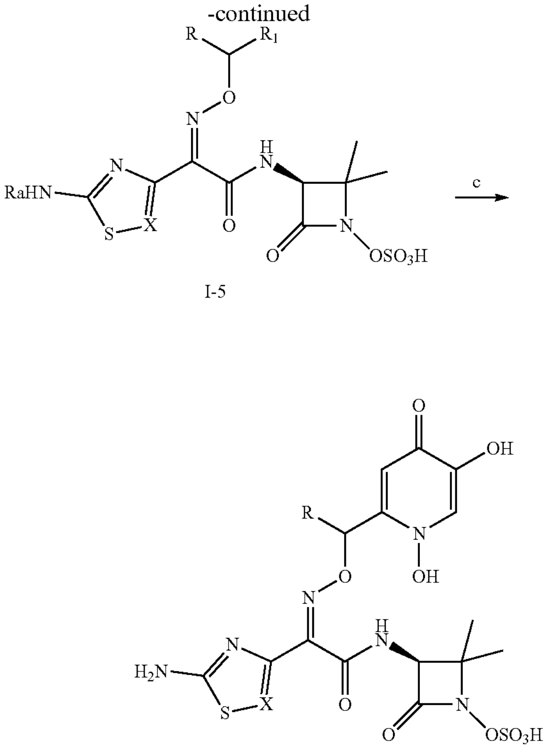

I-5

I in the above reaction scheme (1), X and R are defined as those in claim 1; $R_a$ is an amino protecting group; $R_1$ is

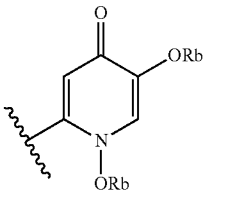

or

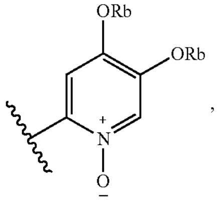

, wherein $R_b$ is a hydroxyl protecting group;

(a) reacting compound I-1 with compound I-2 in a mixed solvent of a polar protic solvent and a non-polar solvent at room temperature for 2 to 6 hours to obtain compound I-3;

(b) reacting compound I-3 with compound I-4 under a condition of a condensing agent and an organic or inorganic base in a polar aprotic solvent as a solvent at room temperature for 4 to 8 hours to obtain compound I-5;

(c) removing the protecting group of compound I-5 via an acid in a non-polar solvent in the presence of a positive ion trapping agent to obtain compound I.

11. The method according to claim 10, wherein the method for synthesizing the key intermediate 1-2 may be selected from one of the following methods:

Method I:

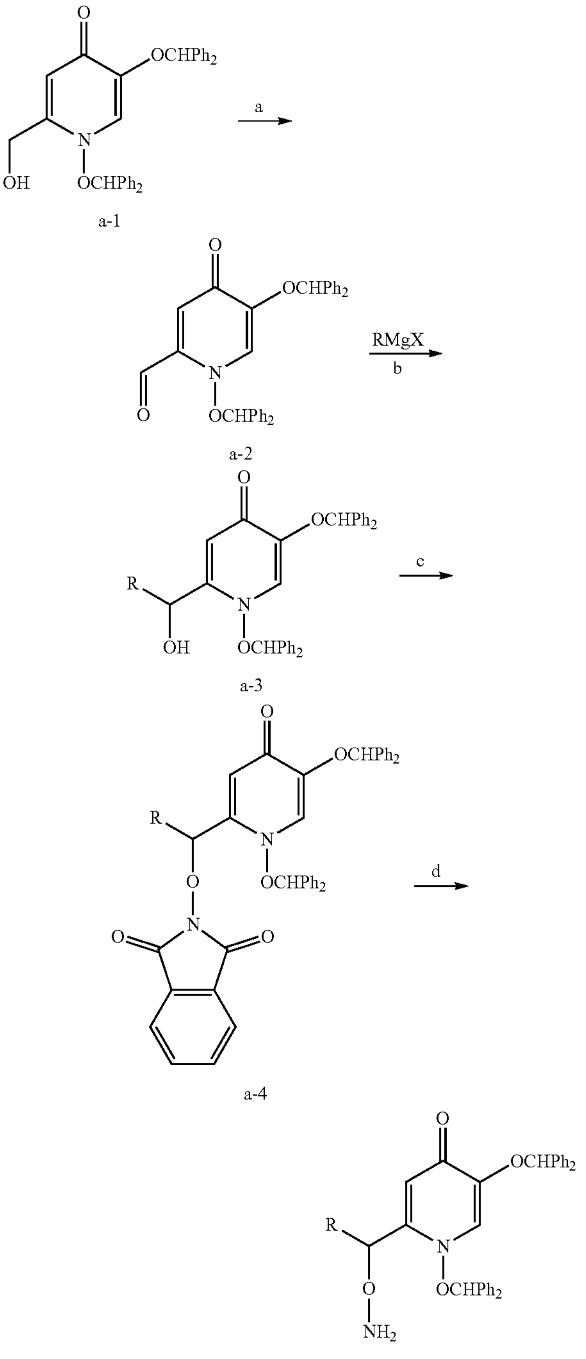

a-1, a-2, a-3, a-4, a-5 wherein R is a $C_{1-4}$ linear alkyl group or a $C_{1-4}$ alkenyl group or a $C_{3-4}$ cycloalkyl group;

(a) oxidizing compound a-1 with an oxidizing agent in a non-polar solvent for 4 to 8 hours to obtain compound a-2, wherein the non-polar solvent is dichloromethane, and the oxidizing agent is a mixture of sulfur trioxide pyridine and dimethyl sulfoxide or a mixture of oxalyl chloride and dimethyl sulfoxide;

(b) reacting compound a-2 with a metal Grignard reagent RMgX in a non-polar solvent at a low temperature of −10 to −20° C. for 4 to 6 hours to obtain compound a-3, wherein the metal Grignard reagent is RMgBr or RMgCl, and the non-polar solvent is tetrahydrofuran;

(c) subjecting to Mitsunobu reaction of compound a-3 and N-hydroxyphthalimide in a non-polar solvent to obtain compound a-4, wherein the non-polar solvent is tetrahydrofuran or 1,4-dioxane;

(d) subjecting to hydrazinolysis of compound a-4 with hydrazine hydrate or aminolysis of compound a-4 with methylamine in a polar protic solvent to obtain a compound a-5, wherein the polar protic solvent is methanol or ethanol;

Method II:

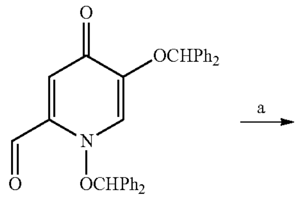

a-2

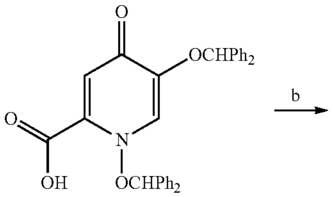

b-1

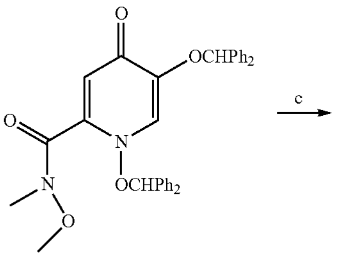

b-2

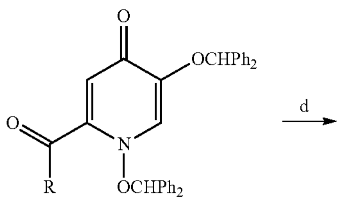

b-3

-continued

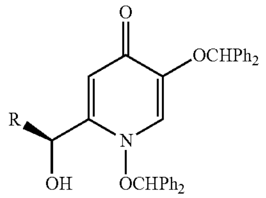

b-4 or

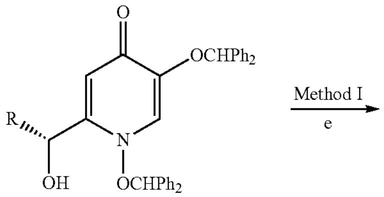

b-5

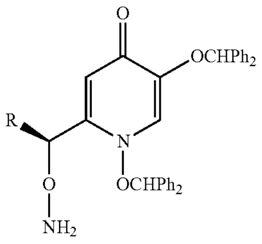

b-6 or

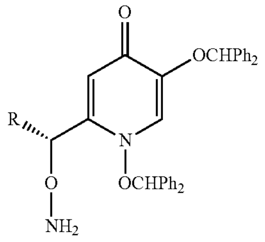

b-7 wherein R is a $C_{1-4}$ linear alkyl group or a $C_{1-4}$ alkenyl group or a $C_{3-4}$ cycloalkyl group;

(a) oxidizing compound a-2 with an oxidizing agent in a mixed solvent of water and a polar aprotic solvent to obtain compound b-1, wherein the polar aprotic solvent is acetonitrile, acetone or 1,4-dioxane, and the oxidizing agent is sodium chlorite;

(b) reacting compound b-1 with N-methyl-N-methoxyamine hydrochloride under a condition of a condensing agent and an organic or inorganic base in a polar aprotic solvent as a solvent at room temperature for 4 to 8 hours to obtain compound b-2, wherein the condensing agent is: a mixture of 2-(7-azabenzotriazoleyl)-N,N,N',N'-tetramethyluronium hexafluorophosphate (HATU) or 1-(3-dimethylaminopropyl)-3-ethylcarbodiimide hydrochloride (EDCI) and 1-hydroxybenzotriazole (HOBT), the organic base is: triethylamine or diisopropylethylamine, the inorganic base is sodium hydrogencarbonate, sodium carbonate or potassium hydrogencarbonate, and the polar aprotic solvent is: dimethyl sulfoxide or N,N-dimethylformamide;

(c) reacting compound b-2 with a metal Grignard reagent RMgX in a non-polar solvent at a low temperature of −10 to −20° C. for 4 to 6 hours to obtain compound b-3, wherein the metal Grignard reagent is RMgBr or RMgCl, and the non-polar solvent is tetrahydrofuran or diethyl ether;

(d) reacting compound b-3 by the action of a transition metal catalyst, a ligand and a hydrogen source in a polar solvent under Ar protection to obtain compound b-4 or b-5, wherein the transition metal catalyst is dichlorobis(4-methylisopropylphenyl)ruthenium (II) or dichloro(pentamethylcyclopentadienyl)rhodium (III) dimer, the ligand is (1R,2R)-(−)—N-(p-methylbenzenesulfonyl)-1,2-diphenylethylenediamine or (1S,2S)-(−)-N-(p-methylbenzenesulfonyl)-1,2-diphenylethylenediamine, the hydrogen source is sodium formate or ammonium formate, and the polar solvent is N,N-dimethylformamide;

(e) subjecting compound b-4 or b-5 to the method described in the method I to obtain compound b-6 or b-7;

Method III:

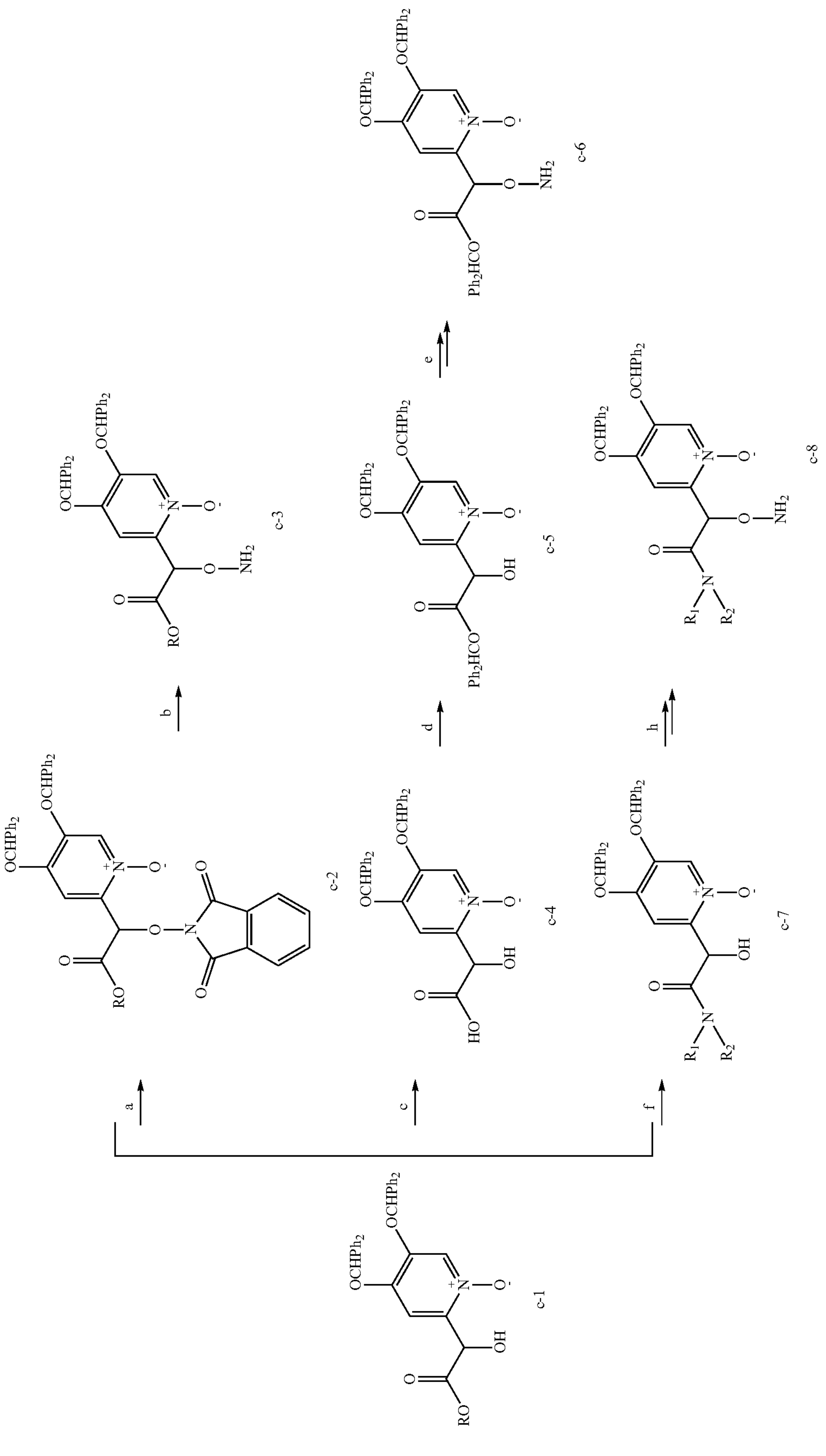
a
b
c
d
e
f
h
c-1
c-2
c-3
c-4
c-5
c-6
c-7
c-8 wherein R is a $C_{1-6}$ linear alkyl group, a $C_{3-6}$ branched alkyl group or a $C_{3-6}$ cycloalkyl group; and $R_1$ and $R_2$ are each independently: a hydrogen; or a $C_{1-6}$ linear alkyl group, a $C_{3-6}$ branched alkyl group or a $C_{3-6}$ cycloalkyl group;

(a) subjecting to Mitsunobu reaction of compound c-1 and N-hydroxyphthalimide in a non-polar solvent to obtain compound c-2, wherein the non-polar solvent is tetrahydrofuran or 1,4-dioxane;

(b) subjecting to hydrazinolysis of compound c-2 with hydrazine hydrate or aminolysis of compound c-2 with methylamine in a polar protic solvent to obtain a compound c-3, wherein the polar protic solvent is methanol or ethanol;

(c) reacting compound c-1 in a mixed polar and non-polar solvents in the presence of an inorganic base at 0° C. to room temperature to obtain a compound c-4, wherein the inorganic base is sodium hydroxide or lithium hydroxide, the polar solvent is water or methanol, and the non-polar solvent is tetrahydrofuran;

(d) reacting compound c-4 with diphenyldiazomethane in a mixed polar and non-polar solvents to obtain compound c-5, wherein the polar solvent is methanol or ethanol, and the non-polar solvent is dichloromethane, ethyl acetate or tetrahydrofuran;

(e) subjecting compound c-5 to the above steps a and b to obtain compound c-6;

(g) subjecting to aminolysis of compound c-1 with $HNR_1R_2$ in a polar protic solvent or a non-polar solvent to obtain compound c-7, wherein the polar protic solvent is a methanol, and the non-polar solvent is tetrahydrofuran;

(g) reacting compound c-4 with amine $HNR_1R_2$ in a polar solvent in the presence of a condensing agent and an organic base at room temperature to obtain a compound c-7, wherein the condensing agent is 2-(7-azabenzotriazoleyl)-N,N,N',N'-tetramethyluronium hexafluorophosphate (HATU) or 1-hydroxybenzotriazole (HOBT), the organic base is triethylamine or diisopropyl ethylamine, and the polar solvent is dichloromethane;

(h) subjecting compound c-7 to the above steps a and b to obtain compound c-8;

the synthetic method of the starting material c-1 in the above reaction scheme is as follows:

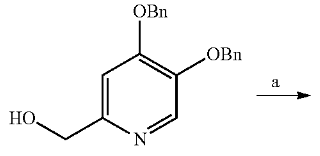

c-9

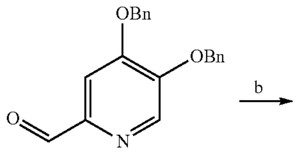

c-10

-continued

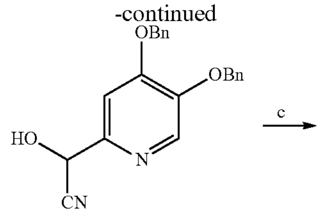

c-11

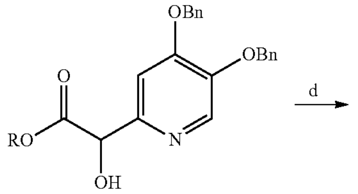

c-12

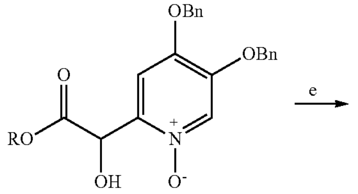

c-13

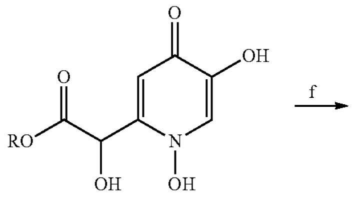

c-14

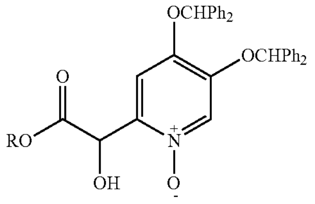

c-1 wherein R is a $C_{1-6}$ linear alkyl group, a $C_{3-6}$ branched alkyl group or a $C_{3-6}$ cycloalkyl group;

(a) oxidizing compound c-9 with an oxidizing agent in a non-polar solvent for 4 to 8 hours to obtain compound c-10, wherein the non-polar solvent is dichloromethane, and the oxidizing agent is a mixture of sulfur trioxide pyridine and dimethyl sulfoxide or a mixture of oxalyl chloride and dimethyl sulfoxide;

(b) reacting compound c-10 with sodium cyanide in a mixed solvent of water and a non-polar solvent to obtain compound c-11, wherein the non-polar solvent is tetrahydrofuran or 1,4-dioxane;

(c) reacting compound c-11 with hydrochloric acid in a polar protic solvent to obtain compound c-12, wherein the polar protic solvent is alcohol ROH;

(d) oxidizing compound c-12 with an oxidizing agent in a non-polar solvent to obtain compound c-13, wherein the non-polar solvent is dichloromethane, the oxidizing agent is m-chloroperoxybenzoic acid (mCPBA) or hydrogen peroxide;

(e) subjecting to deprotecting the benzyl protecting group of compound c-13 in a non-polar solvent under the action of a Lewis acid to obtain compound c-14, wherein the non-polar solvent is dichloromethane, the Lewis acid is boron trichloride or boron tribromide;

(f) reacting compound c-14 with diphenyldiazomethane in a mixed polar and non-polar solvents to obtain compound c-1, wherein the polar solvent is methanol or ethanol, the non-polar solvent is dichloromethane, ethyl acetate or tetrahydrofuran;

Method IV:

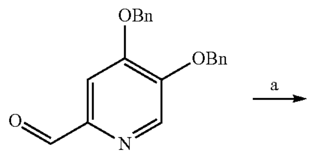

c-10

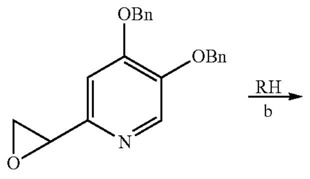

d-1

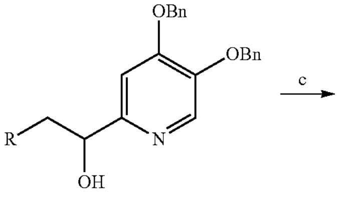

d-2

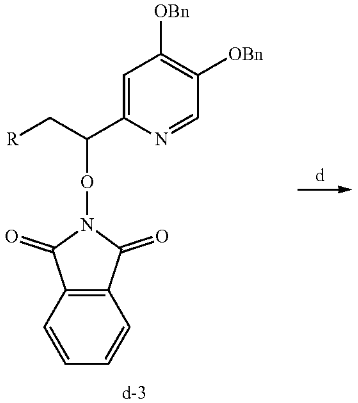

d-3

-continued

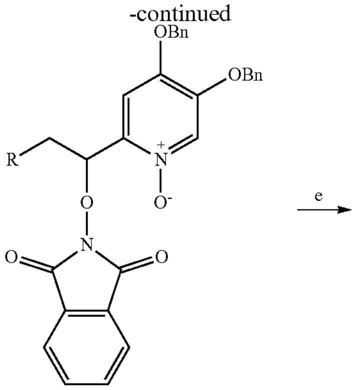

d-4

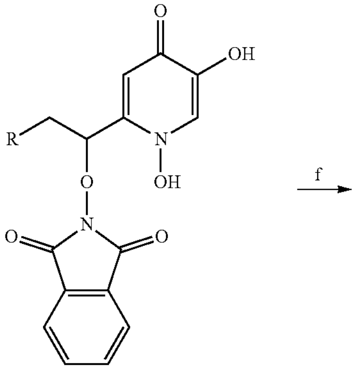

d-5

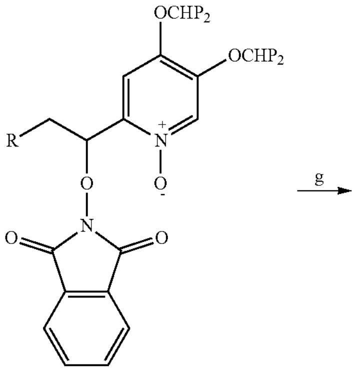

d-6

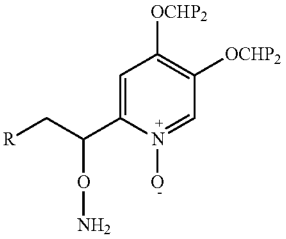

d-7 in the above scheme, R is a hydroxyl group, an amino group, —$OR_1$, —$NR_2R_3$; —$R_1$ is a $C_{1-6}$ linear alkyl group, a $C_{3-6}$ branched alkyl group or a $C_{3-6}$ cycloalkyl group; and $R_2$ and $R_3$ are each independently: a hydrogen or a $C_{1-6}$ linear alkyl group, a $C_{3-6}$ branched alkyl group or a $C_{3-6}$ cycloalkyl group;

(a) reacting compound c-10 with trimethylsulfoxonium iodide or trimethylsulfoxonium iodide under the action of strong alkali in a polar aprotic solvent to obtain compound d-1, wherein the polar aprotic solvent is dimethyl sulfoxide or N,N-dimethylformamide, and the strong alkali is sodium hydride or potassium hydride;

(b) reacting compound d-1 with RH in a non-polar solvent under a strong alkali to obtain compound d-2, wherein the non-polar solvent is tetrahydrofuran, and the strong alkali is sodium hydride, sodium hydroxide or potassium hydroxide;

(c) subjecting to Mitsunobu reaction of compound d-2 and N-hydroxyphthalimide in a non-polar solvent to obtain compound d-3, wherein the non-polar solvent is tetrahydrofuran or 1,4-dioxane;

(d) oxidizing compound d-3 with an oxidizing agent in a non-polar solvent to obtain compound d-4, wherein the non-polar solvent is dichloromethane, and the oxidizing agent is m-chloroperoxybenzoic acid or hydrogen peroxide;

(e) subjecting to deprotecting the benzyl protecting group of compound d-4 under the action of a Lewis acid in a non-polar solvent to obtain compound d-5, wherein the non-polar solvent is dichloromethane, and the Lewis acid is boron trichloride or boron tribromide;

(f) reacting compound d-5 with diphenyldiazomethane in a mixed polar and non-polar solvent to obtain compound d-6, wherein the polar solvent is methanol or ethanol, and the non-polar solvent is dichloromethane, ethyl acetate or tetrahydrofuran;

(g) subjecting to hydrazinolysis of compound d-6 with hydrazine hydrate or aminolysis of compound d-6 with methylamine in a polar protic solvent to obtain a compound d-7, wherein the polar protic solvent is methanol or ethanol;

Method V:

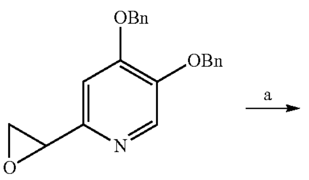

d-1

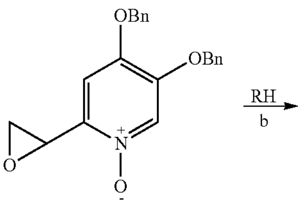

d-8

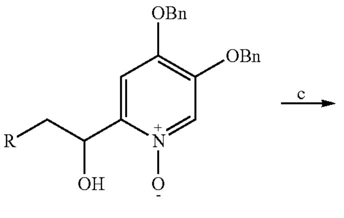

d-9

-continued

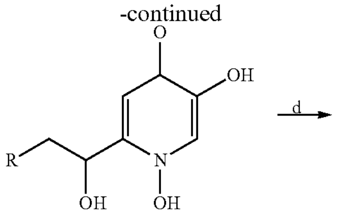

d-10

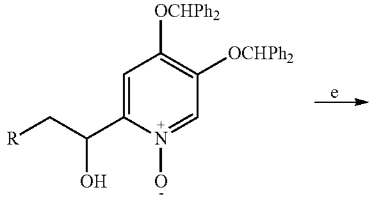

d-11

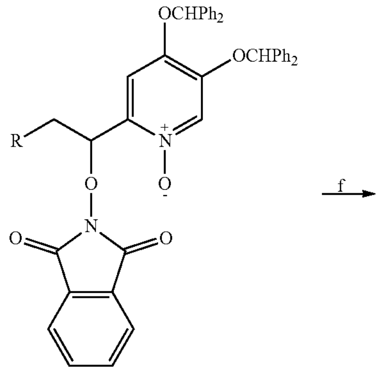

d-12

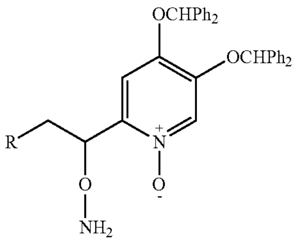

d-13 in the above scheme, R is a hydroxyl group, an amino group, —$OR_1$, —$SR_1$, —$NR_2R_3$; $R_1$ is a $C_{1-6}$ linear alkyl group, a $C_{3-6}$ branched alkyl group or a $C_{3-6}$ cycloalkyl group; and $R_2$ and $R_3$ are each independently: a hydrogen or a $C_{1-6}$ linear alkyl group, a $C_{3-6}$ branched alkyl group or a $C_{3-6}$ cycloalkyl group;

(a) oxidizing compound d-1 with an oxidizing agent in a non-polar solvent to obtain compound d-8, wherein the non-polar solvent is dichloromethane, and the oxidizing agent is m-chloroperoxybenzoic acid or hydrogen peroxide;

(b) reacting compound d-8 with RH in a non-polar solvent under a strong alkali to obtain compound d-9, wherein the non-polar solvent is tetrahydrofuran, and the strong alkali is sodium hydride, sodium hydroxide or potassium hydroxide;

(c) subjecting to deprotecting the benzyl protecting group of compound d-9 in a non-polar solvent under the action of a Lewis acid to obtain compound d-10, wherein the non-polar solvent is dichloromethane, and the Lewis acid is boron trichloride or boron tribromide;

(d) reacting compound d-10 with diphenyldiazomethane in a mixed polar and non-polar solvents to obtain compound d-11, wherein the polar solvent is methanol or ethanol, and the non-polar solvent is dichloromethane, ethyl acetate or tetrahydrofuran;

(e) subjecting to Mitsunobu reaction of compound d-11 and N-hydroxyphthalimide in a non-polar solvent to obtain compound d-12, wherein the non-polar solvent is tetrahydrofuran or 1,4-dioxane;

(f) subjecting to hydrazinolysis of compound d-12 with hydrazine hydrate or aminolysis of compound d-12 with methylamine in a polar protic solvent to obtain a compound d-13, wherein the polar protic solvent is methanol or ethanol;

Method VI:

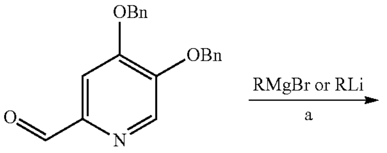

c-10

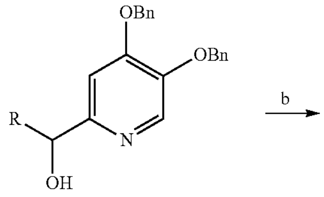

e-1

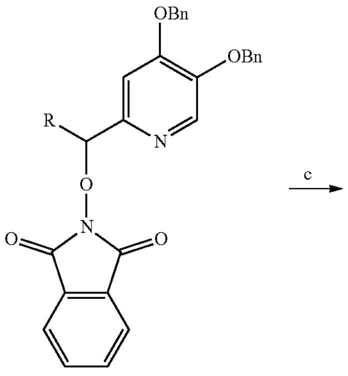

e-2

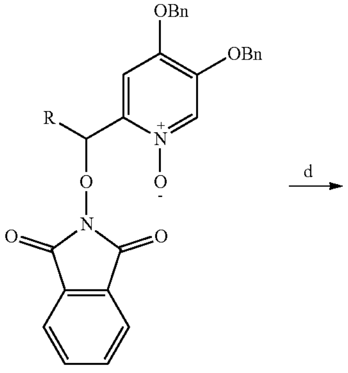

e-3

-continued

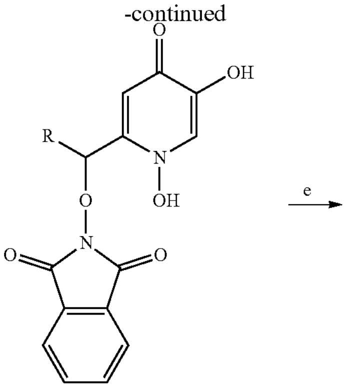

e-4

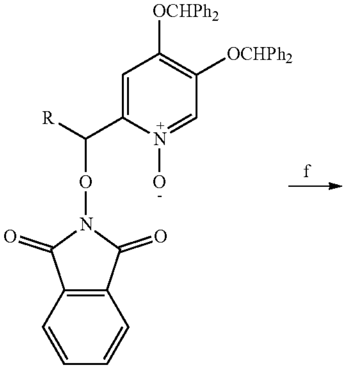

e-5

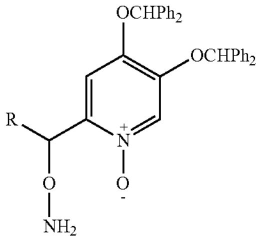

e-6 in the above scheme, R is a $C_{1-6}$ linear alkyl group, a $C_{3-6}$ branched alkyl group, a $C_{3-6}$ cycloalkyl group, a substituted or unsubstituted phenyl group, or a substituted or unsubstituted 5- or 6-membered heteroaryl ring group having 1 to 4 hetero atoms independently selected from the group consisting of N, S and O;

(a) reacting compound c-10 with a Grignard reagent RMgBr or an organolithium reagent RLi in a non-polar solvent to obtain a compound e-1, wherein the non-polar solvent is tetrahydrofuran or methyltetrahydrofuran;

(b) subjecting to Mitsunobu reaction of compound e-1 and N-hydroxyphthalimide in a non-polar solvent to obtain compound e-2, wherein the non-polar solvent is tetrahydrofuran or 1,4-dioxane;

(c) oxidizing compound e-2 with an oxidizing agent in a non-polar solvent obtain compound e-3, wherein the non-polar solvent is dichloromethane, and the oxidizing agent is m-chloroperoxybenzoic acid or hydrogen peroxide;

(d) subjecting to deprotecting the benzyl protecting group of compound e-3 in a non-polar solvent under the action of a Lewis acid to obtain compound e-4, wherein the non-polar solvent is dichloromethane, and the Lewis acid is boron trichloride or boron tribromide;

(e) reacting compound e-4 with diphenyldiazomethane in a mixed polar and non-polar solvents to obtain compound e-5, wherein the polar solvent is methanol or ethanol, and the non-polar solvent is dichloromethane, ethyl acetate or tetrahydrofuran;

(f) subjecting to hydrazinolysis of compound e-5 with hydrazine hydrate or aminolysis of compound e-5 with methylamine in a polar protic solvent to obtain a compound e-6, wherein the polar protic solvent is methanol or ethanol;

Method VII:

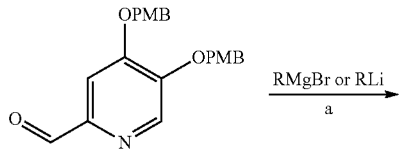

f-1

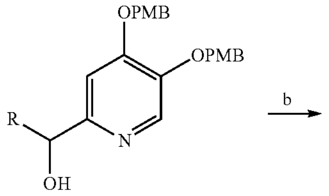

f-2

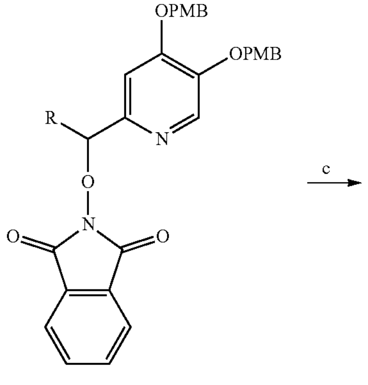

f-3

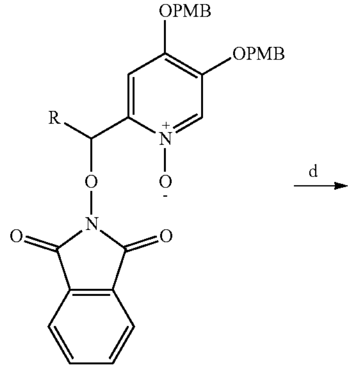

f-4

-continued

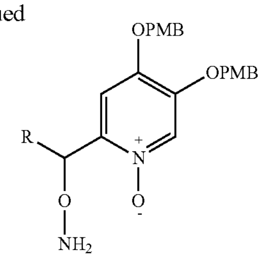

f-5 in the above scheme, R is a $C_{1-6}$ linear alkyl group, a $C_{3-6}$ branched alkyl group, a $C_{3-6}$ cycloalkyl group, a substituted or unsubstituted phenyl group, or a substituted or unsubstituted 5- or 6-membered heteroaryl ring group having 1 to 4 hetero atoms independently selected from the group consisting of N, S and O;

the synthetic method of compound f-1 can refer to the method of compound c-10;

(a) reacting compound f-1 with a Grignard reagent RMgBr or an organolithium reagent RLi in a non-polar solvent to obtain a compound f-2, wherein the non-polar solvent is tetrahydrofuran or methyltetrahydrofuran;

(b) subjecting to Mitsunobu reaction of compound f-2 and N-hydroxyphthalimide in a non-polar solvent to obtain compound f-3, wherein the non-polar solvent is tetrahydrofuran or 1,4-dioxane;

(c) oxidizing compound f-3 with an oxidizing agent in a non-polar solvent obtain compound f-4, wherein the non-polar solvent is dichloromethane, and the oxidizing agent is m-chloroperoxybenzoic acid or hydrogen peroxide;

(d) subjecting to hydrazinolysis of compound f-4 with hydrazine hydrate or aminolysis of compound f-4 with methylamine in a polar protic solvent to obtain a compound f-5, wherein the polar protic solvent is methanol or ethanol;

Method VIII:

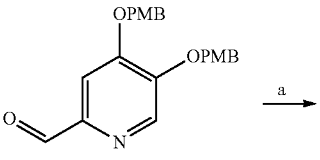

f-1

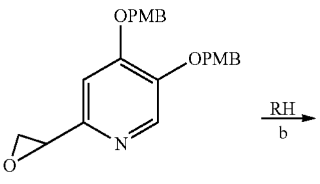

f-6

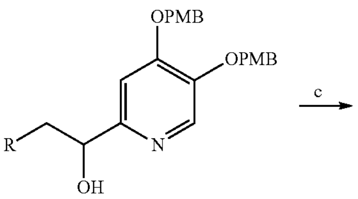

f-7

-continued

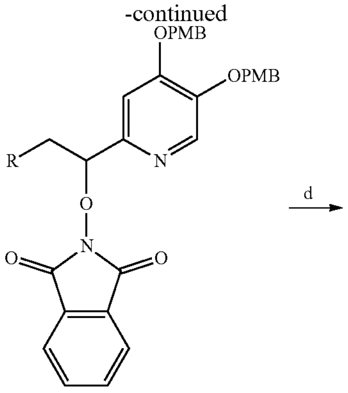

f-8

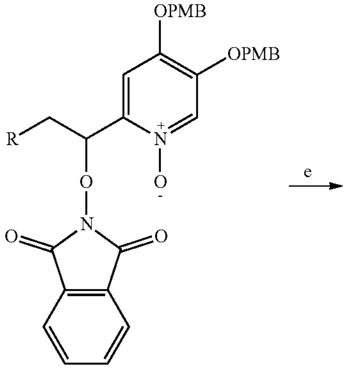

f-9

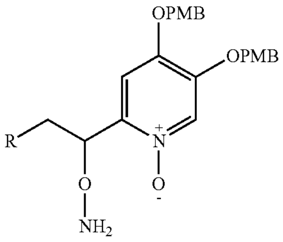

f-10 in the above scheme, R is a hydroxyl group, an amino group, —$OR_1$, —$NR_2R_3$; $R_1$ is a $C_{1-6}$ linear alkyl group, a $C_{3-6}$ branched alkyl group or a $C_{3-6}$ cycloalkyl group; and $R_2$ and $R_3$ are each independently: a hydrogen or a $C_{1-6}$ linear alkyl group, a $C_{3-6}$ branched alkyl group or a $C_{3-6}$ cycloalkyl group;

(a) reacting compound f-1 with trimethylsulfoxonium iodide or trimethylsulfoxonium iodide under the action of strong alkali in a polar aprotic solvent to obtain compound f-6, wherein the polar aprotic solvent is dimethyl sulfoxide or N,N-dimethylformamide, and the strong alkali is sodium hydride or potassium hydride;

(b) reacting compound f-6 with RH in a non-polar solvent under a strong alkali to obtain compound f-7, wherein the non-polar solvent is tetrahydrofuran, and the strong alkali is sodium hydride, sodium hydroxide or potassium hydroxide;

(c) subjecting to Mitsunobu reaction of compound f-7 and N-hydroxyphthalimide in a non-polar solvent to obtain compound f-8, wherein the non-polar solvent is tetrahydrofuran or 1,4-dioxane;

(d) oxidizing compound f-8 with an oxidizing agent in a non-polar solvent to obtain compound f-9, wherein the non-polar solvent is dichloromethane, and the oxidizing agent is m-chloroperoxybenzoic acid or hydrogen peroxide;

(e) subjecting to hydrazinolysis of compound f-9 with hydrazine hydrate or aminolysis of compound d-6 with methylamine in a polar protic solvent to obtain a compound f-10, wherein the polar protic solvent is methanol or ethanol;

method IX:

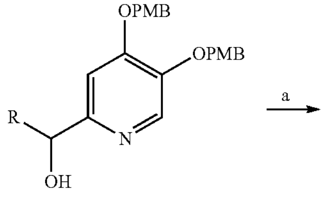

f-2

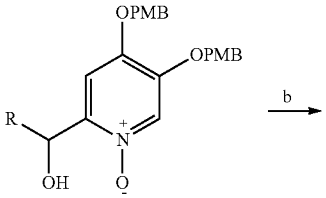

g-1

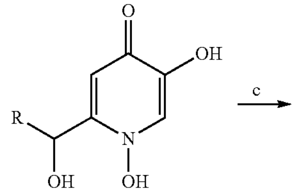

g-2

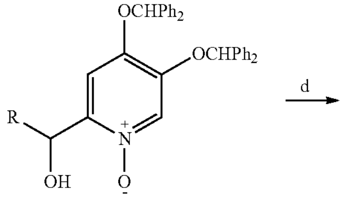

g-3

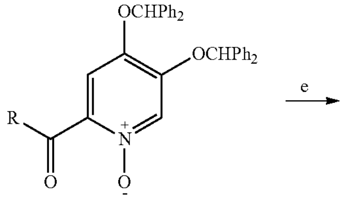

g-4

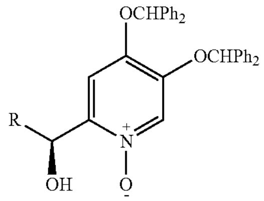

or g-5

-continued

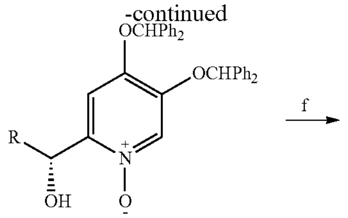

g-6

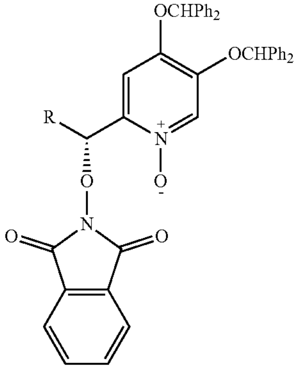

or g-7

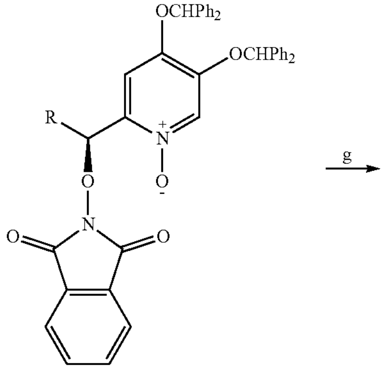

g-8

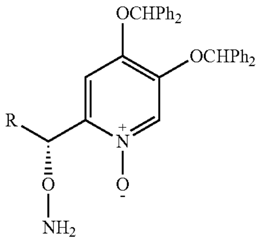

or g-9

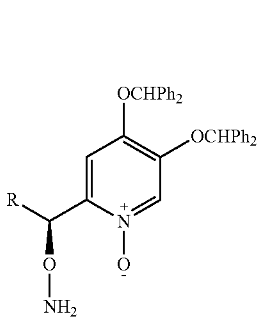

g-10 wherein R is a $C_{1-6}$ linear alkyl group, a $C_{3-6}$ alkenyl group, a $C_{3-6}$ cycloalkyl group, a substituted or unsubstituted phenyl group, or a substituted or unsubstituted 5- or 6-membered heteroaryl ring group having 1 to 4 hetero atoms independently selected from the group consisting of N, S and O;

(a) oxidizing compound f-2 with an oxidizing agent in a non-polar solvent to obtain compound g-1, wherein the non-polar solvent is dichloromethane, and the oxidizing agent is m-chloroperoxybenzoic acid or hydrogen peroxide;

(b) subjecting to deprotecting the benzyl protecting group of compound g-1 in a non-polar solvent under the action of a Lewis acid to obtain compound g-2, wherein the non-polar solvent is dichloromethane, the Lewis acid is boron trichloride or boron tribromide;

(c) reacting compound g-2 with diphenyldiazomethane in a mixed polar and non-polar solvents to obtain compound g-3, wherein the polar solvent is methanol or ethanol; and the non-polar solvent is dichloromethane, ethyl acetate or tetrahydrofuran;

(d) oxidizing compound g-3 with an oxidizing agent in a non-polar solvent for 4 to 8 hours to obtain compound g-4, wherein the non-polar solvent is dichloromethane, and the oxidizing agent is a mixture of sulfur trioxide pyridine and dimethyl sulfoxide or a mixture of oxalyl chloride and dimethyl sulfoxide;

(e) reacting compound g-4 by the action of a transition metal catalyst, a ligand and a hydrogen source in a polar solvent under Ar protection to obtain compound g-5 or g-6, wherein the transition metal catalyst is dichlorobis(4-methylisopropylphenyl)ruthenium (II) or dichloro(pentamethylcyclopentadienyl)rhodium (III) dimer, the ligand is (1R,2R)-(−)—N-(p-methylbenzenesulfonyl)-1,2-diphenylethylenediamine or (1S,2S)-(−)-N-(p-methylbenzenesulfonyl)-1,2-diphenylethylenediamine, the hydrogen source is sodium formate or ammonium formate, and the polar solvent is N,N-dimethylformamide;

(f) subjecting to Mitsunobu reaction of compound g-5 or g-6 and N-hydroxyphthalimide in a non-polar solvent to obtain compound g-7 or g-8, wherein the non-polar solvent is tetrahydrofuran or 1,4-dioxane;

(g) subjecting to hydrazinolysis of compound g-7 or g-8 with hydrazine hydrate or aminolysis of compound g-7 or g-8 with methylamine in a polar protic solvent to obtain a compound g-9 or g-10, wherein the polar protic solvent is methanol or ethanol;

method X:

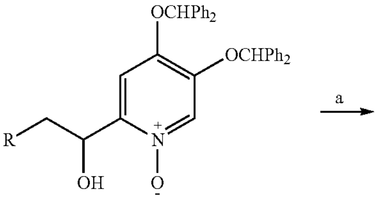

d-11

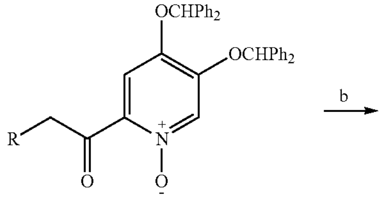

g-11

-continued

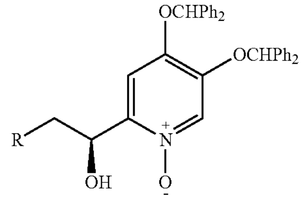

g-12 or

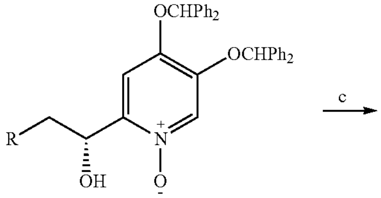

g-13

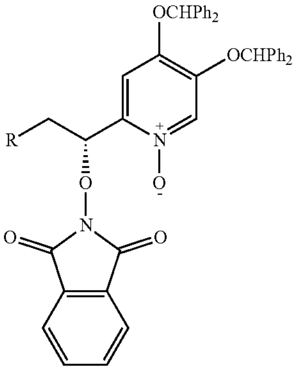

g-14 or

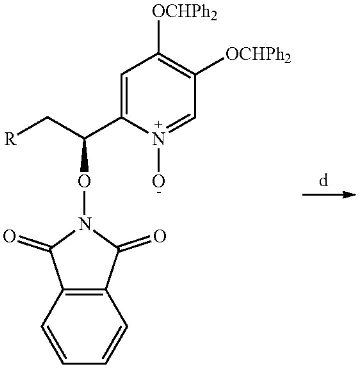

g-15

-continued

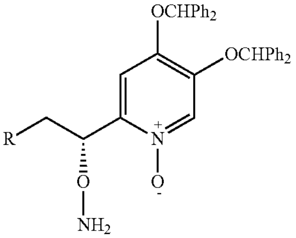

g-16 or

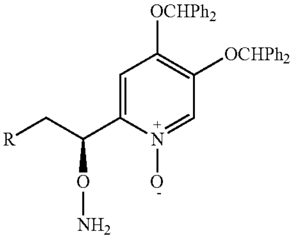

g-17 in the above scheme, R is —$OR_1$, —$SR_1$, —$NR_2R_3$; $R_1$ is a $C_{1-6}$ linear alkyl group, a $C_{3-6}$ branched alkyl group or a $C_{3-6}$ cycloalkyl group; and $R_2$ and $R_3$ are each independently: a hydrogen, a $C_{1-6}$ linear alkyl group, a $C_{3-6}$ branched alkyl group or a $C_{3-6}$ cycloalkyl group;

(a) oxidizing compound d-11 with an oxidizing agent in a non-polar solvent for 4 to 8 hours to obtain compound g-11, wherein the non-polar solvent is dichloromethane, and the oxidizing agent is a mixture of sulfur trioxide pyridine and dimethyl sulfoxide or a mixture of oxalyl chloride and dimethyl sulfoxide;

(b) reacting compound g-11 by the action of a transition metal catalyst, a ligand and a hydrogen source in a polar solvent under Ar protection to obtain compound g-12 or g-13, wherein the transition metal catalyst is dichlorobis(4-methylisopropylphenyl)ruthenium (II) or dichloro(pentamethylcyclopentadienyl)rhodium (III) dimer, the ligand is (1R,2R)-(−)—N-(p-methylbenzenesulfonyl)-1,2-diphenylethylenediamine or (1S,2S)-(−)-N-(p-methylbenzenesulfonyl)-1,2-diphenylethylenediamine, the hydrogen source is sodium formate or ammonium formate, and the polar solvent is N,N-dimethylformamide;

(c) subjecting to Mitsunobu reaction of compound g-12 or g-13 and N-hydroxyphthalimide in a non-polar solvent to obtain compound g-14 or g-15, wherein the non-polar solvent is tetrahydrofuran or 1,4-dioxane;

(d) subjecting to hydrazinolysis of compound g-14 or g-15 with hydrazine hydrate or aminolysis of compound g-14 or g-15 with methylamine in a polar protic solvent to obtain a compound g-16 or g-17, wherein the polar protic solvent is methanol or ethanol.

* * * * *

UNITED STATES PATENT AND TRADEMARK OFFICE

CERTIFICATE OF CORRECTION

PATENT NO. : 10,501,454 B2
APPLICATION NO. : 16/251486
DATED : December 10, 2019
INVENTOR(S) : Yushe Yang et al.

It is certified that error appears in the above-identified patent and that said Letters Patent is hereby corrected as shown below:

In the Claims

Claim 10, Column 170, between Lines 60-65, the compound is shown as:

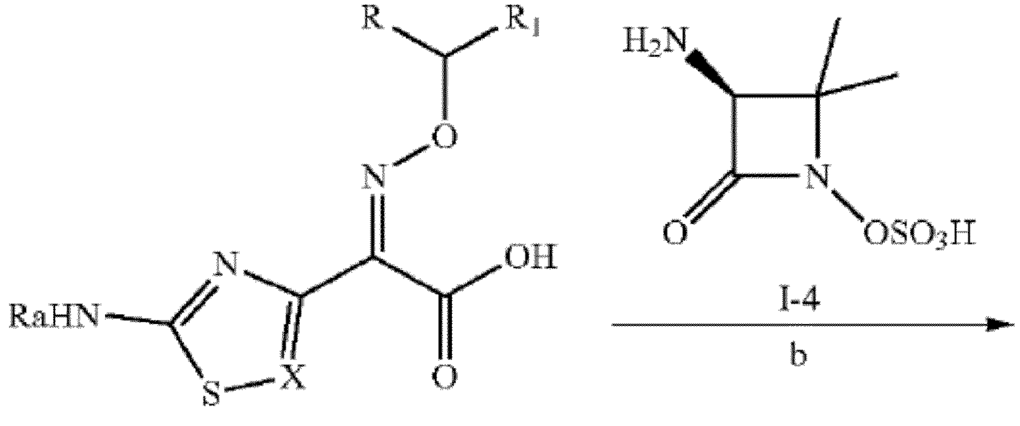

I-3 I-4

Should read:

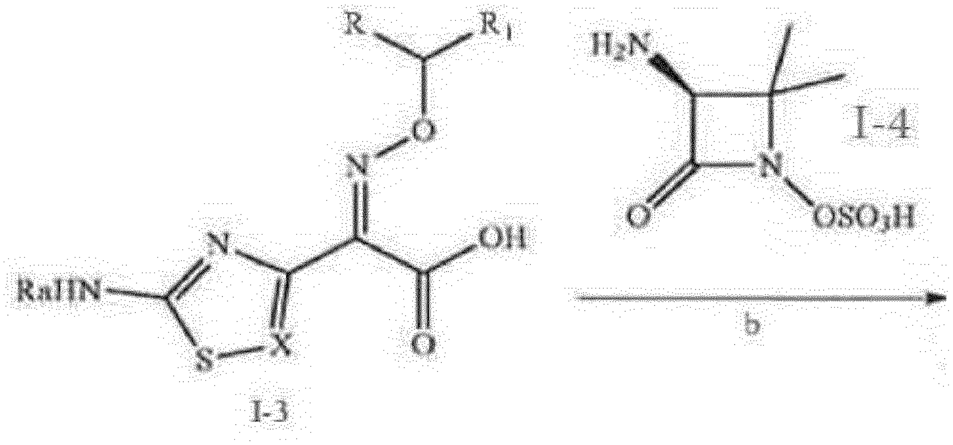

I-3 I-4

Signed and Sealed this
Eighteenth Day of February, 2020

Andrei Iancu
*Director of the United States Patent and Trademark Office*